US011497738B2

(12) United States Patent
Huff et al.

(10) Patent No.: US 11,497,738 B2
(45) Date of Patent: Nov. 15, 2022

(54) DI-SUBSTITUTED PYRAZOLE COMPOUNDS FOR THE TREATMENT OF DISEASES

(71) Applicant: FGH BIOTECH, INC., Houston, TX (US)

(72) Inventors: Joel Huff, Spring Branch, TX (US); Motonari Uesugi, Osaka (JP); John Kincaid, Hayward, CA (US)

(73) Assignee: FGH BIOTECH, INC., Houston, TX (US)

(*) Notice: Subject to any disclaimer, the term of this patent is extended or adjusted under 35 U.S.C. 154(b) by 0 days.

(21) Appl. No.: 16/097,211

(22) PCT Filed: Apr. 28, 2017

(86) PCT No.: PCT/US2017/030261
§ 371 (c)(1),
(2) Date: Oct. 26, 2018

(87) PCT Pub. No.: WO2017/190086
PCT Pub. Date: Nov. 2, 2017

(65) Prior Publication Data
US 2019/0134017 A1    May 9, 2019

Related U.S. Application Data

(60) Provisional application No. 62/330,049, filed on Apr. 29, 2016.

(51) Int. Cl.
| | | |
|---|---|---|
| *A61K 31/4439* | (2006.01) | |
| *C07D 305/08* | (2006.01) | |
| *C07D 231/12* | (2006.01) | |
| *C07D 401/14* | (2006.01) | |
| *C07D 401/04* | (2006.01) | |
| *C07D 307/22* | (2006.01) | |
| *A61P 3/00* | (2006.01) | |
| *A61P 9/00* | (2006.01) | |
| *A61P 35/00* | (2006.01) | |
| *A61K 31/506* | (2006.01) | |

(52) U.S. Cl.
CPC ........ *A61K 31/4439* (2013.01); *A61K 31/506* (2013.01); *A61P 3/00* (2018.01); *A61P 9/00* (2018.01); *A61P 35/00* (2018.01); *C07D 231/12* (2013.01); *C07D 305/08* (2013.01); *C07D 307/22* (2013.01); *C07D 401/04* (2013.01); *C07D 401/14* (2013.01)

(58) Field of Classification Search
CPC ............................ C07D 401/04; C07D 401/14
See application file for complete search history.

(56) References Cited

U.S. PATENT DOCUMENTS

| | | |
|---|---|---|
| 5,712,303 A | 1/1998 | Faraci et al. |
| 5,939,462 A | 8/1999 | Connell et al. |
| 6,130,217 A | 10/2000 | Arnold et al. |
| 6,248,363 B1 | 6/2001 | Patel et al. |
| 8,207,196 B2 | 6/2012 | Uesugi et al. |
| 8,778,976 B2 | 7/2014 | Uesugi et al. |
| 8,927,578 B2 | 1/2015 | Uesugi et al. |
| 9,085,566 B2 | 7/2015 | Uesugi et al. |
| 9,187,485 B2 | 11/2015 | Uesugi et al. |
| 9,212,179 B2 | 12/2015 | Uesugi et al. |
| 9,233,941 B2 | 1/2016 | Uesugi et al. |
| 9,713,613 B2 | 7/2017 | Uesugi et al. |
| 9,873,689 B2 | 1/2018 | Cantrell, Jr. |
| 2002/0065289 A1 | 5/2002 | Kordik et al. |
| 2002/0111353 A1 | 8/2002 | Ledeboer et al. |
| 2003/0055085 A1 | 3/2003 | Van Wagenen et al. |
| 2004/0229927 A1 | 11/2004 | Sircar et al. |
| 2008/0108799 A1 | 5/2008 | Weiss |
| 2008/0280869 A1 | 11/2008 | Almstead et al. |
| 2009/0054491 A1 | 2/2009 | Edwards et al. |
| 2011/0021771 A1 | 1/2011 | Mallais et al. |
| 2011/0046147 A1 | 2/2011 | Hartmann et al. |
| 2011/0112282 A1 | 5/2011 | Roehrig et al. |
| 2012/0252796 A1 | 10/2012 | Pingali et al. |
| 2013/0018053 A1 | 1/2013 | Zhou et al. |
| 2014/0038984 A1 | 2/2014 | Uesugi et al. |
| 2014/0045845 A1 | 2/2014 | Uesugi et al. |
| 2014/0235646 A1 | 8/2014 | Uesugi et al. |
| 2014/0329684 A1* | 11/2014 | Muller ................. C07D 413/04 504/280 |
| 2015/0065519 A1 | 3/2015 | Chakravarty et al. |
| 2015/0210705 A1 | 7/2015 | Jacobsen et al. |
| 2015/0307501 A1 | 10/2015 | Uesugi et al. |
| 2016/0128985 A1 | 5/2016 | Uesugi et al. |
| 2018/0000801 A1 | 1/2018 | Uesugi et al. |
| 2018/0028518 A1 | 2/2018 | Bernales et al. |
| 2018/0051013 A1 | 2/2018 | Pujala et al. |
| 2018/0291013 A1 | 10/2018 | Uesugi et al. |
| 2019/0071434 A1 | 3/2019 | Boxer et al. |
| 2019/0194167 A1* | 6/2019 | Uesugi ..................... A61P 3/10 |

FOREIGN PATENT DOCUMENTS

| | | |
|---|---|---|
| AU | 2004200420 A1 | 9/2004 |
| CN | 105294584 A | 2/2016 |

(Continued)

OTHER PUBLICATIONS

Shimano. FEBS Journal, 2009, 616-621 (Year: 2009).*

(Continued)

*Primary Examiner* — Noble E Jarrell

(74) *Attorney, Agent, or Firm* — Squire Patton Boggs, LLP (US)

(57) ABSTRACT

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and nonalcoholic fatty liver disease (NAFLD) wherein the compound is according to Formula (I).

23 Claims, 7 Drawing Sheets

(56) References Cited

FOREIGN PATENT DOCUMENTS

| | | |
|---|---|---|
| DE | 3406329 | 8/1985 |
| EP | 1698626 A1 | 9/2006 |
| IN | 2816/MUM/2013 | 5/2016 |
| JP | S61-010557 A | 1/1986 |
| JP | 1996181009 | 1/1998 |
| JP | 2006-514095 A | 4/2006 |
| JP | 2008-528700 A | 7/2008 |
| WO | WO 1994/013643 A1 | 6/1994 |
| WO | WO 2001/062737 A1 | 8/2001 |
| WO | WO 03/087061 * | 10/2003 |
| WO | WO 2004/050632 A1 | 6/2004 |
| WO | WO 2005/044194 A2 | 5/2005 |
| WO | WO 2005/063737 A1 | 7/2005 |
| WO | WO 2006/084176 A2 | 8/2006 |
| WO | WO 2007/052843 | 5/2007 |
| WO | WO 2008/090382 | 7/2008 |
| WO | WO 2008/097835 A2 | 8/2008 |
| WO | WO 2009083581 * | 7/2009 |
| WO | WO-2011038261 A * | 3/2011 ........... C07D 401/14 |
| WO | WO 2011/051961 A1 | 5/2011 |
| WO | WO 2011/038261 A1 | 9/2011 |
| WO | WO 2011/109261 A1 | 9/2011 |
| WO | WO 2015/031710 A1 | 3/2015 |
| WO | WO 2015/067646 * | 5/2015 |
| WO | WO 2018/049080 | 3/2018 |

OTHER PUBLICATIONS

Gong. Cancer Epidemiology Biomarkers and Prevention, 2006, 15(10), 1977-1983 (Year: 2006).*
El-Khawass. Journal of the Chinese Chemical Society, 1990, 37, 605-609 (Year: 1990).*
Kumari. Tetrahedron letters, 2012, 53, 1130-1133 (Year: 2012).*
Suri. Green Chemistry, 2012, 14, 2193-2196, supporting information pages S1-S87 (Year: 2012).*
Grosche. Synthesis, 1999, 11, 1961-1970 (Year: 1999).*
U.S. Appl. No. 16/331,505, filed Mar. 7, 2019, Huff et al.
De Barros et al. *Anais da Associacao Brasileira de Quimica* (2001), 50(4), 162-165.
Bellale, Eknath et al., "Diarylthiazole: an antimycobacterial scaffold potentially targeting PrrB-PrrA two-component system", Journal of Medicinal Chemistry Jun. 26, 2014, vol. 57, No. 15, pp. 6572-6582.
Chen, Y et al., "Copper catalyzed synthesis of 1-aryl-1,2,3-triazoles from aryl iodides, alkynes, and sodium azide," Journal of Organometallic Chemistry 2014, 749(31):215-218.
Compounds comprising pyrazole, STN database accessed on Jan. 18, 2019, 236 pages.
International Search Report and Written Opinion dated Nov. 2, 2017 in International Patent Application No. PCT/US2017/030261, 8 pages.
Krishnan et al., "Synthesis of Aryltriazolyl Derivatives," Indian Journal of Chemistry, vol. 26B, Jul. 1987, pp. 616-619.
Ueda, S. et al. Angew. Chem. Int. Ed. 2011, 38, 8944.
Vachal et al., "Highly selective and potent agonists of sphingosine-1-phosphate 1 (SIP$_1$) receptor," *Bioorganic & Medicinal Chemistry Letters*, 16:3684-3687, 2006.
Xu et al., "Design, synthesis, and biologic evaluation of some novel N-arylpyrazole derivatives as cytotxic agents," Medicinal Chemistry Research, 2013, vol. 22, 5610-5616.
Cheng et al. "Glucose-Mediated N-Glycosylation of SCAP is Essential for SREBP-1 Activation and Tumor Growth," *Cancer Cell* 2015,28(5), 569-581.
Du et al. FGFR3 Stimultes Stearoyl CoA Desaturase 1 Activity to Promote Bladder Tumor Growth, Cancer Res Actions 2012, 72(22), 5843-55.
Gabitova et al. "Molecular Pathways: Sterols and Receptor Signaling in Cancer," *Clin Cancer Res*. 2014, 20(1), 28-34.
Kamisuki et al. "A Small Molecule that Blocks Fat Synthesis by Inhibiting the Activation of SREBP," *Chemistry and Biology* 2009, 16, 882-892.
Li et al. "Fatostatin Displays High Antitumor Activity in Prostate Cancer by Blocking SREBP-Regulated Metabolic Pathways and Androgen Receptor Signaling" *Mol Cancer Ther*. 2014, 13(4), 855.
Li et al. "Anti-cancer efficacy of SREBP inhibitor, alone or in combination with docetaxel, in prostate cancer harboring p53 mutations," *Oncotarget*. 2015, 6(38), 41018.
Mason et al. "SCD1 Inhibition Causes Cancer Cell Death Depleting Mono-Unsaturated Fatty Acids," *PLoS ONE* 2012, 7(3), 633823, doi:10.1371/journal.pone.0033823.
Parrales et al. "Unsaturated fatty acids regulate stemness of ovarian cancer cells through NF-κB," *Stem Cell Investig*. 2017, 4, 49.
Southam et al. "Drug Redeployment to Kill Leukemia and Lymphoma Cells by Disrupting SCD1-mediated Synthesis of Monounsaturated Fatty Acids," *Cancer Research* 2015, 75(2), 2530-2540.
Sunami et al. "Lipid Metabolism and Lipid Droplets in Pancreatic Cancer and Stellate Cells" *Cancers* 2018, 10 (3), doi:10.3390/cancers10010003.
Abifadel et al., "Mutations in PCSK9 cause autosomalet dominant hypercholesterolemia", Nat Genet. Jun. 2003;34(2):154-6 (abstract only).
Brown et al., "Stearoyl-coenzyme A desaturase 1 inhibition and the metabolic syndrome: considerations for future drug discovery", Current Opinion in Lipidology 2010, 21:192-197; DOI:10.1097/MOL.0b013e32833854ac.
Cohen et al. "Low LDL Cholesterol in individuals of African descent resulting from frequest nonsense mutations in PCSK9", Nat Genet. Feb. 2005; 37(2):161-5 (abstract only).
Guo et al. "Targeting SREBP-1-driven lipid metabolism to treat cancer," Curr Pharm Des. 2014, 20(15), 2619-2626.
Macdonald et al., "Absence of stearoyl-CoA desaturase-1 ameliorates features of the metabolic syndrome in LDLR-deficient mice", J. Lipid Res. 2008. 49: 217-229. DOI 10.1194/jlr.M700478-JLR200.
Urban et al., Targeting the proprotein convertase subtilisin/ Kexin Type 9 for the Treatment of Dyslipidemia and Atherosclerosis, *J. Am. Coll. Cardiol*. Oct. 15, 2013;62(16):1401-8.
Ali et al., "Input of Isosteric and Bioisosteric Approach in Drug Design", 6 pages, Department of Pharmaceutical Sciences, South Dakota State University, College of Pharmacy, Brookings USA (2013).
Peck et al. "Inhibition of Fatty Acid Desaturation is Detrimental to Cancer Cell Survival in Metabolically Compromised Environments," *Cancer and Mtabolism* 2016, 4:6, 1-18.
Roongta et al. "Cancer Cell Dependency on Unsaturated Fatty Acids Implicates Stearoyl-CoA Desaturase as a Target for Cancer Therapy," *Molecular Cancer Research* 2011, 9(11), 1551-61.
Hachem et al., "The Role of Proprotein Convertase Subtilisin/Kexin Type 9 (PCSK9) in Cardiovscular Homeostasis; A non-systematic Literature Review 2017", Curr Cardiol Rev. 2017 13(4):274-282.
Horton et al. "Molecular Biology of PCSK9: Its Role in LDL Metabolism," *Trends Biochem Sci*. 2007, 32(2), 71-77.
Zhang et al., "Design, synthesis, and biological evaluation of 5-(4-(pyridin-4-yl)-1H-1,2,3-triazol-1-yl)benzonitrile derivatives as xanthine oxidase inhibitors," Chemical Biology & Drug Design 2018, 91(2), 526-533.

* cited by examiner

DI-SUBSTITUTED PYRAZOLE COMPOUNDS FOR THE TREATMENT OF DISEASES

This application is a 371 of International Application No. PCT/US2017/030261 filed Apr. 28, 2017 and which claims priority benefit of U.S. Provisional Patent Application No. 62/330,049 filed Apr. 29, 2016. The contents of which applications are hereby incorporated by reference herein in their entireties.

STATEMENT OF GOVERNMENT RIGHTS

This invention was made with Government support under contract 5R44HL112484-2 awarded by the National Institutes of Health. The Government has certain rights in this invention.

FIELD

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and nonalcoholic fatty liver disease (NAFLD).

BACKGROUND

Metabolic syndrome comprises many cardiovascular risk factors that, occurring together, increase a person's risk of diseases like heart disease, stroke, and type 2 diabetes. These risk factors include hypertension, dyslipidemia, obesity, high blood sugar, pancreatic (β-cell dysfunction, and atherosclerosis. In addition, increasing evidence show a strong link between metabolic syndrome and a variety of cancers including, breast, liver, and prostate (Gabitova et al. *Clin Cancer Res.* 2014, 20(1), 28). Disturbing the balance between energy expenditure and food intake, in addition to predisposing genetic factors, can result in pathological conditions, diseases, or disorders such as obesity, diabetes, and cardiovascular disease. Targeting metabolic pathways, especially those that are related to lipid and fat metabolism, has been used to develop drugs against these diseases (Padwal et al. *Lancet* 2007, 369(9555), 71). Although pharmacological intervention against individual abnormalities associated with metabolic syndrome is possible, it would be of great advantage to target multiple metabolic pathways by lowering lipids (triglycerides and cholesterol), in addition to controlling blood glucose in diabetic patients.

One of the major consequences of metabolic syndrome and obesity in particular is the development of NAFLD. NAFLD is a condition that is caused by excess of fat accumulation in the liver of patients without a history of alcohol abuse. NAFLD is the liver manifestation of metabolic syndrome and has been increasing worldwide in line with the epidemic increase in obesity, type 2 diabetes, and dyslipidemia (Takahashi Y, Fukusato T. Histopathology of nonalcoholic fatty liver disease/nonalcoholic steatohepatitis. *World J Gastroenterol.* 2014 Nov. 14; 20(42):15539-48). NAFLD can be a simple steatosis (triglyceride accumulation in liver) due to shift in de novo fatty acid metabolism to net lipogenesis from lipolysis, or the more serious nonalcoholic steatohepatitis (NASH). NASH is considered the major chronic liver disease, with serious damage to liver such as interlobular inflammation, hepatocellular ballooning and fibrosis and it may lead to liver cirrhosis and hepatocellular carcinoma (Schreuder et al. *World J Gastroenterol* 2008, 14(16), 2474). It is estimated that 15% of the adult population in the US have NAFLD and about 3-4% suffer from NASH (Ekstedt et al. *Hepatology* 2006, 44(4), 865). Currently treatment for NASH is limited to substantial weight loss by methods such as bariatric surgery, insulin sensitizing agents and Vitamin E supplements, in addition to life style modification by diet and exercise.

Another risk factor associated with metabolic syndrome is the development of diabetes mellitus where dyslipidemia, including high levels of LDL cholesterol, is very common in these patients. These patients are at very high risk of developing atherosclerotic cardiovascular disease. Numerous studies including genetic studies support the notion that high levels of LDL are casually implicated in coronary artery disease and that lowering LDL cholesterol reduces the risk of cardiovascular events (Ajufo et al. *Lancet Diabetes Endocrinol.* 2016 May; 4(5):436-46). At the genetic level, familial hypercholesterolemia, a mendelian disorder caused by mutations in LDL Receptor (LDLR) and other genes in LDL-Receptor pathways is associated with high levels of LDL and increased risk of cardiovascular disease (Kolansky et al. *Am J Cardiol.* 2008 Dec. 1; 102(11):1438-43). One of the known genes that was linked to familial hypercholesterolemia is the proprotein convertase subtilisin/kexin type 9 (PCSK 9) which is secreted by hepatocytes (Urban et al. *J. Am. Coll. Cardiol.* 2013 Oct. 15; 62(16):1401-8). It was shown that gain of function in PCSK 9 caused high level of LDL and increased cardiovascular events (Abifadel M et al. *Nat Genet.* 2003 June; 34(2):154-6). On the other hand patients with mutations in this gene had very low level of LDL suggesting that PCSK9 is potential therapeutic target for reducing LDL cholesterol (Cohen et al. *Nat Genet.* 2005 February; 37(2):161-5).

Animals, including humans, rely on fat and carbohydrate as their major energy sources required to sustain their activity needs. A diet varying in fat or carbohydrate contents contributes to energy metabolism of animals including humans. Long chain fatty acids are major sources of energy and important components of the lipids that comprise the cellular membranes. They are derived from food and synthesized de novo from acetyl-CoA. Hence, acetyl-CoA is an intermediate that interrelates glucose and fatty acid metabolism, and is converted to malonyl-CoA by the rate limiting enzyme acetyl-CoA carboxylase (ACC). The synthesis of fatty acids by fatty acid synthase (FAS) requires acetyl-CoA, malonyl-CoA, and NADPH. Malonyl-CoA is the $C_2$ donor in the de novo synthesis of long-chain fatty acids ($C_{14}$-$C_{18}$) and very long chain fatty acids ($C_{20}$-$C_{26}$).

Cholesterol is derived from food and synthesized from acetyl-CoA. The conversion of carbohydrates into acyl glycerides through de novo fatty acid and cholesterol synthesis involves at least 12 and 23 enzymatic reactions, respectively. Expression levels of the genes encoding these enzymes are controlled by three transcription factors, designated sterol regulatory element-binding proteins (SREBPs), SREBP-1a, -1c, and SREBP-2. SREBPs are membrane-bound proteins and are members of a class of the basic helix-loop-helix leucin zipper family of transcription factors. Unlike other leucin zipper members of transcription factors, SREBPs are synthesized as ER-membrane-bound precursors, which need to be proteolytically released by two proteases bound to the Golgi membrane, Site-1 and Site-2 proteases, to generate active forms, nSREBPs, that activate transcription of target genes in the nucleus (DeBose-Boyd et al. *Cell* 1999, 99 (7), 703; Sakai et al. *Cell* 1996, 85, 1037). The proteolytic activation of SREBPs is tightly regulated by sterols that are known to induce the interaction of the SREBP cleavage-activating protein (SCAP) with the ER membrane-bound insulin-induced gene (INSIG), thereby inhibiting the exit of the SREBP/SCAP complex from the ER (Yabe et al. *Proc Natl Acad Sci USA* 2002, 99(20), 12753; Yang et al., *Cell* 2002, 110, 489-500). When sterols accumulate in the ER membranes, the SCAP/SREBP complex fails to exit the ER to the Golgi apparatus, and the proteolytic processing of SREBPs is suppressed. Thus, SREBPs are key lipogenic transcription factors that govern the homeostasis of fat metabolism. Interestingly, SREBP isoforms-1a and -1c have some overlap in target genes, yet they have distinct roles in lipid metabolism (Eberle et al. *Biochimie* 2004, 86 (11), 839).

Recently, numerous studies have shown that SREBPs integrate several cell signals to regulate lipogenesis and other pathways important for diseases such as type II diabetes, dyslipidemia, cancer and the immune response (Shao W and Espenshade P J. *Cell Metab.* 2012, 16, 414). In addition, studies in animal models and humans suggested a strong correlation between upregulation of SREBPs and SREBP-1c in particular and the pathogenesis of these diseases and reducing the activity of SREBPs may be beneficial to treat these diseases and ameliorate their complications (Zhao et al. *Diabetes* 2014, (63) 2464). In addition to life style treatment, individual drugs have been developed to treat these diseases that associated with the metabolic syndrome. The central role of SREBPs in the regulation of lipids and their potential role as a major player in several diseases raised the possibility of novel approaches to treat several risk factors with one drug (Soyal et al. *Trends Pharmacol Sciences* 2015, 36, 406).

Recently, several studies have provided proof of concept for the efficacy of small molecules targeting transcriptional SREBPs activity to treat several components of metabolic syndrome. Betulin, a pentacyclic triterpene that naturally occurs in birch bark, decreased the level of the mature active form of both SREBP-1 and 2 in a human liver Huh-7 cell line, resulting in down regulation of genes involved in cholesterol and fatty acid synthesis (Tang et al. *Cell Metabol.* 2011, 13, 44). These authors presented evidence showing that betulin directly interacts with SCAP. Mice that were fed western diet, which induces obesity, fatty liver and dyslipidemia, and treated with betulin had lower weight gain, and accumulated less fat without affecting food intake (Tang et al. *Cell Metabol.* 2011, 13, 44). In addition, the treated mice had lower triglycerides, cholesterol plasma glucose and improved insulin sensitivity. These metabolic improvements were reflected in reduced levels of hepatic SREBP and its target genes.

Major hallmarks of tumor cells are over expression and increased metabolic activities such as glucose consumption, protein and nucleic acid synthesis and increased de novo fatty acid synthesis (Menendez, J. A., and Lupu, R. *Nat. Rev. Cancer* 2007, 7, 763). It has been shown that, contrary to normal cells, various tumor cells are very active in de novo fatty acid biosynthesis, irrespective of the extracellular lipids, and that de novo fatty acids accounted for all fatty acid esterification in the tumor cells (Medes et al. *Cancer Research* 1953, 13, 27.) Pharmacological and RNAi knock-down approaches against ACC and FAS have been reported (Brusselmans et al. *Cancer Research* 2005, 65, 6719-6725; Kuhajda et al. *Proceedings of the National Academy of Sciences of the United States of America* 2000, 97, 3450-3454; Menendez, et al. *Int J Cancer* 2005, 115, 19-35). These studies showed, that inhibiting these enzymes, induced growth inhibition and an apoptotic effect against breast and prostate cancer cells. In this regard, SREBP-1 and 2 as master regulators of lipid biosynthesis play a major role in tumor growth. In support of the role of SREBP in cancer, several studies have shown that inhibition of SREBP activation using RNAi and a small molecule resulted in significant growth inhibition. On the other hand it was recently reported that glucose-mediated N-glycolsylation of SCAP resulted in its stabilization and activation of SREBP-1 to promote tumor growth in glioblastoma (Cheng et al. 2015). These findings suggest that targeting the SCAP/SREBP complex is a promising approach for treating cancer and metabolic diseases.

Fatostatin is a diarylthiazole small molecule and is the first non-cholesterol molecule that acts on the translocation of SREBPs from the ER to the Golgi, hence affecting the downregulation of the major players in lipid metabolism, including triglyceride (TG) and cholesterol (Kamisuki et al. *Chem. Biol.* 2009, 16, 882-92; Kamisuki et al. *J. Med. Chem.* 2011 54, 4923). Fatostatin derivatives such as FGH10019 bind specifically to SCAP at a distinct site from the sterol-binding domain. As a result of FGH10019 action, SREBPs are retained in the ER, blocking their transportation to the Golgi apparatus, where they are processed by proteases to produce the nuclear active form bHLH. Recently several studies showed that fatostatin derivatives inhibited cell growth in cells and animal models for breast and prostate cancer, thus is validating the potential use of these compounds to treat cancer (Li et al. *Mol. Cancer. Ther.* 2014, 13(4), 855; Li et al. *Oncotarget.* 2015, 6(38), 41018).

However, while fatostatin could provide an important starting point for providing small molecules for new pharmacological interventions to combat metabolic diseases, it has liabilities which may preclude its use as a drug. Thus, small molecules with improved drug-like qualities are needed.

SUMMARY OF THE INVENTION

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and NAFLD.

In one aspect, provided is a Compound of Formula (I):

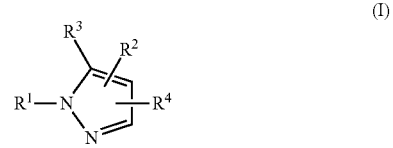

where
R$^1$ is phenyl, pyridinonyl, pyridinyl, pyrimidinyl, pyridazinyl, or pyrazinyl; where the phenyl, pyridinyl, pyrimidinyl, pyridazinyl, and pyrazinyl rings are optionally substituted with 1, 2, or 3 R$^{1a}$ and where the pyridinonyl is substituted on the nitrogen with R$^{1b}$ and is additionally optionally substituted with 1, 2, or 3 R$^{1a}$;

each R$^{1a}$ is independently halo, alkyl, alkenyl, haloalkyl, cycloalkyl, cycloalkylalkyl, heterocycloalkyl, or heterocycloalkylalkyl;

R$^{1b}$ is hydrogen, alkyl, alkenyl, haloalkyl, cycloalkyl, cycloalkylalkyl, heterocycloalkyl, or heterocycloalkylalkyl;

$R^2$ is

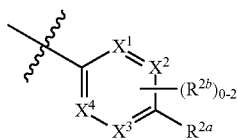

where 0, 1, or 2 of $X^1$-$X^4$ are nitrogen and the remaining are carbon;

$R^{2a}$ is —NR$^{5a}$S(O)$_2$R$^{5b}$ or —NR$^{6a}$R$^{6b}$;

each $R^{2b}$ is independently halo, alkyl, haloalkyl, —NO$_2$, or cyano;

$R^3$ is hydrogen, halo, alkyl, or haloalkyl;

$R^4$ is hydrogen, halo, alkyl, or haloalkyl;

$R^{5a}$ and $R^{6a}$ are independently hydrogen or alkyl; and $R^{5b}$ and $R^{6b}$ are independently alkyl; haloalkyl; cycloalkyl; cycloalkylalkyl; heterocycloalkyl; heterocycloalkylalkyl; and wherein each cycloalkyl, either alone or as part of another group, is independently optionally substituted with one or two groups independently selected from the group consisting of alkyl, halo, and haloalkyl; or a pharmaceutically acceptable salt thereof;

provided that the compound is not N-methyl-6-(1-phenyl-1H-pyrazol-4-yl)pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine.

In another aspect, provided is a Compound according to Formula (II)

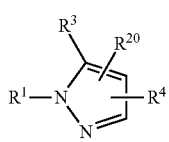

(II)

where $R^1$ is phenyl, pyridinonyl, pyridinyl, pyrimidinyl, pyridazinyl, or pyrazinyl; where the $R^1$ phenyl, pyridinyl, pyrimidinyl, pyridazinyl, and pyrazinyl rings are substituted with one $R^{1a}$ and additionally optionally substituted with a second $R^{1a}$ and additionally optionally substituted with a third $R^{1a}$, and where the pyridinonyl is substituted on the nitrogen with $R^{1b}$ and is additionally optionally substituted with 1, 2, or 3 $R^{1a}$;

each $R^{1a}$ is independently halo, alkyl, alkenyl, haloalkyl, cycloalkyl, cycloalkylalkyl, heterocycloalkyl, or heterocycloalkylalkyl;

$R^{1b}$ is hydrogen, alkyl, alkenyl, haloalkyl, cycloalkyl, cycloalkylalkyl, heterocycloalkyl, or heterocycloalkylalkyl;

$R^{20}$ is

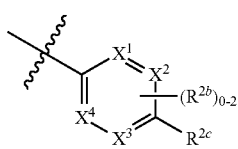

where 0, 1, or 2 of $X^1$-$X^4$ are nitrogen and the remaining are carbon;

each $R^{2b}$ is independently halo, alkyl, haloalkyl, —NO$_2$, or cyano;

$R^{2c}$ is —NO$_2$ or NH$_2$;

$R^3$ is hydrogen or alkyl;

$R^4$ is hydrogen or alkyl;

$R^{5a}$ and $R^{6a}$ are independently hydrogen or alkyl; and $R^{5b}$ and $R^{6b}$ are independently alkyl, haloalkyl, cycloalkyl, cycloalkylalkyl, heterocycloalkyl, heterocycloalkylalkyl; and wherein each cycloalkyl, either alone or as part of another group, is independently optionally substituted with one or two groups independently selected from the group consisting of alkyl, halo, and haloalkyl; or a pharmaceutically acceptable salt thereof;

provided that the compound is not 4-(1-(3-methylpyridin-4-yl)-1H-pyrazol-4-yl)aniline; 4-(1-(2-methylpyridin-4-yl)-1H-pyrazol-4-yl)aniline; or 4-(1-(3-chloropyridin-4-yl)-1H-pyrazol-4-yl)aniline.

In another aspect, provided is a Compound according to Formula (III)

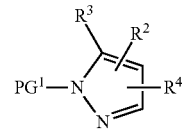

(III)

where

PG$^1$ is a nitrogen protecting group;

$R^2$ is

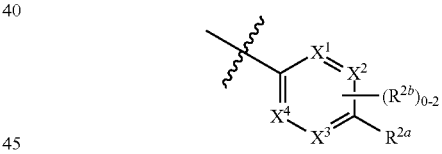

where 0, 1, or 2 of $X^1$-$X^4$ are nitrogen and the remaining are carbon;

$R^{2a}$ is —NR$^{5a}$S(O)$_2$R$^{5b}$, or —NR$^{6a}$R$^{6b}$;

each $R^{2b}$ is independently halo, alkyl, haloalkyl, —NO$_2$, or cyano;

$R^3$ is hydrogen, alkyl, or haloalkyl;

$R^4$ is hydrogen, alkyl, or haloalkyl;

$R^{5a}$ and $R^{6a}$ are independently hydrogen or alkyl;

$R^{5b}$ and $R^{6b}$ are independently alkyl; haloalkyl; cycloalkyl; cycloalkylalkyl; heterocycloalkyl; or heterocycloalkylalkyl; and wherein each cycloalkyl, either alone or as part of another group, is independently optionally substituted with one or two groups independently selected from the group consisting of alkyl, halo, and haloalkyl; or a pharmaceutically acceptable salt thereof.

In another aspect, provided is a compound of Formula (IV)

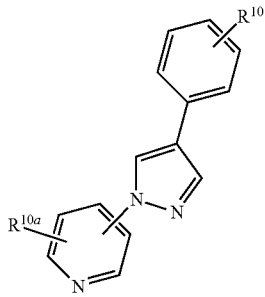

(IV)

wherein $R^{10a}$ is ethyl, n-propyl, isopropyl, —O—$C_{1-3}$ alkyl, —O—$C_{1-3}$ alkoxy, pyrrolidine, or morpholine; $R^{10}$ is H, halogen, —OH, —O—$C_{1-3}$ alkyl, —O—$C_{1-3}$ alkoxy, —OC(O)$R^{10d}$, or —NR$^{10b}$R$^{10c}$; $R^{10d}$ is $C_1$-$C_3$ alkyl or aryl; $R^{10b}$ is H, $C_1$-$C_3$ alkyl, -alkyl-cyclopropane, cyclohexyl, benzyl, or —SO$_2$—R$^{10e}$; $R^{10c}$ is H, $C_1$-$C_3$ alkyl, or —SO$_2$—R$^{10e}$; and $R^{10e}$ is alkyl or cycloalkyl.

In another aspect, provided herein are pharmaceutical compositions, single unit dosage forms, and kits suitable for use in treating disorders associated with abnormal activation of the SREBP pathway which comprise a therapeutically effective amount of a compound provided herein, e.g., of some or any of the embodiments, of Formula (I)-(Im), (100), (200), and (Ia-1)-(Im-1) and specific compounds 1-130, and a pharmaceutically acceptable carrier thereof.

In another aspect, provided herein is a method of treating a condition, disease, or disorder associated with abnormal activation of the SREBP pathway comprising a) administering a therapeutically effective amount of a compound provided herein, e.g., of some or any of the embodiments, of Formula (I)-(Im), (100), (200), and (Ia-1)-(Im-1) and specific compounds 1-130 or a pharmaceutically acceptable salt thereof or b) administering a therapeutically effective amount of a composition comprising a compound provided herein, e.g., of some or any of the embodiments, of Formula (I)-(Im), (100), (200), and (Ia-1)-(Im-1) and specific compounds 1-130 or a pharmaceutically acceptable salt thereof and a pharmaceutically acceptable carrier thereof.

DESCRIPTION OF EXEMPLARY EMBODIMENTS

Definitions

Figure 1A:
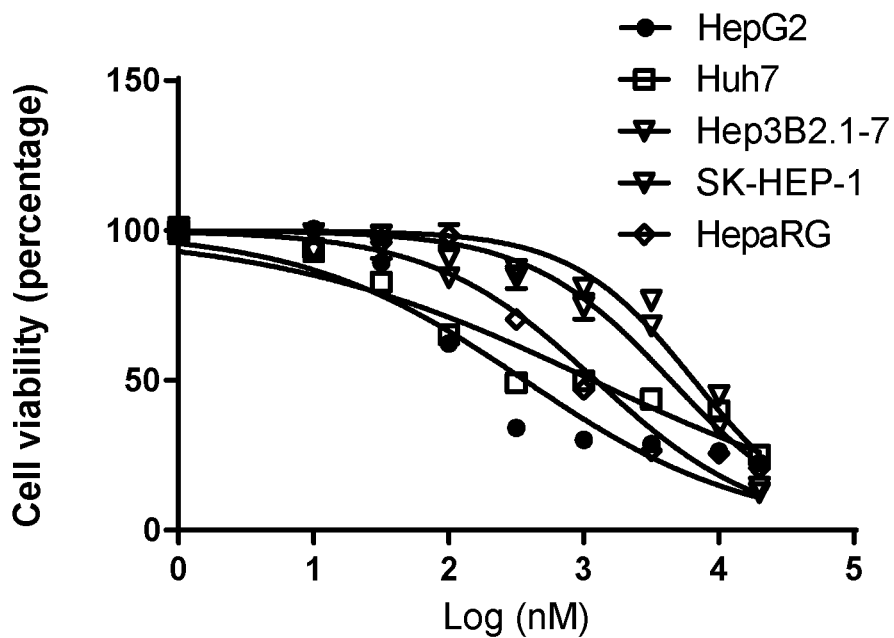
FIG. 1 depicts results for several liver cell lines tested for growth inhibition by a test compound within the scope for Formula I.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being unsubstituted or substituted, the groups in the list of substituents are themselves unsubstituted. For example, a substituted alkyl group can be substituted, for example, with a cycloalkyl group, and the cycloalkyl group is not further substituted unless specified otherwise.

"—O—$C_{1-3}$ Alkoxy" means an —OR group where R is $C_{1-3}$ alkyl substituted with $C_{1-3}$ alkoxy, as defined herein.

"Alkenyl" means a straight or branched hydrocarbon radical having from 2 to 8 carbon atoms and at least one double bond, and in some embodiments, includes ethenyl, propenyl, 1-but-3-enyl, 1-pent-3-enyl, 1-hex-5-enyl, and the like. "Lower alkenyl" means an alkenyl group having one to six carbon atoms.

"Alkyl" means a linear or branched hydrocarbon group having one to eight carbon atoms. "Lower alkyl" means an alkyl group having one to six carbon atoms. In some embodiments, lower alkyl includes methyl, ethyl, propyl, isopropyl, butyl, s-butyl, t-butyl, isobutyl, pentyl, hexyl, and the like. A "$C_0$" alkyl (as in "$C_0$-$C_6$-alkyl") is a covalent bond. "$C_6$ alkyl" refers to, for example, n-hexyl, iso-hexyl, and the like.

"Alkylamino" means a —NHR radical where R is alkyl as defined herein, or an N-oxide derivative thereof. In some embodiments, alkylamino includes methylamino, ethylamino, n- or iso-propylamino, n-, iso-, or tert-butylamino, and methylamino-N-oxide, and the like.

"Amino" means a —NH$_2$.

"Aryl" means a monovalent six- to fourteen-membered, mono- or bi-carbocyclic ring, wherein the monocyclic ring is aromatic and at least one of the rings in the bicyclic ring is aromatic. In some embodiments, aryl is phenyl, naphthyl, or indanyl, and the like.

"Cycloalkyl" means a monocyclic or polycyclic hydrocarbon radical having three to thirteen carbon atoms. The cycloalkyl can be saturated or partially unsaturated, but cannot contain an aromatic ring. In some embodiments, cycloalkyl includes fused, bridged, and spiro ring systems. In some embodiments, cycloalkyl is cyclopropyl, cyclobutyl, cyclopentyl, or cyclohexyl.

"Cycloalkylalkyl" means alkyl group substituted with one or two cycloalkyl group(s), as defined herein. In some embodiments, cycloalkylalkyl includes cyclopropylmethyl, 2-cyclobutyl-ethyl, and the like.

"Dialkylamino" means a —NRR' radical where R and R' are independently alkyl as defined herein, and an N-oxide thereof. In some embodiments, dialkylamino includes dimethylamino, diethylamino, N,N-methylpropylamino and N,N-methylethylamino, and the like.

"Haloalkyl" means an alkyl group, as defined herein, substituted with one or more halogens, for example, one, two, three, four, or five halo atoms. In some embodiments, haloalkyl includes 2,2-difluoroethyl, trifluoromethyl, 2-chloro-1-fluoroethyl, and the like.

"Heteroaryl" means a monocyclic, monovalent aromatic radical of 5 or 6 ring atoms containing one or more heteroatoms, for example one, two, or three ring heteroatoms, independently selected from oxygen, nitrogen, and sulfur and the remaining ring atoms being carbon. Unless stated otherwise, the point of attachment may be located on any atom of any ring of the heteroaryl group, valency rules permitting. In some embodiments, the term heteroaryl includes, but is not limited to, 1,2,4-triazolyl, 1,3,5-triazolyl, pyridinyl, pyrrolyl, imidazolyl, thienyl, furanyl, tetrazoyl, pyrazolyl, pyrazinyl, pyrimidinyl, pyridazinyl, oxazolyl, isooxazolyl, oxadiazolyl, thiazolyl, isothiazolyl, thiadiazolyl, and an N-oxide thereof.

"Heterocycloalkyl" means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the point of attachment of the group may be located on any atom of any ring within the radical, valency rules permitting. In particular, when the point of attachment is located on a nitrogen atom, R$^y$ is absent. In some embodiments, the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and an N-oxide thereof. In some embodiments, the heterocycloalkyl is substituted on the nitrogen with R$^y$ where R$^y$ is alkyl.

"Heterocycloalkylalkyl" means an alkyl group, as defined herein, substituted with one or two heterocycloalkyl group(s), as defined herein.

"Patient" or "subject" includes humans and other animals, particularly mammals, and other organisms. Thus the methods are applicable to both human therapy and veterinary applications. In some embodiments the patient is a mammal, and in other embodiments the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference, or S. M. Berge et al., "Pharmaceutical Salts," *J. Pharm. Sci.* 1977; 66, 1-19 which is also incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid, and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, and aluminum, as salts, and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein, or a salt thereof, that further includes a stoichiometric or non-stoichiometric amount of solvent bound by non-covalent intermolecular forces. In one embodiment, where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "aryl," "alkoxy," "heterocycloalkyl," "heterocyclic," and "heteroaryl," groups optionally comprise deuterium at one or more positions where hydrogen atoms are present, and wherein the deuterium composition of the atom or atoms is other than the natural isotopic composition.

Also as used herein, "alkyl," "cycloalkyl," "aryl," "alkoxy," "heterocycloalkyl," "heterocyclic," and "heteroaryl," groups optionally comprise carbon-13 at an amount other than the natural isotopic composition.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee, and a human), and in certain embodiments, a human. In certain embodiments, the subject is a farm animal (e.g., a horse, a cow, a pig, etc.) or a pet (e.g., a dog or a cat). In certain embodiments, the subject is a human.

"Administration" and variants thereof (e.g., in some embodiments, "administering" a compound) in reference to a compound of the invention means introducing the compound or a prodrug thereof into the system of the animal in need of treatment. When a compound of the invention or prodrug thereof is provided in combination with one or more other active agents (e.g., in some embodiments, surgery, radiation, and chemotherapy, etc.), "administration" and its variants are each understood to include concurrent and sequential introduction of the compound or prodrug thereof and other agents.

"Therapeutically effective amount" is an amount of a compound or composition, that when administered to a patient, is sufficient to effect such treatment for the condition, disease, or disorder, e.g., to ameliorate a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent that is known to be useful for, or has been or is currently being used for the treatment or prevention of a disorder or one or more symptoms thereof.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome, but does not yet experience or display symptoms of the disease, disorder, or syndrome; (ii) inhibiting the disease, disorder, or syndrome, i.e., arresting its development; and (iii) relieving the disease, disorder, or syndrome, e.g., relieving or reducing a symptom thereof, and/or causing regression of the disease, disorder, or syndrome. As is known in the art, adjustments for systemic versus localized delivery, age, body weight, general health, sex, diet, time of administration, drug interaction and the severity of the condition, disease, or disorder may be necessary, and will be ascertainable with routine experimentation by one of ordinary skill in the art. "Treating" or "treatment" of any condition, disease, or disorder refers, in certain embodiments, to ameliorating a condition, disease, or disorder that exists in a subject. In another embodiment, "treating" or "treatment" includes ameliorating at least one physical parameter, which may be indiscernible by the subject. In yet another embodiment, "treating" or "treatment" includes modulating the condition, disease, or disorder, either physically (e.g., stabilization of a discernible symptom) or physiologically (e.g., stabilization of a physical parameter) or both. In yet another embodiment, "treating" or "treatment" includes delaying the onset of the condition, disease, or disorder.

As used herein, the terms "prophylactic agent" and "prophylactic agents" refer to any agent(s) which can be used in the prevention of a condition, disease, or disorder, or one or more symptoms thereof. In certain embodiments, the term "prophylactic agent" includes a compound provided herein. In certain other embodiments, the term "prophylactic agent" does not refer a compound provided herein. In certain embodiments, a prophylactic agent can be an agent that is known to be useful for, or has been or is currently being used to prevent or impede the onset, development, progression, and/or severity of a condition, disease, or disorder.

As used herein, the phrase "prophylactically effective amount" refers to the amount of a therapy (e.g., prophylactic agent) which is sufficient to result in the prevention or reduction of the development, recurrence or onset of one or more symptoms associated with a condition, disease, or disorder, or to enhance or improve the prophylactic effect(s) of another therapy (e.g., another prophylactic agent).

Compounds

The embodiments described herein include the recited compounds as well as a pharmaceutically acceptable salt, hydrate, solvate, stereoisomer, tautomer, or mixture thereof.

In some or any embodiments, the Compound (e.g., of Formula (I), (100), (Ia), (Ib), and (Ih), and any embodiments thereof) is not N-methyl-6-(1-phenyl-1H-pyrazol-4-yl)

pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine.

In one aspect, provided is a Compound of Formula (100):

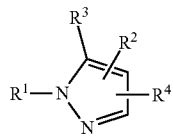

(100)

where
R$^1$ is phenyl, pyridinonyl, pyridinyl, pyrimidinyl, pyridazinyl, or pyrazinyl; where the phenyl, the pyridinyl, pyrimidinyl, pyridazinyl, and pyrazinyl rings are optionally substituted with 1 or 2 R$^{1a}$ and where the pyridinonyl is substituted on the nitrogen with R$^{1b}$ and is additionally optionally substituted with 1 R$^{1a}$;
each R$^{1a}$ is independently halo, alkyl, alkenyl, haloalkyl, cycloalkyl, cycloalkylalkyl, heterocycloalkyl, or heterocycloalkylalkyl;
R$^{1b}$ is hydrogen, alkyl, alkenyl, haloalkyl, cycloalkyl, cycloalkylalkyl, heterocycloalkyl, or heterocycloalkylalkyl;
R$^2$ is

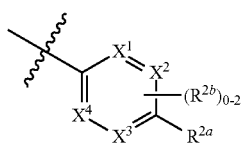

where 0, 1, or 2 of X$^1$-X$^4$ are nitrogen and the remaining are carbon;
R$^{2a}$ is —NR$^{5a}$S(O)$_2$R$^{5b}$ or —NR$^{6a}$R$^{6b}$;
each R$^{2b}$ is independently halo, alkyl, haloalkyl, —NO$_2$, or cyano;
R$^3$ is hydrogen, halo, alkyl, or haloalkyl;
R$^4$ is hydrogen, halo, alkyl, or haloalkyl;
R$^{5a}$ and R$^{6a}$ are independently hydrogen or alkyl; and
R$^{5b}$ and R$^{6b}$ are independently alkyl; haloalkyl; cycloalkyl where the cycloalkyl is optional substituted with 1 or 2 alkyl groups; cycloalkylalkyl; heterocycloalkyl; heterocycloalkylalkyl; or
a pharmaceutically acceptable salt thereof;
provided that the compound is not N-methyl-6-(1-phenyl-1H-pyrazol-4-yl)pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine.

In another aspect, provided is a Compound according to Formula (200)

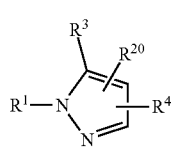

(200)

where
R$^1$ is phenyl, pyridinonyl, pyridinyl, pyrimidinyl, pyridazinyl, or pyrazinyl; where the R$^1$ phenyl, pyridinyl, pyrimidinyl, pyridazinyl, and pyrazinyl rings are substituted with one R$^{1a}$ and additionally optionally substituted with a second R$^{1a}$, and where the pyridinonyl is substituted on the nitrogen with R$^{1b}$ and is additionally optionally substituted with 1 R$^{1a}$;
each R$^{1a}$ is independently halo, alkyl, haloalkyl, or heterocycloalkyl;
R$^{1b}$ is hydrogen, alkyl, haloalkyl, cycloalkyl, cycloalkylalkyl, or heterocycloalkyl;
R$^{20}$ is

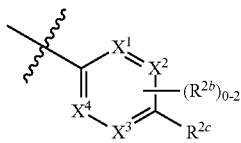

where 0, 1, or 2 of X$^1$-X$^4$ are nitrogen and the remaining are carbon; each R$^{2b}$ is independently halo, alkyl, haloalkyl, —NO$_2$, or cyano;
R$^{2c}$ is —NO$_2$ or NH$_2$;
R$^3$ is hydrogen or alkyl;
R$^4$ is hydrogen or alkyl;
R$^{5a}$ and R$^{6a}$ are independently hydrogen or alkyl; and
R$^{5b}$ and R$^{6b}$ are independently alkyl, haloalkyl, cycloalkyl, cycloalkylalkyl, heterocycloalkyl, heterocycloalkylalkyl; or
a pharmaceutically acceptable salt thereof;
provided that the compound is not 4-(1-(3-methylpyridin-4-yl)-1H-pyrazol-4-yl)aniline; 4-(1-(2-methylpyridin-4-yl)-1H-pyrazol-4-yl)aniline; or 4-(1-(3-chloropyridin-4-yl)-1H-pyrazol-4-yl)aniline.

In another aspect, provided is a Compound according to Formula (300)

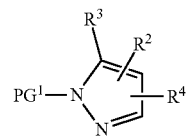

(300)

where
PG$^1$ is a nitrogen protecting group;
R$^2$ is

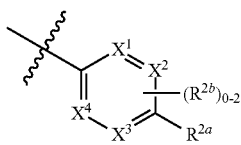

where 0, 1, or 2 of X$^1$-X$^4$ are nitrogen and the remaining are carbon;
R$^{2a}$ is —NR$^{5a}$S(O)$_2$R$^{5b}$, or —NR$^{6a}$R$^{6b}$;
each R$^{2b}$ is independently halo, alkyl, haloalkyl, —NO$_2$, or cyano;
R$^3$ is hydrogen or alkyl;
R$^4$ is hydrogen or alkyl;
R$^{5a}$ and R$^{6a}$ are independently hydrogen or alkyl;
R$^{5b}$ and R$^{6b}$ are independently alkyl; haloalkyl; cycloalkyl; cycloalkylalkyl where the cycloalkyl is optionally substituted with 1 or 2 alkyl groups; heterocycloalkyl; or heterocycloalkylalkyl; or
a pharmaceutically acceptable salt thereof.

In one embodiment, provided is a Compound of Formula (I):

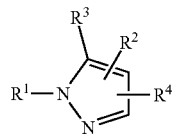
(I)

where
R$^1$ is phenyl, pyridinonyl, or pyridinyl; where the phenyl, pyridinonyl, and pyridinyl rings are optionally substituted with 1 R$^{1a}$ and where the pyridinonyl is substituted on the nitrogen with R$^{1b}$;
R$^{1a}$ is alkyl, haloalkyl, or heterocycloalkyl;
R$^{1b}$ is alkyl, haloalkyl, or cycloalkylalkyl;
R$^2$ is

R$^{2a}$ is —NR$^{5a}$S(O)$_2$R$^{5b}$ or —NR$^{6a}$R$^{6b}$;
R$^{2b}$ is halo, alkyl, haloalkyl, or cyano;
R$^3$ is hydrogen or alkyl;
R$^4$ is hydrogen or alkyl;
R$^{5a}$ and R$^{6a}$ are hydrogen; and
R$^{5b}$ and R$^{6b}$ are independently alkyl; haloalkyl; cycloalkyl where the cycloalkyl is optionally substituted with 1 or 2 alkyl groups; cycloalkylalkyl; or heterocycloalkyl; or
a pharmaceutically acceptable salt thereof.

In one embodiment, provided is a Compound of Formula (I):

(I)

where
R$^1$ is phenyl, pyridinonyl, or pyridinyl; where the phenyl, pyridinonyl, and pyridinyl rings are optionally substituted with 1 R$^{1a}$ and where the pyridinonyl is substituted on the nitrogen with R$^{1b}$;
R$^{1a}$ is alkyl, haloalkyl, or heterocycloalkyl;
R$^{1b}$ is alkyl;
R$^2$ is

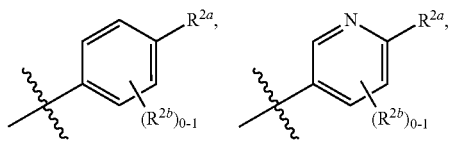

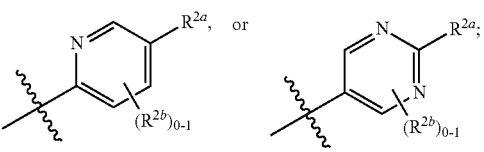

R$^{2a}$ is —NR$^{5a}$S(O)$_2$R$^{5b}$ or —NR$^{6a}$R$^{6b}$;
R$^{2b}$ is halo, alkyl, haloalkyl, or cyano;
R$^3$ is hydrogen or alkyl;
R$^4$ is hydrogen or alkyl;
R$^{5a}$ and R$^{6a}$ are hydrogen; and
R$^{5b}$ and R$^{6b}$ are independently alkyl; haloalkyl; cycloalkyl; cycloalkylalkyl; or heterocycloalkyl; or
a pharmaceutically acceptable salt thereof.

In some or any embodiments, the Compound (e.g., of Formula (I), (100), (Ia), (Ic), (Ie), (If), (Ia-1), (Ic-1), and (Ie-1), and any embodiments thereof) is not

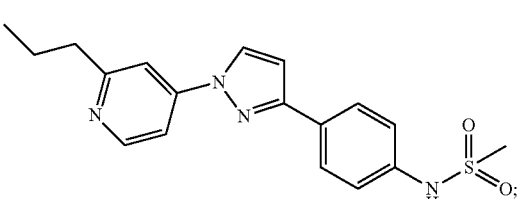

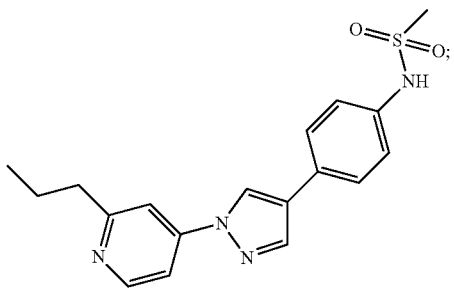

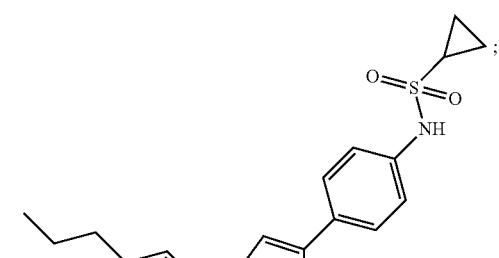

-continued

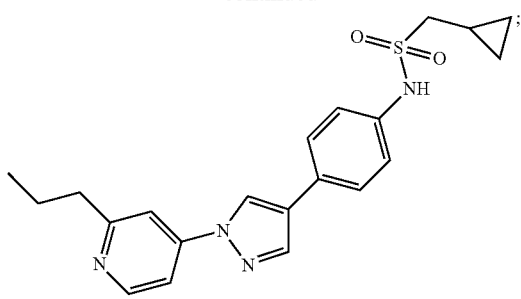

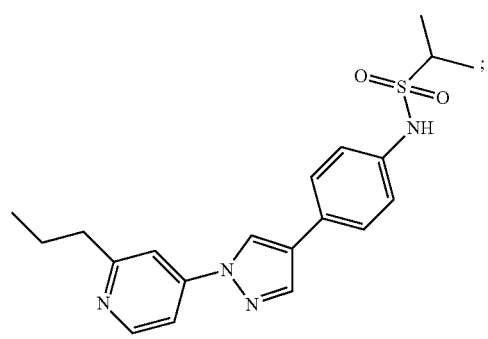

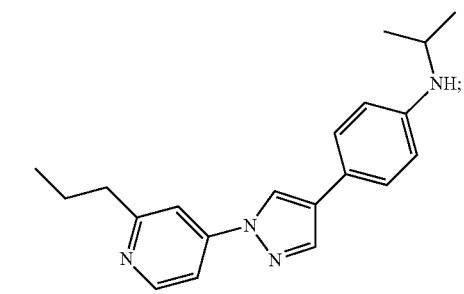

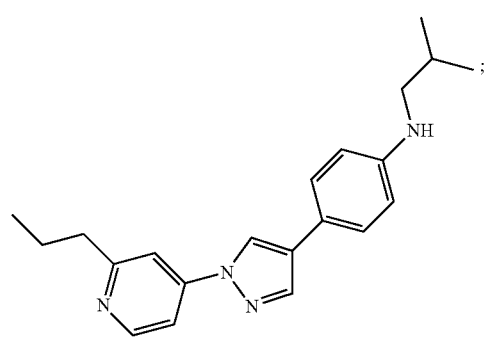

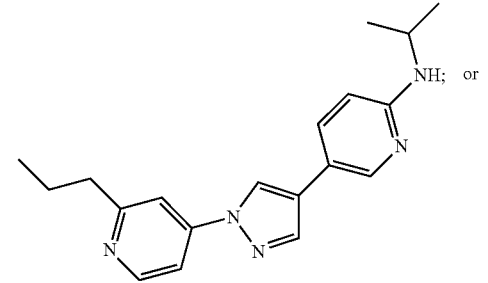

-continued

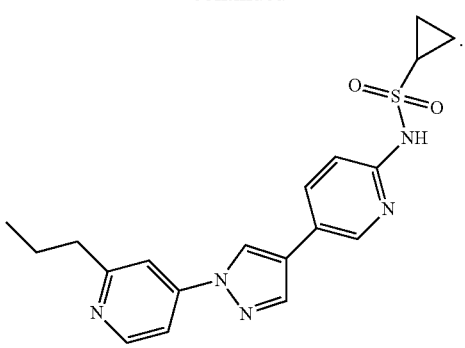

In some or any embodiments, the Compound (e.g., of Formula (I), (100), (Ia), (Ic), (Ie), (If), (Ia-1), (Ic-1), and (Ie-1), and any embodiments thereof) is not a pharmaceutically acceptable salt of one of the specific compounds in this paragraph.

In some or any embodiments, the Compound (e.g., of Formula (I), (100), (Ia), (Ib), (Ic), (Ie), (If), (Ih), (Ia-1), (Ic-1), and (Ie-1), and any embodiments thereof) is not N-methyl-6-(1-phenyl-1H-pyrazol-4-yl)pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine; and not

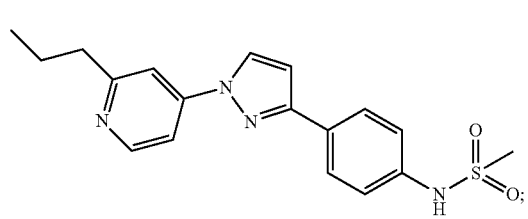

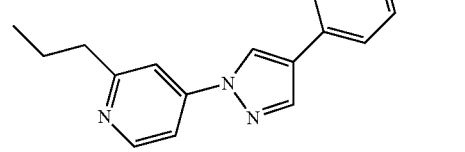

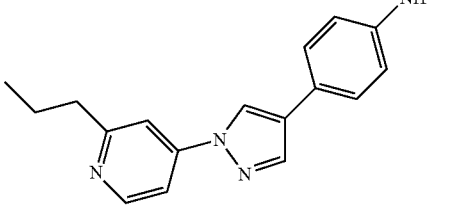

-continued

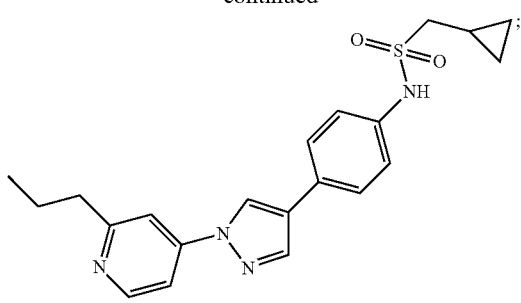

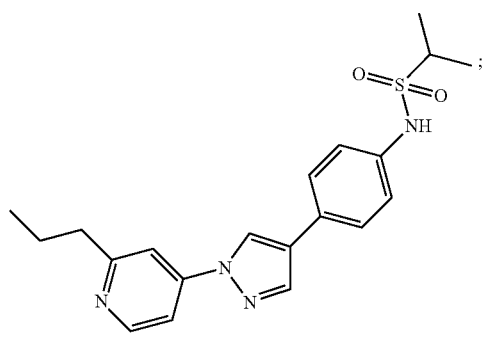

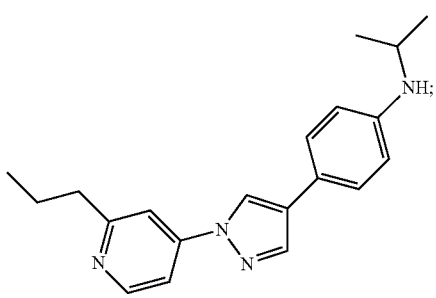

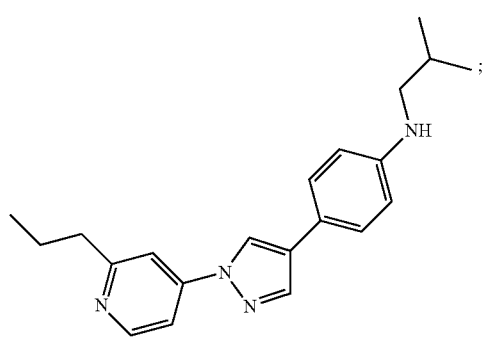

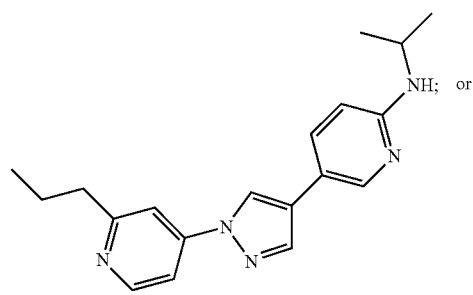

-continued

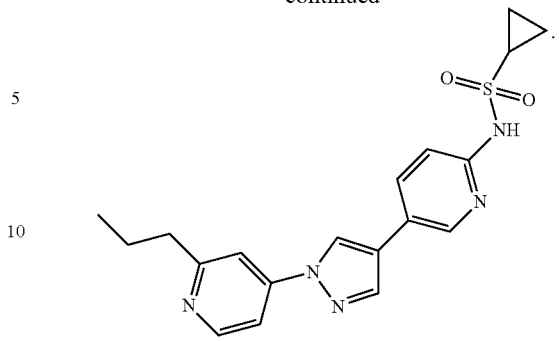

In some embodiments, the Compound (e.g., of Formula (I), (100), (Ia), (Ib), (Ic), (Ie), (If), (Ih), (Ia-1), (Ic-1), and (Ie-1), and any embodiments thereof) is not a pharmaceutically acceptable salt of one of the specific compounds in this paragraph.

A Compound according to Formula (Ia):

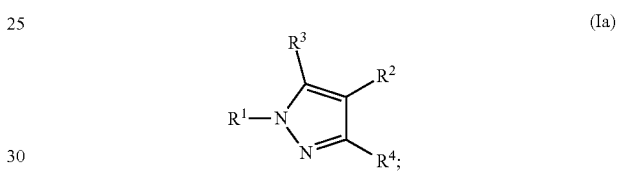

(Ia)

where $R^1$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ia) is that where $R^2$ is

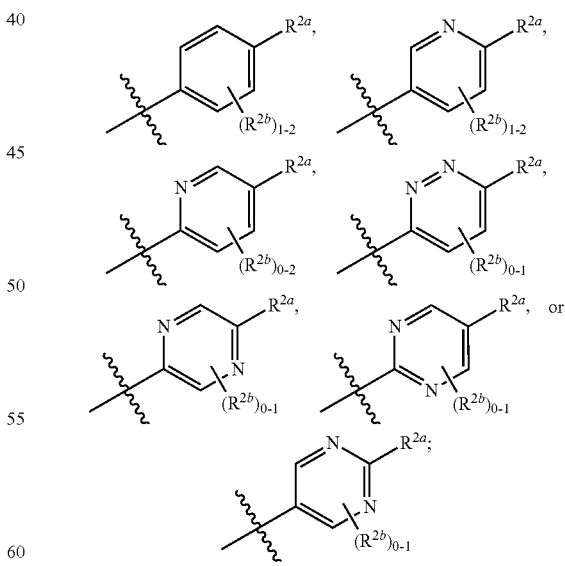

and all other groups are as defined in the Summary of the Invention for a Compound of Formula (I) or in any embodiments described herein. In some or any embodiments, the Compound of Formula (Ia) is that where $R^3$ and $R^4$ are hydrogen.

In some or any embodiments, the Compound is according to Formula (Ib):

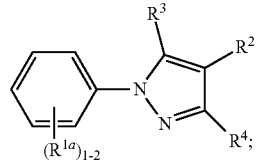
(Ib)

where $R^{1a}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ib) is that where $R^2$ is

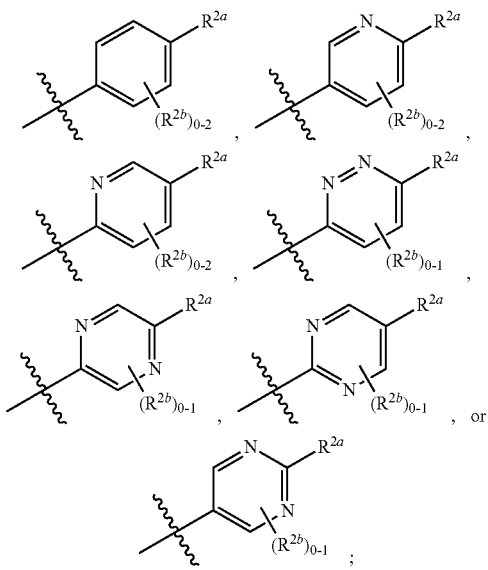

and all other groups are as defined in the Summary of the Invention for a Compound of Formula (I) or in any embodiments described herein. In some or any embodiments, the Compound of Formula (Ib) is that where $R^3$ and $R^4$ are hydrogen.

In some or any embodiments, the Compound is according to Formula (Ic):

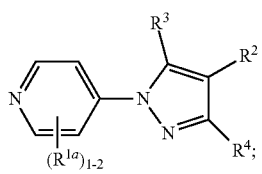
(Ic)

where $R^{1a}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ic) is that where $R^2$ is

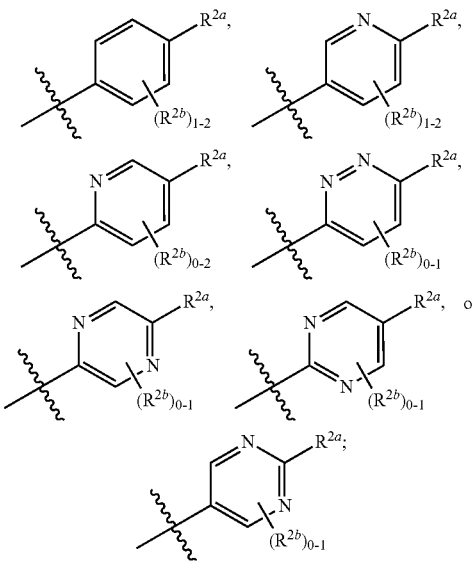

and all other groups are as defined in the Summary of the Invention for a Compound of Formula (I) or in any embodiments described herein. In some or any embodiments, the Compound of Formula (Ic) is that where $R^3$ and $R^4$ are hydrogen.

In some or any embodiments, the Compound is according to Formula (Id):

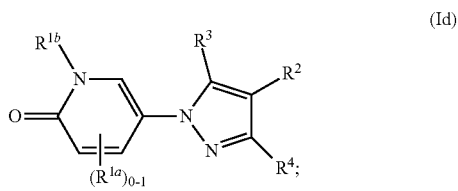
(Id)

where $R^{1a}$, $R^{1b}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Id) is that where $R^2$ is

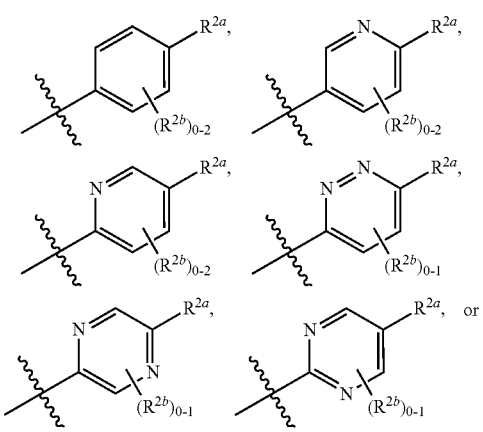

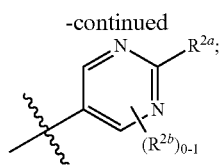

and all other groups are as defined in the Summary of the Invention for a Compound of Formula (I) or in any embodiments described herein. In some or any embodiments, the Compound of Formula (Id) is that where $R^2$ is

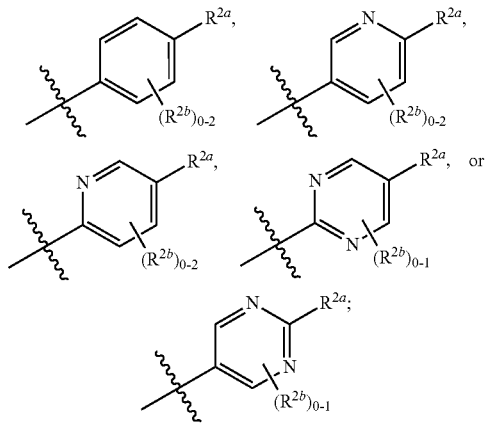

and all other groups are as defined in the Summary of the Invention for a Compound of Formula (I) or in any embodiments described herein. In some or any embodiments, the Compound of Formula (Id) is that where $R^2$ is

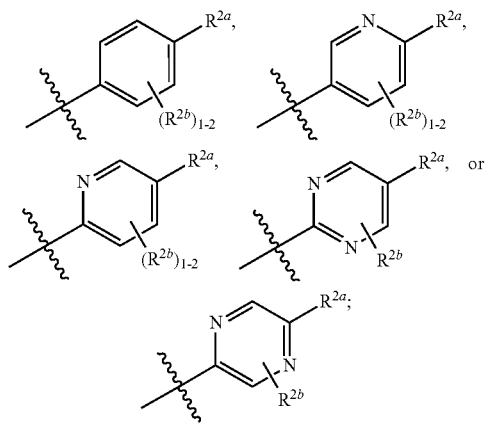

and all other groups are as defined in the Summary of the Invention for a Compound of Formula (I) or in any embodiments described herein. In some or any embodiments, the Compound of Formula (Id) is that where $R^2$ is

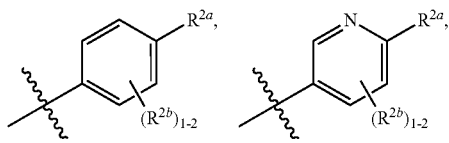

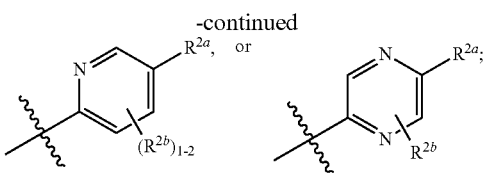

and all other groups are as defined in the Summary of the Invention for a Compound of Formula (I) or in any embodiments described herein. In some or any embodiments, the Compound of Formula (Id) is that where $R^2$ is

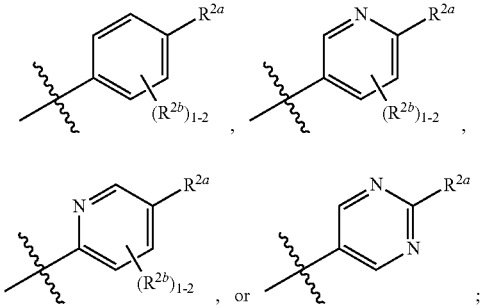

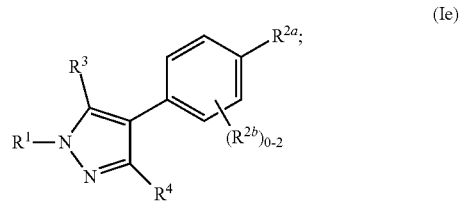

and all other groups are as defined in the Summary of the Invention for a Compound of Formula (I) or in any embodiments described herein. In some or any embodiments, the Compound of Formula (Id) is that where $R^3$ and $R^4$ are hydrogen.

In some or any embodiments, the Compound is according to Formula (Ie):

(Ie)

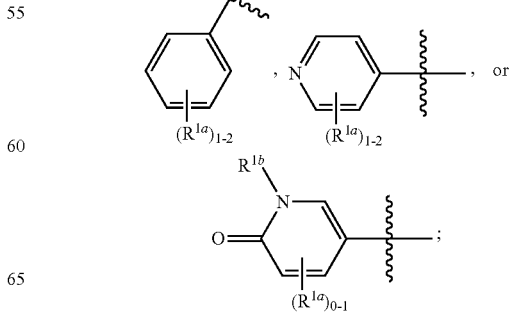

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ie) is that wherein $R^1$ is and all other groups are as defined in the Summary of the Invention for a Compound of Formula (I) or in any embodiments described herein. In some or any embodiments, the Compound of Formula (Ie) is that wherein R¹ is

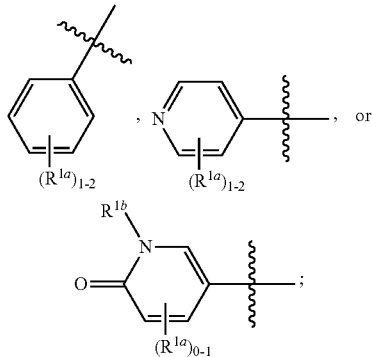

and all other groups are as defined in the Summary of the Invention for a Compound of Formula (I) or in any embodiments described herein. In some or any embodiments, the Compound of Formula (Ie) is that where $R^3$ and $R^4$ are hydrogen. In some or any embodiments, the Compound of Formula (Ie) is that where one $R^{2b}$ is present.

In some or any embodiments, the Compound is according to Formula (If):

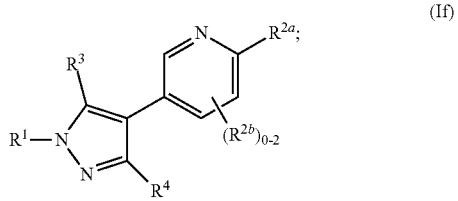

(If)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (If) is that wherein $R^1$ is

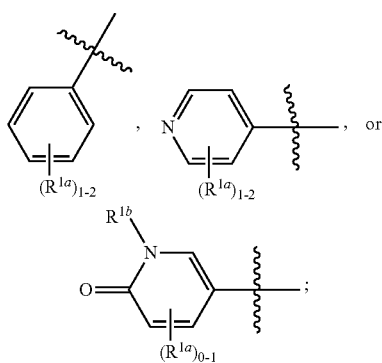

and all other groups are as defined in the Summary of the Invention for a Compound of Formula (I) or in any embodiments described herein. In some or any embodiments, the Compound of Formula (If) is that wherein $R^1$ is

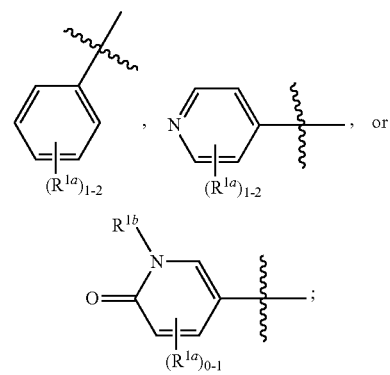

and all other groups are as defined in the Summary of the Invention for a Compound of Formula (I) or in any embodiments described herein. In some or any embodiments, the Compound of Formula (If) is that where $R^3$ and $R^4$ are hydrogen. In some or any embodiments, the Compound of Formula (If) is that where one $R^{2b}$ is present.

In some or any embodiments, the Compound is according to Formula (Ig):

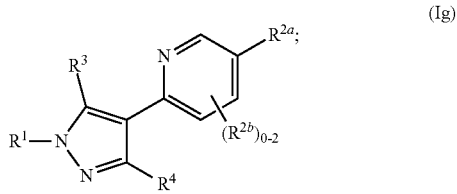

(Ig)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ig) is that wherein $R^1$ is

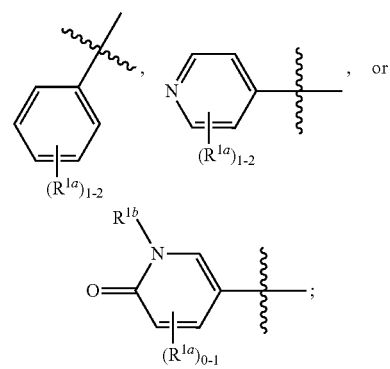

and all other groups are as defined in the Summary of the Invention for a Compound of Formula (I) or in any embodiments described herein. In some or any embodiments, the Compound of Formula (Ig) is that where $R^3$ and $R^4$ are hydrogen. In some or any embodiments, the Compound of Formula (Ig) is that where one $R^{2b}$ is present.

In some or any embodiments, the Compound is according to Formula (Ih):

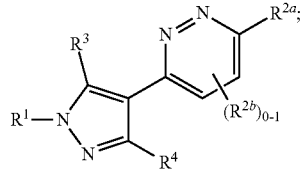
(Ih)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ih) is that wherein $R^1$ is

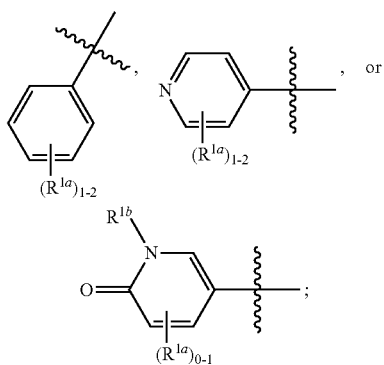

and all other groups are as defined in the Summary of the Invention for a Compound of Formula (I) or in any embodiments described herein. In some or any embodiments, the Compound of Formula (Ih) is that where $R^3$ and $R^4$ are hydrogen. In some or any embodiments, the Compound of Formula (Ih) is that where one $R^{2b}$ is present.

In some or any embodiments, the Compound is according to Formula (Ij):

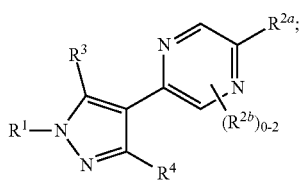
(Ij)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ij) is that wherein $R^1$ is

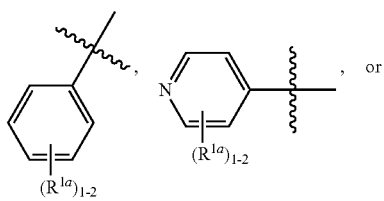

and all other groups are as defined in the Summary of the Invention for a Compound of Formula (I) or in any embodiments described herein. In some or any embodiments, the Compound of Formula (Ij) is that where $R^3$ and $R^4$ are hydrogen. In some or any embodiments, the Compound of Formula (Ij) is that where one $R^{2b}$ is present.

In some or any embodiments, the Compound is according to Formula (Ik):

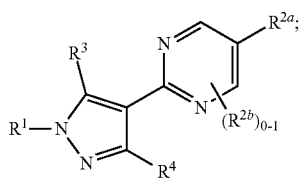
(Ik)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ik) is that wherein $R^1$ is

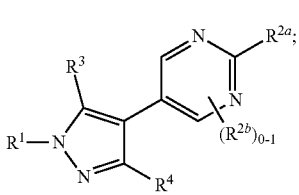

and all other groups are as defined in the Summary of the Invention for a Compound of Formula (I) or in any embodiments described herein. In some or any embodiments, the Compound of Formula (Ik) is that where $R^3$ and $R^4$ are hydrogen. In some or any embodiments, the Compound of Formula (Ik) is that where one $R^{2b}$ is present.

In some or any embodiments, the Compound is according to Formula (Im):

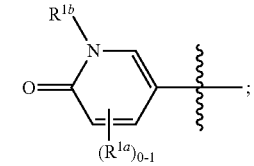
(Im)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Im) is that wherein $R^1$ is

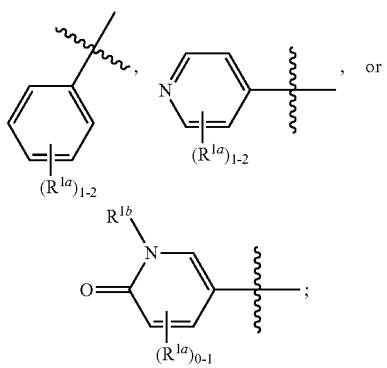

and all other groups are as defined in the Summary of the Invention for a Compound of Formula (I) or in any embodiments described herein. In some or any embodiments, the Compound of Formula (Im) is that where $R^3$ and $R^4$ are hydrogen. In some or any embodiments, the Compound of Formula (Im) is that where one $R^{2b}$ is present. In some or any embodiments, the Compound of Formula (Im) is that where no $R^{2b}$ is present.

In some or any embodiments, the Compound of Formula (I), (100), (Ia), (Ib), or (Ih) is not N-methyl-6-(1-phenyl-1H-pyrazol-4-yl)pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine.

In some or any embodiments, the Compound of Formula (I), (100), (Ia), (Ib), (Ic), (Ie), (If), or (Ih) is not N-methyl-6-(1-phenyl-1H-pyrazol-4-yl)pyridazin-3-amine; N-ethyl-6-(1-phenyl-1H-pyrazol-4-yl)pyridazin-3-amine; or N-propyl-6-(1-phenyl-1H-pyrazol-4-yl)pyridazin-3-amine; and not

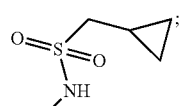

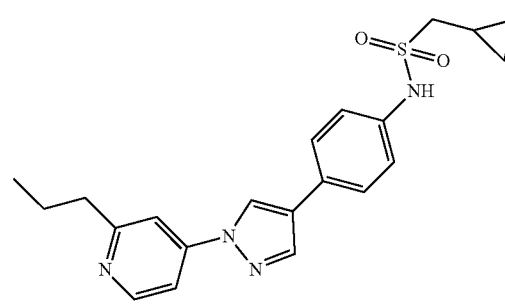

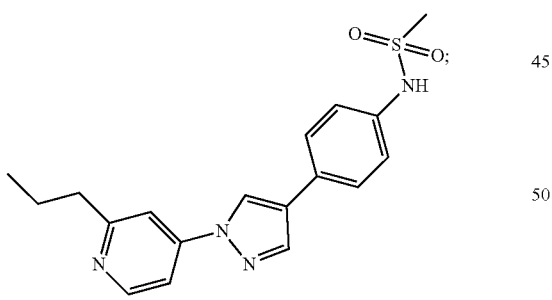

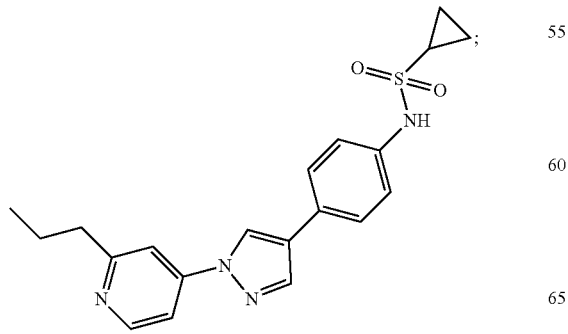

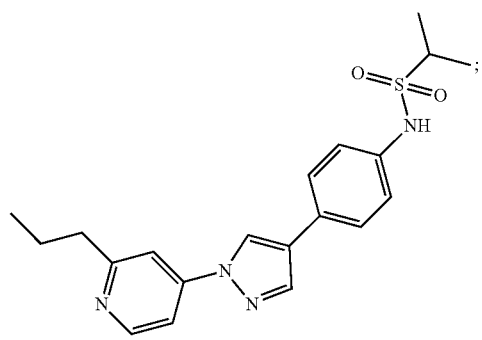

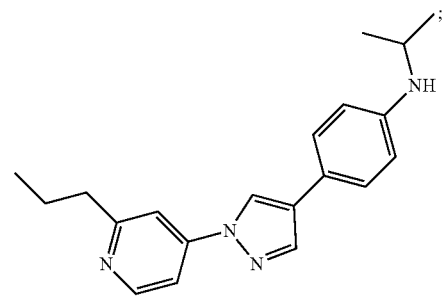

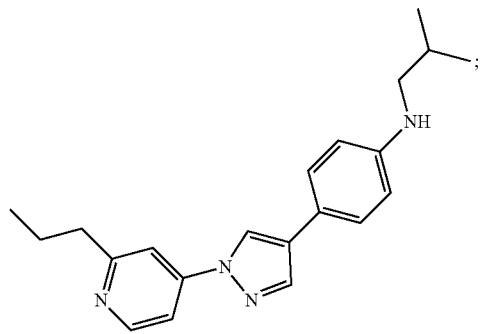

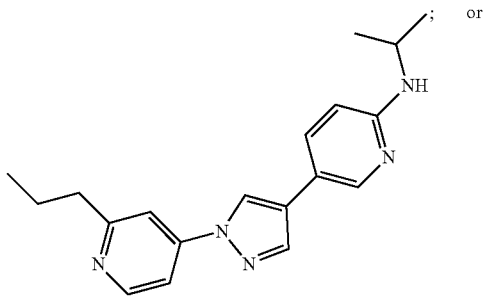

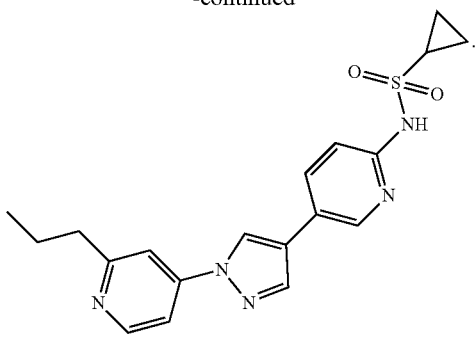

In some or any embodiments, the Compound (e.g., of Formula (I), (100), (Ia), (Ib), (Ic), (Ie), (If), or (Ih), and any embodiments thereof) is not a pharmaceutically acceptable salt of one of the specific compounds in this paragraph.

In some or any embodiments, the Compound of Formula (I)-(Im), (100), or (Ia-1)-(Im-1) is that where $R^3$ and $R^4$ are hydrogen; $R^3$ and $R^4$ are alkyl; or one of $R^3$ and $R^4$ is hydrogen and the other is alkyl; and all other groups are as defined in the Summary of the Invention for a Compound of Formula (I) or in any embodiments described herein. In some or any embodiments, the Compound of Formula (I)-(Im), (100), or (Ia-1)-(Im-1) is that where $R^3$ and $R^4$ are hydrogen; $R^3$ and $R^4$ are methyl; $R^3$ is hydrogen and $R^4$ is methyl; or $R^3$ is methyl and $R^4$ is hydrogen; and all other groups are as defined in the Summary of the Invention for a Compound of Formula (I) or in any embodiments described herein. In some or any embodiments, the Compound of Formula (I)-(Im), (100), or (Ia-1)-(Im-1) is that where $R^3$ and $R^4$ are hydrogen; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is phenyl, pyridinonyl, or pyridinyl; where the phenyl and pyridinyl rings are optionally substituted with 1 or 2 $R^{1a}$ and where the pyridinonyl is substituted on the nitrogen with $R^{1b}$ and is additionally optionally substituted with 1 $R^{1a}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is pyridinonyl substituted on the nitrogen with $R^{1b}$ and additionally optionally substituted with 1 $R^{1a}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is phenyl optionally substituted with 1 or 2 $R^{1a}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is pyridinyl optionally substituted with 1 or 2 $R^{1a}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is pyrimidinyl optionally substituted with 1 or 2 $R^{1a}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is pyridazinyl optionally substituted with 1 or 2 $R^a$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is pyrazinyl optionally substituted with 1 or 2 $R^{1a}$; and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

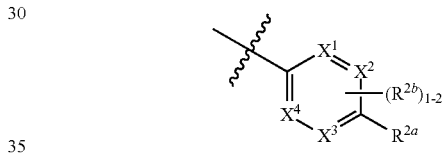

where 0, 1, or 2 of $X^1$-$X^4$ are nitrogen and the remaining are carbon; and all other groups are as defined in the Summary of the Invention for a Compound of Formula (I) or in any embodiments described herein. In some of any embodiment, the Compound of Formula (I), (Ia), (Ib), (Ic), (Id), (100), (Ia-1), (Ib-1), (Ic-1), or (Id-1) is that where $R^2$ is

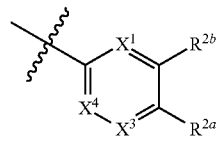

where 0, 1, or 2 of $X^1$, $X^3$, and $X^4$ are nitrogen and the remaining are carbon; and all other groups are as defined in the Summary of the Invention for a Compound of Formula (I) or in any embodiments described herein. In some of any embodiment, the Compound of Formula (I), (Ia), (Ib), (Ic), (Id), (100), (Ia-1), (Ib-1), (Ic-1), or (Id-1) is that where $R^2$ is

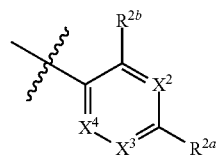

where 0, 1, or 2 of $X^2$, $X^3$, and $X^4$ are nitrogen and the remaining are carbon; and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

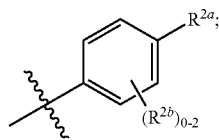

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

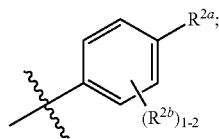

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

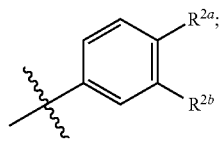

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

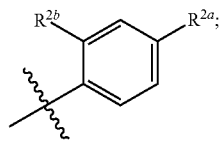

and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

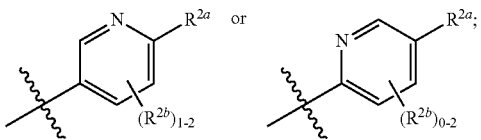

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

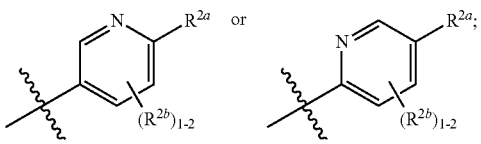

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

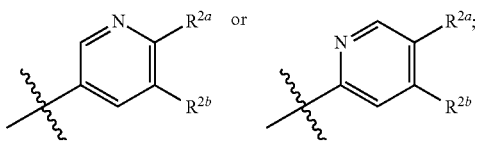

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

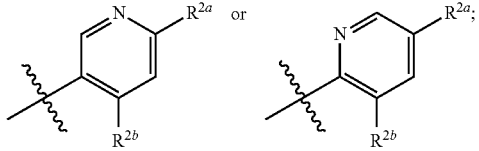

and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

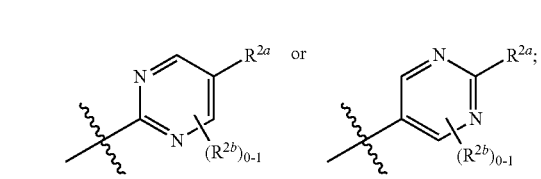

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

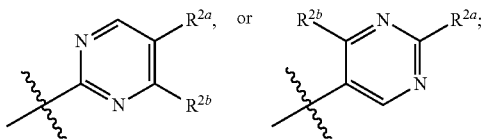

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

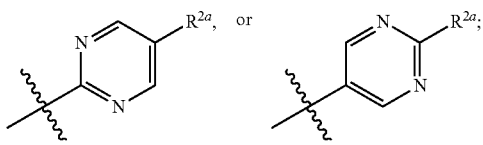

and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

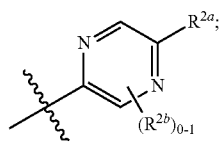

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

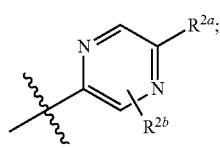

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

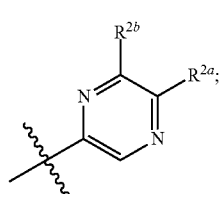

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

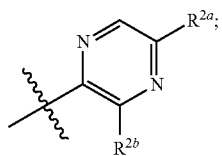

and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

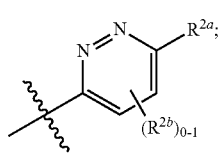

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

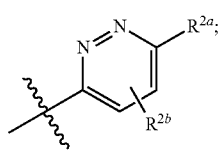

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

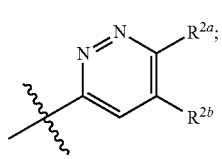

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

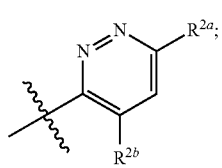

and all other groups are as defined in the Summary of the Invention for a Compound of Formula (I) or in any embodiments described herein.

In some or any embodiments, the Compound of Formula (I), (Ia), (Ib), (Ic), (Id), (100), (Ia-1), (Ib-1), (Ic-1), or (Id-1) is that where $R^2$ is

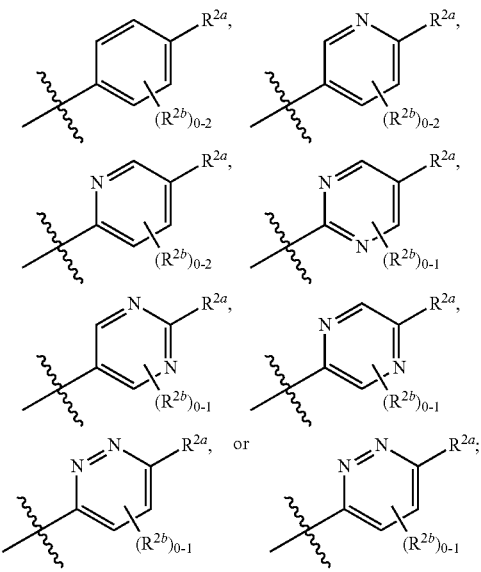

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

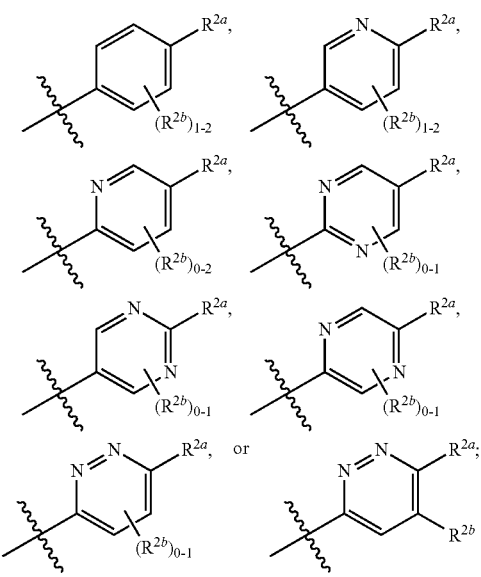

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

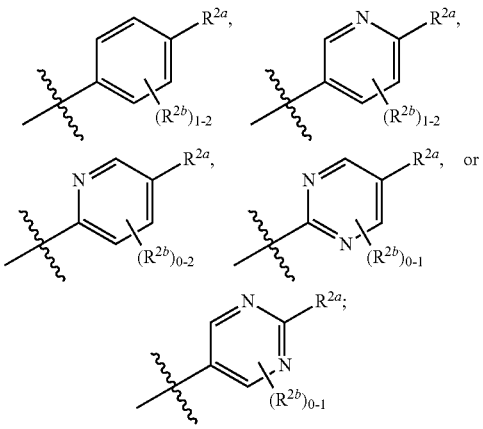

and all other groups are as defined in the Summary of the Invention for a Compound of Formula (I) or in any embodiments described herein. In some or any embodiments, the Compound of Formula (I), (Ia), (Ib), (Ic), (Id), (100), (Ia-1), (Ib-1), (Ic-1), or (Id-1) is that where $R^2$ is

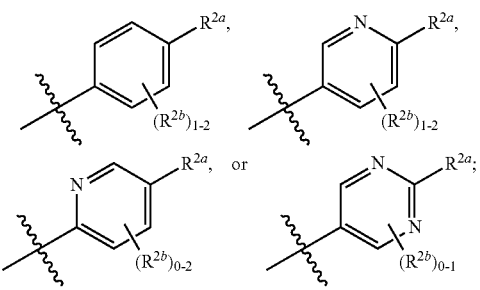

and all other groups are as defined in the Summary of the Invention for a Compound of Formula (I) or in any embodiments described herein.

In some or any embodiments, the Compound of Formula (I)-(Im), (100), or (Ia-1)-(Im-1) is that where $R^{2a}$ is —NR$^{5a}$S(O)$_2$R$^{5b}$; and all other groups are as defined in the Summary of the Invention for a Compound of Formula (I) or in any embodiments described herein. In some or any embodiments, the Compound of Formula (I)-(Im), (100), or (Ia-1)-(Im-1) is that where $R^{2a}$ is —NHS(O)$_2$R$^{5b}$; and all other groups are as defined in the Summary of the Invention for a Compound of Formula (I) or in any embodiments described herein.

In some or any embodiments, the Compound of Formula (I)-(Im), (100), or (Ia-1)-(Im-1) is that where $R^{2a}$ is —NR$^{6a}$R$^{6b}$; and all other groups are as defined in the Summary of the Invention for a Compound of Formula (I) or in any embodiments described herein. In some or any embodiments, the Compound of Formula (I)-(Im), (100), or (Ia-1)-(Im-1) is that where $R^{2a}$ is —NHR$^{6b}$; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is phenyl, pyridinonyl, or pyridinyl; where the phenyl and pyridinyl rings are optionally substituted with 1 or 2 $R^{1a}$ and where the pyridinonyl is substituted on the nitrogen with $R^{1b}$ and is additionally optionally substituted with 1 $R^{1a}$; $R^3$ and $R^4$ are hydrogen; and all other groups are as defined in the Summary of the Invention for a Compound of Formula (I) or in any embodiments described herein.

In some or any embodiments, the Compound of Formula (I), (Ia), (Ie), (If), (Ig), (Ih), (Ij), (Ik), (Im), (100), (Ia-1), (Ie-1), (If-1), (Ig-1), (Ih-1), (Ij-1), (Ik-1), or (Im-1) is that where $R^1$ is phenyl, pyridinonyl, or pyridinyl; where the phenyl and pyridinyl rings are substituted with 1 or 2 $R^{1a}$ and where the pyridinonyl is substituted on the nitrogen with $R^{1b}$ and is additionally optionally substituted with 1 $R^{1a}$; $R^3$ and $R^4$ are hydrogen; and all other groups are as defined in the Summary of the Invention for a Compound of Formula (I) or in any embodiments described herein.

In some or any embodiments, the Compound of Formula (I), (Ia), (Id), (Ie), (If), (Ig), (Ih), (Ij), (Ik), (Im), (100), (Ia-1), (Id-1), (Ie-1), (If-1), (Ig-1), (Ih-1), (Ij-1), (Ik-1), or (Im-1) is that where $R^1$ is pyridinonyl substituted on the nitrogen with $R^{1b}$ and additionally optionally substituted with 1 $R^{1a}$; and $R^{1b}$ is alkyl, haloalkyl, cycloalkylalkyl, or heterocycloalkylalkyl where the heterocycloalkyl is substituted with $R^y$ where $R^y$ is hydrogen, alkyl, hydroxy, alkoxy, acyl, or alkylsulfonyl; and all other groups are as defined in the Summary of the Invention for a Compound of Formula (I) or in any embodiments described herein.

In some or any embodiments, provided is a Compound of Formula (I), (Ia), (Id), (Ie), (If), (Ig), (Ih), (Ij), (Ik), (Im), (100), (Ia-1), (Id-1), (Ie-1), (If-1), (Ig-1), (Ih-1), (Ij-1), (Ik-1), or (Im-1) where $R^{1b}$ and additionally optionally substituted with 1 $R^{1a}$; and $R^{1b}$ is alkyl, haloalkyl, cycloalkylalkyl, or heterocycloalkylalkyl where the heterocycloalkyl is substituted with $R^y$ where $R^y$ is hydrogen, alkyl, hydroxy, alkoxy, acyl, or alkylsulfonyl; and all other groups are as defined in the Summary of the Invention for a Compound of Formula (I) or in any embodiments described herein. In some or any embodiments, provided is a Compound of Formula (I), (Ia), (Id), (Ie), (If), (Ig), (Ih), (Ij), (Ik), (Im), (100), (Ia-1), (Id-1), (Ie-1), (If-1), (Ig-1), (Ih-1), (Ij-1), (Ik-1), or (Im-1) where $R^{1b}$ and additionally optionally substituted with 1 $R^{1a}$; and $R^{1b}$ is alkyl, haloalkyl, cycloalkylalkyl, or heterocycloalkylalkyl where the heterocycloalkyl is substituted with alkyl; and all other groups are as defined in the Summary of the Invention for a Compound of Formula (I) or in any embodiments described herein.

In some or any embodiments, the Compound of Formula (I), (100), (Ia), or (Ia-1) is that where $R^1$ is phenyl, pyridinonyl, or pyridinyl; where the phenyl and pyridinyl rings are optionally substituted with 1 or 2 $R^{1a}$ and where the pyridinonyl is substituted on the nitrogen with $R^{1b}$ and is additionally optionally substituted with 1 $R^a$; $R^3$ and $R^4$ are hydrogen; $R^2$ is

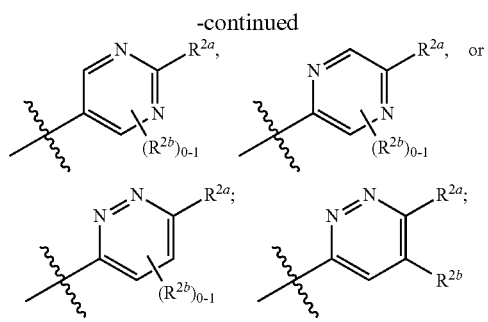

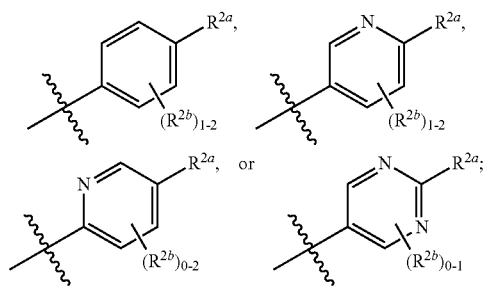

and all other groups are as defined in the Summary of the Invention for a Compound of Formula (I) or in any embodiments described herein.

In some or any embodiments, the Compound of Formula (I), (100), (Ia), or (Ia-1) is that where $R^1$ is phenyl, pyridinonyl, or pyridinyl; where the phenyl and pyridinyl rings are optionally substituted with 1 or 2 $R^{1a}$ and where the pyridinonyl is substituted on the nitrogen with $R^{1b}$ and is additionally optionally substituted with 1 $R^{1a}$; $R^3$ and $R^4$ are hydrogen; $R^2$ is

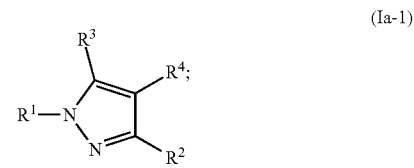

and all other groups are as defined in the Summary of the Invention for a Compound of Formula (I) or in any embodiments described herein.

A Compound according to Formula (Ia-1):

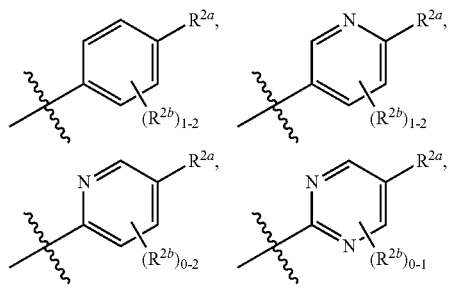

(Ia-1)

where $R^1$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ia-1) is that where $R^2$ is

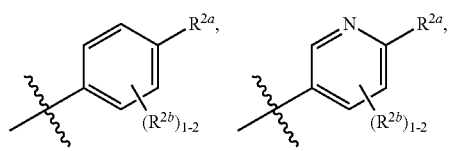

-continued

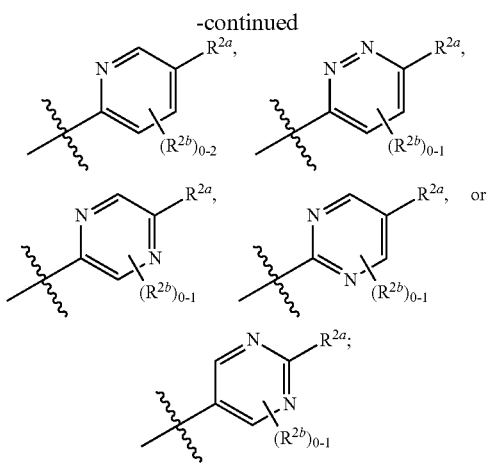

and all other groups are as defined in the Summary of the Invention for a Compound of Formula (I) or in any embodiments described herein. In some or any embodiments, the Compound of Formula (Ia-1) is that where $R^2$ is

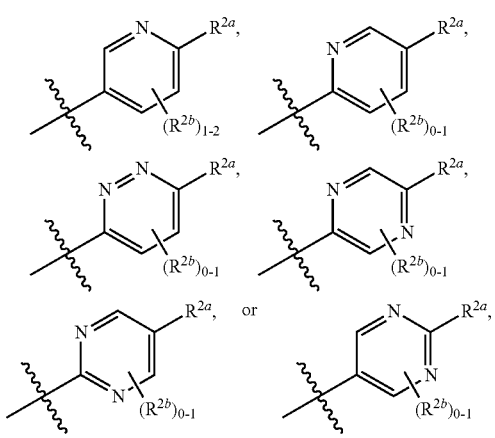

and all other groups are as defined in the Summary of the Invention for a Compound of Formula (I) or in any embodiments described herein. In some or any embodiments, the Compound of Formula (Ia-1) is that where $R^3$ and $R^4$ are hydrogen.

In some or any embodiments, the Compound is according to Formula (Ib-1):

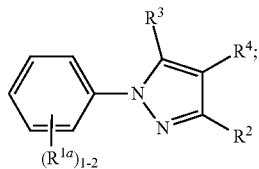

(Ib-1)

where $R^{1a}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ib-1) is that where $R^2$ is

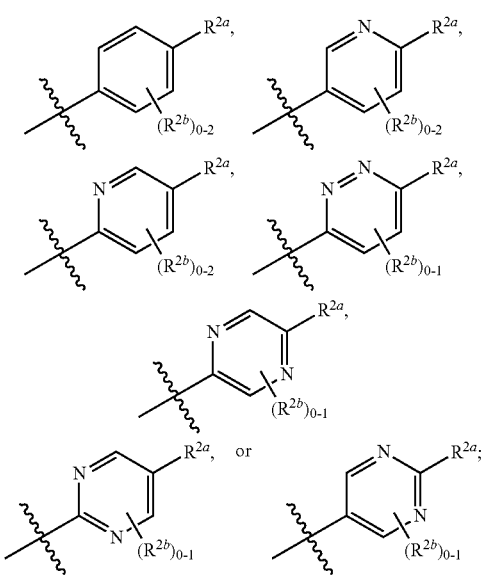

and all other groups are as defined in the Summary of the Invention for a Compound of Formula (I) or in any embodiments described herein. In some or any embodiments, the Compound of Formula (Ib-1) is that where $R^2$ is

and all other groups are as defined in the Summary of the Invention for a Compound of Formula (I) or in any embodiments described herein. In some or any embodiments, the Compound of Formula (Ib-1) is that where $R^3$ and $R^4$ are hydrogen.

In some or any embodiments, the Compound is according to Formula (Ic-1):

(Ic-1)

where $R^{1a}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ic-1) is that where $R^2$ is

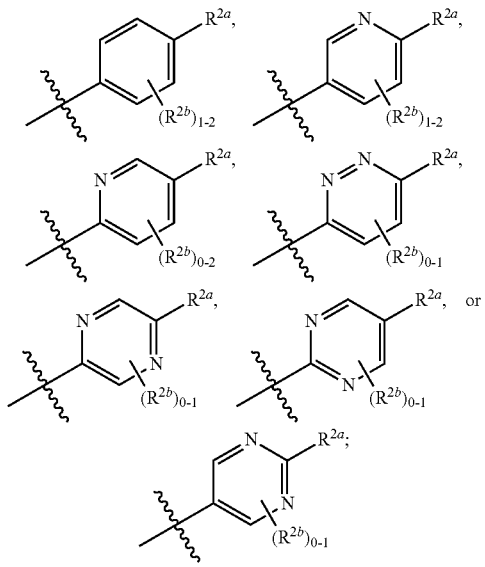

and all other groups are as defined in the Summary of the Invention for a Compound of Formula (I) or in any embodiments described herein. In some or any embodiments, the Compound of Formula (Ic-1) is that where $R^2$ is

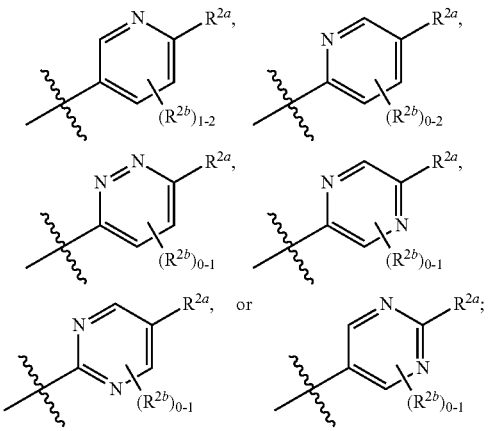

and all other groups are as defined in the Summary of the Invention for a Compound of Formula (I) or in any embodiments described herein. In some or any embodiments, the Compound of Formula (Ic-1) is that where $R^3$ and $R^4$ are hydrogen.

In some or any embodiments, the Compound is according to Formula (Id-1):

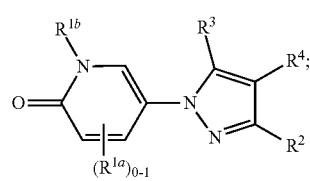

(Id-1)

where $R^{1a}$, $R^{1b}$, $R^2$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Id-1) is that where $R^2$ is

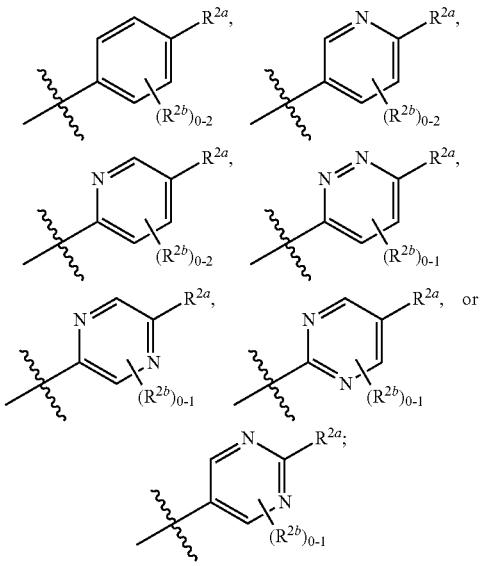

and all other groups are as defined in the Summary of the Invention for a Compound of Formula (I) or in any embodiments described herein. In some or any embodiments, the Compound of Formula (Id-1) is that where $R^2$ is

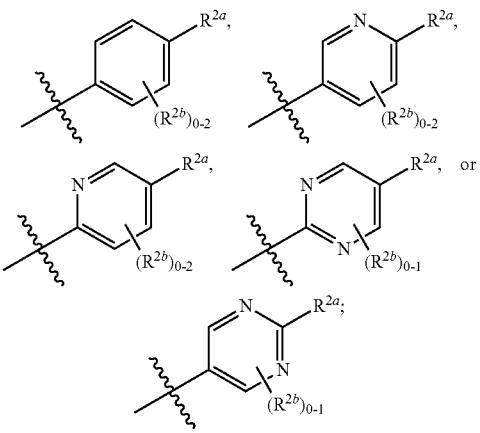

and all other groups are as defined in the Summary of the Invention for a Compound of Formula (I) or in any embodiments described herein. In some or any embodiments, the Compound of Formula (Id-1) is that where $R^2$ is

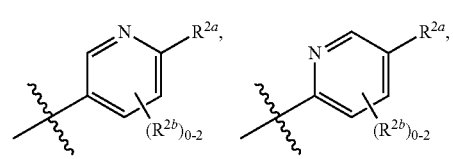

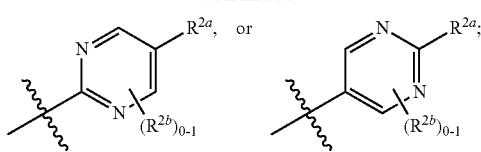

and all other groups are as defined in the Summary of the Invention for a Compound of Formula (I) or in any embodiments described herein. In some or any embodiments, the Compound of Formula (Id-1) is that where $R^2$ is

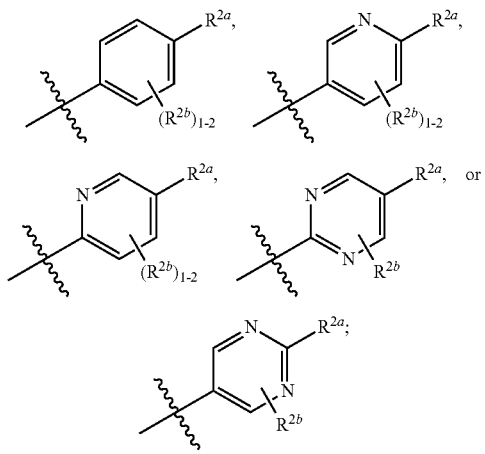

and all other groups are as defined in the Summary of the Invention for a Compound of Formula (I) or in any embodiments described herein. In some or any embodiments, the Compound of Formula (Id-1) is that where $R^2$ is

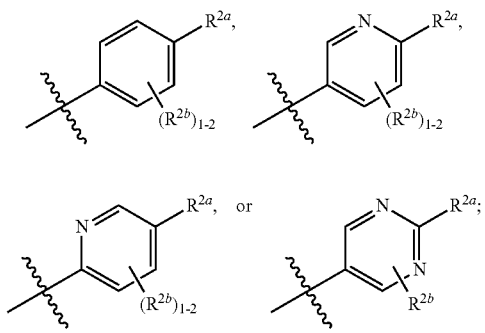

and all other groups are as defined in the Summary of the Invention for a Compound of Formula (I) or in any embodiments described herein. In some or any embodiments, the Compound of Formula (Id-1) is that where $R^2$ is

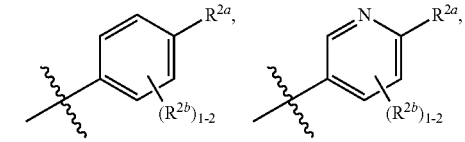

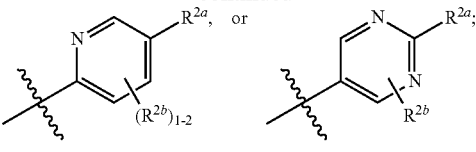

and all other groups are as defined in the Summary of the Invention for a Compound of Formula (I) or in any embodiments described herein. In some or any embodiments, the Compound of Formula (Id-1) is that where $R^3$ and $R^4$ are hydrogen.

In some or any embodiments, the Compound is according to Formula (Ie-1):

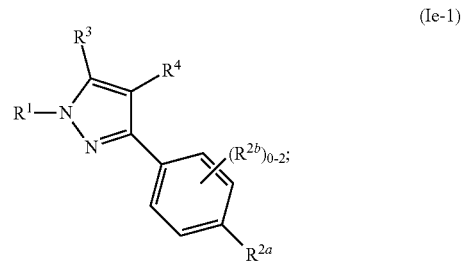

(Ie-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ie-1) is that wherein $R^1$ is

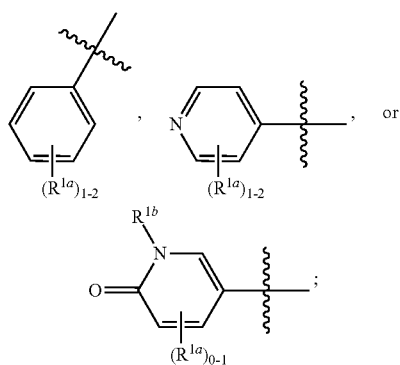

and all other groups are as defined in the Summary of the Invention for a Compound of Formula (I) or in any embodiments described herein. In some or any embodiments, the Compound of Formula (Ie-1) is that wherein $R^1$ is

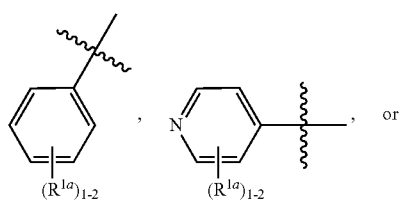

-continued

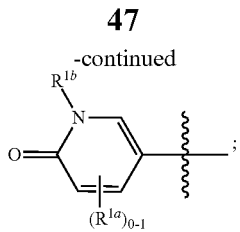

and all other groups are as defined in the Summary of the Invention for a Compound of Formula (I) or in any embodiments described herein. In some or any embodiments, the Compound of Formula (Ie-1) is that where $R^3$ and $R^4$ are hydrogen. In some or any embodiments, the Compound of Formula (Ie-1) is that where one $R^{2b}$ is present.

In some or any embodiments, the Compound is according to Formula (If-1):

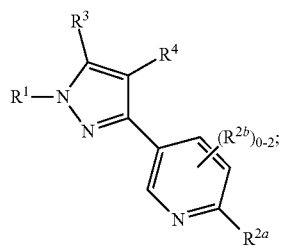

(If-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (If-1) is that wherein $R^1$ is

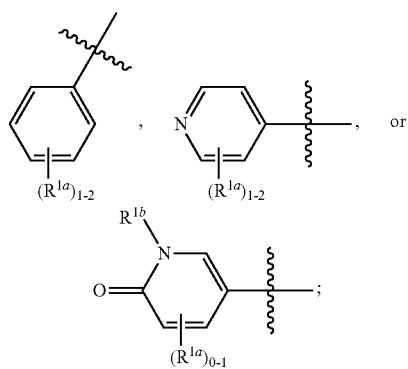

and all other groups are as defined in the Summary of the Invention for a Compound of Formula (I) or in any embodiments described herein. In some or any embodiments, the Compound of Formula (If-1) is that wherein $R^1$ is

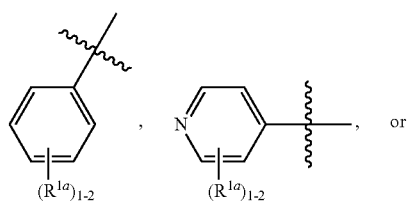

-continued

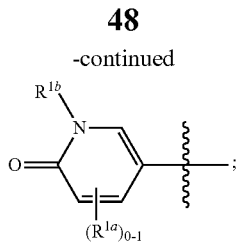

and all other groups are as defined in the Summary of the Invention for a Compound of Formula (I) or in any embodiments described herein. In some or any embodiments, the Compound of Formula (If-1) is that where $R^3$ and $R^4$ are hydrogen. In some or any embodiments, the Compound of Formula (If-1) is that where one $R^{2b}$ is present.

In some or any embodiments, the Compound is according to Formula (Ig-1):

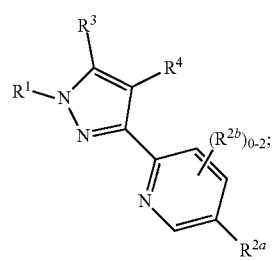

(Ig-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ig-1) is that wherein $R^1$ is

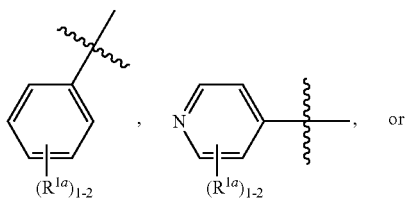

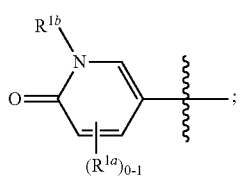

and all other groups are as defined in the Summary of the Invention for a Compound of Formula (I) or in any embodiments described herein. In some or any embodiments, the Compound of Formula (Ig-1) is that where $R^3$ and $R^4$ are hydrogen. In some or any embodiments, the Compound of Formula (Ig-1) is that where one $R^{2b}$ is present.

In some or any embodiments, the Compound is according to Formula (Ih-1):

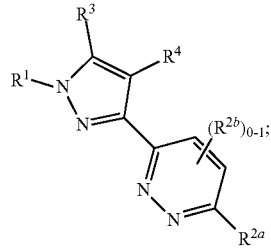
(Ih-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ih-1) is that wherein $R^1$ is

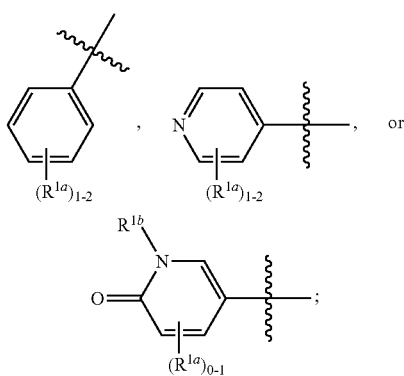

and all other groups are as defined in the Summary of the Invention for a Compound of Formula (I) or in any embodiments described herein. In some or any embodiments, the Compound of Formula (Ih-1) is that where $R^3$ and $R^4$ are hydrogen. In some or any embodiments, the Compound of Formula (Ih-1) is that where one $R^{2b}$ is present.

In some or any embodiments, the Compound is according to Formula (Ij-1):

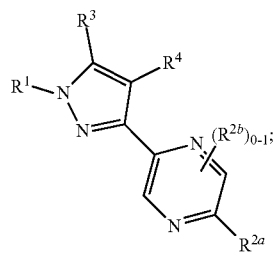
(Ij-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ij-1) is that wherein $R^1$ is

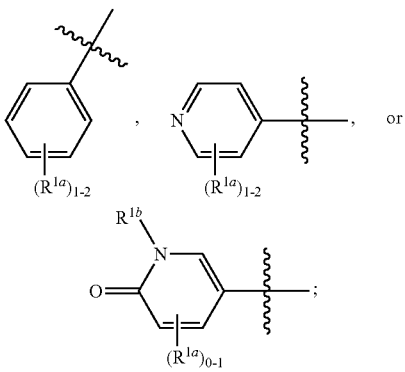

and all other groups are as defined in the Summary of the Invention for a Compound of Formula (I) or in any embodiments described herein. In some or any embodiments, the Compound of Formula (Ij-1) is that where $R^3$ and $R^4$ are hydrogen. In some or any embodiments, the Compound of Formula (Ij-1) is that where one $R^{2b}$ is present.

In some or any embodiments, the Compound is according to Formula (Ik-1):

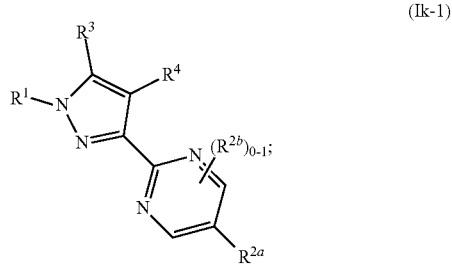
(Ik-1)

where $R^1$, $R^{2a}$, $R^{2b}$, $R^3$, $R^4$, and all other groups are as defined in the Summary of the Invention for a Compound of Formula (I) or in any embodiments described herein; or a pharmaceutically acceptable salt thereof. In some or any embodiments, the Compound of Formula (Ik-1) is that wherein $R^1$ is

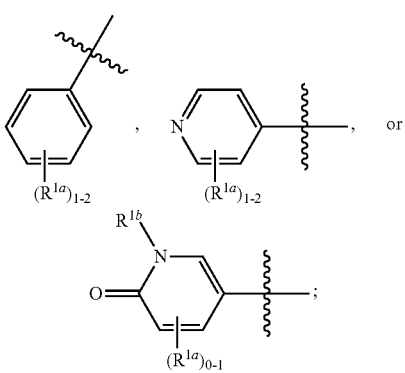

and all other groups are as defined in the Summary of the Invention for a Compound of Formula (I) or in any embodiments described herein. In some or any embodiments, the Compound of Formula (Ik-1) is that where $R^3$ and $R^4$ are hydrogen. In some or any embodiments, the Compound of Formula (Ik-1) is that where one $R^{2b}$ is present.

In some or any embodiments, the Compound is according to Formula (Im-1):

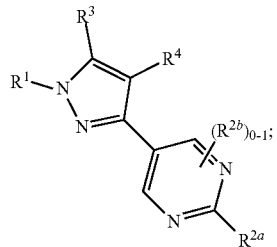

(Im-1)

where R¹, R²ᵃ, R²ᵇ, R³, R⁴, and all other groups are as defined in the Summary of the Invention for a Compound of Formula (I) or in any embodiments described herein; or a pharmaceutically acceptable salt thereof. In some or any embodiments, the Compound of Formula (Im-1) is that wherein R¹ is

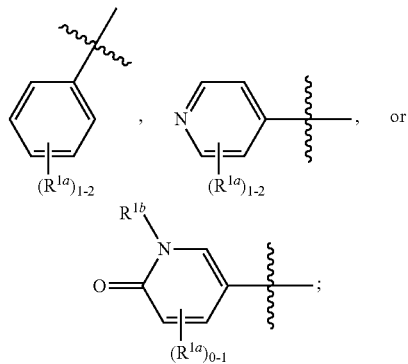

and all other groups are as defined in the Summary of the Invention for a Compound of Formula (I) or in any embodiments described herein. In some or any embodiments, the Compound of Formula (Im-1) is that where R³ and R⁴ are hydrogen. In some or any embodiments, the Compound of Formula (Im-1) is that where one R²ᵇ is present. In some or any embodiments, the Compound of Formula (Im-1) is that where no R²ᵇ is present.

In some or any embodiments, the Compound of Formula (II) or (200) is not

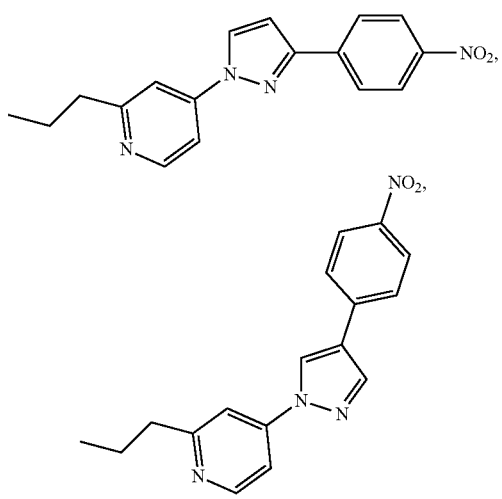

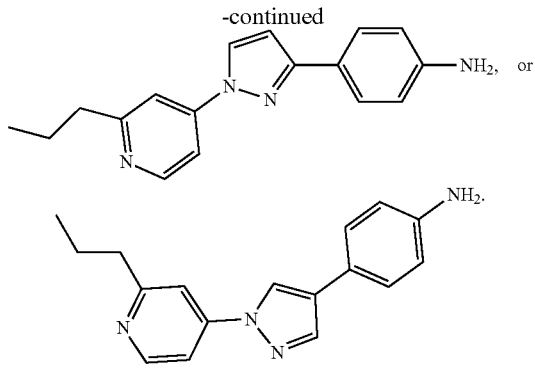

In some or any embodiments, the Compound (e.g., of Formula (II) and (200), and any embodiments thereof) is not a pharmaceutically acceptable salt of one of the specific compounds in this paragraph.

In some or any embodiments, provided is a Compound according to any of the following formula:

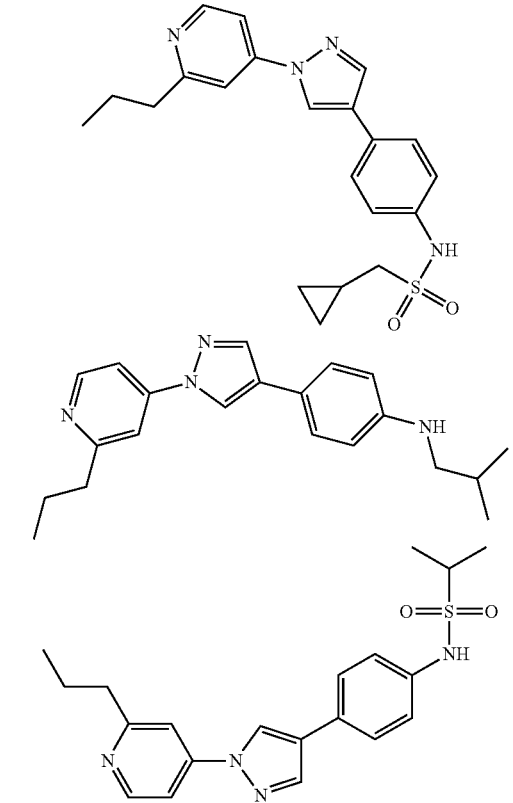

53
-continued
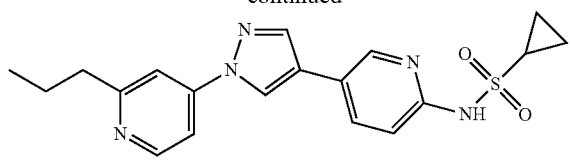
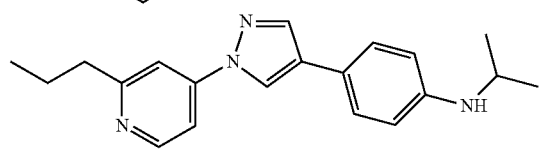
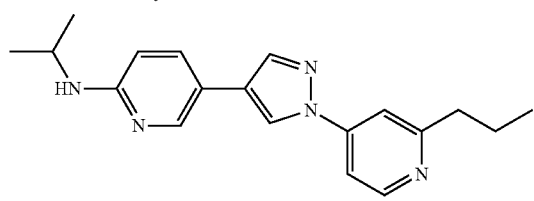
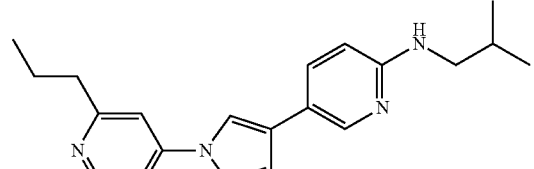
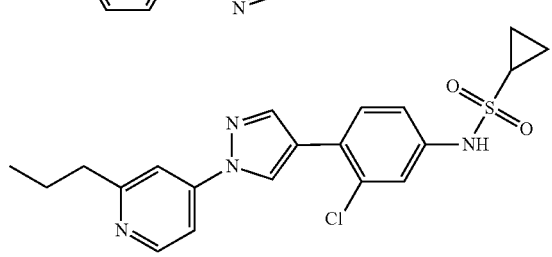
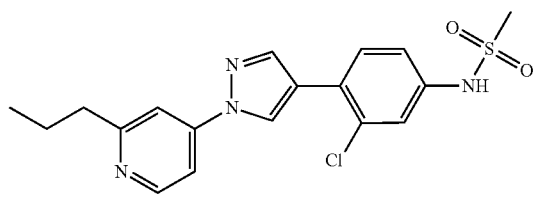
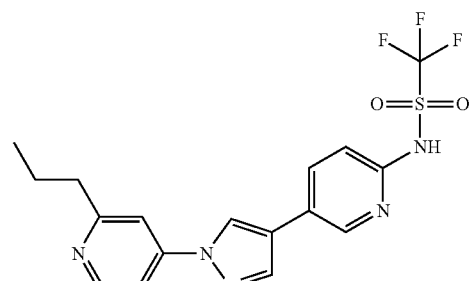
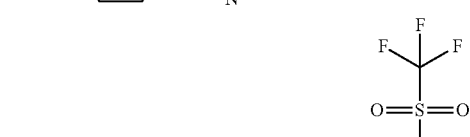
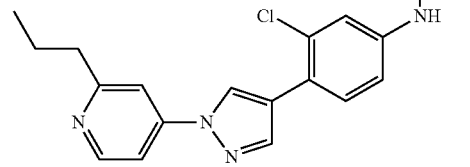
54
-continued
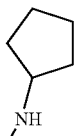
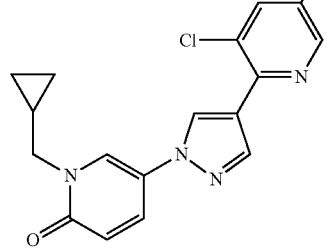
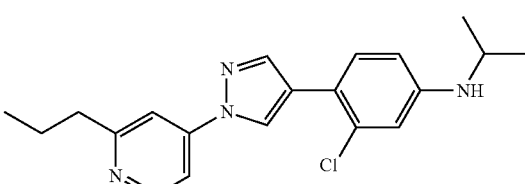
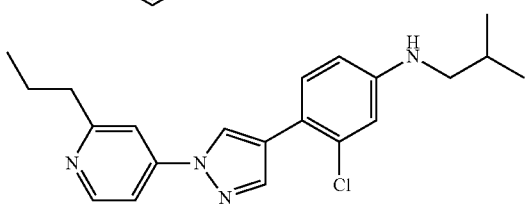
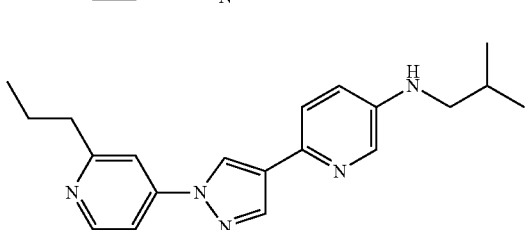
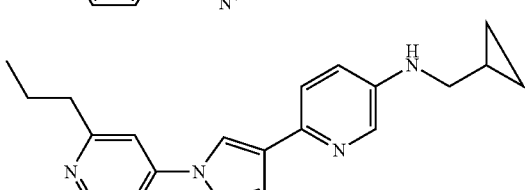
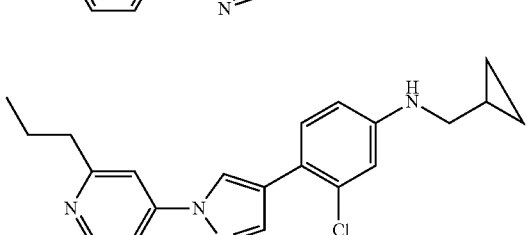
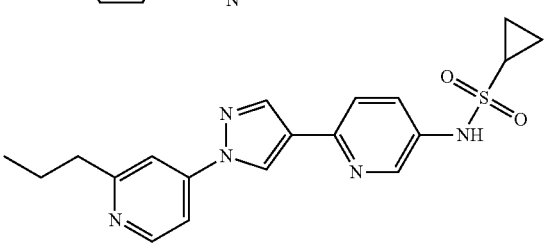

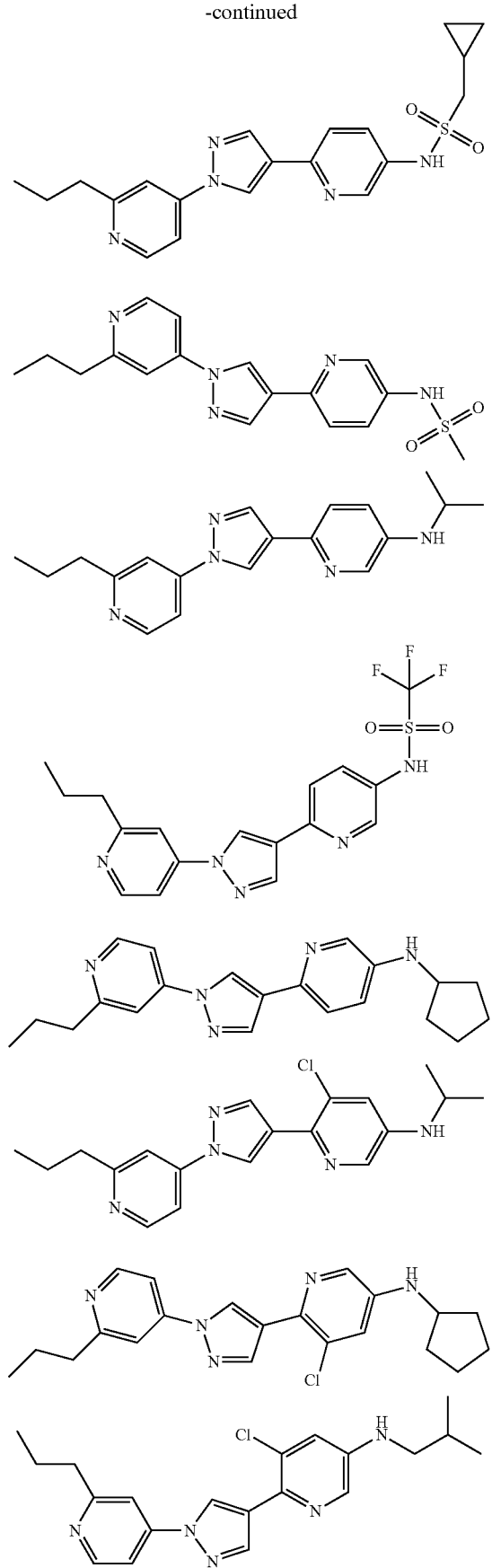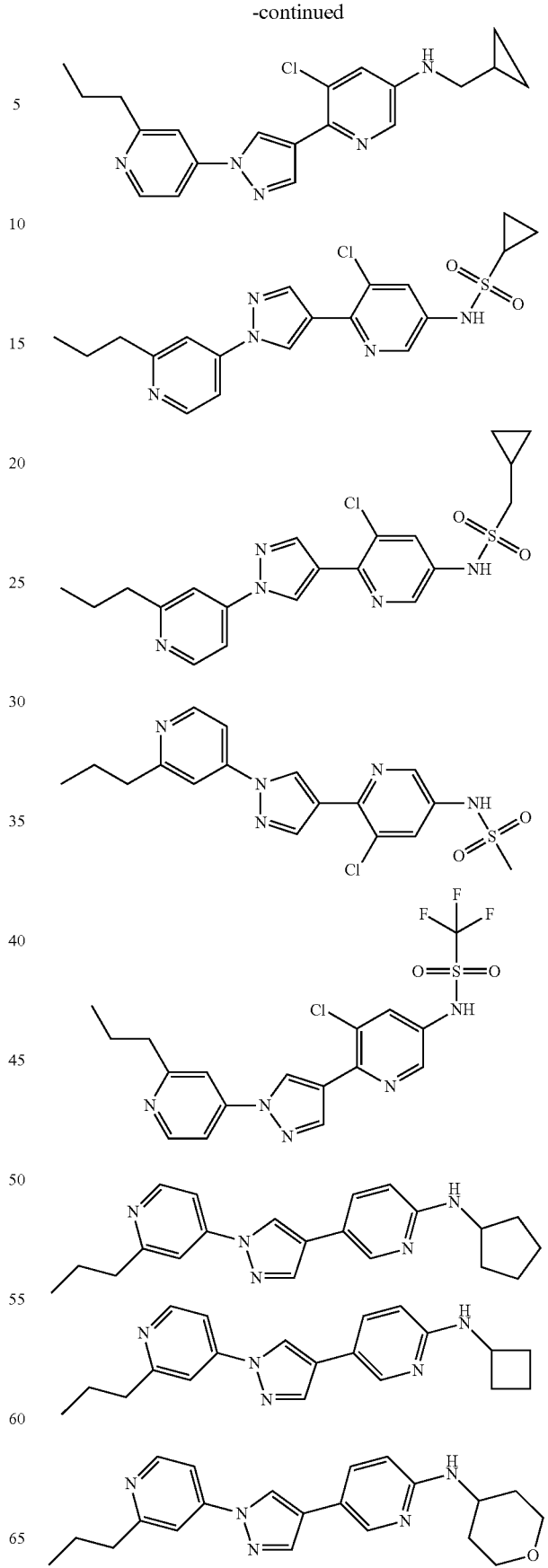

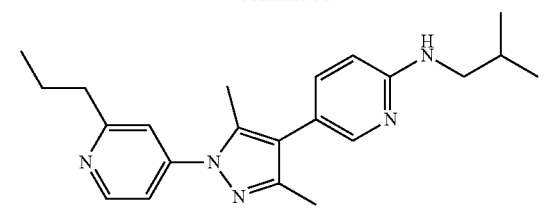
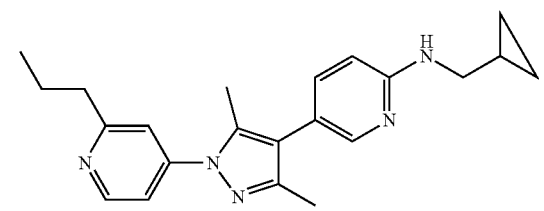
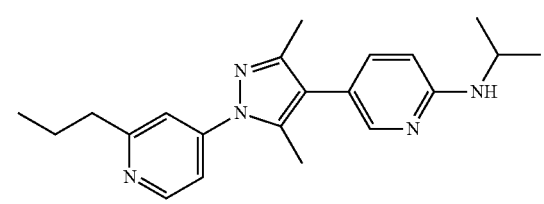
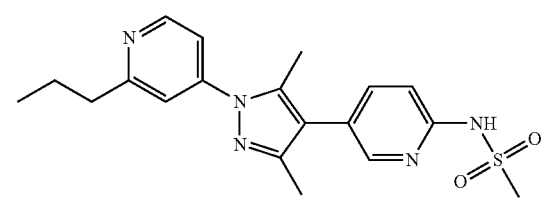
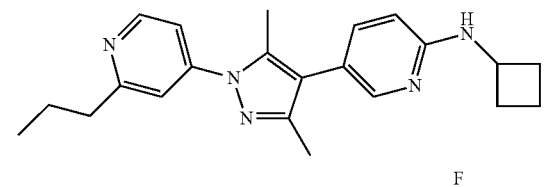
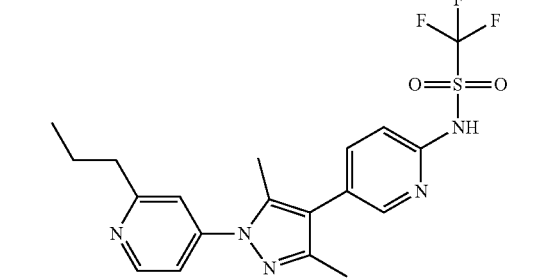
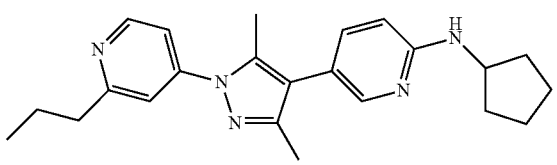
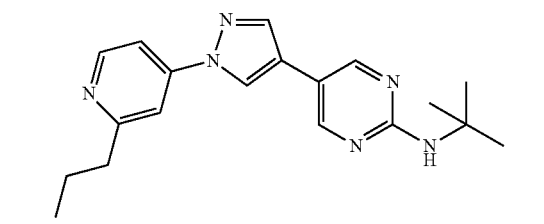
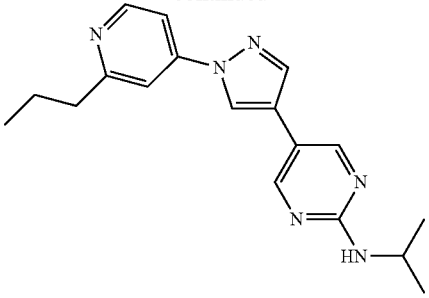
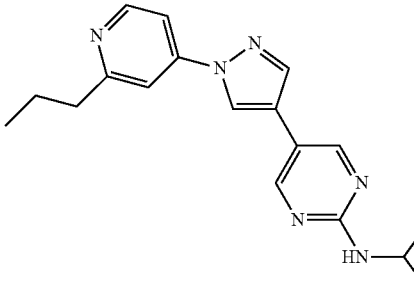
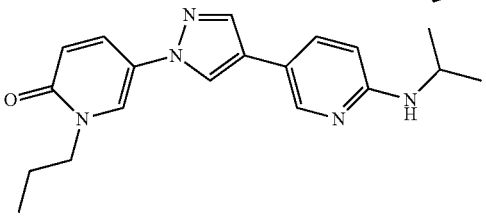
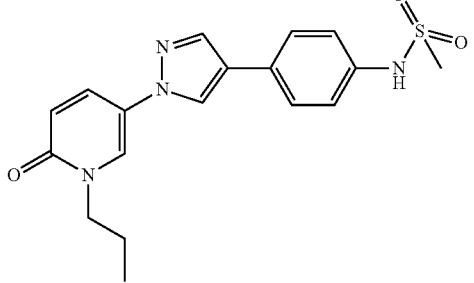
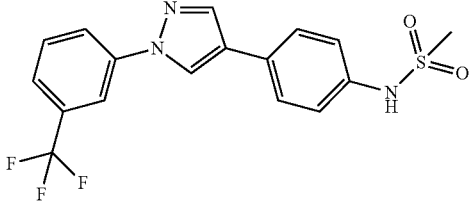
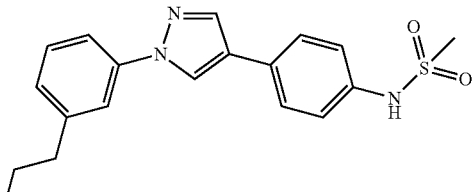
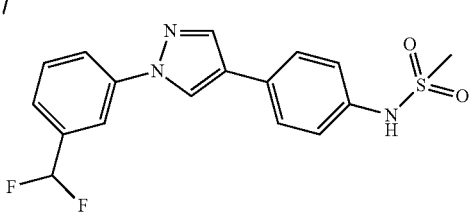

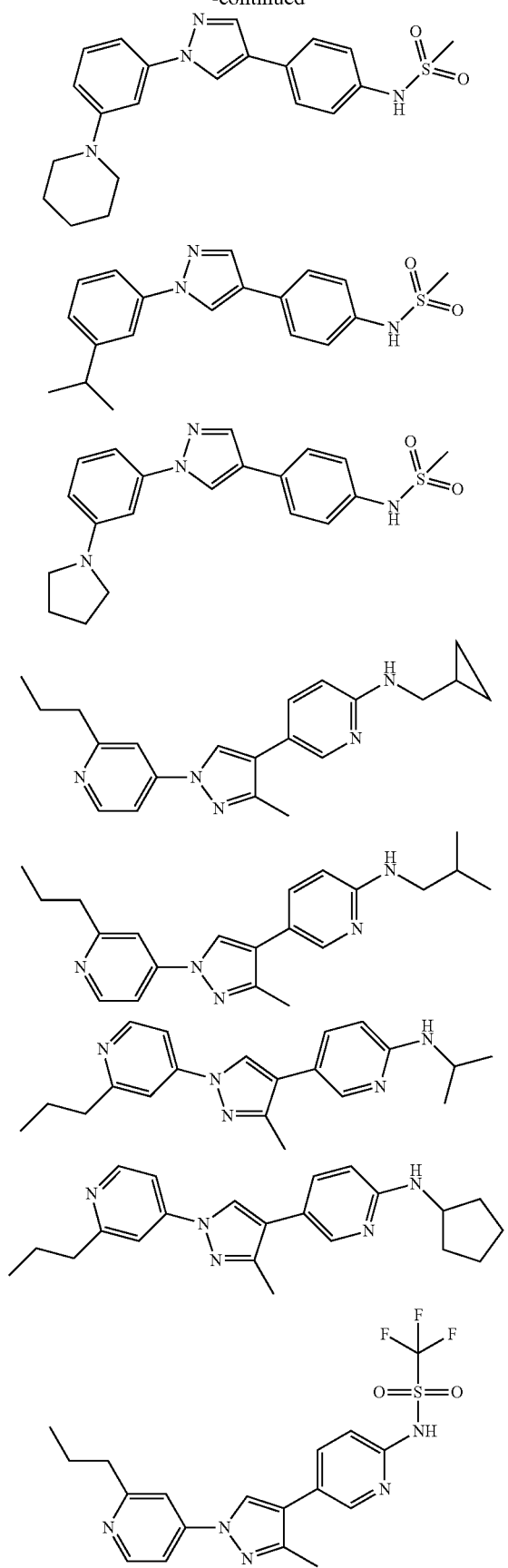
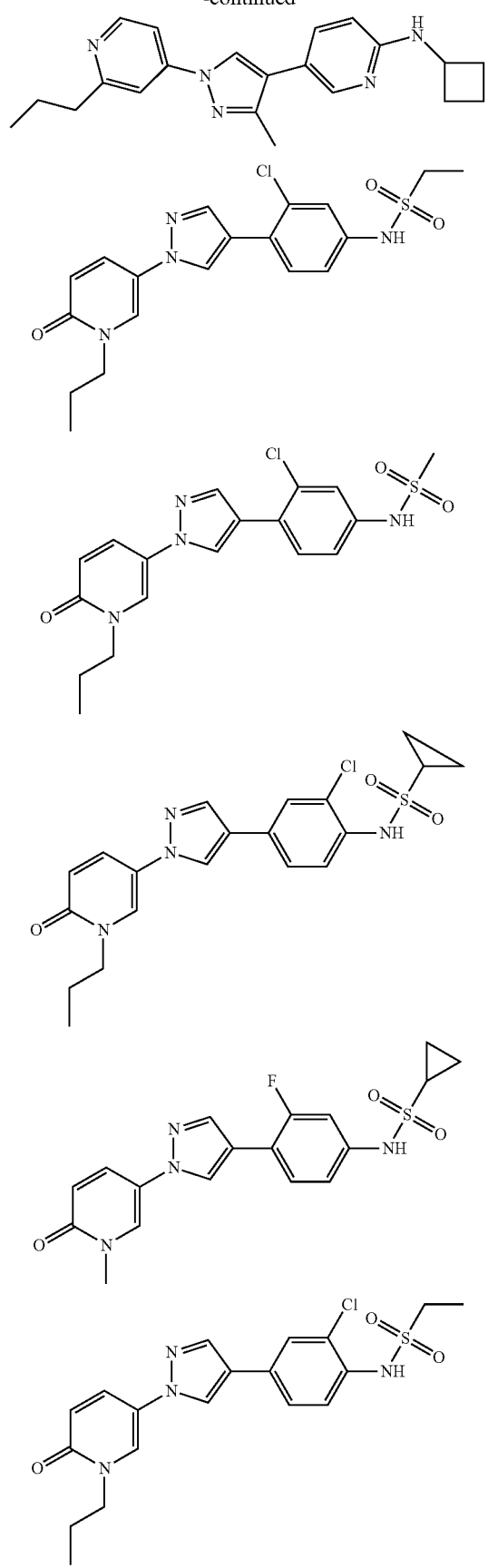

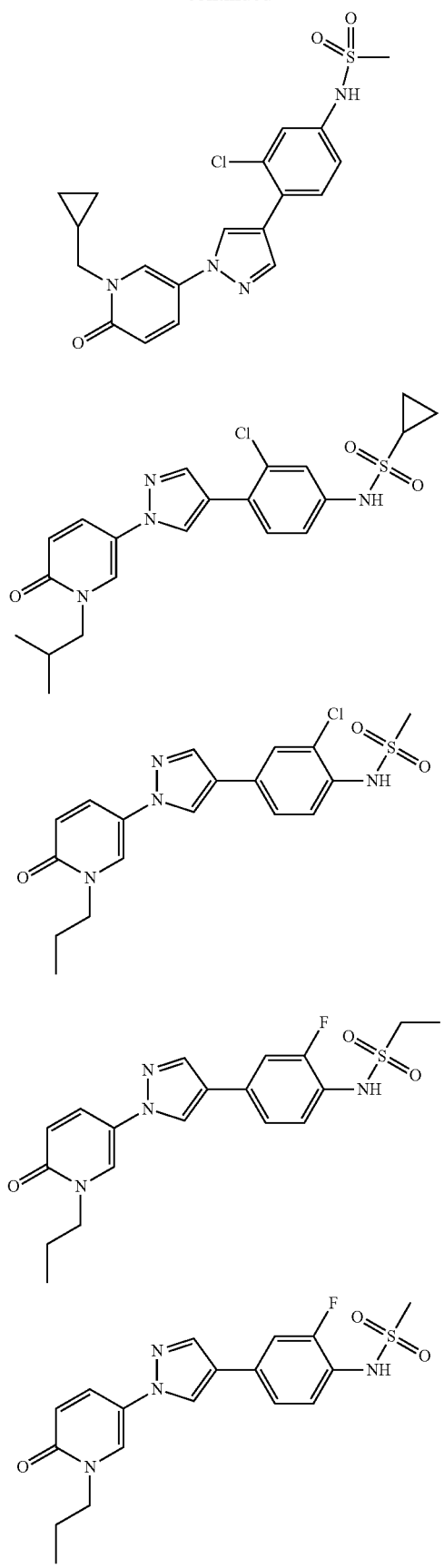
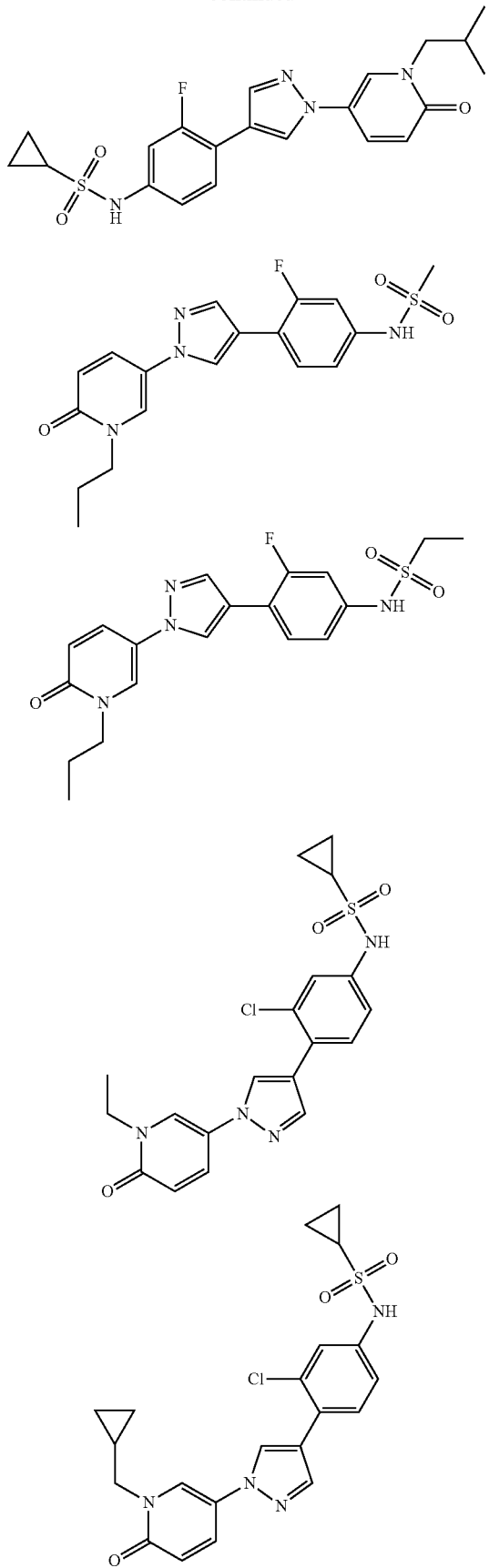

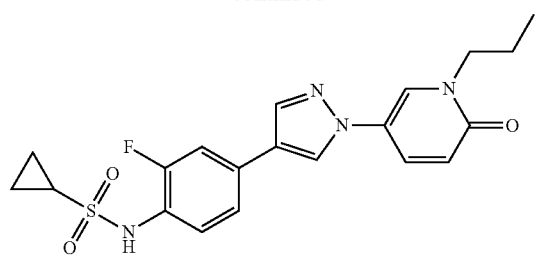
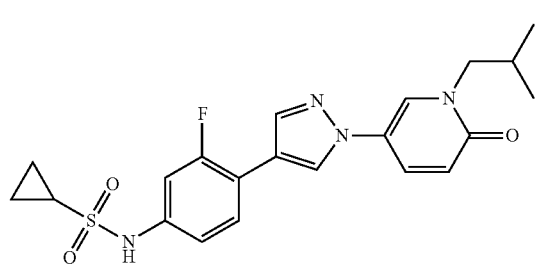
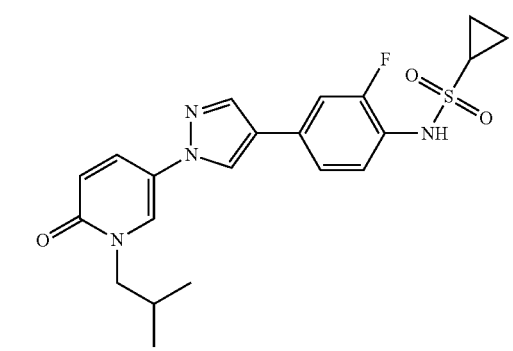
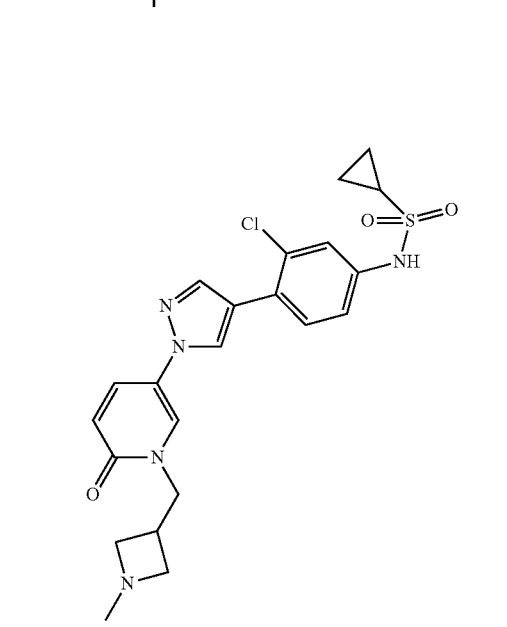
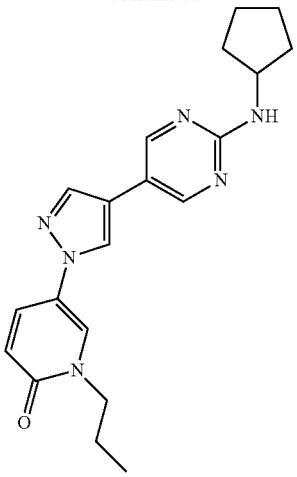
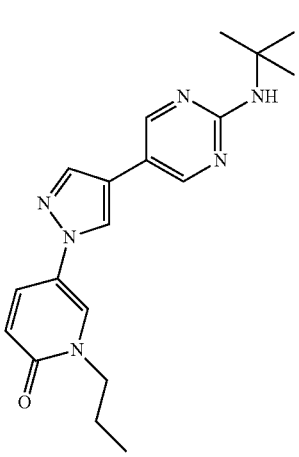
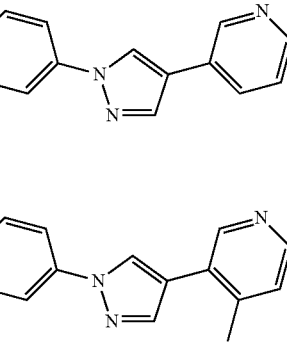
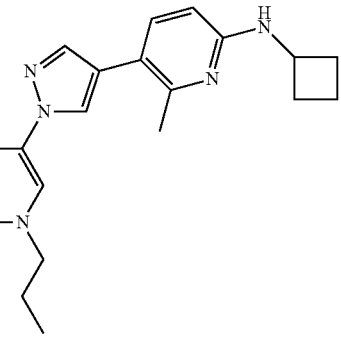

-continued
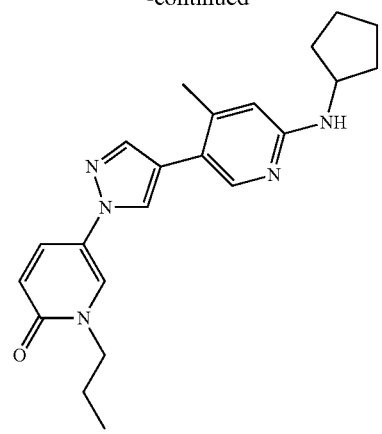
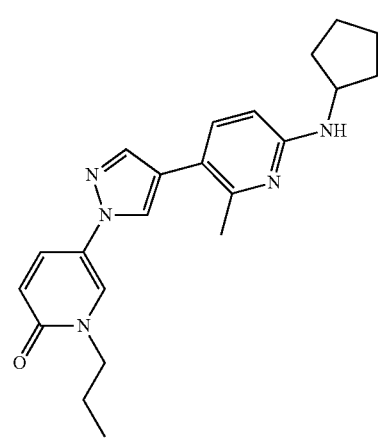
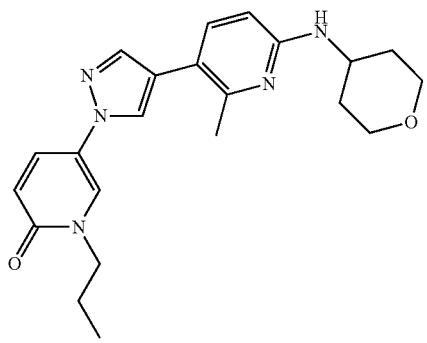
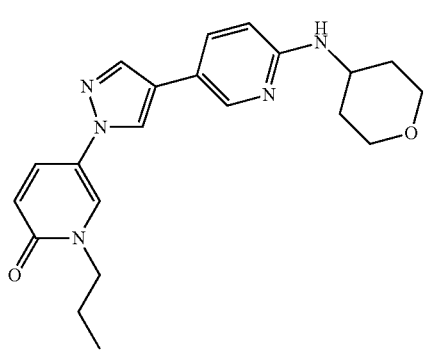
-continued
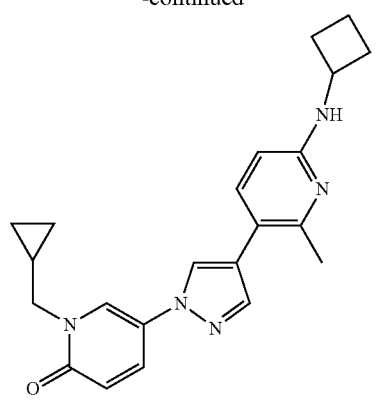
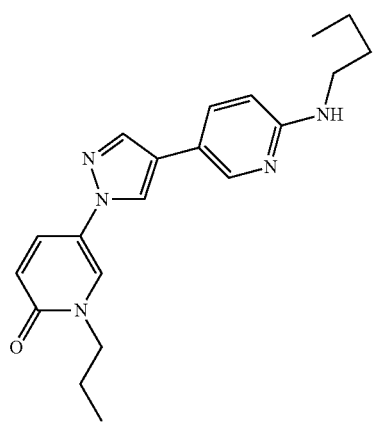
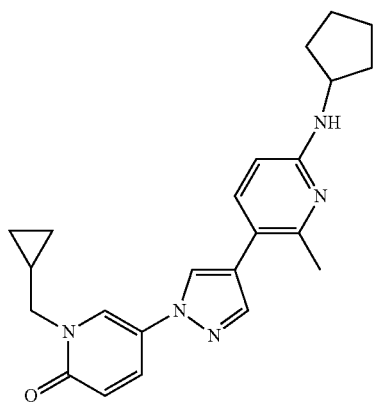
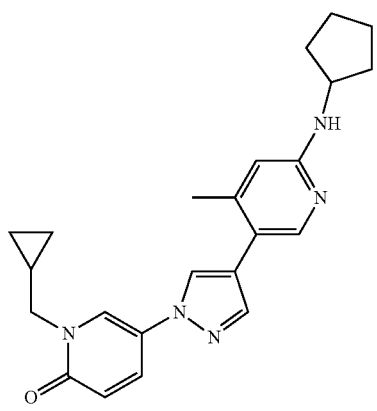

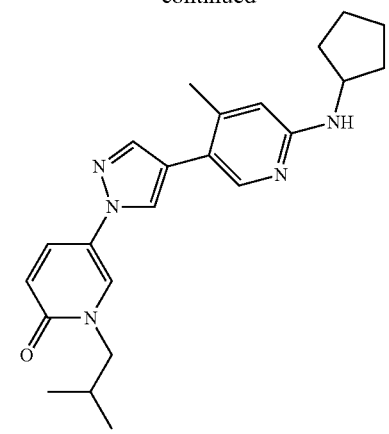
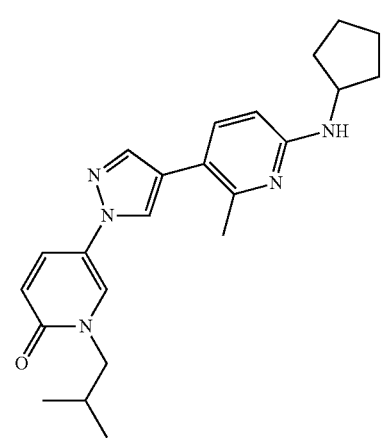
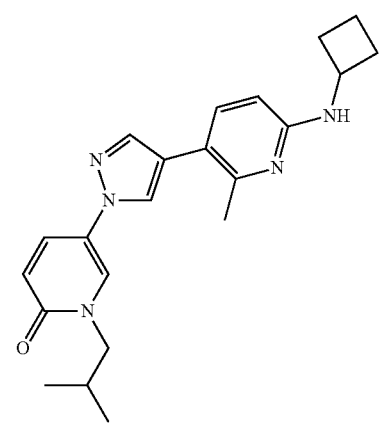
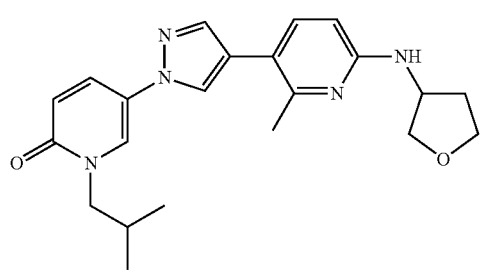
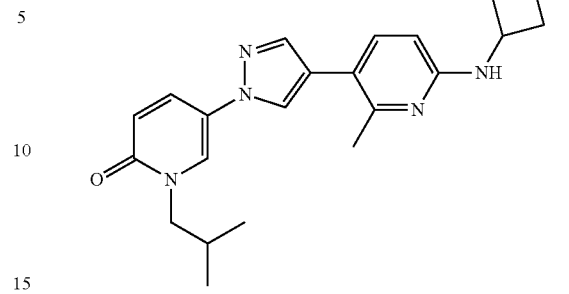
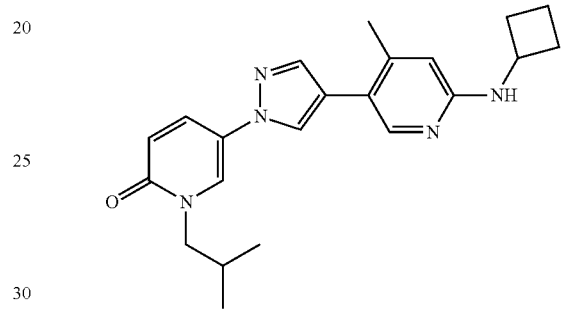
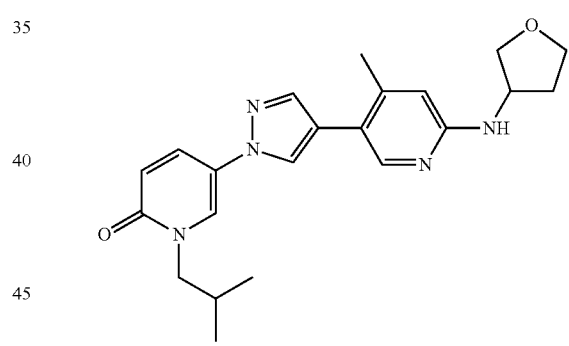
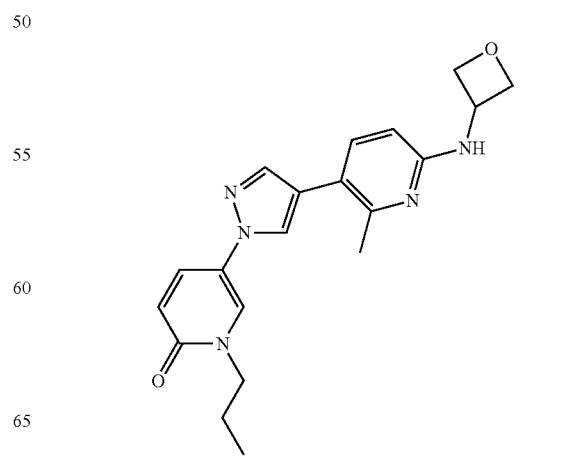

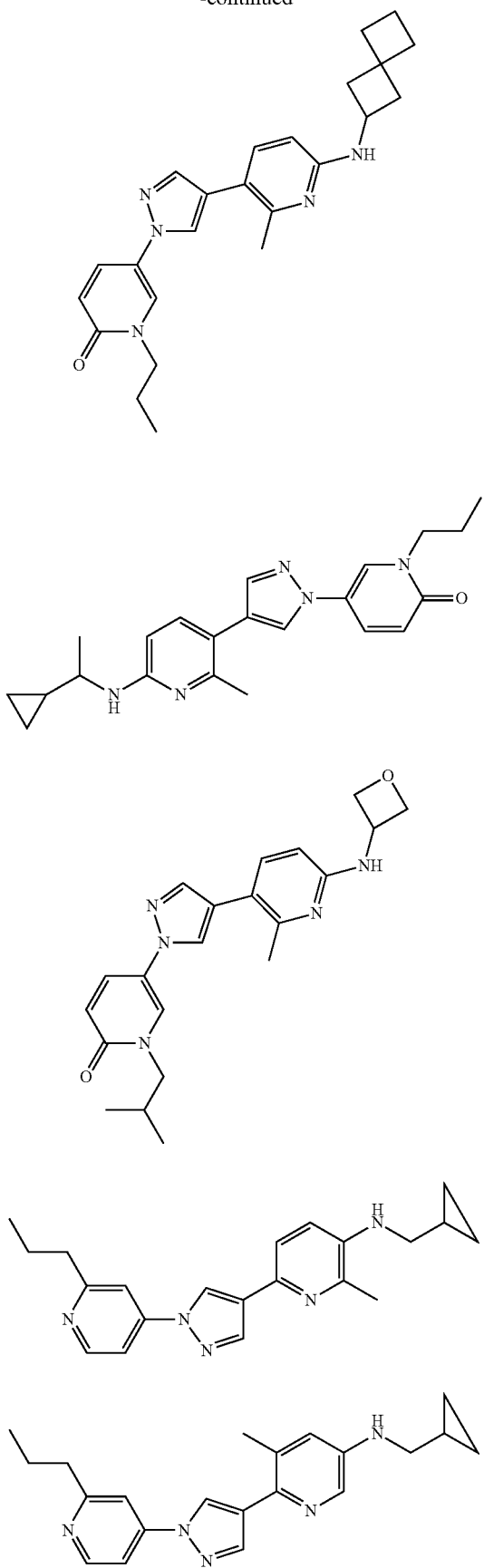
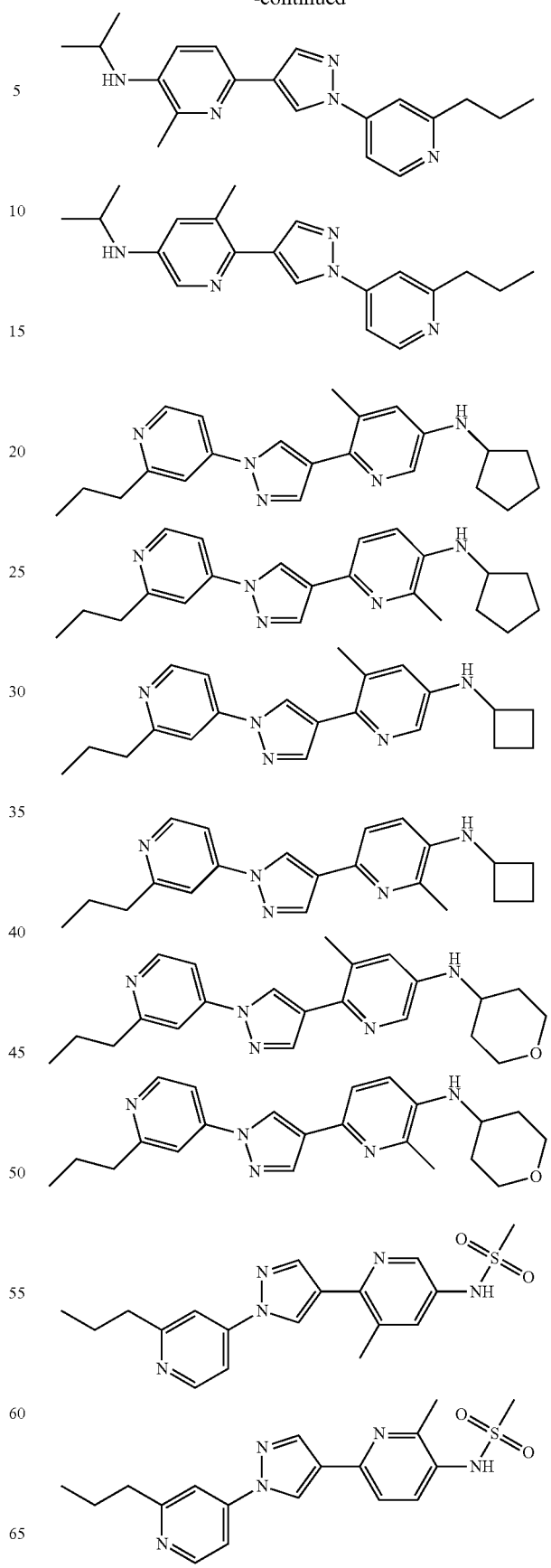

71
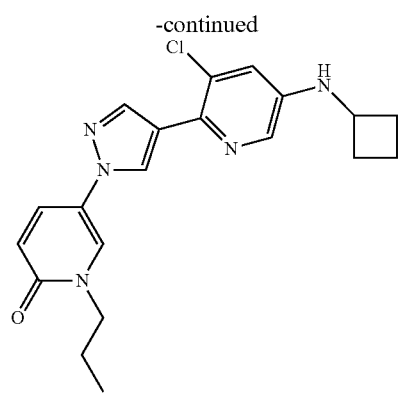
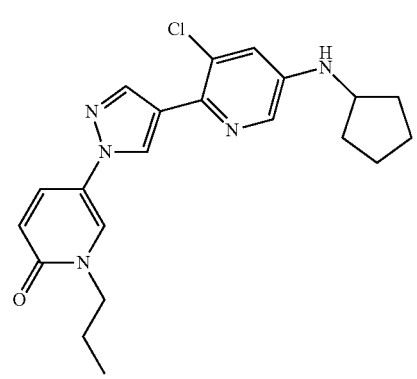
72
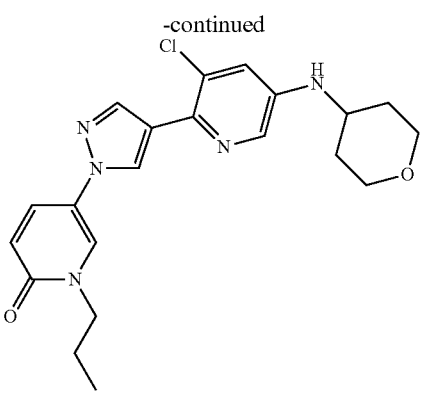
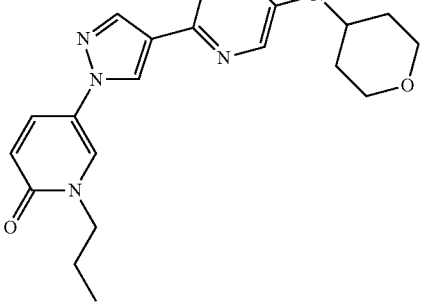
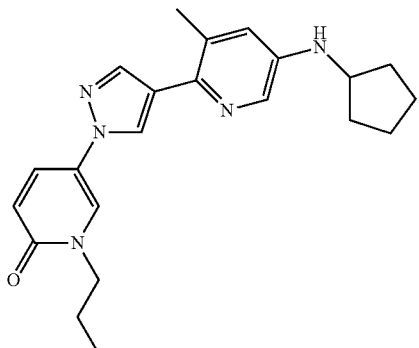
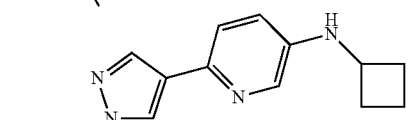
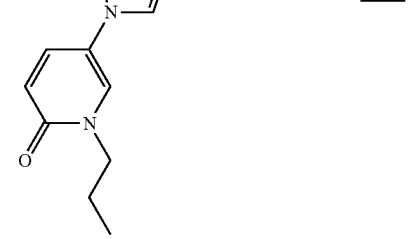

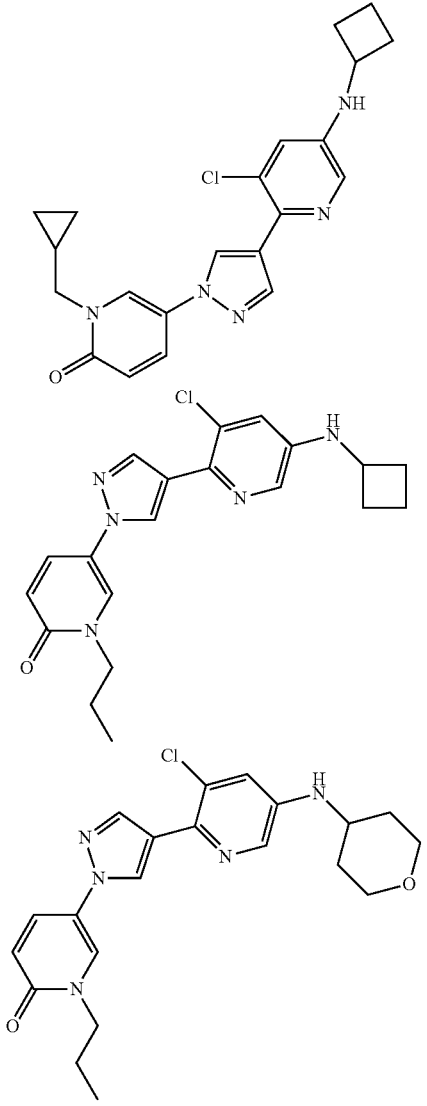

In some embodiments, provided herein are:
(a) compounds as described herein, e.g., of Formula (I)-(Im), (100), (200), (I)-(Im), and (Ia-1)-(Im-1) and Examples 1-130 and Embodiment A, and pharmaceutically acceptable salts and compositions thereof;
(b) compounds as described herein, e.g., of Formula (I)-(Im), (100), (200), (I)-(Im), and (Ia-1)-(Im-1) and Examples 1-130 and Embodiment A, and pharmaceutically acceptable salts and compositions thereof for use in the treatment of a condition, disease, or disorder associated with abnormal activation of the SREBP pathway;
(c) processes for the preparation of compounds as described herein, e.g., of Formula (I)-(Im), (100), (200), (I)-(Im), and (Ia-1)-(Im-1) and Examples 1-130 and Embodiment A, as described in more detail elsewhere herein;
(d) pharmaceutical formulations comprising a compound as described herein, e.g., of Formula (I)-(Im), (100), (200), (I)-(Im), and (Ia-1)-(Im-1) and Examples 1-130 and Embodiment A, or a pharmaceutically acceptable salt thereof together with a pharmaceutically acceptable carrier;
(e) a method for the treatment of a condition, disease, or disorder associated with abnormal activation of the SREBP pathway in a subject that includes the administration of an effective treatment amount of a compound as described herein, e.g., of Formula (I)-(Im), (100), (200), (I)-(Im), and (Ia-1)-(Im-1) and Examples 1-130 and Embodiment A, its pharmaceutically acceptable salt or composition;
(f) pharmaceutical formulations comprising a compound as described herein, e.g., of Formula (I)-(Im), (100), (200), (I)-(Im), and (Ia-1)-(Im-1) and Examples 1-130 and Embodiment A, or a pharmaceutically acceptable salt thereof together with one or more other effective agents for treating a condition, disease, or disorder associated with abnormal activation of the SREBP pathway, optionally in a pharmaceutically acceptable carrier; or
(g) a method for the treatment of a condition, disease, or disorder associated with abnormal activation of the SREBP pathway in a subject that includes the administration of an effective treatment amount of a compound as described herein, e.g., of Formula (I)-(Im), (100), (200), (I)-(Im), and (Ia-1)-(Im-1) and Examples 1-130 and Embodiment A, its pharmaceutically acceptable salt or composition in combination and/or alternation with one or more agent for the treatment of a condition, disease, or disorder associated with abnormal activation of the SREBP pathway.

Optically Active Compounds

It is appreciated that compounds provided herein may have one or more chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (e.g., in certain embodiments, by resolution of the racemic form by recrystallization techniques, by synthesis from optically-active starting materials, by chiral synthesis, or by chromatographic separation using a chiral stationary phase).

In certain embodiments, methods to obtain optically active materials are known in the art, and include at least the following.
i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;
ii) simultaneous crystallization—a technique whereby the individual stereoisomers are separately crystallized from a solution of the racemate, possible only if the latter is a conglomerate in the solid state;
iii) enzymatic resolutions—a technique whereby partial or complete separation of a racemate by virtue of differing rates of reaction for the stereoisomers with an enzyme;
iv) enzymatic asymmetric synthesis—a synthetic technique whereby at least one step of the synthesis uses an enzymatic reaction to obtain an stereoisomerically pure or enriched synthetic precursor of the desired stereoisomer;
v) chemical asymmetric synthesis—a synthetic technique whereby the desired stereoisomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary is later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

Isotopically Enriched Compounds

Also provided herein are isotopically enriched compounds, including but not limited to isotopically enriched di-substituted pyrazoles.

Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et al. Food Cosmet. Toxicol., 20: 393 (1982); Lijinsky et al. J. Nat. Cancer Inst., 69: 1127 (1982); Mangold et al. Mutation Res. 308: 33 (1994); Gordon et al. Drug Metab. Dispos., 15: 589 (1987); Zello et. al. Metabolism, 43: 487 (1994); Gately et. al. J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e., the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al. Adv. Drug Res., vol. 14, pp. 1-36 (1985); Kushner et al. Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art.

Additional steps and reagents not provided in the Exemplary Preparation Scheme would be known to those of skill in the art. Exemplary methods of preparation are described in detail in the Examples herein.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of Formula (I)-(Im) (100), (200), (I)-(Im), and (Ia-1)-(Im-1) and 1-130 and Embodiment A, if appropriate in a salt form, either used alone or in the form of a combination with one or more compatible and pharmaceutically acceptable carriers, such as diluents or adjuvants, or with another agent for the treatment of a condition, disease, or disorder associated with abnormal activation of the SREBP pathway.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semisynthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Any embodiment described for "excipient". Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition, disease, or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a condition, disease, or disorder associated with abnormal activation of the SREBP pathway in a subject by administering, to a subject in need thereof, an effective amount of a compound provided herein, or a pharmaceutically acceptable salt thereof. The amount of the compound or composition which will be effective in the treatment of a disorder or one or more symptoms thereof will vary with the nature and severity of the condition, disease, or disorder, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the condition, disease, or disorder described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different conditions, diseases, or disorders, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiments, the daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, bout 350 mg/kg, about 375 mg/kg, about 400 mg/kg, about 425 mg/kg, about 450 mg/kg, about 475 mg/kg, about 500 mg/kg, or about 600 mg/kg. In certain embodiments, the daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, about 150-250 mg/kg, about 250-300 mg/kg, about 300-350 mg/kg, about 300-400 mg/kg, about 200-400 mg/kg, about 100-300 mg/kg, or about 400-500 mg/kg.

In certain embodiment, the twice daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, or about 300 mg/kg. In certain embodiments, the twice daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, or about 150-250 mg/kg In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In certain embodiments, dosages of the second agents to be used in a combination therapy are provided herein. In certain embodiments, dosages lower than those which have been or are currently being used to treat a condition, disease, or disorder associated with abnormal activation of the SREBP pathway are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J.; which are incorporated herein by reference in their entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a condition, disease, or disorder associated with abnormal activation of the SREBP pathway. The kits can include a compound or composition provided herein, a second agent or composition, and instructions providing information to a health care provider regarding usage for treating a condition, disease, or disorder associated with abnormal activation of the SREBP pathway. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a condition, disease, or disorder associated with abnormal activation of the SREBP pathway in a subject, which comprises contacting the subject with a therapeutically effective amount of a di-substituted pyrazole disclosed herein, e.g., a di-substituted pyrazole of Formula (I)-(Im) (100), (200), (I)-(Im), and (Ia-1)-(Im-1) and 1-130 and Embodiment A, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In certain embodiments, provided herein are methods for treating a condition, disease, or disorder associated with abnormal activation of the SREBP pathway in a subject. In certain embodiments, the methods encompass the step of administering to the subject in need thereof an amount of a compound effective for the treatment of a condition, disease, or disorder associated with abnormal activation of the SREBP pathway in combination with a second agent. The compound can be any compound as described herein, and the second agent can be any second agent described in the art or herein. In certain embodiments, the compound is in the form of a pharmaceutical composition or dosage form, as described elsewhere herein.

Diseases which can be treated with the Compound according to any of the Formula described herein, including Compounds 1-130 and Embodiment A, include metabolic syndrome, hypertension, type 2 diabetes, dyslipidemia, obesity, pancreatic B-cell dysfunction, atherosclerosis, cell proliferative disease, reducing body weight, increasing thermogenesis, metabolic diseases, hyperlipidemia, a lipoprotein related disease, combined hyoerlipidemia (elevated cholesterol and triglycerides), Frederickson Type IIb, familial combined hyperlipidemia (inherited form of combined hyperlipidemia), familial hypertriglyceridemia, Frederickson Type IV, hyperlipoproteinemia Type V, mixed hyperlipidemia, Aquired hyperlipidemia, Fatty Liver Disease, Nonalcoholic Steatohepatitis, Neutral Lipid Storage Diseases, Chanarin-Dorfman Syndrome, Tissue Inflammation such as Cutaneous Psoriasis (associated with Metabolic syndrome), coronary artery disease (atherosclerosis), post myocardial infarction management, peripheral vascular disease, cerebrovascular disease—thrombotic, type II diabetes mellitus, diabetic nephropathy, cancer, hepatocellular carcinoma—not amenable to surgical or locoregional therapy, glioblastoma multiforme, prostate cancer, breast cancer, post-menopausal breast carcinoma, pancreatic adenocarcinoma, ovarian cancer, and B cell lymphoma.

Diseases which can be treated with the Compound according to any of the Formula described herein, including Compounds 1-130 and Embodiment A, include hyperlipidemia, a lipoprotein related disease, combined hyoerlipidemia (elevated cholesterol and triglycerides), Frederickson Type IIb, familial combined hyperlipidemia (inherited form of combined hyperlipidemia), familial hypertriglyceridemia, Frederickson Type IV, hyperlipoproteinemia Type V, mixed hyperlipidemia, Aquired hyperlipidemia, Fatty Liver Disease, Nonalcoholic Steatohepatitis, Neutral Lipid Storage Diseases, Chanarin-Dorfman Syndrome, Tissue Inflammation such as Cutaneous Psoriasis (associated with Metabolic syndrome), coronary artery disease (atherosclerosis), post myocardial infarction management, peripheral vascular disease, cerebrovascular disease—thrombotic, type II diabetes mellitus, diabetic nephropathy, cancer, hepatocellular carcinoma—not amenable to surgical or locoregional therapy, glioblastoma multiforme, prostate cancer, breast cancer, post-menopausal breast carcinoma, pancreatic adenocarcinoma, ovarian cancer, and B cell lymphoma.

Additional cancers which can be treated with the Compound according to any of the Formula described herein, including Compounds 1-130 and Embodiment A, include a cancer selected from the group consisting of lung cancer, a digestive and gastrointestinal cancer, gastrointestinal stromal tumor, gastrointestinal carcinoid tumor, colon cancer, rectal cancer, anal cancer, bile duct cancer, small intestine cancer, stomach (gastric) cancer, esophageal cancer, gall bladder cancer, liver cancer, pancreatic cancer, appendix cancer, breast cancer, ovarian cancer, renal cancer, cancer of the central nervous system, skin cancer, a lymphoma, choriocarcinoma, head and neck cancer, osteogenic sarcoma, and a blood cancer.

Assay Methods

Compounds can be assayed for efficacy in treating a condition, disease, or disorder associated with abnormal activation of the SREBP pathway according to any assay known to those of skill in the art. Exemplary assay methods are provided elsewhere herein.

Second Therapeutic Agents

In certain embodiments, the compounds and compositions provided herein are useful in methods of treatment of a condition, disease, or disorder associated with abnormal activation of the SREBP pathway, that comprise further administration of a second agent. The second agent can be any agent known to those of skill in the art to be effective for the treatment of a condition, disease, or disorder associated with abnormal activation of the SREBP pathway, including those currently approved by the United States Food and Drug Administration, or other similar body of a country foreign to the United States.

In some embodiments, the disease is cancer and the second agent is a cancer treatment. In some embodiments, the disease is cancer and the second agent is a chemotherapeutic agent. In some embodiments, the chemotherapeutic agent is selected from an alkylating agent (e.g. cyclophosphamide, mechlorethamine, chlorambucil, melphalan, dacarbazine (DTIC), a nitrosoureas, temozolomide (oral dacarbazine); an anthracycline (e.g. daunorubicin, doxorubicin, liposomal doxorubicin, epirubicin, idarubicin, mitoxantrone, and valrubicin); a cytoskeletal disruptor (a taxane, e.g. paclitaxel, Albumin-bound paclitaxel and docetaxel); epothilone; an Histone Deacetylase inhibitor (e.g. vorinostat and romidepsin); an inhibitor of Topoisomerase I (e.g. irinotecan and topotecan); an inhibitor of Topoisomerase II (e.g. etoposide, teniposide, and tafluposide); a kinase inhibitor (e.g. sorafenib, cobimetinib, cabozantanib, lapatinib, bortezomib, erlotinib, gefitinib, imatinib, vemurafenib, and vismodegib); a nucleotide analog and precursor analog (e.g. azacitidine, azathioprine, capecitabine, cytarabine, doxifluridine, fluorouracil, gemcitabine, hydroxyurea, mercaptopurine, methotrexate, and tioguanine); a peptide antibiotic (e.g. bleomycin and actinomycin); a platinum agent (e.g. carboplatin, cisplatin, and oxaliplatin); a retinoid (e.g. tretinoin, alitretinoin, and bexarotene); a vinca alkaloid or derivative (e.g. Capecitabine, vinblastine, vincristine, vindesine, and vinorelbine); eribulin; ixabepilone; radiation; bevacizumab; olaparib; an aromatase inhibitor (e.g. letrozole, anastrozole, and exemestane); rituximab; ibritumomab; prednisone; and enzalutamide.

In some embodiments, the disease is cancer and the second agent is a kinase inhibitor e.g. sorafenib, cobimetinib, cabozantanib, lapatinib, bortezomib, erlotinib, gefitinib, imatinib, vemurafenib, and vismodegib. In some embodiments, the disease is cancer and the second agent is a kinase inhibitor such as sorafenib or erlotinib.

In some embodiments, the disease is breast cancer (e.g. pos-menopausal breast carcinoma) and the second agent is radiation, docetaxel, paclitaxel, platinum agents (cisplatin, carboplatin), vinorelbine, capecitabine, liposomal doxorubicin, gemcitabine, mitoxantrone, ixabepilone, albumin-bound paclitaxel, eribulin, trastuzumab, pertuzimab, ado-trastuzumab, lapatinib, bevacizumab, olaparib, radiation, an aromatase inhibitor (e.g. letrozole, anastrozole, and exemestane), or tamoxifen.

In some embodiments, the disease is liver cancer (e.g. hepatocellular carcinoma, hepatocellular carcinoma not amenable to surgical or locoregional therapy) and the second agent is sorafenib.

In some embodiments, the disease is prostate cancer and the second agent is radiation, abiraterone, or enzalutamide.

In some embodiments, the disease is pancreatic adenocarcinoma and the second agent is radiation.

In some embodiments, the disease is ovarian cancer and the second agent is bevacizumab, olaparib, radiation, an aromatase inhibitor (e.g. letrozole, anastrozole, and exemestane), or tamoxifen.

In some embodiments, the disease is B cell lymphoma and the second agent is rituximab, radiation, ibritumomab, cyclophosphamide, doxorubicin, vincristine, or prednisone.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of a condition, disease, or disorder associated with abnormal activation of the SREBP pathway. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition, disease, or disorder associated with abnormal activation of the SREBP pathway to be treated. It is to be further understood that for any particular subject, specific dosage regimens and schedules should be adjusted over time according to the individual need and the professional judgment of the person administering or supervising the administration of the compositions.

General Scheme 1
General reaction scheme for sulfonylation or reductive amination of aromatic and heteroaromatic amines

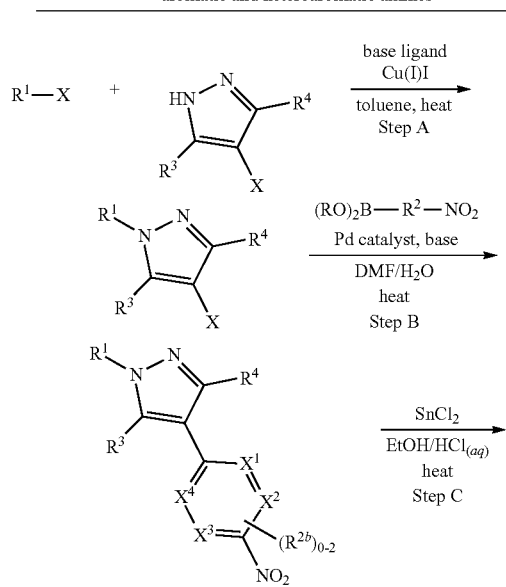

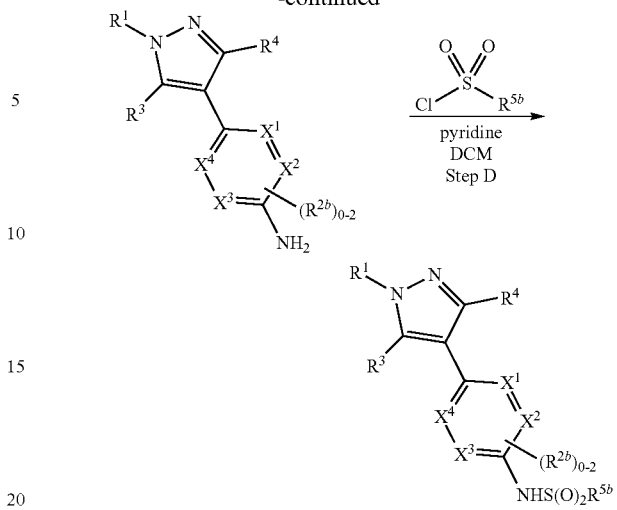

General Scheme 1 describes the preparation of a Compound of Formula (I) where $R^1$ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; each X is independently a leaving group such as halo (in some embodiments, bromo); each R is hydrogen, each R is linear alkyl, or the two R are alkyl and together with the atoms to which they are attached form a cyclic boronic acid or ester; and all other groups are as defined in the Summary of the invention or in any embodiments described herein.

General Scheme 2
General reaction schemes for Aromatic and heteroaromatic amines intermediates

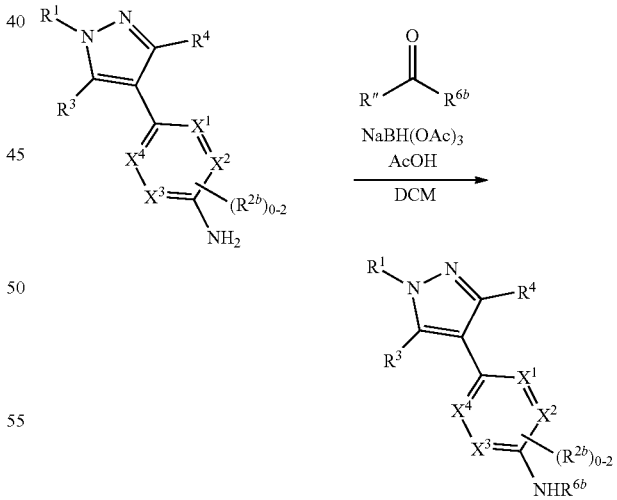

General Scheme 2 describes the preparation of a Compound of Formula (I) where $R^1$ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; $R^{6b}$ is alkyl, haloalkyl, cycloalkyl, cycloalkylalkyl, heterocycloalkyl, or heterocycloalkylalkyl), and additionally optionally substituted with 1 or 2 $R^{2b}$; R" is H or alkyl; and all other groups are as defined in the Summary of the invention or in any embodiments described herein.

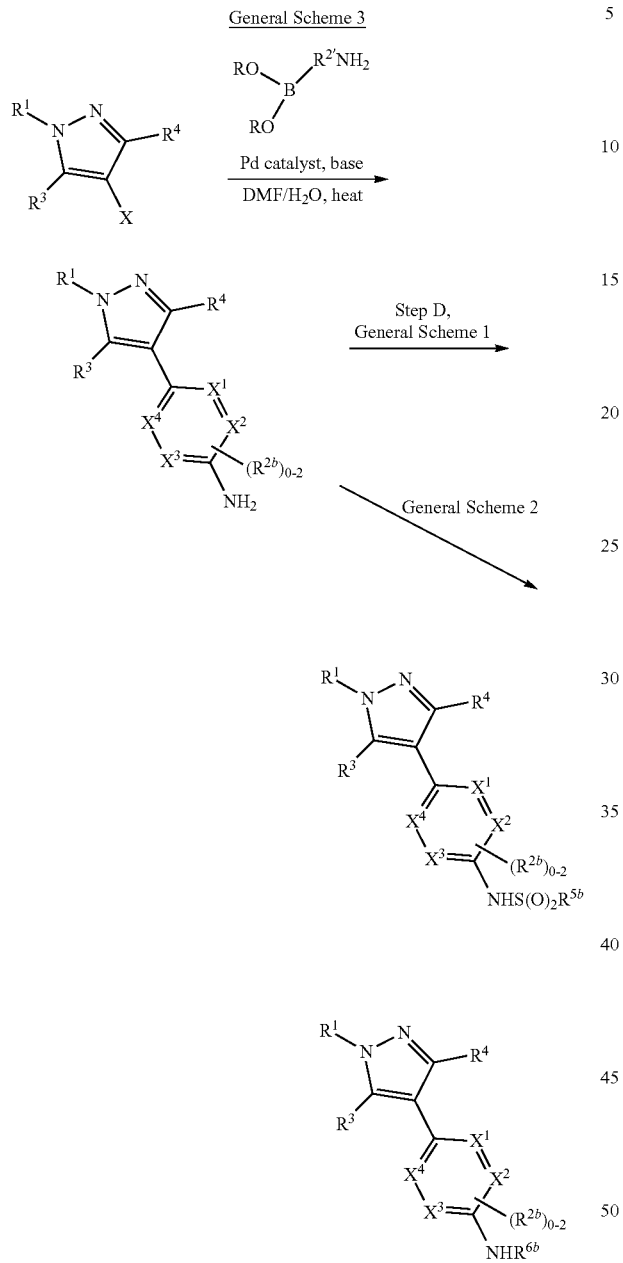

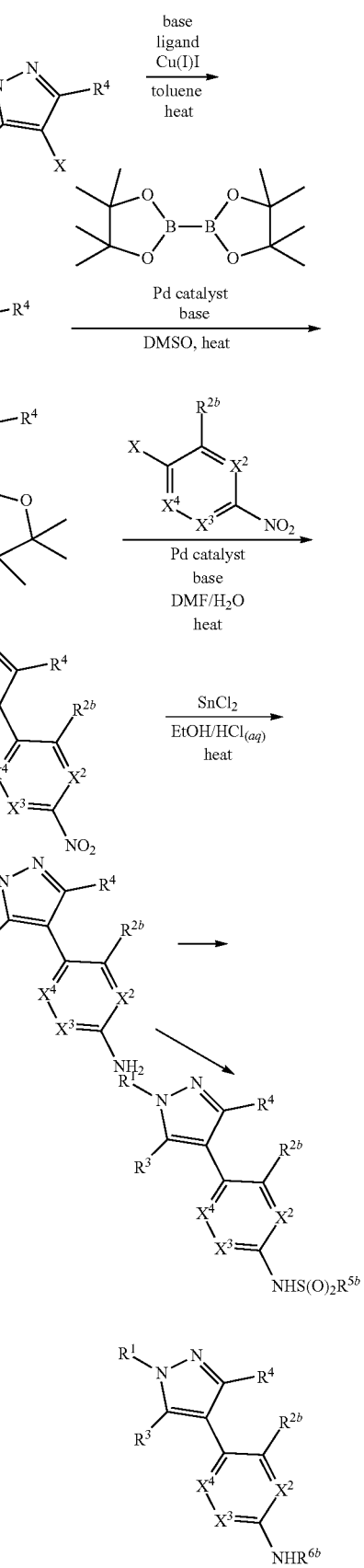

General Scheme 3 describes the preparation of a Compound of Formula (I) where $R^1$ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; X is a leaving group such as halo (in some embodiments, bromo); each R is hydrogen, each R is linear alkyl, or the two R are alkyl and together with the atoms to which they are attached form a cyclic boronic acid or ester; and all other groups are as defined in the Summary of the invention or in any embodiments described herein; where the —$NH_2$ is further derivatized according to Step D in General Scheme 1 or according to General Scheme 2.

General Scheme 4 describes the preparation of a Compound of Formula (I) where R¹ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; each X is independently a leaving group such as halo (in some embodiments, bromo); and all other groups are as defined in the Summary of the invention or in any embodiments described herein; where the —NH₂ is further derivatized according to Step D in General Scheme 1 or according to General Scheme 2.

General Scheme 5 describes the preparation of a Compound of Formula (I) where R¹ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; X is a leaving group such as halo (in some embodiments, bromo); each R is hydrogen, each R is linear alkyl, or the two R are alkyl and together with the atoms to which they are attached form a cyclic boronic acid or ester; and all other groups are as defined in the Summary of the invention or in any embodiments described herein; where the —NH₂ is further derivatized according to Step D in General Scheme 1 or according to General Scheme 2.

General Scheme 5

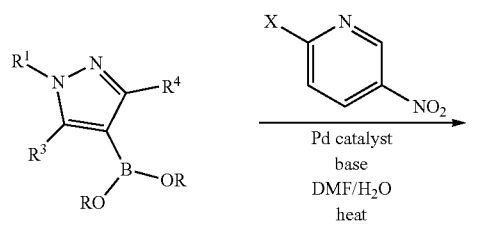

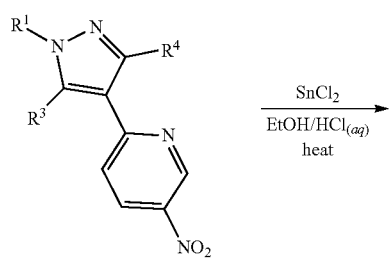

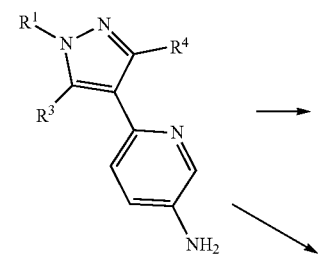

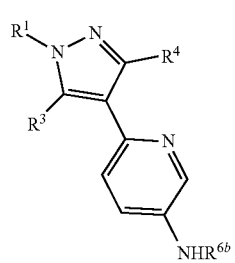

General Scheme 6

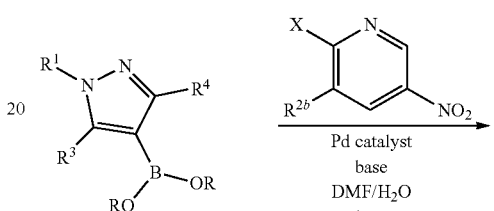

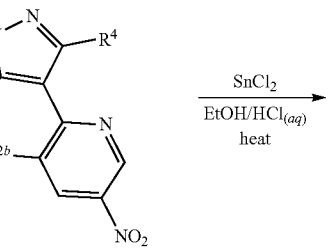

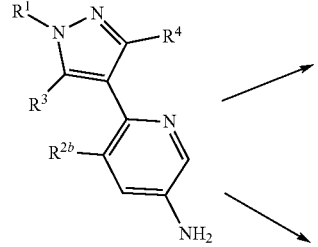

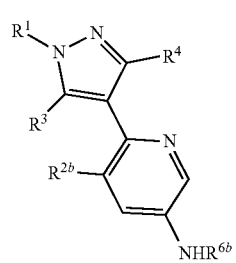

General Scheme 6 describes the preparation of a Compound of Formula (I) where $R^1$ is phenyl, pyridinyl, pyrimidinyl, pyridazinyl, or pyrazinyl; where the phenyl, pyridinyl, pyrimidinyl, pyridazinyl, and pyrazinyl rings are optionally substituted with 1 or 2 $R^{1a}$; X is a leaving group such as halo (in some embodiments, bromo); each R is hydrogen, each R is linear alkyl, or the two R are alkyl and together with the atoms to which they are attached form a cyclic boronic acid or ester; and all other groups are as defined in the Summary of the invention or in any embodiments described herein; where the —$NH_2$ is further derivatized according to Step D in General Scheme 1 or according to General Scheme 2.

General Scheme 8

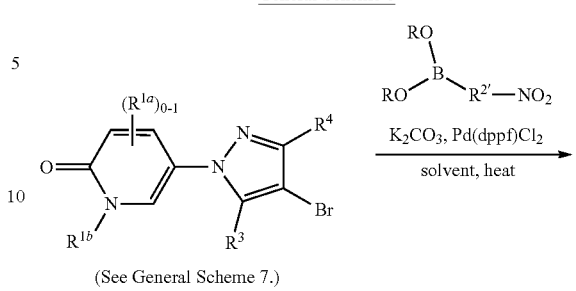

(See General Scheme 7.)

General Scheme 7

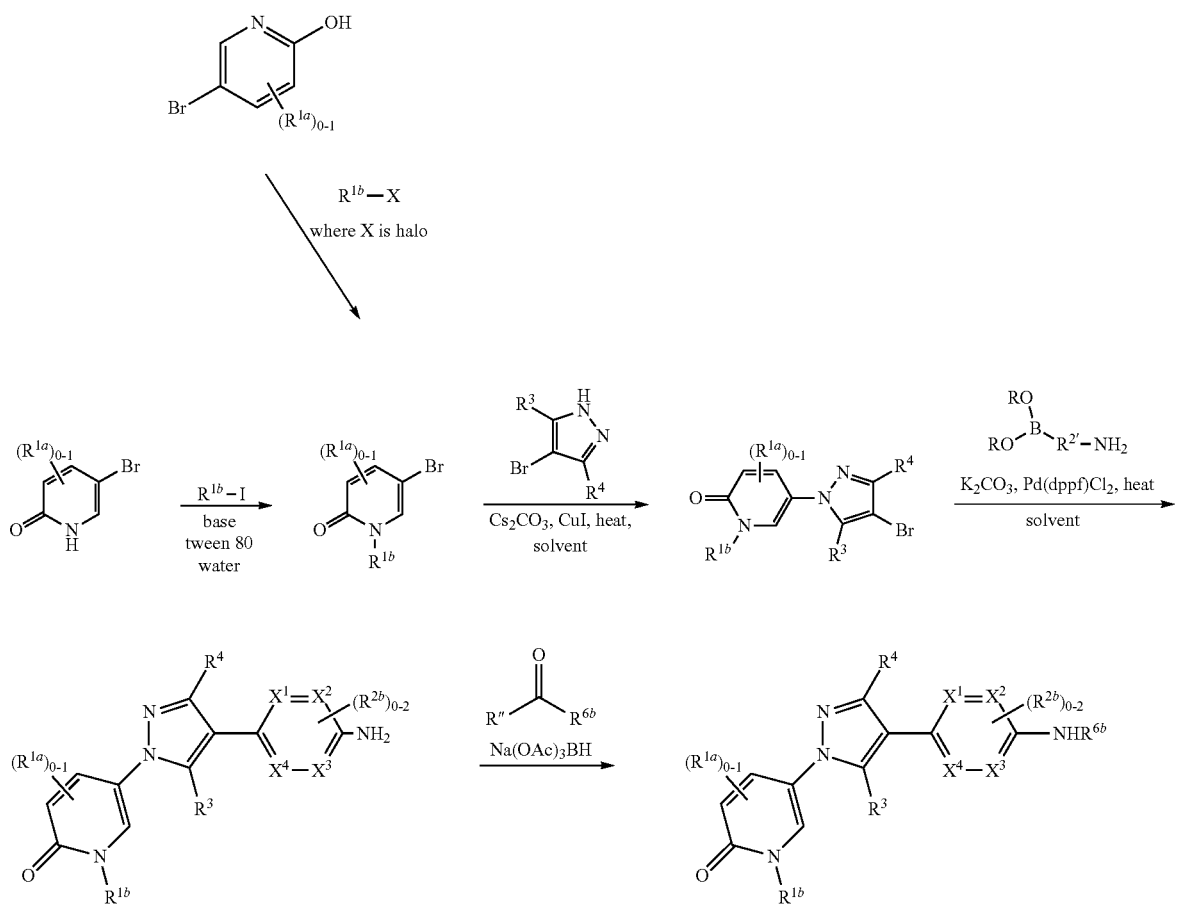

General Scheme 7 describes the preparation of a Compound of Formula (I) where $R^{6b}$ is alkyl, haloalkyl, cycloalkyl, cycloalkylalkyl, heterocycloalkyl, or heterocycloalkylalkyl; R" is H or alkyl; $R^{2'}$ is and all other groups are as defined in the Summary of the invention or in any embodiments described herein.

-continued

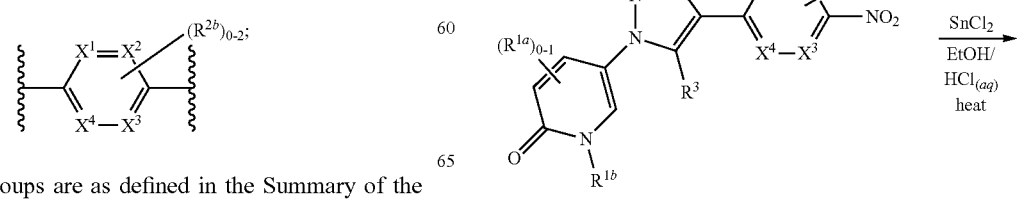

101
-continued
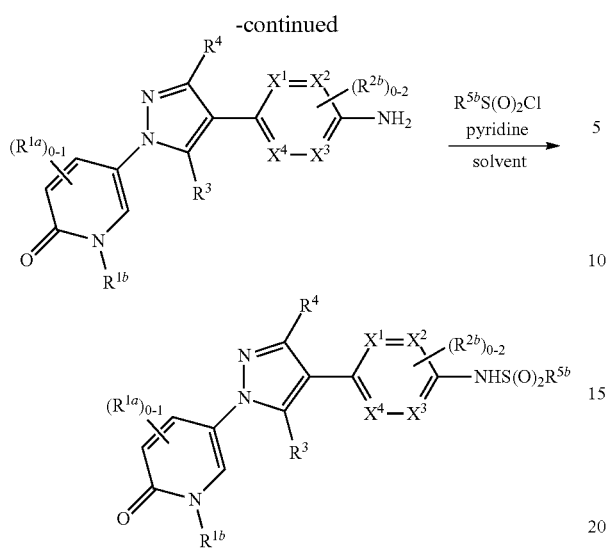
102
General Scheme 8 describes the preparation of a Compound of Formula (I) where $R^{5b}$ is alkyl, haloalkyl, cycloalkylalkyl, or heterocycloalkylalkyl; $R^{2t}$ is
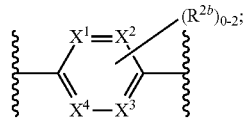
and all other groups are as defined in the Summary of the invention or in any embodiments described herein.
General Scheme 9
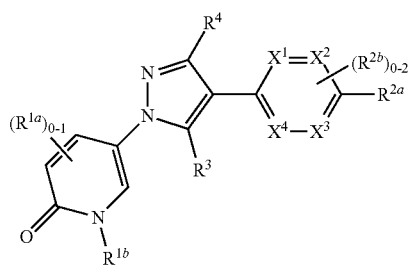
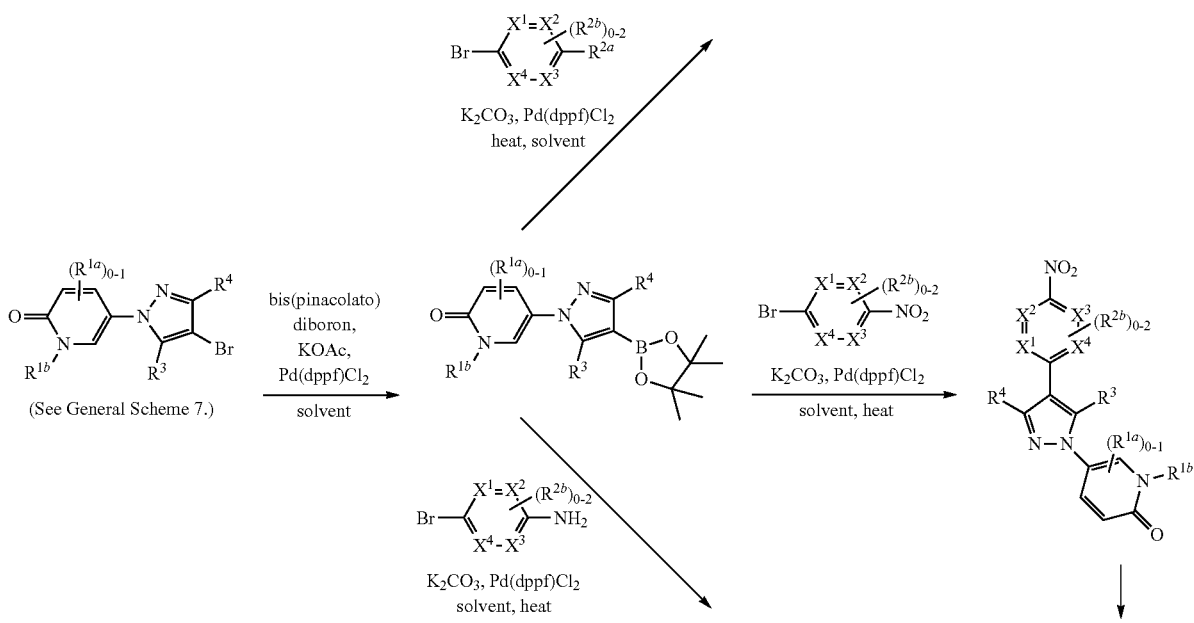

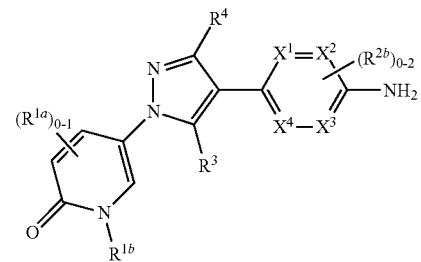

↓ ketone or aldehyde
Na(OAc)₃BH

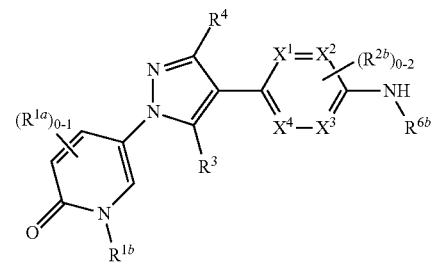

General Scheme 9 describes the preparation of a Compound of Formula (I) where $R^1$ is pyridinonyl substituted with one $R^{1b}$ and optionally substituted with one $R^{1a}$; other groups are as defined in the Summary of the invention or in any embodiments described herein.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl₃ (deuterated chloroform); AcOH (acetic acid); DCM (dichloromethane); DMSO (dimethylsulfoxide); DMSO-d₆ (deuterated dimethylsulfoxide); EtOAc (ethyl acetate); MeOH (methanol); Tces (2,2,2-trichloroethoxysulfonyl); —Si(tert-Bu)(Ph)₂ and —Si'BuPh₂ (tert-butyl-diphenylsilyl); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Example 1: N-(4-(1-(2-propylpyridin-4-yl)-1H-pyrazol-4-yl)phenyl)cyclopropanesulfonamide

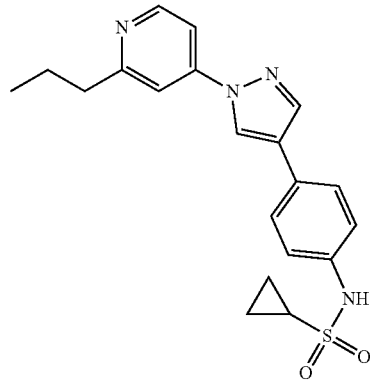 [SMILES: CCCc1cc(-n2cc(-c3ccc(NS(=O)(=O)C4CC4)cc3)cn2)ccn1]

Step 1:
4-(4-bromo-1H-pyrazol-1-yl)-2-propylpyridine

To a stirred solution of 4-bromo-2-(n-propyl)pyridine (4.00 g, 20.0 mmol), 3-bromopyrazole (3.526 g, 24.0 mmol), potassium carbonate (5.526 g, 40.0 mmol) in anhydrous toluene (40 mL) under argon were added trans-N,N'-dimethyl-1,2-cyclohexanediamine (0.63 mL, 4.0 mmol) and copper(I) iodide (0.190 g, 1.0 mmol). The mixture was stirred at 100° C. overnight. After cooling, the mixture was partitioned between ethyl acetate and water. The layers were separated and the aqueous layer was extracted twice with ethyl acetate. The combined organics were washed with brine and dried over MgSO₄. The solvents were removed and resulting residue was dissolved in DCM and loaded to silica gel column (80 g, 0-40% ethyl acetate/hexanes). The title compound was obtained as a thick oil (2.89 g, 54.3%). LC/MS: 268.1 [M+1]$^+$; $^1$H NMR (300 MHz, CDCl$_3$): δ 8.59 (d, J=5.1 Hz, 1H), 8.06 (s, 1H), 7.73 (s, 1H), 7.49 (d, J=1.8 Hz, 1H), 7.38 (dd, J=5.7, 2.4 Hz, 1H), 2.84 (t, J=7.5 Hz, 2H), 1.85-1.78 (m, 2H), 1.00 (t, J=7.5 Hz, 3H).

Step 2: 4-(4-(4-nitrophenyl)-1H-pyrazol-1-yl)-2-propylpyridine

A solution of 4-(4-bromo-1H-pyrazol-1-yl)-2-propylpyridine (2.370 g, 8.9 mmol), 4-Nitrophenylboronic acid (1.858 g, 11.1 mmol), potassium carbonate (13.36 mL of a 2.0 molar aqueous solution, 26.7 mmol) in DMF (20 mL) was stirred at room temperature for 5 minutes, then palladium diacetate (300 mg) was then added and the flask was flushed with argon and stirred at 90° C. for 4 hours. After cooling, the mixture was partitioned between ethyl acetate (100 mL) and water. The organic layer was washed with brine, dried over Na$_2$SO$_4$ and concentrated. The residue was purified by silica gel column (0-45% ethyl acetate/hexanes) to afford the desired product as a yellow solid (1.2 g, 43.7%). $^1$H-NMR (300 MHz, CDCl$_3$): δ 8.62 (d, J=4.8 Hz, 1H), 8.39-8.36 (m, 2H), 8.28-8.25 (m, 2H), 8.13 (s, 1H), 7.81-7.71 (m, 3H), 2.88 (t, J=7.8 Hz, 2H), 1.88-1.81 (m, 2H), 1.03 (t, J=7.8 Hz, 3H).

Step 3: 4-(1-(2-propylpyridin-4-yl)-1H-pyrazol-4-yl)aniline

To a suspension of 4-(4-(4-nitrophenyl)-1H-pyrazol-1-yl)-2-propylpyridine (1.2 g, 3.9 mmol) in Ethanol (70 mL), was added Tin(II) chloride (2.435 g, 12.8 mmol) followed by hydrogen chloride (5 mL), and the reaction was heated to 80° C. for 5 hours to give a yellow suspension. After the reaction had cooled to ambient temperature, it was poured into an ice-cold solution of 10.0 g potassium hydroxide in 100 mL of water and diluted with 75 mL of ethyl acetate, the layers separated, and the aqueous layer was extracted with ethyl acetate (3×30 mL). The combined organics were dried over sodium sulfate and concentrated. The residue was purified by silica gel column (0-100% ethyl acetate/hexanes) to afford the desired product as a yellow solid (0.64 g, 59.1%). $^1$H-NMR (300 MHz, CDCl$_3$): δ 8.57 (d, J=6.0 Hz, 1H), 8.14 (s, 1H), 7.97 (s, 1H), 7.55 (s, 1H), 7.44 (dd, J=5.4, 1.8 Hz, 1H), 7.37 (d, J=8.7 Hz, 2H), 6.75 (d, J=8.1 Hz, 2H), 3.75 (bs, 2H), 2.85 (t, J=7.7 Hz, 2H), 1.87-1.79 (m, 2H), 1.02 (t, J=7.4 Hz, 3H).

Step 4: N-(4-(1-(2-propylpyridin-4-yl)-1H-pyrazol-4-yl)phenyl)cyclopropanesulfonamide A solution of 4-(1-(2-propylpyridin-4-yl)-1H-pyrazol-4-yl)aniline (0.09 g, 0.3 mmol) and Pyridine (78 µL, 1.0 mmol) in Dichloromethane (5 mL) was cooled to 0° C. Then, Cyclopropanesulfonyl chloride (99 µL, 1.0 mmol) was added, and reaction mixture was allowed to warm to room temperature overnight to give a clear reddish brown solution. Reaction mixture was cooled back to 0° C., and it was quenched with saturated sodium bicarbonate. The layers were separated, and the aqueous layer was extracted with dichloromethane (2×20 mL). The combined organics were dried over Na$_2$SO$_4$ and concentrated. The resulting residue was purified by silica gel chromatography (0-50% ethyl acetate/hexanes). The title compound was obtained as a yellow solid (0.056 g, 43.8%). LC/MS: [M+1]$^+$, 383.0; $^1$H NMR (300 MHz, CDCl$_3$): δ 8.60 (d, J=5.4 Hz, 1H), 8.25 (s, 1H), 8.03 (s, 1H), 7.58-7.47 (m, 4H), 7.34 (s, 1H), 7.31 (s, 1H), 6.38 (brs, 1H), 2.87 (t, J=7.7 Hz, 2H), 2.54-2.50 (m, 1H), 1.88-1.80 (m, 2H), 1.26-1.19 (m, 3H), 1.05-0.99 (m, 4H).

Example 2: 1-cyclopropyl-N-(4-(1-(2-propylpyridin-4-yl)-1H-pyrazol-4-yl)phenyl)methanesulfonamide

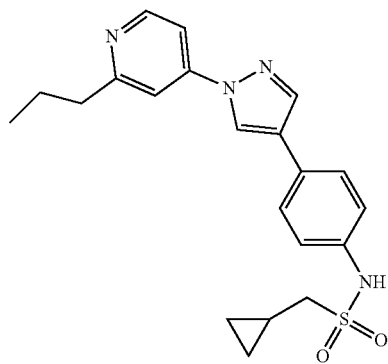 [SMILES: CCCc1cc(-n2cc(-c3ccc(NS(=O)(=O)CC4CC4)cc3)cn2)ccn1]

A solution of 4-(1-(2-propylpyridin-4-yl)-1H-pyrazol-4-yl)aniline (0.090 g, 0.3 mmol) and Pyridine (78 µL, 1.0 mmol) in Dichloromethane (5 mL) was cooled to 0° C. Then cyclopropylmethanesulfonyl chloride (150 mg, 1.0 mmol) was added, and reaction mixture was allowed to warm to room temperature overnight to give a clear reddish brown solution. The reaction mixture was cooled back to 0° C., and it was quenched with saturated sodium bicarbonate. The layers were separated, and the aqueous layer was extracted with dichloromethane (2×20 mL). The combined organics were dried over Na$_2$SO$_4$ and concentrated. The resulting residue was purified by silica gel chromatography (0-50% ethyl acetate/hexanes). The title compound was obtained as a yellow solid (0.089 g, 67.9%). LC/MS: [M+1]$^+$, 397.1; $^1$H NMR (300 MHz, CDCl$_3$): δ 8.60 (d, J=5.7 Hz, 1H), 8.23 (s, 1H), 8.01 (s, 1H), 7.57-7.46 (m, 4H), 7.31-7.27 (m, 2H), 6.78 (brs, 1H), 3.08 (d, J=7.5 Hz, 2H), 2.86 (t, J=7.5 Hz, 2H), 1.90-1.77 (m, 2H), 1.26-1.12 (m, 1H), 1.02 (t, J=7.4 Hz, 3H), 0.74-0.68 (m, 2H), 0.35-0.30 (m, 2H)

Example 3: N-isobutyl-4-(1-(2-propylpyridin-4-yl)-1H-pyrazol-4-yl)aniline

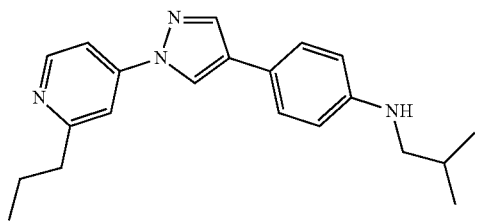 [SMILES: CCCc1cc(-n2cc(-c3ccc(NCC(C)C)cc3)cn2)ccn1]

To a solution of 4-(1-(2-propylpyridin-4-yl)-1H-pyrazol-4-yl)aniline (0.10 g, 0.4 mmol) in dichloroethane (5 mL) was added isobutyraldehyde (0.039 mL, 0.4 mmol), acetic acid (0.031 mL, 0.5 mmol) and Sodium triacetoxyborohydride (0.152 g, 0.7 mmol). The reaction was stirred at room temperature for 4 hours. The mixture was diluted with sat. sodium bicarbonate solution and dichloromethane. The organic layer was washed with brine, dried over anhydrous sodium sulfate, filtered and concentrated. The resulting residue was purified by silica gel chromatography (0-50% ethyl acetate/hexanes). The title compound was obtained as a yellow oil (0.097 g, 79.5%). LC-MS: 335.2 [M+1]$^+$; $^1$H NMR (300 MHz, CDCl$_3$): δ 8.57 (d, J=5.4 Hz, 1H), 8.12 (s, 1H), 7.96 (s, 1H), 7.56-7.55 (m, 1H), 7.44 (dd, J=5.4, 1.8 Hz, 1H), 7.38 (d, J=8.1 Hz, 2H), 6.66 (d, J=8.7 Hz, 2H), 3.84 (brs, 1H), 2.98 (d, J=6.6 Hz, 2H), 2.85 (t, J=7.7 Hz, 2H), 1.97-1.77 (m, 3H), 1.04-0.99 (m, 9H).

Example 4: N-(4-(1-(2-propylpyridin-4-yl)-1H-pyrazol-4-yl)phenyl)propane-2-sulfonamide

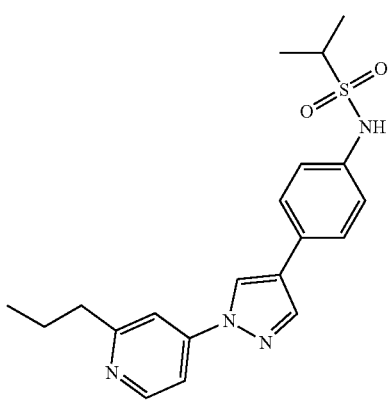 [SMILES: CCCc1cc(-n2cc(-c3ccc(NS(=O)(=O)C(C)C)cc3)cn2)ccn1]

A solution of 4-(1-(2-propylpyridin-4-yl)-1H-pyrazol-4-yl)aniline (0.080 g, 0.3 mmol) and Pyridine (70 μL, 0.9 mmol) in Dichloromethane (5 mL) was cooled to 0° C. Then, propane-2-sulfonyl chloride (97 μL, 0.9 mmol) was added, and reaction mixture was allowed to warm to room temperature overnight to give a clear reddish brown solution. The reaction mixture was cooled back to 0° C., and it was quenched with saturated sodium bicarbonate. The layers were separated, and the aqueous layer was extracted with dichloromethane (2×20 mL). The combined organics were dried over Na$_2$SO$_4$ and concentrated. The resulting residue was purified by silica gel chromatography (0-50% ethyl acetate/hexanes). The title compound was obtained as a yellow solid (0.038 g, 33.4%). LC/MS: 385.1 [M+1]$^+$; $^1$H NMR (300 MHz, CDCl$_3$): δ 8.60 (d, J=5.7 Hz, 1H), 8.23 (s, 1H), 8.01 (s, 1H), 7.58-7.46 (m, 4H), 7.31 (s, 2H), 6.40 (brs, 1H), 3.37-3.30 (m, 1H), 2.86 (t, J=7.5 Hz, 2H), 1.87-1.80 (m, 2H), 1.44 (d, J=6.6 Hz, 6H), 1.02 (t, J=7.4 Hz, 3H).

Example 5: N-(5-(1-(2-propylpyridin-4-yl)-1H-pyrazol-4-yl)pyridin-2-yl)cyclopropanesulfonamide

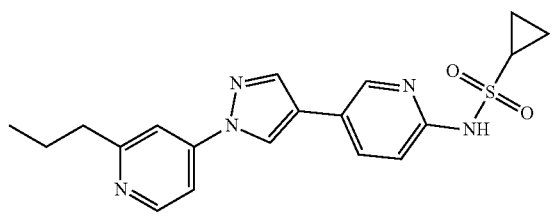 [SMILES: CCCc1cc(-n2cc(-c3ccc(NS(=O)(=O)C4CC4)nc3)cn2)ccn1]

Step 1: 5-(1-(2-propylpyridin-4-yl)-1H-pyrazol-4-yl)pyridin-2-amine

A solution of 4-(4-bromo-1H-pyrazol-1-yl)-2-propylpyridine (0.510 g, 1.9 mmol), 5-(4,4,5,5-tetramethyl-1,3,2-dioxaborolan-2-yl)pyridin-2-amine (0.485 g, 2.2 mmol) and 2.0 M sodium carbonate (2.9 mL, 5.7 mmol) in DMF (10 mL) was stirred at room temperature for 5 minutes, then tetrakis(triphenylphosphine) palladium(0) (50 mg) was then added and the flask was flushed with argon and stirred at 110° C. for overnight. After cooling, the mixture was partitioned between ethyl acetate (100 mL) and water. The organic layer was washed with brine, dried over sodium sulfate and concentrated. The residue was purified by silica gel chromatography (25 g, 0-30% ethyl acetate/hexanes) to afford the desired product as a light yellow solid (0.35 g, 65.4%). $^1$H NMR (300 MHz, CDCl$_3$): δ 8.58 (d, J=5.7 Hz, 1H), 8.31 (m, 1H), 8.17 (s, 1H), 7.96 (s, 1H), 7.63 (d, J=6.9 Hz, 1H), 7.56 (s, 1H), 7.46 (d, J=8.1 Hz, 1H), 6.59 (d, J=8.1 Hz, 1H), 4.57 (brs, 2H), 2.85 (t, J=7.7 Hz, 2H), 1.87-1.79 (m, 2H), 1.04 (t, J=7.4 Hz, 3H).

Step 2: N-(5-(1-(2-propylpyridin-4-yl)-1H-pyrazol-4-yl)pyridin-2-yl)cyclopropanesulfonamide A solution of 5-(1-(2-propylpyridin-4-yl)-1H-pyrazol-4-yl)pyridin-2-amine (0.080 g, 0.3 mmol) and Pyridine (69 μL, 0.9 mmol) in Dichloromethane (6 mL) was cooled to 0° C. Then, Cyclopropanesulfonyl chloride (88 μL, 0.9 mmol) was added, and the reaction mixture was allowed to warm to RT overnight to give a clear reddish brown solution. The reaction mixture was cooled back to 0° C., and it was quenched with saturated sodium bicarbonate. The layers were separated, and the aqueous layer was extracted with dichloromethane (2×20 mL). The combined organics were dried over Na$_2$SO$_4$ and concentrated. The resulting residue was purified by silica gel chromatography (0-50% ethyl acetate/hexanes). The title compound was obtained as a yellow solid (0.019 g, 16.9%). LC/MS: [M+1]$^+$, 384.1; $^1$HNMR (300 MHz, CDCl$_3$): δ 8.62 (d, J=5.4 Hz, 1H), 8.53 (s, 1H), 8.27 (s, 1H), 8.03 (s, 1H), 7.88-7.86 (m, 1H), 7.58 (s, 1H), 7.49-7.46 (m, 2H), 2.87 (t, J=7.7 Hz, 2H), 2.74-2.62 (m, 1H), 1.88-1.80 (m, 2H), 1.29-1.26 (m, 3H), 1.05-1.00 (m, 4H).

Example 6: N-isopropyl-4-(1-(2-propylpyridin-4-yl)-1H-pyrazol-4-yl)aniline

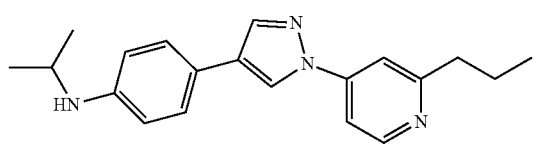 [SMILES: CCCc1cc(-n2cc(-c3ccc(NC(C)C)cc3)cn2)ccn1]

To a solution of 4-(1-(2-propylpyridin-4-yl)-1H-pyrazol-4-yl)aniline (0.080 g, 0.3 mmol) in dichloroethane (5 mL) was added acetone (106 μL, 1.4 mmol), acetic acid (25 μL, 0.4 mmol) and sodium triacetoxyborohydride (0.182 g, 0.9 mmol). The reaction was stirred at room temperature overnight. The reaction mixture partitioned between dichloromethane and saturated sodium bicarbonate solution. The layers were separated and the aqueous layer was extracted twice with dichloromethane. The combined organics were dried over MgSO$_4$. The solvents were removed and the resulting residue was purified by silica gel chromatography (0-60% ethyl acetate/hexanes). The title compound was obtained as a yellow solid (0.074 g, 79.1%). LC/MS: 321.2 [M+1]+; ¹H NMR (300 MHz, CDCl₃): δ 8.57 (d, J=6.0 Hz, 1H), 8.12 (s, 1H), 7.96 (s, 1H), 7.44 (dd, J=5.7, 2.1 Hz, 1H), 7.46-7.43 (m, 1H), 7.38 (d, J=8.1 Hz, 2H), 6.64 (d, J=8.4 Hz, 2H), 3.72-3.58 (m, 1H), 2.85 (t, J=8.0 Hz, 2H), 1.87-1.77 (m, 2H), 1.25 (d, J=6.0 Hz, 6H), 1.01 (t, J=7.4 Hz, 3H).

Example 7: N-isopropyl-5-(1-(2-propylpyridin-4-yl)-1H-pyrazol-4-yl)pyridin-2-amine

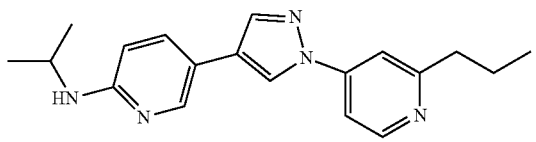 [SMILES: CCCc1cc(-n2cc(-c3ccc(NC(C)C)nc3)cn2)ccn1]

To a solution of 5-(1-(2-propylpyridin-4-yl)-1H-pyrazol-4-yl)pyridin-2-amine (0.47 g, 1.7 mmol) in dichloroethane (40 mL) was added acetone (618 µL, 8.4 mmol), acetic acid (144 µL, 2.5 mmol) and Sodium triacetoxyborohydride (1.065 g, 5.0 mmol). The reaction was stirred at room temperature overnight. The reaction mixture partitioned between dichloromethane and saturated sodium bicarbonate solution. The layers were separated and the aqueous layer was extracted twice with dichloromethane. The combined organics were dried over MgSO₄. The solvents were removed and the resulting residue was purified by silica gel chromatography (0-60% ethyl acetate/hexanes). The title compound was obtained as an off-white solid (87 mg, 16.0%). LC/MS: 322.1 [M+1]+; ¹H NMR (300 MHz, CDCl₃): δ 8.58 (d, J=6.0 Hz, 1H), 8.32 (d, J=2.4 Hz, 1H), 8.14 (s, 1H), 7.95 (s, 1H), 7.60 (dd, J=6.0, 2.4 Hz, 1H), 7.56 (s, 1H), 7.45 (dd, J=5.7, 1.8 Hz, 1H), 6.44 (d, J=8.1 Hz, 1H), 4.47 (brs, 1H), 3.96-3.89 (m, 1H), 2.85 (t, J=7.7 Hz, 2H), 1.87-1.79 (m, 2H), 1.27 (d, J=6.3 Hz, 6H), 1.01 (t, J=7.4 Hz, 3H).

Example 8: N-isobutyl-5-(1-(2-propylpyridin-4-yl)-1H-pyrazol-4-yl)pyridin-2-amine

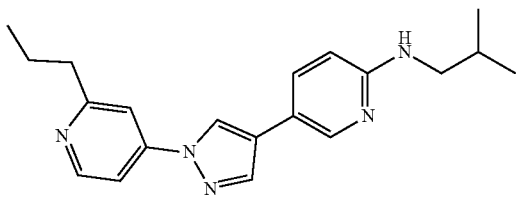 [SMILES: CCCc1cc(-n2cc(-c3ccc(NCC(C)C)nc3)cn2)ccn1]

To a solution of 5-(1-(2-propylpyridin-4-yl)-1H-pyrazol-4-yl)pyridin-2-amine (0.200 g, 0.7 mmol) in dichloroethane (10 mL) was added isobutyraldehyde (79 µL, 0.9 mmol), acetic acid (61 µL, 1.1 mmol) and Sodium triacetoxyborohydride (0.302 g, 1.4 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The resulting residue was purified by silica gel chromatography (0-50% ethyl acetate/hexanes). The title compound was obtained as an off-white solid (77 mg, 32.5%). LC/MS: 336.2 [M+1]+;

¹H NMR (300 MHz, CDCl₃): δ 8.58 (d, J=5.4 Hz, 1H), 8.31 (d, J=1.8 Hz, 1H), 8.14 (s, 1H), 7.95 (s, 1H), 7.60 (dd, J=8.7, 2.1 Hz, 1H), 7.56 (s, 1H), 7.52-7.44 (m, 1H), 6.46 (d, J=8.7 Hz, 1H), 4.72 (brs, 1H), 3.13 (t, J=6.2 Hz, 2H), 2.85 (t, J=7.7 Hz, 2H), 1.97-1.77 (m, 3H), 1.04-0.99 (m, 9H).

Example 9: N-(3-chloro-4-(1-(2-propylpyridin-4-yl)-1H-pyrazol-4-yl)phenyl)methanesulfonamide

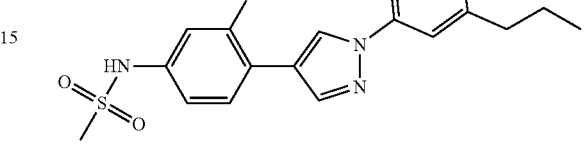

Step 1: 2-propyl-4-(4-(4,4,5,5-tetramethyl-1,3,2-dioxaborolan-2-yl)-1H-pyrazol-1-yl)pyridine To a stirred solution of 4-(4-bromo-1H-pyrazol-1-yl)-2-propylpyridine (2.100 g, 7.9 mmol) in DMSO (35 mL) was added 4,4,4',4',5,5,5',5'-octamethyl-2,2'-bi(1,3,2-dioxaborolane) (3.006 g, 11.8 mmol) and potassium acetate (2.323 g, 23.7 mmol) followed by 1,1'-bis(diphenylphosphino)ferrocenedichloro palladium(II) dichloromethane complex (190 mg) and the flask was flushed with argon and stirred at 70° C. for overnight. After cooling, the mixture was partitioned between ethyl acetate (100 mL) and saturated sodium bicarbonate. The organic layer was washed with brine, dried over Na₂SO₄ and concentrated. The product was obtained as a yellow oil (3.0 g). The crude was directly used in subsequent reactions without further purification. LC/MS: [M+1]+, 314.2.

Step 2: 4-(4-(2-chloro-4-nitrophenyl)-1H-pyrazol-1-yl)-2-propylpyridine

A mixture of crude 2-propyl-4-(4-(4,4,5,5-tetramethyl-1,3,2-dioxaborolan-2-yl)-1H-pyrazol-1-yl)pyridine (3.0 g, 6.7 mmol), 1-bromo-2-chloro-4-nitrobenzene (2.378 g, 10.1 mmol) and 2.0 M sodium carbonate (10.06 mL, 20.1 mmol) in DMF (30 mL) was stirred at room temperature for 5 minutes, then tetrakis(triphenylphosphine) palladium(0) (160 mg) was then added and the flask was flushed with argon and stirred at 110° C. for overnight. After cooling, the mixture was partitioned between ethyl acetate (200 mL) and water. The organic layer was washed with brine, dried over Na₂SO₄ and concentrated. The residue was purified by silica gel chromatography (0-30% ethyl acetate/hexanes) to afford the desired product as a light yellow solid (1.14 g, 49%). LC/MS: [M+1]+, 343.2; ¹H-NMR (300 MHz, CDCl₃): δ 8.62 (d, J=4.8 Hz, 1H), 8.58 (s, 1H), 8.41 (s, 1H), 8.21-8.16 (m, 2H), 7.72 (d, J=9.0 Hz, 1H), 7.60 (s, 1H), 7.52-7.50 (m, 1H), 2.88 (t, J=7.8 Hz, 2H), 1.90-1.78 (m, 2H), 1.04 (t, J=7.8 Hz, 3H).

Step 3: 3-chloro-4-(1-(2-propylpyridin-4-yl)-1H-pyrazol-4-yl)aniline

To a suspension of 4-(4-(2-chloro-4-nitrophenyl)-1H-pyrazol-1-yl)-2-propylpyridine (1.100 g, 3.2 mmol) in ethanol (70 mL), was added Tin(II) chloride (2.008 g, 10.6 mmol) followed by concentrated hydrogen chloride (5 mL), and the reaction was heated to 80° C. for 8 hours to give a yellow suspension. After the reaction had cooled to ambient temperature, it was poured into an ice-cold solution of 10.0 g potassium hydroxide in 100 mL of water and diluted with 75 mL of ethyl acetate, the layers separated, and the aqueous layer was extracted with ethyl acetate (3×30 mL). The combined organics were dried over sodium sulfate and concentrated. The residue was purified by silica gel chromatography (0 to 100% ethyl acetate/hexanes) to afford the desired product as a yellow solid (0.84 g, 84%). LC/MS: [M+1]$^+$, 313.1; $^1$H-NMR (300 MHz, CDCl$_3$): δ 8.58 (d, J=6.0 Hz, 1H), 8.31 (s, 1H), 7.99 (s, 1H), 7.56 (s, 1H), 7.46 (dd, J=5.7, 1.8 Hz, 1H), 7.29 (d, J=8.1 Hz, 1H), 6.82 (d, J=1.8 Hz, 1H), 6.64 (dd, J=8.4, 2.4 Hz, 1H), 3.82 (s, 2H), 2.85 (t, J=7.7 Hz, 2H), 1.87-1.79 (m, 2H), 1.01 (t, J=7.4 Hz, 3H).

Step 4: N-(3-chloro-4-(1-(2-propylpyridin-4-yl)-1H-pyrazol-4-yl)phenyl)methanesulfonamide A round bottom flask was charged with 3-chloro-4-(1-(2-propylpyridin-4-yl)-1H-pyrazol-4-yl)aniline (0.08 g, 0.26 mmol), dichloromethane (5 mL) and Pyridine (0.0310 mL, 0.38 mmol) and the reaction mixture cooled to 0° C. Methanesulfonyl chloride (0.03 mL, 0.38 mmol) was slowly added under nitrogen and the reaction mixture was stirred at 0° C. for 30 minutes. The mixture was allowed to warm to room temperature and stirred for additional 3 hours. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as an off-white solid (0.049 g, 47%). LC/MS: [M+1]$^+$, 391.0; $^1$HNMR (300 MHz, CDCl3), δ 8.61 (d, J=5.4 Hz, 1H), 8.40 (s, 1H), 8.05 (s, 1H), 7.58 (d, J=1.5 Hz, 1H), 7.53-7.47 (m, 2H), 7.40 (d, J=2.4 Hz, 1H), 7.21 (dd, J=8.7, 2.4 Hz, 1H), 6.76 (brs, 1H), 3.10 (s, 3H), 2.87 (t, J=7.7 Hz, 2H), 1.87-1.80 (m, 2H), 1.02 (t, J=7.7 Hz, 3H).

Example 10: N-(3-chloro-4-(1-(2-propylpyridin-4-yl)-1H-pyrazol-4-yl)phenyl)cyclopropanesulfonamide

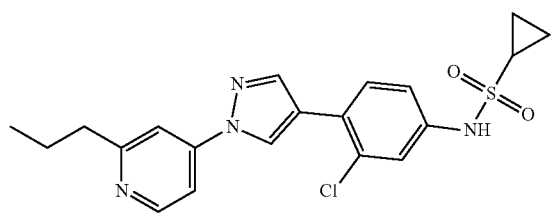 [SMILES: CCCc1cc(-n2cc(-c3ccc(NS(=O)(=O)C4CC4)cc3Cl)cn2)ccn1]

A solution of 3-chloro-4-(1-(2-propylpyridin-4-yl)-1H-pyrazol-4-yl)aniline (0.076 g, 0.2 mmol) and Pyridine (58 µL, 0.7 mmol) in Dichloromethane (5 mL) was cooled to 0° C. Then, Cyclopropanesulfonyl chloride (73 µL, 0.7 mmol) was added, and the reaction mixture was allowed to warm to room temperature overnight to give a clear reddish brown solution. The reaction mixture was cooled back to 0° C., and it was quenched with saturated sodium bicarbonate. The layers were separated, and the aqueous layer was extracted with dichloromethane (2×20 mL). The combined organics were dried over Na$_2$SO$_4$ and concentrated. The residue was purified by silica gel chromatography (0-50% ethyl acetate/hexanes). The title compound was obtained as an off-white solid (0.072 g, 72%). LC/MS: [M+1]+, 417.0; $^1$HNMR (300 MHz, CDCl$_3$): δ 8.61 (d, J=6.0 Hz, 1H), 8.41 (s, 1H), 8.05 (s, 1H), 7.58 (d, J=1.5 Hz, 1H), 7.51-7.48 (m, 2H), 7.42 (d, J=1.8 Hz, 1H), 7.26-7.22 (m, 1H), 6.60 (brs, 1H), 2.86 (t, J=7.7 Hz, 2H), 2.58-2.54 (m, 1H), 1.87-1.80 (m, 2H), 1.32-1.23 (m, 2H), 1.08-0.99 (m, 5H).

Example 11: N-(3-chloro-4-(1-(2-propylpyridin-4-yl)-1H-pyrazol-4-yl)phenyl)-1,1,1-trifluoromethanesulfonamide

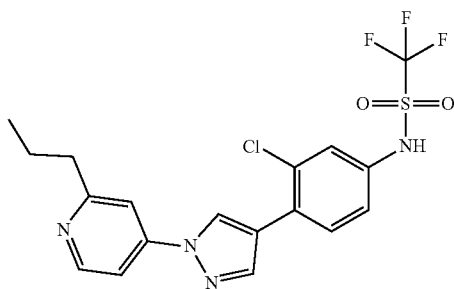 [SMILES: CCCc1cc(-n2cc(-c3ccc(NS(=O)(=O)C(F)(F)F)cc3Cl)cn2)ccn1]

Pyridine (0.078 mL, 1.0 mmol) was added dropwise to a solution of triflic anhydride (0.11 mL, 0.6 mmol) at 0° C. under nitrogen in dichloromethane (5 mL) over 10 minutes. The reaction mixture was stirred at the same temperature for 30 minutes. A solution of 3-chloro-4-(1-(2-propylpyridin-4-yl)-1H-pyrazol-4-yl)aniline (0.100 g, 0.3 mmol) in dichlormethane (3 mL) was added dropwise over 20 minutes. The reaction was then allowed to come to room temperature and stirred for 1 hour. Upon completion, ice water was added and the dichloromethane layer was separated. The aqueous was extracted with dichloromethane (2×50 mL). The dichloromethane extracts were combined and dried over anhydrous sodium sulfate and concentrated under reduced pressure. The residue was purified by silica gel chromatography (0-70% ethyl acetate/hexanes). The title compound was obtained as a yellow solid (0.036 g, 24.9%). LC/MS: [M+1]$^+$, 445.0; $^1$HNMR (300 MHz, CDCl3), δ 8.61 (d, J=5.4 Hz, 1H), 8.43 (s, 1H), 8.06 (s, 1H), 7.60-7.47 (m, 4H), 7.31-7.30 (m, 1H), 2.86 (t, J=7.5 Hz, 2H), 1.86-1.79 (m, 2H), 1.01 (t, J=7.2 Hz, 3H).

Example 12: 1,1,1-trifluoro-N-(5-(1-(2-propylpyridin-4-yl)-1H-pyrazol-4-yl)pyridin-2-yl)methanesulfonamide

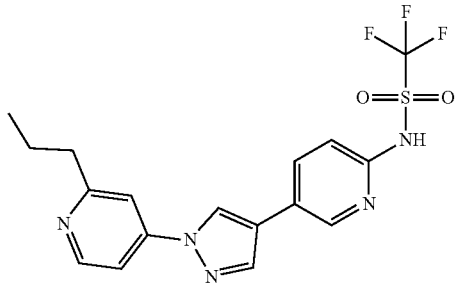 [SMILES: CCCc1cc(-n2cc(-c3ccc(NS(=O)(=O)C(F)(F)F)nc3)cn2)ccn1]

Pyridine (0.078 mL, 1.0 mmol) was added dropwise to a solution of triflic anhydride (0.108 mL, 0.6 mmol) at 0° C. under nitrogen in dichloromethane (5 mL) over 10 minutes. The reaction mixture was stirred at the same temperature for 30 minutes. A solution of 5-(1-(2-propylpyridin-4-yl)-1H-pyrazol-4-yl)pyridin-2-amine (0.090 g, 0.3 mmol) in dichloromethane (3 mL) was added dropwise over 20 min. The reaction was then allowed to come to room temperature and stirred for 1 hour. Upon completion, ice water was added and the dichloromethane layer was separated. The aqueous layer was extracted with dichloromethane (2×50 mL). The dichloromethane extracts were combined and dried over anhydrous sodium sulfate and concentrated under reduced. The residue was purified by silica gel chromatography (4 g, 0-70% ethyl acetate/hexanes). The title compound was obtained as a yellow solid (0.015 g, 11.3%). LC/MS: [M+1]$^+$, 412.0; $^1$HNMR (300 MHz, CDCl3): δ 8.65 (d, J=5.4 Hz, 1H), 8.39 (s, 1H), 8.32 (s, 1H), 8.18-7.96 (m, 3H), 7.60 (s, 1H), 7.53 (d, J=5.4 Hz, 1H), 2.89 (t, J=7.7 Hz, 2H), 1.89-1.81 (m, 2H), 1.03 (t, J=7.4 Hz, 3H).

Example 13: 3-chloro-N-isopropyl-4-(1-(2-propylpyridin-4-yl)-1H-pyrazol-4-yl)aniline

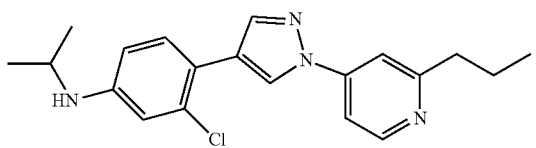 [SMILES: CCCc1cc(-n2cc(-c3ccc(NC(C)C)cc3Cl)cn2)ccn1]

To a solution of 3-chloro-4-(1-(2-propylpyridin-4-yl)-1H-pyrazol-4-yl)aniline (0.150 g, 0.5 mmol) in dichloroethane (5 mL) was added Acetone (176 μL, 2.4 mmol), acetic acid (41 μL, 0.7 mmol) and Sodium triacetoxyborohydride (0.303 g, 1.4 mmol). The reaction was stirred at room temperature overnight. The reaction mixture partitioned between dichloromethane and saturated sodium bicarbonate solution. The layers were separated and the aqueous layer was extracted twice with dichloromethane. The combined organics were dried over MgSO$_4$. The solvents were removed and the residue was purified by silica gel chromatography (0-30% ethyl acetate/hexanes). The title compound was obtained as a yellow oil (91 mg, 53%). LC/MS: 355.2 [M+1]+; $^1$H NMR (300 MHz, CDCl$_3$): δ 8.57 (d, J=5.4 Hz, 1H), 8.30 (s, 1H), 7.99 (s, 1H), 7.56 (d, J=1.8 Hz, 1H), 7.46 (dd, J=5.4, 2.1 Hz, 1H), 7.30 (s, 1H), 6.69 (d, J=2.4 Hz, 1H), 6.53 (dd, J=8.7 and 2.4 Hz, 1H), 3.67-3.62 (m, 1H), 2.85 (t, J=7.7 Hz, 2H), 1.87-1.79 (m, 2H), 1.25 (d, J=5.7 Hz, 6H), 1.01 (t, J=7.2 Hz, 3H).

Example 14: 3-chloro-N-isobutyl-4-(1-(2-propylpyridin-4-yl)-1H-pyrazol-4-yl)aniline

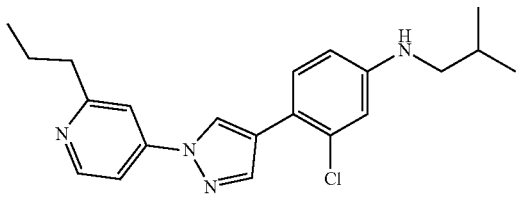 [SMILES: CCCc1cc(-n2cc(-c3ccc(NCC(C)C)cc3Cl)cn2)ccn1]

To a solution of 3-chloro-4-(1-(2-propylpyridin-4-yl)-1H-pyrazol-4-yl)aniline (0.075 g, 0.2 mmol) in dichloroethane (5 mL) was added isobutyraldehyde (26 μL, 0.3 mmol), acetic acid (21 μL, 0.4 mmol) and sodium triacetoxyborohydride (0.101 g, 0.5 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-50% ethyl acetate/hexanes). The title compound was obtained as a yellow oil (0.076 g, 83.2%). LC/MS: 369.2 [M+1]+; $^1$H NMR (300 MHz, CDCl$_3$): δ 8.57 (d, J=6.0 Hz, 1H), 8.30 (s, 1H), 7.99 (s, 1H), 7.57 (d, J=1.8 Hz, 1H), 7.46 (dd, J=8.7, 1.8 Hz, 1H), 7.30 (s, 1H), 6.70 (d, J=2.1 Hz, 1H), 6.55 (dd, J=9.0, 2.4 Hz, 1H), 3.90 (brs, 1H), 2.96-2.87 (m, 2H), 2.85 (t, J=7.7 Hz, 2H), 1.94-1.79 (m, 3H), 1.03-0.99 (m, 9H).

Example 15: N-isobutyl-6-(1-(2-propylpyridin-4-yl)-1H-pyrazol-4-yl)pyridin-3-amine

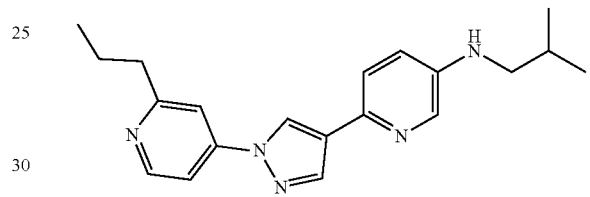

Step 1: 4-(4-(5-nitropyridin-2-yl)-1H-pyrazol-1-yl)-2-propylpyridine

A solution of crude 2-propyl-4-(4-(4,4,5,5-tetramethyl-1,3,2-dioxaborolan-2-yl)-1H-pyrazol-1-yl)pyridine (3.00 g, 5.3 mmol), 2-Bromo-5-nitropyridine (2.182 g, 10.5 mmol) and 2.0 M sodium carbonate (7.902 mL, 15.8 mmol) in DMF (30 mL) was stirred at room temperature for 5 minutes, then tetrakis(triphenylphosphine) palladium(0) (130 mg) was then added and the flask was flushed with argon and stirred at 110° C. for overnight. After cooling, the mixture was partitioned between ethyl acetate (200 mL) and water. The organic layer was washed with brine, dried over Na$_2$SO$_4$ and concentrated. The residue was purified by silica gel chromatography (0-60% ethyl acetate/hexanes) to afford the desired product as a light yellow solid (1.38 g). $^1$H-NMR (300 MHz, CDCl$_3$): δ 9.44 (d, J=2.1 Hz, 1H), 8.74 (s, 1H), 8.65 (d, J=6.0 Hz, 1H), 8.52 (dd, J=9.0, 2.4 Hz, 1H), 8.31 (s, 1H), 7.72 (d, J=8.1 Hz, 1H), 7.62 (d, J=1.8 Hz, 1H), 7.53 (dd, J=5.1 and 2.1 Hz, 1H), 2.88 (t, J=7.8 Hz, 2H), 1.88-1.80 (m, 2H), 1.02 (t, J=7.8 Hz, 3H).

Step 2: 6-(1-(2-propylpyridin-4-yl)-1H-pyrazol-4-yl)pyridin-3-amine

To a suspension of 4-(4-(5-nitropyridin-2-yl)-1H-pyrazol-1-yl)-2-propylpyridine (1.380 g, 4.5 mmol) in Ethanol (100 mL), was added Tin(II) chloride (2.791 g, 14.7 mmol) followed by concentrated hydrogen chloride (6 mL), and the reaction was heated to 80° C. for 6 hrs to give a yellow solution. After the reaction had cooled to ambient temperature, it was poured into an ice-cold solution of 10.0 g potassium hydroxide in 100 mL of water and diluted with 75 mL of ethyl acetate, the layers separated, and the aqueous layer was extracted with ethyl acetate (3×30 mL). The combined organics were dried over sodium sulfate and concentrated. The residue was purified by silica gel chromatography (0-15% methanol/dichloromethane) to afford the desired product as a yellow solid. $^1$H-NMR (300 MHz, CDCl$_3$): δ 8.57 (d, J=6.0 Hz, 1H), 8.14 (s, 1H), 7.97 (s, 1H), 7.55 (s, 1H), 7.44 (dd, J=5.4 and 1.8 Hz, 1H), 7.37 (d, J=8.7 Hz, 2H), 6.75 (d, J=8.1 Hz, 2H), 3.75 (bs, 2H), 2.85 (t, J=7.7 Hz, 2H), 1.87-1.79 (m, 2H), 1.02 (t, J=7.4 Hz, 3H).

Step 3: 4-(4-(5-nitropyridin-2-yl)-1H-pyrazol-1-yl)-2-propylpyridine

To a solution of 6-(1-(2-propylpyridin-4-yl)-1H-pyrazol-4-yl)pyridin-3-amine (0.080 g, 0.3 mmol) in dichloroethane (5 mL) was added isobutyraldehyde (31 μL, 0.3 mmol), acetic acid (25 μL, 0.4 mmol) and sodium triacetoxyborohydride (0.181 g, 0.9 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-50% ethyl acetate/hexanes). The title compound was obtained as an off-white solid (59 mg, 61.4%). LC/MS: 336.2 [M+1]+; $^1$H NMR (300 MHz, CDCl$_3$): δ 8.57 (d, J=5.4 Hz, 1H), 8.45 (s, 1H), 8.12 (s, 1H), 8.04 (d, J=2.7 Hz, 1H), 7.58 (s, 1H), 7.48 (dd, J=6.0 and 1.8 Hz, 1H), 7.38 (d, J=8.1 Hz, 1H), 6.93 (dd, J=9.0 and 3.0 Hz, 1H), 3.86 (brs, 1H), 3.00 (t, J=5.6 Hz, 2H), 2.84 (t, J=7.7 Hz, 2H), 1.96-1.79 (m, 3H), 1.04-0.98 (m, 9H).

Example 16: N-(cyclopropylmethyl)-6-(1-(2-propylpyridin-4-yl)-1H-pyrazol-4-yl)pyridin-3-amine

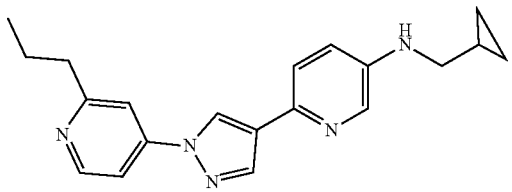 [SMILES: CCCc1cc(-n2cc(-c3ccc(NCC4CC4)cn3)cn2)ccn1]

To a solution of 6-(1-(2-propylpyridin-4-yl)-1H-pyrazol-4-yl)pyridin-3-amine (0.080 g, 0.3 mmol) in dichloroethane (5 mL) was added 95.0% cyclopropanecarbaldehyde (27 μL, 0.3 mmol), acetic acid (25 μL, 0.4 mmol) and sodium triacetoxyborohydride (0.181 g, 0.9 mmol). The reaction was stirred at room temperature for 4 hours. The mixture was diluted with saturated sodium bicarbonate and DCM. The organic layer was washed with brine, dried over anhydrous sodium sulfate, filtered and concentrated. The residue was purified by silica gel chromatography (0-50% ethyl acetate/hexanes). The title compound was obtained as a light yellow solid (39 mg, 40.8%). LC/MS: 334.2 [M+1]+; $^1$H NMR (300 MHz, CDCl$_3$): δ 8.57 (d, J=6.0 Hz, 1H), 8.46 (s, 1H), 8.12 (s, 1H), 8.05 (d, J=2.7 Hz, 1H), 7.58 (s, 1H), 7.47 (d, J=5.7 Hz, 1H), 7.38 (d, J=8.7 Hz, 1H), 6.93 (dd, J=9.0 and 3.0 Hz, 1H), 3.86 (brs, 1H), 3.02 (d, J=7.2 Hz, 2H), 2.84 (t, J=7.7 Hz, 2H), 1.86-1.78 (m, 2H), 1.17-1.09 (m, 1H), 1.01 (t, J=7.2 Hz, 3H), 0.64-0.58 (m, 2H), 0.32-0.27 (m, 2H).

Example 17: 3-chloro-N-(cyclopropylmethyl)-4-(1-(2-propylpyridin-4-yl)-1H-pyrazol-4-yl)aniline

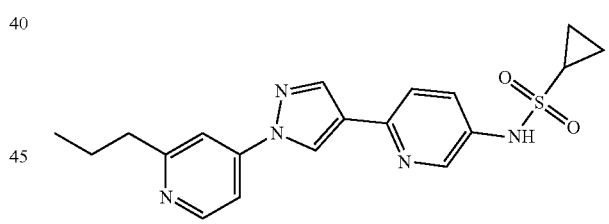

To a solution of 3-chloro-4-(1-(2-propylpyridin-4-yl)-1H-pyrazol-4-yl)aniline (0.088 g, 0.3 mmol) in dichloroethane (5 mL) was added 95.0% cyclopropanecarbaldehyde (26 μL, 0.3 mmol), acetic acid (24 μL, 0.4 mmol) and sodium triacetoxyborohydride (0.178 g, 0.8 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-50% ethyl acetate/hexanes). The title compound was obtained as a white solid (40 mg, 38.5%). LC/MS: 367.2 [M+1]+; $^1$H NMR (300 MHz, CDCl$_3$): δ 8.57 (d, J=6.0 Hz, 1H), 8.30 (s, 1H), 7.99 (s, 1H), 7.56 (s, 1H), 7.46 (d, J=5.1 Hz, 1H), 7.29 (d, J=8.7 Hz, 1H), 6.71 (s, 1H), 6.57 (d, J=8.7 Hz, 1H), 3.98 (brs, 1H), 2.99 (d, J=6.6 Hz, 2H), 2.85 (t, J=7.7 Hz, 2H), 1.89-1.77 (m, 2H), 1.12-1.08 (m, 1H), 1.01 (t, J=7.2 Hz, 3H), 0.62-0.57 (m, 2H), 0.30-0.25 (m, 2H).

Example 18: N-(6-(1-(2-propylpyridin-4-yl)-1H-pyrazol-4-yl)pyridin-3-yl)cyclopropanesulfonamide A solution of 6-(1-(2-propylpyridin-4-yl)-1H-pyrazol-4-yl)pyridin-3-amine (0.075 g, 0.3 mmol) and Pyridine (65 μL, 0.8 mmol) in Dichloromethane (5 mL) was cooled to 0° C. Then, Cyclopropanesulfonyl chloride (82 μL, 0.8 mmol) was added and reaction mixture was allowed to warm to room temperature overnight to give a yellow suspension. The reaction mixture was quenched with saturated sodium bicarbonate. The layers were separated, and the aqueous layer was extracted with dichloromethane (2×20 mL). The combined organics were dried over Na$_2$SO$_4$ and concentrated. The residue was purified by silica gel chromatography (0-50% ethyl acetate/hexanes). The title compound was obtained as a light yellow solid (51 mg, 49.5%). LC/MS: [M+1]+, 384.1; $^1$HNMR (300 MHz, CDCl$_3$): δ 8.60 (d, J=6.0 Hz, 1H), 8.57 (s, 1H), 8.46 (s, 1H), 8.19 (s, 1H), 7.77 (d, J=5.4 Hz, 1H), 7.59-7.48 (m, 3H), 6.38 (brs, 1H), 2.85 (t, J=7.5 Hz, 2H), 2.53-2.49 (m, 1H), 1.86-1.79 (m, 2H), 1.22-1.18 (m, 2H), 1.04-0.98 (m, 5H).

Example 19: 1-cyclopropyl-N-(6-(1-(2-propylpyridin-4-yl)-1H-pyrazol-4-yl)pyridin-3-yl)methanesulfonamide

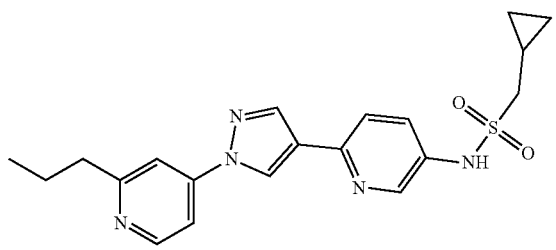 [SMILES: CCCc1cc(-n2cc(-c3ccc(NS(=O)(=O)CC4CC4)cn3)cn2)ccn1]

A solution of 6-(1-(2-propylpyridin-4-yl)-1H-pyrazol-4-yl)pyridin-3-amine (0.075 g, 0.3 mmol) and Pyridine (65 µL, 0.8 mmol) in Dichloromethane (5 mL) was cooled to 0° C. Then, cyclopropylmethanesulfonyl chloride (91 mg, 0.6 mmol) was added and reaction mixture was allowed to warm to room temperature overnight to give a reddish brown suspension. The reaction mixture was quenched with saturated sodium bicarbonate. The layers were separated, and the aqueous layer was extracted with dichloromethane (2×20 mL). The combined organics were dried over $Na_2SO_4$ and concentrated. The residue was purified by silica gel chromatography (0-50% ethyl acetate/hexanes). The title compound was obtained as an off-white solid (29 mg, 27.1%). LC/MS: [M+1]+, 398.1; $^1$HNMR (300 MHz, $CDCl_3$): δ 8.61 (d, J=6.0 Hz, 1H), 8.56 (s, 1H), 8.42 (s, 1H), 8.19 (s, 1H), 7.78 (d, J=1.5 Hz, 1H), 7.60-7.49 (m, 3H), 6.51 (brs, 1H), 3.09 (d, J=6.9 Hz, 2H), 2.86 (t, J=7.7 Hz, 2H), 1.87-1.79 (m, 2H), 1.20-1.18 (m, 1H), 1.02 (t, J=7.2 Hz, 3H), 0.75-0.72 (m, 2H), 0.37-0.35 (m, 2H).

Example 20: N-(6-(1-(2-propylpyridin-4-yl)-1H-pyrazol-4-yl)pyridin-3-yl)methanesulfonamide

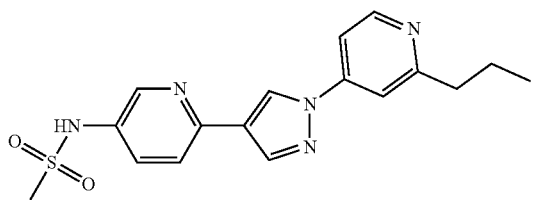 [SMILES: CCCc1cc(-n2cc(-c3ccc(NS(C)(=O)=O)cn3)cn2)ccn1]

A round bottom flask was charged with 6-(1-(2-propylpyridin-4-yl)-1H-pyrazol-4-yl)pyridin-3-amine (0.100 g, 0.4 mmol), dichloromethane (5 mL) and Pyridine (0.087 mL, 1.1 mmol) and the reaction mixture cooled to 0° C. Methanesulfonyl chloride (0.083 mL, 1.1 mmol) was slowly added under nitrogen and the reaction mixture was stirred at 0° C. for 30 minutes. The mixture was allowed to warm to room temperature and stirred for additional 3 hours. The mixture was diluted with saturated sodium bicarbonate and dichloromethane. The organic layer was washed with brine, dried over anhydrous sodium sulfate, filtered and concentrated. The residue was purified by silica gel chromatography (0-70% ethyl acetate/hexanes). The title compound was obtained as an off-white solid (56 mg, 43.8%). LC/MS: [M+1]$^+$, 358.1; $^1$HNMR (300 MHz, CDCl3), δ 8.61 (d, J=5.4 Hz, 1H), 8.57 (s, 1H), 8.45 (s, 1H), 8.21 (s, 1H), 7.76 (dd, J=9.0 and 3.0 Hz, 1H), 7.61-7.50 (m, 3H), 6.46 (brs, 1H), 3.09 (s, 3H), 2.86 (t, J=7.7 Hz, 2H), 1.87-1.80 (m, 2H), 1.02 (t, J=7.4 Hz, 3H).

Example 21: N-isopropyl-6-(1-(2-propylpyridin-4-yl)-1H-pyrazol-4-yl)pyridin-3-amine

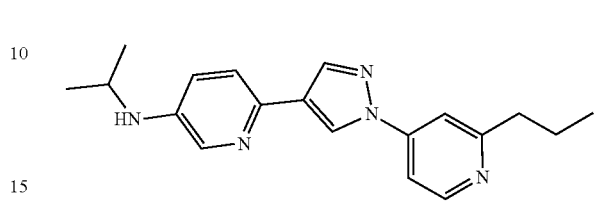

To a solution of 6-(1-(2-propylpyridin-4-yl)-1H-pyrazol-4-yl)pyridin-3-amine (0.080 g, 0.3 mmol) in dichloroethane (10 mL) was added acetone (105 µL, 1.4 mmol), acetic acid (25 µL, 0.4 mmol) and sodium triacetoxyborohydride (0.181 g, 0.9 mmol). The reaction was stirred at room temperature overnight. The reaction mixture partitioned between dichloromethane and saturated sodium bicarbonate solution. The layers were separated and the aqueous layer was extracted twice with dichloromethane. The combined organics were dried over $MgSO_4$. The residue was purified by silica gel chromatography (0-60% ethyl acetatehexanes). The title compound was obtained as an off-white solid (30 mg, 32.1%). LC/MS: 322.2 [M+1]+; $^1$H NMR (300 MHz, $CDCl_3$): δ 8.57 (d, J=6.0 Hz, 1H), 8.45 (d, J=2.4 Hz, 1H), 8.12 (s, 1H), 8.02 (s, 1H), 7.59 (s, 1H), 7.48 (d, J=6.0 Hz, 1H), 7.39 (d, J=8.1 Hz, 1H), 6.94-6.91 (m, 1H), 3.70-3.66 (m, 2H), 2.84 (t, J=7.7 Hz, 2H), 1.86-1.76 (m, 2H), 1.27 (d, J=6.0 Hz, 6H), 1.01 (t, J=7.4 Hz, 3H).

Example 22: 1,1,1-trifluoro-N-(6-(1-(2-propylpyridin-4-yl)-1H-pyrazol-4-yl)pyridin-3-yl)methanesulfonamide

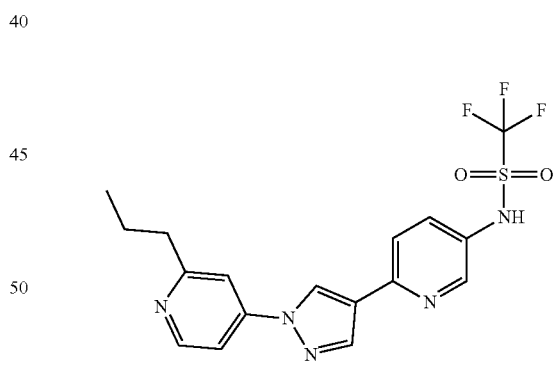

Pyridine (0.087 mL, 1.1 mmol) was added dropwise to a solution of triflic anhydride (0.181 mL, 1.1 mmol) at 0° C. under nitrogen in dichloromethane (5 mL) over 10 minutes. The reaction mixture was stirred at the same temperature for 30 minutes. A solution of 6-(1-(2-propylpyridin-4-yl)-1H-pyrazol-4-yl)pyridin-3-amine (0.100 g, 0.4 mmol) in dichloromethane (3 mL) was added dropwise over 20 minutes. The reaction was then allowed to come to room temperature and stirred for 1 hour. Upon completion, ice water was added and the dichloromethane layer was separated. The aqueous was extracted with dichloromethane (2×50 mL). The dichloromethane extracts were combined and dried over anhydrous sodium sulfate and concentrated under reduced pressure. The residue was purified by silica gel chromatography (0-70% ethyl acetate/hexanes). The title compound was obtained as a brown solid (55 mg, 36.3%). LC/MS: [M+1]+, 412.0; ¹HNMR (300 MHz, DMSO-d6): δ 9.31 (s, 1H), 8.67 (d, J=6.0 Hz, 1H), 8.45 (s, 1H), 8.24 (s, 1H), 8.03-7.96 (m, 2H), 7.74-7.65 (m, 2H), 2.85 (t, J=7.4 Hz, 2H), 1.81-1.73 (m, 2H), 0.94 (t, J=7.2 Hz, 3H).

Example 23: N-cyclopentyl-6-(1-(2-propylpyridin-4-yl)-1H-pyrazol-4-yl)pyridin-3-amine

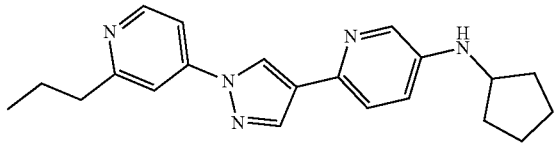 [SMILES: CCCc1cc(-n2cc(-c3ccc(NC4CCCC4)cn3)cn2)ccn1]

To a solution of 6-(1-(2-propylpyridin-4-yl)-1H-pyrazol-4-yl)pyridin-3-amine (0.075 g, 0.3 mmol) in dichloroethane (5 mL) was added Cyclopentanone (0.112 mL, 1.3 mmol), acetic acid (0.022 mL, 0.4 mmol) and sodium triacetoxyborohydride (0.160 g, 0.8 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as an off-white solid (40 mg, 42.9%). LC/MS: [M+1]+, 348.2; ¹HNMR (300 MHz, CDCl3): δ 8.57 (d, J=5.4 Hz, 1H), 8.45 (s, 1H), 8.12 (s, 1H), 8.03 (s, 1H), 7.58 (s, 1H), 7.47 (d, J=5.4 Hz, 1H), 7.38 (d, J=8.1 Hz, 1H), 6.93 (d, J=7.2 Hz, 1H), 3.84-3.80 (m, 2H), 2.84 (t, J=7.7 Hz, 2H), 2.08-2.04 (m, 2H), 1.86-1.50 (m, 8H), 1.01 (t, J=7.2 Hz, 3H).

Example 24: 5-chloro-N-isopropyl-6-(1-(2-propylpyridin-4-yl)-1H-pyrazol-4-yl)pyridin-3-amine

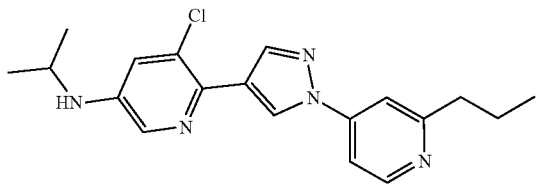 [SMILES: CCCc1cc(-n2cc(-c3ncc(NC(C)C)cc3Cl)cn2)ccn1]

Step 1: 3-chloro-5-nitro-2-(1-(2-propylpyridin-4-yl)-1H-pyrazol-4-yl)pyridine

A solution of crude 2-propyl-4-(4-(4,4,5,5-tetramethyl-1,3,2-dioxaborolan-2-yl)-1H-pyrazol-1-yl)pyridine (1.400 g, 2.5 mmol), 2-bromo-3-chloro-5-nitropyridine (1.191 g, 4.9 mmol) and 2.0 M sodium carbonate (3.7 mL, 7.4 mmol) in DMF (8 mL) was stirred at room temperature for 5 minutes, then tetrakis(triphenylphosphine) palladium(0) (60 mg) was then added and the flask was flushed with argon and stirred at 110° C. for overnight. After cooling, the mixture was partitioned between ethyl acetate (200 mL) and water. The organic layer was washed with brine, dried over Na₂SO₄ and concentrated. The residue was purified by silica gel chromatography (0-40% ethyl acetate/hexanes) to afford the desired product as a yellow solid (0.63 g). LC/MS: [M+1]+, 344.1; ¹H-NMR (300 MHz, CDCl₃): δ 9.35 (s, 1H), 8.97 (s, 1H), 8.67-8.59 (m, 3H), 7.64 (s, 1H), 7.55 (d, J=5.4 Hz, 1H), 2.89 (t, J=7.8 Hz, 2H), 1.89-1.81 (m, 2H), 1.03 (t, J=7.8 Hz, 3H).

Step 2: 5-chloro-6-(1-(2-propylpyridin-4-yl)-1H-pyrazol-4-yl)pyridin-3-amine

To a yellow suspension of 3-chloro-5-nitro-2-(1-(2-propylpyridin-4-yl)-1H-pyrazol-4-yl)pyridine (0.630 g, 1.8 mmol) in Ethanol (50 mL), was added Tin(II) chloride (1.147 g, 6.0 mmol) followed by concentrated hydrogen chloride (3 mL), and the reaction was heated to 80° C. for 6 hrs to give a yellow solution. After the reaction had cooled to ambient temperature, it was poured into an ice-cold solution of 10.0 g potassium hydroxide in 100 mL of water and diluted with 75 mL of ethyl acetate, the layers separated, and the aqueous layer was extracted with ethyl acetate (3×30 mL). The combined organics were dried over sodium sulfate and concentrated to afford the desired product as a yellow solid (0.53 g, 92%). LC/MS: [M+1]+, 314.2; ¹H-NMR (300 MHz, CDCl₃): δ 8.64 (s, 1H), 8.58 (d, J=5.1 Hz, 1H), 8.41 (s, 1H), 8.05 (d, J=2.4 Hz, 1H), 7.60 (s, 1H), 7.50 (d, J=6.0 Hz, 1H), 7.09 (d, J=2.4 Hz, 1H), 3.85 (bs, 2H), 2.85 (t, J=7.7 Hz, 2H), 1.87-1.79 (m, 2H), 1.01 (t, J=7.4 Hz, 3H).

Step 3: 5-chloro-N-isopropyl-6-(1-(2-propylpyridin-4-yl)-1H-pyrazol-4-yl)pyridin-3-amine To a solution of 5-chloro-6-(1-(2-propylpyridin-4-yl)-1H-pyrazol-4-yl)pyridin-3-amine (0.065 g, 0.2 mmol) in dichloroethane (10 mL) was added Acetone (76 μL, 1.0 mmol), acetic acid (24 μL, 0.4 mmol) and sodium triacetoxyborohydride (0.144 g, 0.7 mmol). The reaction was stirred at room temperature overnight. The reaction mixture partitioned between dichloromethane and saturated sodium bicarbonate solution. The layers were separated and the aqueous layer was extracted twice with dichloromethane. The combined organic layers were dried over MgSO₄. The solvents were removed and the residue was purified by silica gel chromatography (0-60% ethyl acetate/hexanes). The title compound was obtained as a yellow solid (49 mg, 66.5%). LC/MS: 356.2 [M+1]+; ¹H NMR (300 MHz, CDCl₃): δ 8.61 (s, 1H), 8.58 (d, J=5.4 Hz, 1H), 8.39 (s, 1H), 7.95 (d, J=2.4 Hz, 1H), 7.59 (s, 1H), 7.49 (dd, J=5.4 and 1.5 Hz, 1H), 6.93 (d, J=3.0 Hz, 1H), 3.74-3.62 (m, 2H), 2.85 (t, J=7.7 Hz, 2H), 1.87-1.77 (m, 2H), 1.28 (d, J=6.0 Hz, 6H), 1.01 (t, J=7.4 Hz, 3H).

Example 25: 5-chloro-N-cyclopentyl-6-(1-(2-propylpyridin-4-yl)-1H-pyrazol-4-yl)pyridin-3-amine

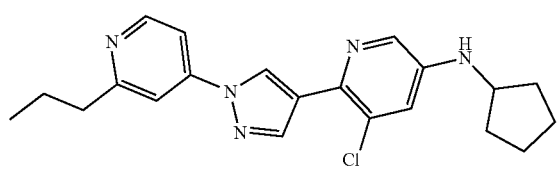 [SMILES: CCCc1cc(-n2cc(-c3ncc(NC4CCCC4)cc3Cl)cn2)ccn1]

To a solution of 5-chloro-6-(1-(2-propylpyridin-4-yl)-1H-pyrazol-4-yl)pyridin-3-amine (0.065 g, 0.2 mmol) in dichloroethane (5 mL) was added Cyclopentanone (0.092 mL, 1.0 mmol), acetic acid (0.024 mL, 0.4 mmol) and sodium triacetoxyborohydride (0.144 g, 0.7 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as an off-white solid (22 mg, 27.8%). LC/MS: [M+1]$^+$, 382.2; $^1$HNMR (300 MHz, CDCl3): δ 8.61 (s, 1H), 8.58 (d, J=5.4 Hz, 1H), 8.40 (s, 1H), 7.96 (d, J=1.5 Hz, 1H), 7.59 (s, 1H), 7.49 (d, J=5.4 Hz, 1H), 6.95 (d, J=2.4 Hz, 1H), 3.89-3.80 (m, 2H), 2.85 (t, J=7.7 Hz, 2H), 2.09-2.05 (m, 2H), 1.87-1.50 (m, 8H), 1.02 (t, J=7.5 Hz, 3H).

Example 26: 5-chloro-N-isobutyl-6-(1-(2-propylpyridin-4-yl)-1H-pyrazol-4-yl)pyridin-3-amine

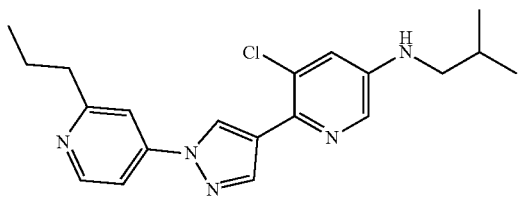 [SMILES: CCCc1cc(-n2cc(-c3ncc(NCC(C)C)cc3Cl)cn2)ccn1]

To a solution of 5-chloro-6-(1-(2-propylpyridin-4-yl)-1H-pyrazol-4-yl)pyridin-3-amine (0.065 g, 0.2 mmol) in dichloroethane (5 mL) was added isobutyraldehyde (23 μL, 0.2 mmol), acetic acid (24 μL, 0.4 mmol) and sodium triacetoxyborohydride (0.144 g, 0.7 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-40% ethyl acetate/hexanes). The title compound was obtained as a yellow solid (41 mg, 53.3%). LC/MS: 370.2 [M+1]+; $^1$H NMR (300 MHz, CDCl$_3$): δ 8.61 (s, 1H), 8.58 (d, J=6.0 Hz, 1H), 8.39 (s, 1H), 7.98 (d, J=2.4 Hz, 1H), 7.59 (s, 1H), 7.50 (dd, J=5.7 and 1.5 Hz, 1H), 6.93 (d, J=2.4 Hz, 1H), 3.99-3.95 (m, 1H), 2.98 (t, J=6.3 Hz, 2H), 2.85 (t, J=7.7 Hz, 2H), 1.98-1.79 (m, 3H), 1.04-0.99 (m, 9H).

Example 27: 5-chloro-N-(cyclopropylmethyl)-6-(1-(2-propylpyridin-4-yl)-1H-pyrazol-4-yl)pyridin-3-amine

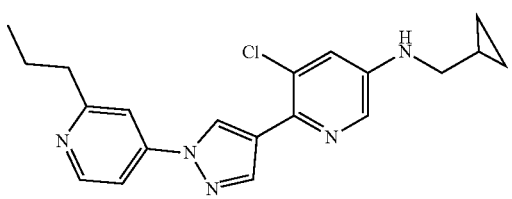 [SMILES: CCCc1cc(-n2cc(-c3ncc(NCC4CC4)cc3Cl)cn2)ccn1]

To a solution of 5-chloro-6-(1-(2-propylpyridin-4-yl)-1H-pyrazol-4-yl)pyridin-3-amine (0.065 g, 0.2 mmol) in dichloroethane (5 mL) was added 95.0% cyclopropanecarbaldehyde (20 μL, 0.2 mmol), acetic acid (24 μL, 0.4 mmol) and sodium triacetoxyborohydride (0.144 g, 0.7 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-40% ethyl acetate/hexanes). The title compound was obtained as a yellow solid (62 mg, 81%). LC/MS: 368.2 [M+1]$^+$; $^1$H NMR (300 MHz, CDCl$_3$): δ 8.62 (s, 1H), 8.58 (d, J=5.4 Hz, 1H), 8.40 (s, 1H), 7.99 (d, J=3.0 Hz, 1H), 7.59 (s, 1H), 7.49 (dd, J=5.1 and 1.5 Hz, 1H), 6.94 (d, J=2.4 Hz, 1H), 4.05 (brs, 1H), 3.03-2.99 (m, 2H), 2.85 (t, J=7.7 Hz, 2H), 1.87-1.79 (m, 2H), 1.15-1.11 (m, 1H), 1.01 (t, J=7.4 Hz, 3H), 0.66-0.60 (m, 2H), 0.33-0.29 (m, 2H).

Example 28: N-(5-chloro-6-(1-(2-propylpyridin-4-yl)-1H-pyrazol-4-yl)pyridin-3-yl)cyclopropanesulfonamide

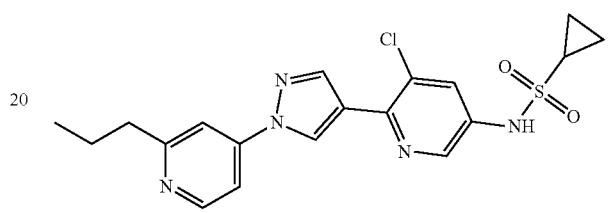

A solution of 5-chloro-6-(1-(2-propylpyridin-4-yl)-1H-pyrazol-4-yl)pyridin-3-amine (0.065 g, 0.2 mmol) and Pyridine (50 μL, 0.6 mmol) in Dichloromethane (7 mL) was cooled to 0° C. Then, Cyclopropanesulfonyl chloride (63 μL, 0.6 mmol) was added, and reaction mixture was allowed to warm to room temperature overnight to give a yellow suspension. The reaction mixture was quenched with saturated sodium bicarbonate. The layers were separated, and the aqueous layer was extracted with dichloromethane (2×20 mL). The combined organics were dried over Na$_2$SO$_4$ and concentrated. The residue was purified by silica gel chromatography (0-50% ethyl acetate/hexanes). The title compound was obtained as an off-white solid (38 mg, 42.7%). LC/MS: [M+1]$^+$, 418.1; $^1$HNMR (300 MHz, CDCl$_3$): δ 8.78 (s, 1H), 8.61 (d, J=5.4 Hz, 1H), 8.50 (s, 1H), 8.41 (s, 1H), 7.85 (s, 1H), 7.61 (s, 1H), 7.51 (d, J=4.8 Hz, 1H), 6.50 (brs, 1H), 2.87 (t, J=7.7 Hz, 2H), 2.58-2.55 (m, 1H), 1.87-1.80 (m, 2H), 1.29-1.25 (m, 2H), 1.10-0.99 (m, 5H).

Example 29: N-(5-chloro-6-(1-(2-propylpyridin-4-yl)-1H-pyrazol-4-yl)pyridin-3-yl)-1-cyclopropylmethanesulfonamide

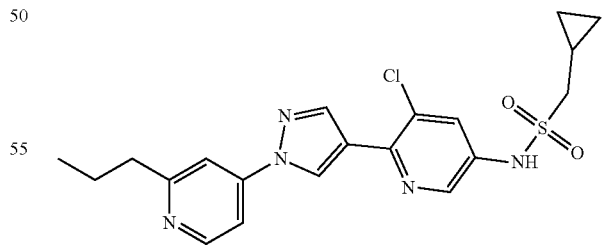

A solution of 5-chloro-6-(1-(2-propylpyridin-4-yl)-1H-pyrazol-4-yl)pyridin-3-amine (0.065 g, 0.2 mmol) and Pyridine (50 μL, 0.6 mmol) in Dichloromethane (7 mL) was cooled to 0° C. Then, cyclopropylmethanesulfonyl chloride (67 mg, 0.4 mmol) was added, and reaction mixture was allowed to warm to room temperature overnight to give a reddish brown suspension. The reaction mixture was quenched with saturated sodium bicarbonate. The layers were separated, and the aqueous layer was extracted with dichloromethane (2×20 mL). The combined organics were dried over $Na_2SO_4$ and concentrated. The residue was purified by silica gel chromatography (0-50% ethyl acetate/hexanes). The title compound was obtained as an off-white solid (35 mg, 38.2%). LC/MS: [M+1]$^+$, 431.9; $^1$HNMR (300 MHz, CDCl$_3$): δ 8.76 (s, 1H), 8.61 (d, J=5.4 Hz, 1H), 8.48 (s, 1H), 8.36 (d, J=2.4 Hz, 1H), 7.86 (d, J=2.4 Hz, 1H), 7.61 (s, 1H), 7.51 (dd, J=5.4 and 1.8 Hz, 1H), 6.71 (brs, 1H), 3.13 (d, J=6.9 Hz, 2H), 2.87 (t, J=7.7 Hz, 2H), 1.90-1.78 (m, 2H), 1.27-1.16 (m, 1H), 1.02 (t, J=7.2 Hz, 3H), 0.79-0.73 (m, 2H), 0.40-0.35 (m, 2H).

Example 30: N-(5-chloro-6-(1-(2-propylpyridin-4-yl)-1H-pyrazol-4-yl)pyridin-3-yl)methanesulfonamide

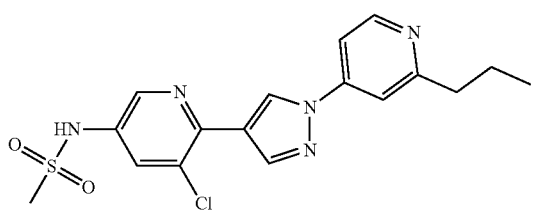 [SMILES: CCCc1cc(-n2cc(-c3ncc(NS(C)(=O)=O)cc3Cl)cn2)ccn1]

A round bottom flask was charged with 5-chloro-6-(1-(2-propylpyridin-4-yl)-1H-pyrazol-4-yl)pyridin-3-amine (0.080 g, 0.3 mmol), dichloromethane (7 mL) and Pyridine (0.062 mL, 0.8 mmol) and the reaction mixture cooled to 0° C. Methanesulfonyl chloride (0.059 mL, 0.8 mmol) was slowly added under nitrogen and the reaction mixture was stirred at 0° C. for 30 minutes. The mixture was allowed to warm to room temperature and stirred for additional 3 hours. The mixture was diluted with saturated sodium bicarbonate and dichloromethane. The organic layer was washed with brine, dried over anhydrous sodium sulfate, filtered and concentrated. The residue was purified by silica gel chromatography (0-70% ethyl acetate/hexanes). The title compound was obtained as an off-white solid (75 mg, 75.1%). LC/MS: [M+1]+, 392.0; $^1$HNMR (300 MHz, CDCl3): δ 8.78 (s, 1H), 8.62 (d, J=6.0 Hz, 1H), 8.49 (s, 1H), 8.38 (d, J=2.4 Hz, 1H), 7.84 (d, J=2.1 Hz, 1H), 7.61 (d, J=1.8 Hz, 1H), 7.51 (dd, J=5.7 and 2.1 Hz, 1H), 6.60 (brs, 1H), 3.13 (s, 3H), 2.87 (t, J=7.7 Hz, 2H), 1.88-1.80 (m, 2H), 1.02 (t, J=7.4 Hz, 3H).

Example 31: N-(5-chloro-6-(1-(2-propylpyridin-4-yl)-1H-pyrazol-4-yl)pyridin-3-yl)-1,1,1-trifluoromethanesulfonamide

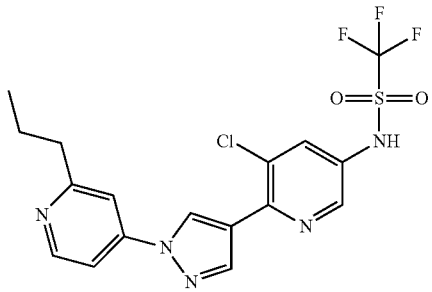 [SMILES: CCCc1cc(-n2cc(-c3ncc(NS(=O)(=O)C(F)(F)F)cc3Cl)cn2)ccn1]

Pyridine (0.054 mL, 0.7 mmol) was added dropwise to a solution of triflic anhydride (0.113 mL, 0.7 mmol) at 0° C. under nitrogen in dichloromethane (5 mL) over 10 minutes. The reaction mixture was stirred at the same temperature for 30 minutes. A solution of 5-chloro-6-(1-(2-propylpyridin-4-yl)-1H-pyrazol-4-yl)pyridin-3-amine (0.070 g, 0.2 mmol) in dichloromethane (3 mL) was added dropwise over 20 min. The reaction was then allowed to come to room temperature and stirred for 1 hour. Upon completion, ice water was added and the dichloromethane layer was separated. The aqueous was extracted with dichloromethane (2×50 mL). The dichloromethane extracts were combined and dried over anhydrous sodium sulfate and concentrated under reduced pressure. The residue was purified by silica gel chromatography (0-15% methanol/dichlormethane). The title compound was obtained as a brown solid (17 mg, 16.9%). LC/MS: [M+1]$^+$, 445.9; $^1$HNMR (300 MHz, DMSO-d6): δ 8.80 (s, 1H), 8.62 (d, J=6.0 Hz, 1H), 8.51 (s, 1H), 8.44 (s, 1H), 7.82 (s, 1H), 7.63 (s, 1H), 7.54 (d, J=5.1 Hz, 1H), 2.87 (t, J=7.7 Hz, 2H), 1.88-1.84 (m, 2H), 1.01 (t, J=7.4 Hz, 3H).

Example 32: N-cyclopentyl-5-(1-(2-propylpyridin-4-yl)-1H-pyrazol-4-yl)pyridin-2-amine

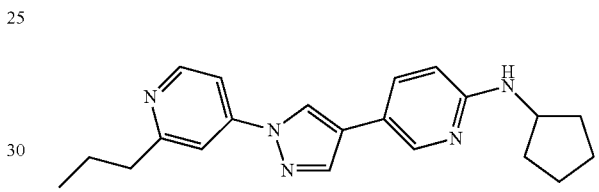

To a solution of 5-(1-(2-propylpyridin-4-yl)-1H-pyrazol-4-yl)pyridin-2-amine (0.080 g, 0.3 mmol) in dichloroethane (5 mL) was added Cyclopentanone (0.152 mL, 1.7 mmol), acetic acid (0.033 mL, 0.6 mmol) and Sodium triacetoxyborohydride (0.181 g, 0.9 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as a light yellow oil (12 mg, 11.5%). LC/MS: [M+1]$^+$, 348.1; $^1$HNMR (300 MHz, CDCl3): δ 8.58 (d, J=5.4 Hz, 1H), 8.30 (s, 1H), 8.14 (s, 1H), 7.95 (s, 1H), 7.64-7.45 (m, 3H), 6.47 (d, J=9.0 Hz, 1H), 4.78 (brs, 1H), 4.02-4.01 (m, 1H), 2.85 (t, J=7.7 Hz, 2H), 2.09-2.05 (m, 2H), 1.87-1.50 (m, 8H), 1.01 (t, J=7.5 Hz, 3H).

Example 33: N-cyclobutyl-5-(1-(2-propylpyridin-4-yl)-1H-pyrazol-4-yl)pyridin-2-amine

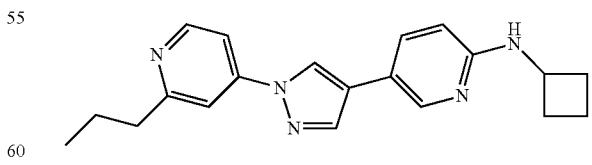

To a solution of 5-(1-(2-propylpyridin-4-yl)-1H-pyrazol-4-yl)pyridin-2-amine (0.080 g, 0.3 mmol) in dichloroethane (5 mL) was added cyclobutanone (0.111 mL, 1.7 mmol), acetic acid (0.033 mL, 0.6 mmol) and Sodium triacetoxyborohydride (0.181 g, 0.9 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as a light yellow solid (26 mg, 26.9%). LC/MS: [M+1]$^+$, 334.1; $^1$HNMR (300 MHz, CDCl3): δ 8.58 (d, J=5.4 Hz, 1H), 8.31 (s, 1H), 8.14 (s, 1H), 7.95 (s, 1H), 7.62-7.56 (m, 2H), 7.45 (d, J=5.7 Hz, 1H), 6.39 (d, J=9.0 Hz, 1H), 4.87 (brs, 1H), 4.19-4.12 (m, 1H), 2.85 (t, J=7.7 Hz, 2H), 2.48-2.45 (m, 2H), 1.95-1.79 (m, 6H), 1.02 (t, J=7.4 Hz, 3H).

Example 34: 5-(3,5-dimethyl-1-(2-propylpyridin-4-yl)-1H-pyrazol-4-yl)-N-isobutylpyridin-2-amine

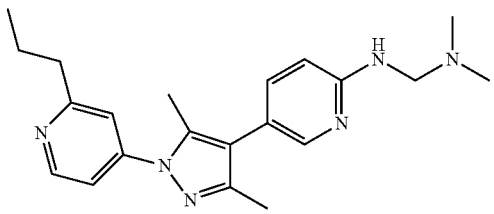 [SMILES: CCCc1cc(-n2nc(C)c(-c3ccc(NCN(C)C)nc3)c2C)ccn1]

Step 1: 4-(4-bromo-3,5-dimethyl-1H-pyrazol-1-yl)-2-propylpyridine

A microwave vial was charged with 4-bromo-2-(n-propyl)pyridine (2.030 g, 10.1 mmol), 4-bromo-3,5-dimethylpyrazole (1.776 g, 10.1 mmol), copper(I) iodide (0.386 g, 2.0 mmol), cesium carbonate (9.917 g, 30.4 mmol) and DMA (5 mL) and the reaction mixture heated to 140° C. for 16 hours. The reaction mixture was cooled to room temperature and diluted with water and extracted with ethyl acetate (2×100 mL). The organic solvents were washed with water, brine and dried over MgSO4. The solvents were evaporated to dryness and the resultant residue was purified by flash chromatography (0-50% ethyl acetate in hexanes). The collected fractions were dried to evaporation to give the product as colorless oil (1.25 g, 42%)). LC/MS: [M+2]$^+$, 296.0; $^1$HNMR (300 MHz, CDCl3): δ 8.59 (d, J=5.1 Hz, 1H), 7.31 (s, 1H), 7.22 (dd, J=5.4 and 1.8 Hz, 1H), 2.82 (t, 7.5 Hz, 2H), 2.43 (s, 3H), 2.30 (s, 3H), 1.83-1.75 (m, 2H), 0.99 (t, J=7.5 Hz, 3H).

Step 2: 5-(3,5-dimethyl-1-(2-propylpyridin-4-yl)-1H-pyrazol-4-yl)pyridin-2-amine A solution of 4-(4-bromo-3,5-dimethyl-1H-pyrazol-1-yl)-2-propylpyridine (0.400 g, 1.4 mmol), 5-(4,4,5,5-tetramethyl-1,3,2-dioxaborolan-2-yl)pyridin-2-amine (0.299 g, 1.4 mmol) and 2.0 M sodium carbonate (2.039 mL, 4.1 mmol) in DMF (10 mL) was stirred at room temperature for 5 minutes, and tetrakis(triphenylphosphine)palladium(0) (0.032 g, 0.03 mmol) was added and the flask was degassed and flushed with argon. This process was repeated three times and the reaction mixture stirred at 110° C. overnight. After cooling, the mixture was diluted with water and extracted with ethyl acetate (3×50 mL). The combined organic layer was washed with brine, dried over MgSO4 and concentrated. The residue was purified by silica gel chromatography (0-20% dichloromethane in Methanol) to afford the desired product (0.38 g, 73%). LC/MS: [M+1]$^+$, 308.1; 1H NMR (300 MHz, CDCl3): δ 8.60 (d, J=5.7 Hz, 1H), 7.71-7.31 (m, 4H), 6.62 (d, J=8.7 Hz, 1H), 4.53 (bs, 2H), 2.85 (t, J=7.2 Hz, 2H), 2.40 (s, 3H), 2.30 (s, 3H), 1.86-1.78 (m, 2H), 1.00 (t, J=6.3 Hz, 3H).

Step 3: 5-(3,5-dimethyl-1-(2-propylpyridin-4-yl)-1H-pyrazol-4-yl)-N-isobutylpyridin-2-amine To a solution of 5-(3,5-dimethyl-1-(2-propylpyridin-4-yl)-1H-pyrazol-4-yl)pyridin-2-amine (0.095 g, 0.2 mmol) in dichloroethane (5 mL) was added isobutyraldehyde (27 µL, 0.3 mmol), acetic acid (21 µL, 0.4 mmol) and sodium triacetoxyborohydride (0.156 g, 0.7 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-50% ethyl acetate/hexanes). The title compound was obtained as a white oil (29 mg, 31.6%). LC/MS: 364.0 [M+1]+; $^1$H NMR (300 MHz, CDCl$_3$): δ 8.59 (d, J=5.7 Hz, 1H), 8.03 (s, 1H), 7.69-7.40 (m, 3H), 6.48 (d, J=8.1 Hz, 1H), 4.76 (bs, 1H), 3.14 (t, J=6.2 Hz, 2H), 2.84 (t, J=7.7 Hz, 2H), 2.40 (s, 3H), 2.30 (s, 3H), 1.96-1.79 (m, 3H), 1.04-0.98 (m, 9H).

Example 35: N-(cyclopropylmethyl)-5-(3,5-dimethyl-1-(2-propylpyridin-4-yl)-1H-pyrazol-4-yl)pyridin-2-amine

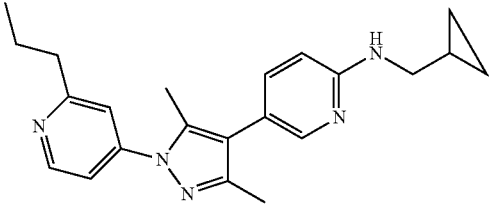 [SMILES: CCCc1cc(-n2nc(C)c(-c3ccc(NCC4CC4)nc3)c2C)ccn1]

To a solution of 5-(3,5-dimethyl-1-(2-propylpyridin-4-yl)-1H-pyrazol-4-yl)pyridin-2-amine (0.095 g, 0.2 mmol) in dichloroethane (5 mL) was added cyclopropanecarbaldehyde (23 µL, 0.3 mmol), acetic acid (21 µL, 0.4 mmol) and sodium triacetoxyborohydride (0.156 g, 0.7 mmol, 3.0 equiv.). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-40% ethyl acetate/hexanes). The title compound was obtained as a white solid (54 mg, 59.2%). LC/MS: 362.2 [M+1]$^+$; $^1$H NMR (300 MHz, CDCl$_3$): δ 8.59 (d, J=5.1 Hz, 1H), 8.03 (d, J=1.8 Hz, 1H), 7.71-7.36 (m, 3H), 6.49 (d, J=8.7 Hz, 1H), 4.74 (bs, 1H), 3.19 (t, J=6.2 Hz, 2H), 2.84 (t, J=7.7 Hz, 2H), 2.40 (s, 3H), 2.30 (s, 3H), 1.86-1.78 (m, 2H), 1.15-1.10 (m, 1H), 1.01 (t, J=7.2 Hz, 3H), 0.60-0.56 (m, 2H), 0.32-0.29 (m, 2H).

Example 36: 5-(3,5-dimethyl-1-(2-propylpyridin-4-yl)-1H-pyrazol-4-yl)-N-isopropylpyridin-2-amine

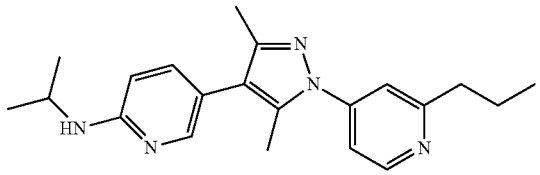 [SMILES: CCCc1cc(-n2nc(C)c(-c3ccc(NC(C)C)nc3)c2C)ccn1]

To a solution of 5-(3,5-dimethyl-1-(2-propylpyridin-4-yl)-1H-pyrazol-4-yl)pyridin-2-amine (80% pure by NMR, 0.095 g, 0.2 mmol) in dichloroethane (10 mL) was added acetone (91 µL, 1.2 mmol), acetic acid (21 µL, 0.4 mmol) and sodium triacetoxyborohydride (0.156 g, 0.7 mmol). The reaction was stirred at room temperature overnight. The reaction mixture partitioned between dichloromethane and sat'd sodium bicarbonate solution. The layers were separated and the aqueous layer was extracted twice with dichloromethane. The combined organics were dried over MgSO$_4$. The solvents were removed and resulting residue was purified by silica gel chromatography (0-60% ethyl acetate/hexanes). The title compound was obtained as a white oil (26 mg, 28.9%). LC/MS: 350.2 [M+1]$^+$; $^1$H NMR (300 MHz, CDCl$_3$): δ 8.59 (d, J=5.1 Hz, 1H), 8.02 (s, 1H), 7.71-7.29 (m, 3H), 6.46 (d, J=9.0 Hz, 1H), 4.50 (bs, 1H), 3.94-3.88 (m, 1H), 2.85 (t, J=7.7 Hz, 2H), 2.40 (s, 3H), 2.30 (s, 3H), 1.86-1.78 (m, 2H), 1.29 (d, J=6.6 Hz, 6H), 1.01 (t, J=7.2 Hz, 3H).

Example 37: N-(5-(3,5-dimethyl-1-(2-propylpyridin-4-yl)-1H-pyrazol-4-yl)pyridin-2-yl)methanesulfonamide

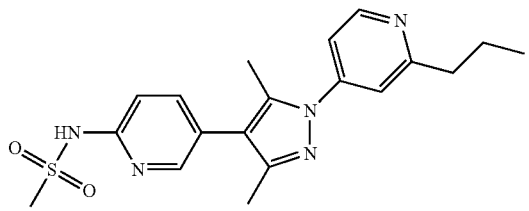 [SMILES: CCCc1cc(-n2nc(C)c(-c3ccc(NS(C)(=O)=O)nc3)c2C)ccn1]

A round bottom flask was charged with 5-(3,5-dimethyl-1-(2-propylpyridin-4-yl)-1H-pyrazol-4-yl)pyridin-2-amine (0.060 g, 0.2 mmol), dichloromethane (7 mL) and Pyridine (0.047 mL, 0.6 mmol) and the reaction mixture cooled to 0° C. Methanesulfonyl chloride (0.045 mL, 0.6 mmol) was slowly added under nitrogen and the reaction mixture was stirred at 0° C. for 30 minutes. The mixture was allowed to warm to room temperature and stirred for additional 3 hours. The mixture was diluted with saturated sodium bicarbonate and dichloromethane. The organic layer was washed with brine, dried over anhydrous sodium sulfate, filtered and concentrated. The residue was purified by silica gel chromatography (0-70% ethyl acetate/hexanes). The title compound was obtained as an off-white solid (14 mg, 17.7%). LC/MS: [M+1]$^+$, 386.1; $^1$HNMR (300 MHz, CDCl3): δ 8.63 (d, J=5.1 Hz, 1H), 8.25 (s, 1H), 7.67 (dd, J=8.4, 2.1 Hz, 1H), 7.36-7.30 (m, 3H), 3.26 (s, 3H), 2.86 (t, J=7.7 Hz, 2H), 2.42 (s, 3H), 2.33 (s, 3H), 1.86-1.78 (m, 2H), 1.01 (t, J=7.4 Hz, 3H).

Example 38: N-cyclobutyl-5-(3,5-dimethyl-1-(2-propylpyridin-4-yl)-1H-pyrazol-4-yl)pyridin-2-amine

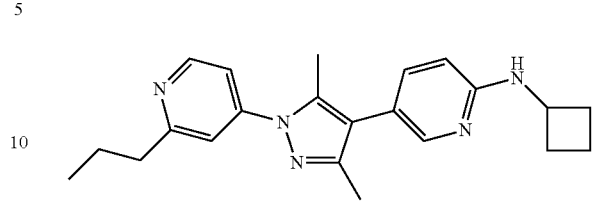

To a solution of 5-(3,5-dimethyl-1-(2-propylpyridin-4-yl)-1H-pyrazol-4-yl)pyridin-2-amine (0.070 g, 0.2 mmol) in dichloroethane (5 mL) was added cyclobutanone (0.172 mL, 2.3 mmol), acetic acid (0.039 mL, 0.7 mmol) and Sodium triacetoxyborohydride (0.288 g, 1.4 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as a light yellow solid (35 mg, 41%). LC/MS: [M+1]+, 362.3; $^1$HNMR (300 MHz, CDCl3): δ 8.59 (d, J=5.7 Hz, 1H), 8.01 (s, 1H), 7.40-7.37 (m, 3H), 6.42 (d, J=9.0 Hz, 1H), 4.19-4.16 (m, 1H), 2.84 (t, J=7.7 Hz, 2H), 2.48-2.45 (m, 2H), 2.40 (s, 3H), 2.30 (s, 3H), 1.94-1.78 (m, 6H), 1.01 (t, J=7.2 Hz, 3H).

Example 39: N-(5-(3,5-dimethyl-1-(2-propylpyridin-4-yl)-1H-pyrazol-4-yl)pyridin-2-yl)-1,1,1-trifluoromethanesulfonamide

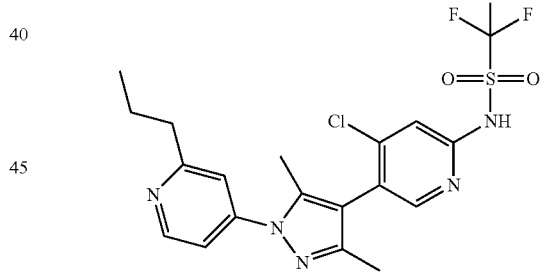

Pyridine (0.062 mL, 0.8 mmol) was added dropwise to a solution of triflic anhydride (0.129 mL, 0.8 mmol) at 0° C. under nitrogen in dichloromethane (5 mL) over 10 minutes. The reaction mixture was stirred at the same temperature for 30 minutes. A solution of 5-(3,5-dimethyl-1-(2-propylpyridin-4-yl)-1H-pyrazol-4-yl)pyridin-2-amine (0.080 g, 0.3 mmol) in dichloromethane (3 mL) was added dropwise over 20 minutes. The reaction was then allowed to come to room temperature and stirred for 1 hour. Upon completion, ice water was added and the dichloromethane layer was separated. The aqueous was extracted with dichloromethane (2×50 mL). The dichloromethane extracts were combined and dried over anhydrous sodium sulfate and concentrated under reduced pressure. The residue was purified by silica gel chromatography (0-15% methanol/dichloromethane). The title compound was obtained as a brown solid (53 mg, 44.1%). LC/MS: [M+1]$^+$, 440.2; $^1$HNMR (300 MHz, CDCl3): δ 8.66 (d, J=5.4 Hz, 1H), 8.23 (s, 1H), 7.98 (s, 2H), 7.37-7.30 (m, 2H), 2.88 (t, J=7.7 Hz, 2H), 2.45 (s, 3H), 2.36 (s, 3H), 1.87-1.80 (m, 2H), 1.02 (t, J=7.4 Hz, 3H).

Example 40: N-cyclopentyl-5-(3,5-dimethyl-1-(2-propylpyridin-4-yl)-1H-pyrazol-4-yl)pyridin-2-amine

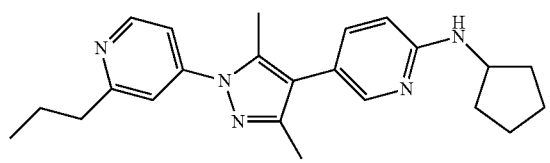 [SMILES: CCCc1cc(-n2nc(C)c(-c3ccc(NC4CCCC4)nc3)c2C)ccn1]

To a solution of 5-(3,5-dimethyl-1-(2-propylpyridin-4-yl)-1H-pyrazol-4-yl)pyridin-2-amine (0.080 g, 0.2 mmol) in dichloroethane (5 mL) was added Cyclopentanone (0.184 mL, 2.1 mmol), acetic acid (0.036 mL, 0.6 mmol) and sodium triacetoxyborohydride (0.264 g, 1.2 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as a light oil (17 mg, 21.2%). LC/MS: [M+1]$^+$, 376.3; $^1$HNMR (300 MHz, CDCl3): δ 8.59 (d, J=5.7 Hz, 1H), 8.02 (s, 1H), 7.40-7.31 (m, 3H), 6.50 (d, J=8.1 Hz, 1H), 4.82 (s, 1H), 4.03-3.98 (m, 1H), 2.85 (t, J=7.7 Hz, 2H), 2.40 (s, 3H), 2.30 (s, 3H), 2.10-2.07 (m, 2H), 1.86-1.65 (m, 8H), 1.01 (t, J=7.2 Hz, 3H).

Example 41: N-(tert-butyl)-5-(1-(2-propylpyridin-4-yl)-1H-pyrazol-4-yl)pyrimidin-2-amine

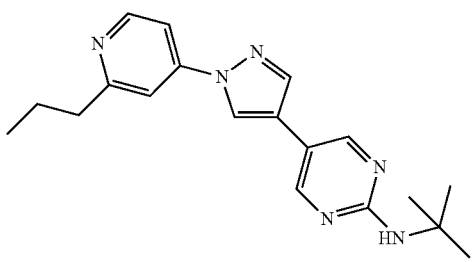 [SMILES: CCCc1cc(-n2cc(-c3cnc(NC(C)(C)C)nc3)cn2)ccn1]

A solution of 2-propyl-4-(4-(4,4,5,5-tetramethyl-1,3,2-dioxaborolan-2-yl)-1H-pyrazol-1-yl)pyridine (80% pure by LC/MS, 0.100 g, 0.3 mmol), 5-bromo-N-(tert-butyl)pyrimidin-2-amine (0.090 g, 0.4 mmol) and sodium carbonate (0.383 mL, 0.8 mmol) in DMF (6 mL) was stirred at room temperature for 5 minutes, then tetrakis(triphenylphosphine) palladium(0) (10 mg) was then added and the flask was flushed with argon and stirred at 110° C. for overnight. The reaction mixture partitioned between dichloromethane and saturated sodium bicarbonate solution. The layers were separated and the aqueous layer was extracted twice with dichloromethane. The combined organics were dried over MgSO$_4$. The solvents were removed and resulting residue was purified by silica gel chromatography (0-30% ethyl acetate/hexanes) two times. The title compound was obtained as a yellow solid (16 mg, 18.5%). LC/MS: 337.3 [M+1]+; $^1$H NMR (300 MHz, CDCl$_3$): δ 8.60 (d, J=5.1 Hz, 1H), 8.47 (s, 2H), 8.16 (s, 1H), 7.94 (s, 1H), 7.56 (d, J=1.8 Hz, 1H), 7.45 (dd, J=5.4 and 1.8 Hz, 1H), 5.24 (brs, 1H), 2.86 (t, J=7.7 Hz, 2H), 1.87-1.80 (m, 2H), 1.45 (s, 9H), 1.02 (t, J=7.2 Hz, 3H).

Example 42: N-isopropyl-5-(1-(2-propylpyridin-4-yl)-1H-pyrazol-4-yl)pyrimidin-2-amine

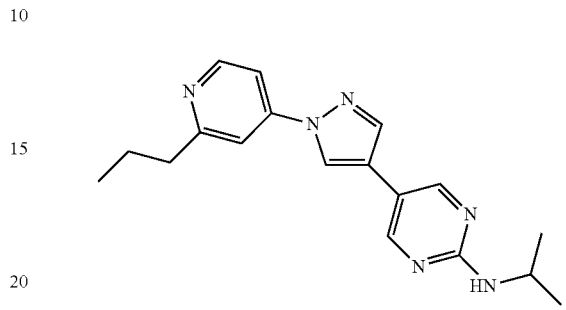

A solution of 2-propyl-4-(4-(4,4,5,5-tetramethyl-1,3,2-dioxaborolan-2-yl)-1H-pyrazol-1-yl)pyridine (80% pure by LC/MS 0.100 g, 0.3 mmol), 5-bromo-N-isopropylpyrimidin-2-amine (0.084 g, 0.4 mmol) and 2.0 M sodium carbonate (0.383 mL, 0.8 mmol) in DMF (6 mL) was stirred at room temperature for 5 minutes, then tetrakis(triphenylphosphine) palladium(0) (10 mg) was then added and the flask was flushed with argon and stirred at 110° C. for overnight. The reaction mixture partitioned between dichloromethane and saturated sodium bicarbonate solution. The layers were separated and the aqueous layer was extracted twice with dichloromethane. The combined organics were dried over MgSO$_4$. The solvents were removed and resulting residue was purified by silica gel chromatography (0-30% ethyl acetate/hexanes) two times. The title compound was obtained as a yellow solid (32 mg, 38.1%). LC/MS: 323.3 [M+1]+; $^1$H NMR (300 MHz, CDCl$_3$): δ 8.60 (d, J=5.1 Hz, 1H), 8.48 (s, 2H), 8.16 (s, 1H), 7.94 (s, 1H), 7.71-7.45 (m, 2H), 5.05 (bs, 1H), 4.21-4.14 (m, 1H), 2.86 (t, J=7.7 Hz, 2H), 1.87-1.77 (m, 2H), 1.28 (d, J=6.3 Hz, 6H), 1.02 (t, J=7.2 Hz, 3H).

Example 43: N-cyclopentyl-5-(1-(2-propylpyridin-4-yl)-1H-pyrazol-4-yl)pyrimidin-2-amine

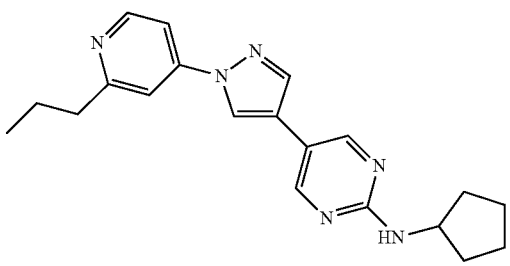 [SMILES: CCCc1cc(-n2cc(-c3cnc(NC4CCCC4)nc3)cn2)ccn1]

A solution of 2-propyl-4-(4-(4,4,5,5-tetramethyl-1,3,2-dioxaborolan-2-yl)-1H-pyrazol-1-yl)pyridine (80% pure by LC/MS 0.100 g, 0.3 mmol), 5-bromo-N-cyclopentylpyrimidin-2-amine (0.090 g, 0.4 mmol) and 2.0 M sodium carbonate (0.383 mL, 0.8 mmol) in DMF (6 mL) was stirred at room temperature for 5 minutes, then tetrakis(triphenylphosphine) palladium(0) (10 mg) was then added and the flask was flushed with argon and stirred at 110° C. for overnight. The reaction mixture partitioned between dichloromethane and sat'd sodium bicarbonate solution. The layers were separated and the aqueous layer was extracted twice with dichloromethane. The combined organics were dried over MgSO$_4$. The solvents were removed and resulting residue was purified by silica gel chromatography (0-60% ethyl acetate/hexanes) two times. The title compound was obtained as a yellow solid (73 mg, 79.6%). LC/MS: 349.3 [M+1]+; $^1$H NMR (300 MHz, CDCl$_3$): δ 8.60 (d, J=5.7 Hz, 1H), 8.48 (s, 2H), 8.16 (s, 1H), 7.94 (s, 1H), 7.71-7.46 (m, 2H), 5.19 (bs, 1H), 4.32-4.29 (m, 1H), 2.86 (t, J=7.7 Hz, 2H), 2.11-2.06 (m, 2H), 1.87-1.68 (m, 6H), 1.53-1.50 (m, 2H), 1.02 (t, J=7.2 Hz, 3H).

Example 44: 5-(4-(6-(isopropylamino)pyridin-3-yl)-1H-pyrazol-1-yl)-1-propylpyridin-2(1H)-one

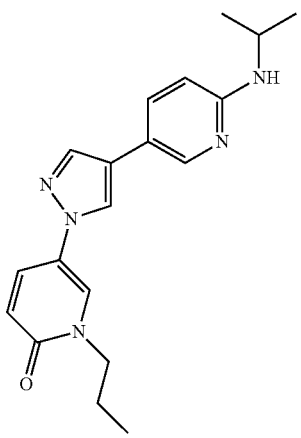 [SMILES: CCCn1cc(-n2cc(-c3ccc(NC(C)C)nc3)cn2)ccc1=O]

Step 1: 5-bromo-1-propylpyridin-2(1H)-one

A round bottom flask was charged with 2-hydroxy-5-bromopyridine (1.000 g, 5.7 mmol), 1-iodopropane (2.81 mL, 28.7), potassium carbonate (3.972 g, 28.7 mmol) and tween 80 (2% w/w in water, 10 mL) and the reaction mixture was heated to 70° C. overnight. The reaction mixture was diluted with water and extracted with ethyl acetate (3×50 mL) and the combined organics were washed with brine and dried over MgSO4. The solvents were evaporated to dryness and the residue purified by flash chromatography (silica gel, 0-50% ethyl acetate in hexanes). The desired fractions were evaporated to dryness to give the compound as colorless oil. LC/MS: [M$^+$] and [M+2]$^+$216.1 and 218.1; $^1$H NMR (300 MHz, DMSO-d6): δ 8.00 (d, J=2.7 Hz, 1H), 7.49 (dd, J=9.9 and 3.0 Hz, 1H), 6.34 (d, J=10.2 Hz, 1H), 3.79 (t, J=6.9 Hz, 2H), 1.64-1.57 (m, 2H), 0.82 (t, J=7.5 Hz, 3H).

Step 2: 5-(4-bromo-1H-pyrazol-1-yl)-1-propylpyridin-2(1H)-one

To a stirred solution of 5-bromo-1-propylpyridin-2(1H)-one (1.029 g, 4.8 mmol), cesium carbonate (4.655 g, 14.3 mmol), 3-bromopyrazole (0.700 g, 4.8 mmol), in anhydrous DMA (3 mL) under argon was added and copper(I) iodide (0.181 g, 1.0 mmol). The mixture was stirred at 120° C. overnight. After cooling, the mixture was diluted with water and extracted with ethyl acetate (3×20 mL). The combined organics were washed with brine and dried over MgSO4. The solvents were dried to evaporation and the residue purified by flash chromatography (0-100% ethyl acetate in hexanes). The pure fractions were collected and dried to give the product as a liquid (320 mg, 24%). LC/MS: [M+1]+ 282.1; $^1$H NMR (300 MHz, CDCl$_3$): δ 8.25 (d, J=2.4 Hz, 1H), 7.84-7.76 (m, 2H), 7.66 (dd, J=9.9 and 2.4 Hz, 1H), 7.56 (dd, J=8.7 and 2.4 Hz, 1H) 6.68 (d, J=9.9 Hz, 1H), 6.55 (d, J=8.1 Hz, 1H), 4.51 (bs, 2H), 3.96 (t, J=7.8 Hz, 2H), 1.87-1.80 (m, 2H), 0.99 (t, J=7.5 Hz, 3H).

Step 3: 5-(4-(6-aminopyridin-3-yl)-1H-pyrazol-1-yl)-1-propylpyridin-2(1H)-one

A microwave vial was charged with 5-(4-bromo-1H-pyrazol-1-yl)-1-propylpyridin-2(1H)-one (0.300 g, 1.1 mmol), 5-(4,4,5,5-tetramethyl-1,3,2-dioxaborolan-2-yl)pyridin-2-amine (0.278 g, 1.3 mmol), potassium carbonate (0.525 g, 3.8 mmol), dioxan (12 mL) and water (3 mL) and the flask was degassed and flushed with argon. PdCl$_2$(dppf) (0.104 g, 0.1 mmol) was added and the reaction flask was again degassed and flushed with argon. The reaction mixture was then heated to 100° C. for 45 minutes in a microwave. The reaction was cooled to room temperature and quenched with sat. NaHCO$_3$ and extracted with ethyl acetate (3×40 mL). The combined organics were washed with water, brine and dried over MgSO4. The solvents were evaporated to dryness and the residue purified by flash chromatography (silica gel, 0-60% ethyl acetates in hexanes) to give the product as a brown oil (220 mg, 70%). LC/MS: [M+1]$^+$ 296.2; $^1$H NMR (300 MHz, CDCl$_3$): δ 8.26 (d, J=1.8 Hz, 1H), 7.83 (d, J=5.1 Hz, 2H), 7.76 (d, J=3.0 Hz, 1H), 7.66 (dd, J=9.9 and 3.0 Hz, 1H), 7.57 (8.7 and 2.4 HZ, 1H), 6.68 (d, J=9.3 Hz, 1H), 6.56 (d, J=8.7 Hz, 1H), 4.49 (s, 2H), 3.97 (t, J=7.2 Hz, 2H), 1.88-1.80 (m, 2H), 1.00 (t, J=6.9 Hz, 3H).

Step 4: 5-(4-(6-(isopropylamino)pyridin-3-yl)-1H-pyrazol-1-yl)-1-propylpyridin-2(1H)-one A round bottom flask was charged with 5-(4-(6-amino-pyridin-3-yl)-1H-pyrazol-1-yl)-1-propylpyridin-2(1H)-one (0.140 g, 0.5 mmol), acetone (0.171 mL, 2.4 mmol.), acetic acid (0.040 mL, 0.7 mmol), sodium triacetoxyborohydride (0.500 g, 2.4 mmol) and 1,2-dichloroethane (5 mL). The reaction was stirred at 40° C. under argon for 30 minutes. The reaction mixture was cooled and quenched with saturated NaHCO$_3$ (10 mL) and extracted with dichloromethane (3×50 mL). The combined organics were washed with the water, brine and dried over MgSO4. The solvents were evaporated under reduced pressure to dryness and the residue purified by flash chromatography (silica gel, 0-20% methanol in dichloromethane) to afford the product as tan colored solid (19 mg, 12%). LC/MS: 338.2 [M+1]$^+$. $^1$H NMR (300 MHz, CDCl$_3$): δ 8.26 (d, J=1.8 Hz, 1H), 7.83-7.75 (m, 3H), 7.66 (dd, J=9.9 & 3.0 Hz, 1H), 7.54 (dd, J=8.7 & 3.0 Hz, 1H), 6.68 (d, J=9.9 Hz, 1H), 6.41 (d, J=8.7 Hz, 1H), 4.44 (d, J-8.1 Hz, 1H), 3.99-3.87 (m, 3H), 1.88-1.62 (m, 2H), 1.26 (d, J=6.6 Hz, 6H), 1.00 (t, J=6.9 Hz, 3H).

Example 45: N-(4-(1-(6-oxo-1-propyl-1,6-dihydropyridin-3-yl)-1H-pyrazol-4-yl)phenyl)methanesulfonamide

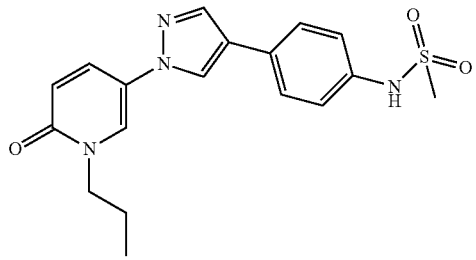 [SMILES: CCCn1cc(-n2cc(-c3ccc(NS(C)(=O)=O)cc3)cn2)ccc1=O]

Step 1: 5-(4-(4-nitrophenyl)-1H-pyrazol-1-yl)-1-propylpyridin-2(1H)-one

A microwave vial was charged with 5-(4-bromo-1H-pyrazol-1-yl)-1-propylpyridin-2(1H)-one (0.300 g, 1.1 mmol), 4-Nitrophenylboronic acid (0.177 g, 1.1 mmol), potassium carbonate (0.441 g, 3.2 mmol), dioxan (12 mL) and water (3 mL) and the flask was degassed and flushed with argon. PdCl$_2$(dppf) (0.104 g, 0.1 mmol) was added and the reaction flask was again degassed and flushed with argon. The reaction mixture was then heated to 100° C. for 45 minutes in a microwave. The reaction was cooled to room temperature and quenched with sat. NaHCO3 and extracted with ethyl acetate (3×20 mL). The combined organics were washed with water, brine and dried over MgSO4. The solvents were evaporated to dryness and the residue purified by flash chromatography (silica gel, 0-100% ethyl acetates in hexanes) to give the product as a solid (320 mg, 93%). LC/MS: [M+1]$^+$325.1; $^1$H NMR (300 MHz, CDCl$_3$): δ 8.28-8.25 (m, 2H), 8.03 (d, J=3.6 Hz, 2H), 7.81 (d, J=2.4 Hz, 1H), 7.69-7.65 (m, 3H), 6.70 (d, J=9.9 Hz, 1H), 3.980 (t, J=7.5 Hz, 2H), 1.89-1.81 (m, 2H), 1.01 (t, J=7.5 Hz, 3H).

Step 2: 5-(4-(4-aminophenyl)-1H-pyrazol-1-yl)-1-propylpyridin-2(1H)-one

A round bottom flask was charged with 5-(4-(4-nitrophenyl)-1H-pyrazol-1-yl)-1-propylpyridin-2(1H)-one (0.345 g, 1.2 mmol), ethanol (20 mL) and Tin(II) chloride (0.666 g, 3.5 mmol) was added and the reaction mixture heated to 85° C. for 45 minutes. The reaction mixture was cooled and poured into 50 mL of 2M KOH. This was extracted with ethyl acetate (3×50 mL). The combined organics were washed with brine and dried over MgSO$_4$. The solvents were evaporated to give the product as pale brown solid which was used in the next reaction without further purification (290 mg, 93%). LC/MS: 295.2 [M+1]+; $^1$H NMR (300 MHz, CDCl$_3$): δ 7.84 (s, 1H), 7.78 (s, 1H), 7.75 (d, J=3.0 Hz, 1H), 7.65 (dd, J=9.9 and 3.0 Hz, 1H), 7.39-7.29 (m, 2H), 6.74-6.66 (m, 3H), 3.96 (t, J=7.5 Hz, 2H), 1.88-1.80 (m, 2H), 0.99 (t, J=6.9 Hz, 3H).

Step 3: N-(4-(1-(6-oxo-1-propyl-1,6-dihydropyridin-3-yl)-1H-pyrazol-4-yl)phenyl)methanesulfonamide A round bottom flask was charged with 5-(4-(4-aminophenyl)-1H-pyrazol-1-yl)-1-propylpyridin-2(1H)-one (0.120 g, 0.4 mmol), dichloromethane (4 mL) and Pyridine (0.148 mL, 1.8 mmol) and methanesulfonyl chloride (0.142 mL, 1.8 mmol) were added at 0° C. under argon. The reaction mixture was stirred at that temperature for 30 minutes. The reaction was quenched with sat. NaHCO$_3$ and extracted with dichloromethane (3×50 mL). The combined organics were washed with water, brine and dried over MgSO$_4$. The solvents were evaporated to dryness and the residue was purified by flash chromatography (silica gel, 0-100% ethyl acetate in hexanes) to give the product as tan colored solid (26 mg, 19%). LC/MS: 373.1 [M+1]$^+$. $^1$H NMR (300 MHz, CDCl$_3$): δ 7.91 (d, J=6.0 Hz, 2H), 7.79 (d, J=2.7 Hz, 1H), 7.67 (dd, J=9.9 & 3.0 Hz, 1H), 7.52 (d, J=9.0 Hz, 2H), 7.27 (1H), 6.71 (d, J=9.9 Hz, 1H), 6.37 (s, 1H), 3.98 (t, J=6.9 Hz, 2H), 3.05 (s, 3H), 1.90-1.83 (m, 2H), 1.02 (t, J=6.9 Hz, 3H).

Example 46: N-(4-(1-(3-(trifluoromethyl)phenyl)-1H-pyrazol-4-yl)phenyl)methanesulfonamide

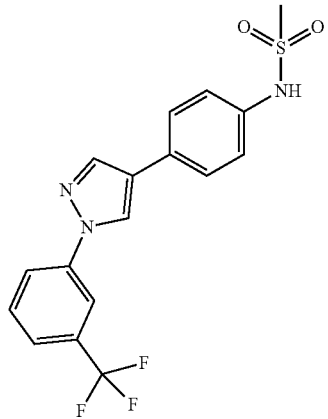 [SMILES: CS(=O)(=O)Nc1ccc(-c2cnn(-c3cccc(C(F)(F)F)c3)c2)cc1]

Step 1: 4-bromo-1-(3-(trifluoromethyl)phenyl)-1H-pyrazole

To a stirred mixture of m-bromobenzotrifluoride (0.500 g, 2.2 mmol), 3-bromopyrazole (0.327 g, 2.2 mmol), potassium carbonate (0.921 g, 6.7 mmol), in anhydrous toluene (3 mL) under argon were added trans-N,N'-dimethyl-1,2-cyclohexanediamine (0.035 mL, 0.2 mmol) and copper(I) iodide (0.021 g, 0.1 mmol,). The mixture was stirred at 120° C. for 2 hours. The reaction mixture was cooled to room temperature and quenched with water and extracted with ethyl acetate (3×25 mL). The combined organics were washed with brine and dried over MgSO$_4$. The solvents were evaporated to dryness and the residue purified by flash chromatography (silica gel, 0-60% ethyl acetate in hexane) to afford the product as colorless oil (0.13 g, 20%). $^1$H NMR (300 MHz, CDCl$_3$): δ 7.99 (s, 1H), 7.94 (s, 1H), 7.84-7.82 (m, 1H), 7.70 (s, 1H), 7.61-7.56 (m, 2H).

Step 2: N-(4-(1-(3-(trifluoromethyl)phenyl)-1H-pyrazol-4-yl)phenyl)methanesulfonamide A microwave vial was charged with 4-bromo-1-(3-(trifluoromethyl)phenyl)-1H-pyrazole (0.130 g, 0.4 mmol), N-4-methanesulfonamidephenylboronic acid (0.096 g, 0.4 mmol), dioxan (8 mL) and water (2 mL) and the flask was degassed and flushed with argon. PdCl$_2$(dppf) (0.037 g, 0.04 mmol.) was added and the reaction flask was again degassed and flushed with argon. The reaction mixture was then heated to 100° C. in a microwave for 45 minutes. The reaction was cooled to room temperature and quenched with sat. NaHCO₃ and extracted with ethyl acetate (3×50 mL). The combined organics were washed with water, brine and dried over MgSO₄. The solvents were evaporated to dryness and the residue purified by flash chromatography (silica gel, 0-60% ethyl acetate in hexane) to afford the product as white solid (125 mg, 73%). LC/MS: [M+1]⁺382.0; ¹H NMR (300 MHz, CDCl₃): δ 8.18 (s, 1H), 8.02 (s, 1H), 7.99 (s, 1H), 7.94 (d, J-8.1 Hz, 1H), 7.65-7.55 (m, 4H), 7.30-7.26 (m, 2H), 6.40 (s, 1H), 3.04 (s, 3H).

Using the procedure of Example 46 and commercially available aryl bromides in place of m-bromobenzotrifluoride for step 1 of Example 46, the following examples were prepared.

| Ex. No. | Name | Structure | Analytical data |
|---|---|---|---|
| 47 | N-(4-(1-(3-propylphenyl)-1H-pyrazol-4-yl)phenyl)methanesulfonamide | 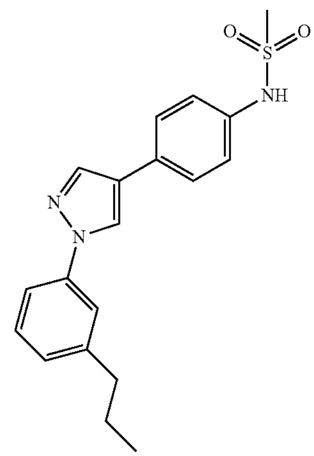 [SMILES: CCCc1cccc(-n2cc(-c3ccc(NS(C)(=O)=O)cc3)cn2)c1] | LC/MS: 356.1 [M + 1]⁺; ¹H NMR (300 MHz, CDCl₃): δ 8.14 (s, 1H), 7.96 (s, 1H0, 7.58-7.50 (s, 4H), 7.38 (t, J = 8.1 Hz, 1H), 7.27-7.25 (m, 2H), 7.14 (d, J = 8.4 Hz, 1H), 6.33 (bs, 1H), 3.04 (s, 3H), 2.67 (t, J = 7.8 Hz, 2H), 1.75-1.67 (m, 2H), 0.97 (t, J = 7.5 Hz, 3H). |
| 48 | N-(4-(1-(3-(difluoromethyl)phenyl)-1H-pyrazol-4-yl)phenyl)methanesulfonamide | 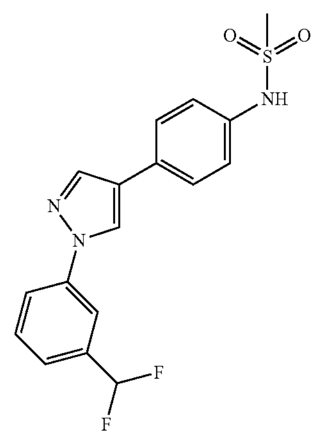 [SMILES: CS(=O)(=O)Nc1ccc(-c2cnn(-c3cccc(C(F)F)c3)c2)cc1] | LC/MS: 364.1 [M + 1]⁺; ¹H NMR (300 MHz, CDCl₃): δ 8.18 (s, 1H), 7.99 (s, 1H), 7.91 (s, 1H, 7.86 (d, J = 8.1 Hz, 1H), 7.61-7.54 (m, 3H), 7.47-7.44 (m, 1H), 7.29 (s, 1H), 6.72 (t, J = 56.1 Hz, 1H), 6.42 (s, 1H), 3.05 (s, 3H). |
| 49 | N-(4-(1-(3-(piperidin-1-yl)phenyl)-1H-pyrazol-4-yl)phenyl)methanesulfonamide | 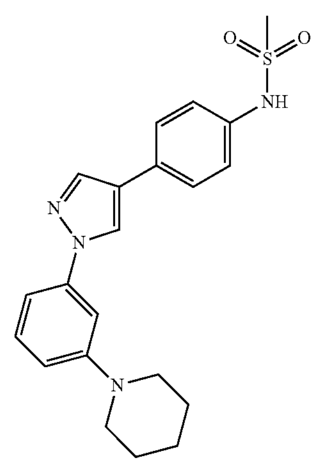 [SMILES: CS(=O)(=O)Nc1ccc(-c2cnn(-c3cccc(N4CCCCC4)c3)c2)cc1] | LC/MS: 397.2 [M + 1]⁺; ¹H NMR (300 MHz, CDCl₃): δ 8.11 (s, 1H), 7.94 (s, 1H), 7.55 (d, J = 8.1 Hz, 2H), 7.33-7.24 (m, 4H), 7.06 (d, J = 6.9 Hz, 1H), 6.87 (dd, J = 8.4 and 2.4 Hz, 1H), 6.36 (s, 1H), 3.26 (t, J = 4.8 Hz, 4H), 3.03 (s, 3H), 1.76-1.71 (m, 4H), 1.62-1.60 (m, 2H). |

| Ex. No. | Name | Structure | Analytical data |
|---|---|---|---|
| 50 | N-(4-(1-(3-isopropylphenyl)-1H-pyrazol-4-yl)phenyl)methanesulfonamide | 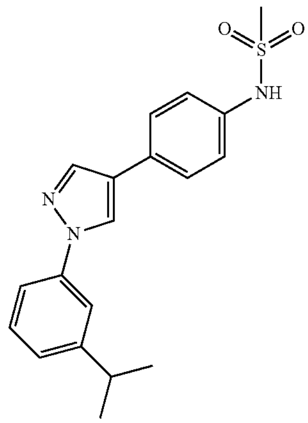 [SMILES: CC(C)c1cccc(-n2cc(-c3ccc(NS(C)(=O)=O)cc3)cn2)c1] | LC/MS: 356.1 [M + 1]+; 1H NMR (300 MHz, CDCl3): δ 8.14 (s, 1H), 7.96 (s, 1H), 7.62 (s, 1H), 7.57-7.48 (m, 3H), 7.39 (t, J = 7.5 Hz, 1H), 7.20 (d, J = 6.9 Hz, 1H), 6.34 (s, 1H), 3.04 (s, 3H), 3.04-2.97 (m, 1H), 1.31 (d, J = 6.3 Hz, 6H). |
| 51 | N-(4-(1-(3-(pyrrolidin-1-yl)phenyl)-1H-pyrazol-4-yl)phenyl)methanesulfonamide | 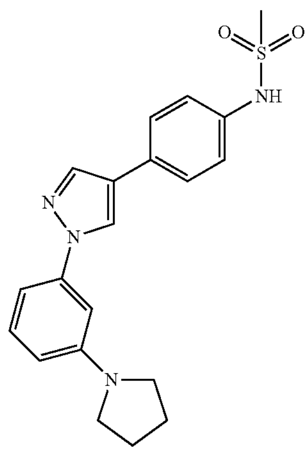 [SMILES: CS(=O)(=O)Nc1ccc(-c2cnn(-c3cccc(N4CCCC4)c3)c2)cc1] | LC/MS: 383.1 [M + 1]+; 1H NMR (300 MHz, CDCl3): δ 8.12 (s, 1H), 7.95 (s, 1H), 7.55 (d, J = 8.4 Hz, 2H), 7.31-7.24 (m, 3H), 6.95-6.90 (m, 2H), 6.51 (dd, J = 8.4 and 2.4 Hz, 1H), 6.34 (s, 1H), 3.36 (t, J = 6.3 Hz, 4H), 3.03 (s, 3H), 2.06-2.02 (m, 4H). |

Example 52: 5-(1-(2-propylpyridin-4-yl)-1H-pyrazol-4-yl)-N-(tetrahydro-2H-pyran-4-yl)pyridin-2-amine

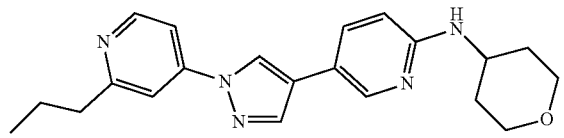 [SMILES: CCCc1cc(-n2cc(-c3ccc(NC4CCOCC4)nc3)cn2)ccn1]

To a solution of 5-(1-(2-propylpyridin-4-yl)-1H-pyrazol-4-yl)pyridin-2-amine (0.080 g, 0.3 mmol) in dichloroethane (5 mL) was added tetrahydro-4H-pyran-4-one (0.159 mL, 1.7 mmol), acetic acid (0.033 mL, 0.6 mmol) and Sodium triacetoxyborohydride (0.181 g, 0.9 mmol). The reaction was stirred at room temperature overnight. The mixture was diluted with saturated sodium bicarbonate and dichloromethane. The organic layer was washed with brine, dried over anhydrous sodium sulfate, filtered and concentrated. The residue was purified by silica gel chromatography (0-60% ethyl acetate/hexanes). The title compound was obtained as a light yellow solid (15 mg, 14.3%). LC/MS: [M+1]+, 364.3; 1HNMR (300 MHz, CDCl3): δ 8.58 (d, J=5.7 Hz, 1H), 8.33 (s, 1H), 8.14 (s, 1H), 7.95 (s, 1H), 7.61-7.56 (m, 2H), 7.45 (d, J=2.1 Hz, 1H), 6.46 (d, J=8.7 Hz, 1H), 4.48 (brs, 1H), 4.05-3.93 (m, 3H), 3.57 (t, J=11.1 Hz, 2H), 2.85 (t, J=7.7 Hz, 2H), 2.10-2.06 (m, 2H), 1.87-1.80 (m, 2H), 1.60-1.50 (m, 2H), 1.02 (t, J=7.4 Hz, 3H).

Example 53: N-isobutyl-5-(3-methyl-1-(2-propylpyridin-4-yl)-1H-pyrazol-4-yl)pyridin-2-amine

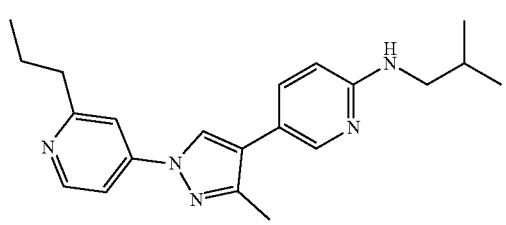 [SMILES: CCCc1cc(-n2cc(-c3ccc(NCC(C)C)nc3)c(C)n2)ccn1]

Step 1: 4-(4-bromo-3-methyl-1H-pyrazol-1-yl)-2-propylpyridine

A microwave vial was charged with 4-bromo-2-(n-propyl)pyridine (2.030 g, 10.1 mmol), 4-bromo-3-methyl-1H-pyrazole (1.776 g, 11.0 mmol), copper(I) iodide (0.386 g, 2.0 mmol), cesium carbonate (9.917 g, 30.4 mmol), and DMA (5 mL) and the sealed reaction mixture was heated to 140° C. for 16 hours. The reaction mixture was cooled to room temperature and diluted with water and extracted with ethyl acetate (2×100 mL). The organic solvents were washed with water, brine and dried over MgSO4. The solvents were evaporated to dryness and the resultant residue was purified by silica gel chromatography (0-50% ethyl acetate in hexanes). The collected fractions were dried to evaporation to give the product which contained approximately 20% by 1H NMR of its regioisomer, 4-(4-bromo-5-methyl-1H-pyrazol-1-yl)-2-propylpyridine, as colorless oil (1.4 g, 49%). LC/MS: [M+2]+282.1; $^1$HNMR (300 MHz, CDCl3): δ 8.53 (d, J=6.0 Hz, 1H), 7.97 (s, 1H), 7.44 (d, J=2.4 Hz, 1H), 7.32 (dd, J=5.7 and 2.1 Hz, 1H), 2.81 (t, J=7.5 Hz, 2H), 2.34 (s, 3H), 1.85-1.74 (m, 2H), 0.97 (t, J=7.2 Hz, 3H).

Step 2: 5-(3-methyl-1-(2-propylpyridin-4-yl)-1H-pyrazol-4-yl)pyridin-2-amine

A solution of 4-(4-bromo-3-methyl-1H-pyrazol-1-yl)-2-propylpyridine (0.600 g, 2.1 mmol), 5-(4,4,5,5-tetramethyl-1,3,2-dioxaborolan-2-yl)pyridin-2-amine (0.471 g, 2.1 mmol), and 2.0 M sodium carbonate (3.212 mL, 6.4 mmol) in DMF (10 mL) was stirred at room temperature for 5 minutes, and tetrakis(triphenylphosphine)palladium(0) (0.050 g, 0.04 mmol) was added. The flask was degassed and flushed with argon. This process was repeated three times and the reaction mixture stirred at 110° C. overnight. After cooling, the mixture was diluted with water and extracted with ethyl acetate (3×50 mL). The combined organic layer was washed with brine, dried over MgSO4 and concentrated. The residue was purified by silica gel column (0-20% methanol/dichloromethane) to afford the desired product (210 mg, 33%). LC/MS: [M+1]+294.1; $^1$H NMR (300 MHz, CDCl3): δ 8.55 (d, J=5.1 Hz, 1H), 8.18 (s, 1H), 7.99 (s, 1H), 7.54-7.52 (m, 2H), 7.41-7.39 (m, 1H), 6.60 (d, J=9.0 Hz, 1H), 4.52 (bs, 2H), 2.83 (t, J=6.9 Hz, 2H), 2.45 (s, 3H), 1.86-1.77 (m, 2H), 1.01 (t, J=6.9 Hz, 3H).

Step 3

To a solution of 5-(3-methyl-1-(2-propylpyridin-4-yl)-1H-pyrazol-4-yl)pyridin-2-amine (0.070 g, 0.2 mmol) in dichloroethane (5 mL) was added isobutyraldehyde (26 μL, 0.3 mmol), acetic acid (20 μL, 0.4 mmol) and sodium triacetoxyborohydride (0.148 g, 0.7 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The residue was purified by silica gel chromatography (0-50% ethyl acetate/hexanes). The title compound was obtained as a light yellow oil (30 mg, 36.7%). LC/MS: 350.3 [M+1]+; $^1$H NMR (300 MHz, CDCl$_3$): δ 8.54 (d, J=5.1 Hz, 1H), 8.18 (s, 1H), 7.98 (s, 1H), 7.52 (s, 1H), 7.50 (s, 1H), 7.39 (d, J=5.4 Hz, 1H), 6.47 (d, J=9.0 Hz, 1H), 4.76 (brs, 1H), 3.14 (t, J=5.9 Hz, 2H), 2.83 (t, J=7.7 Hz, 2H), 2.45 (s, 3H), 1.96-1.79 (m, 3H), 1.03-0.98 (m, 9H).

Using the procedure of Example 53 and commercially available aldehydes or ketones in place of m-isobutyraldehyde for step 3 of Example 53, the following examples were prepared:

| Ex. | Name | Structure | Analytical data |
|---|---|---|---|
| 54 | N-(cyclopropylmethyl)-5-(3-methyl-1-(2-propylpyridin-4-yl)-1H-pyrazol-4-yl)pyridin-2-amine | 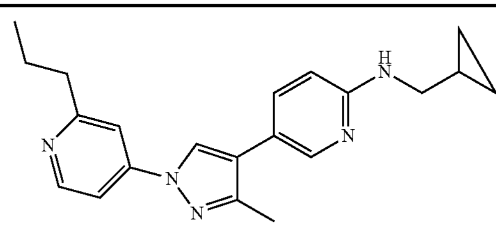 | LC-MS: 348.3 [M + 1]+; $^1$H NMR (300 MHz, CDCl$_3$): δ 8.54 (d, J = 5.4 Hz, 1H), 8.19 (s, 1H), 7.98 (s, 1H), 7.52 (s, 1H), 7.50 (s, 1H), 7.38 (d, J = 5.4 Hz, 1H), 6.47 (d, J = 8.7 Hz, 1H), 4.76 (brs, 1H), 3.18 (t, J = 5.6 Hz, 2H), 2.83 (t, J = 7.7 Hz, 2H), 2.45 (s, 3H), 1.86-1.78 (m, 2H), 1.17-1.09 (m, 1H), 1.01 (t, J = 7.2 Hz, 3H), 0.60-0.57 (m, 2H), 0.30-0.28 (m, 2H). |
| 55 | N-cyclopentyl-5-(3-methyl-1-(2-propylpyridin-4-yl)-1H-pyrazol-4-yl)pyridin-2-amine | 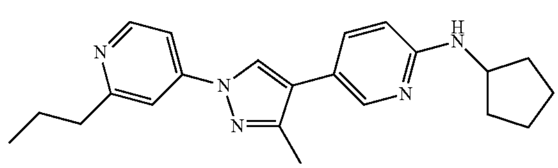 [SMILES: CCCc1cc(-n2cc(-c3ccc(NC4CCCC4)nc3)c(C)n2)ccn1] | LC/MS: [M + 1]+, 362.3; $^1$HNMR (300 MHz, CDCl3), δ 8.54 (d, J = 5.7 Hz, 1H), 8.18 (s, 1H), 7.98 (s, 1H), 7.52-7.50 (m, 2H), 7.39 (d, J = 5.1 Hz, 1H), 6.48 (d, J = 5.1 Hz, 1H), 4.70 (brs, 1H), 4.06-4.00 (m, 1H), 2.83 (t, J = 7.7 Hz, 2H), 2.45 (s, 3H), 2.10-2.06 (m, 2H), 1.86-1.70 (m, 8H), 1.01 (t, J = 7.2 Hz, 3H) |

| Ex. | Name | Structure | Analytical data |
|---|---|---|---|
| 56 | N-isopropyl-5-(3-methyl-1-(2-propylpyridin-4-yl)-1H-pyrazol-4-yl)pyridin-2-amine | 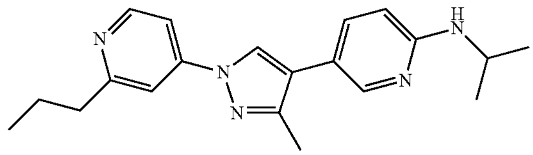 | LC/MS: [M + 1]$^+$, 362.3; $^1$HNMR (300 MHz, CDCl3), δ 8.54 (d, J = 5.7 Hz, 1H), 8.18 (s, 1H), 7.98 (s, 1H), 7.52-7.50 (m, 2H), 7.39 (d, J = 5.1 Hz, 1H), 6.48 (d, J = 5.1 Hz, 1H), 4.70 (brs, 1H), 4.06-4.00 (m, 1H), 2.83 (t, J = 7.7 Hz, 2H), 2.45 (s, 3H), 2.10-2.06 (m, 2H), 1.86-1.70 (m, 8H), 1.01 (t, J = 7.2 Hz, 3H). |
| 57 | N-cyclobutyl-5-(3-methyl-1-(2-propylpyridin-4-yl)-1H-pyrazol-4-yl)pyridin-2-amine | 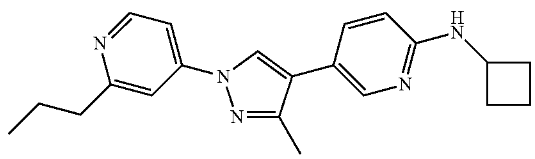 [SMILES: CCCc1cc(-n2cc(-c3ccc(NC4CCC4)nc3)c(C)n2)ccn1] | LC/MS: [M + 1]$^+$, 348.3; $^1$HNMR (300 MHz, CDCl3), δ 8.54 (d, J = 5.7 Hz, 1H), 8.17 (s, 1H), 7.97 (s, 1H), 7.52-7.40 (m, 3H), 6.40 (d, J = 5.1 Hz, 1H), 4.90 (brs, 1H), 4.19-4.16 (m, 1H), 2.83 (t, J = 7.7 Hz, 2H), 2.48-2.45 (m, 5H), 1.94-1.78 (m, 6H), 1.01 (t, J = 7.2 Hz, 3H) |

Example 58: 1,1,1-trifluoro-N-(5-(3-methyl-1-(2-propylpyridin-4-yl)-1H-pyrazol-4-yl)pyridin-2-yl)methanesulfonamide

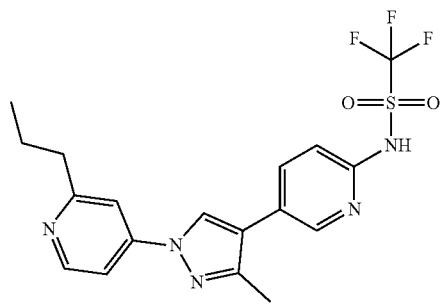 [SMILES: CCCc1cc(-n2cc(-c3ccc(NS(=O)(=O)C(F)(F)F)nc3)c(C)n2)ccn1]

Pyridine (0.046 mL, 0.6 mmol) was added dropwise to a solution of triflic anhydride (0.097 mL, 0.6 mmol) at 0° C. under nitrogen in dichloromethane (5 mL) over 10 minutes. The reaction mixture was stirred at the same temperature for 30 minutes. A solution of 5-(3-methyl-1-(2-propylpyridin-4-yl)-1H-pyrazol-4-yl)pyridin-2-amine (0.060 g, 0.2 mmol) in dichloromethane (3 mL) was added dropwise over 20 minutes. The reaction was then allowed to come to room temperature and stirred for 1 hour. Upon completion, ice water was added and the dichloromethane layer was separated. The aqueous was extracted with dichloromethane (2×50 mL). The dichloromethane extracts were combined and dried over anhydrous sodium sulfate and concentrated under reduced pressure. The resulting residue was purified by reverse phase Prep HPLC. The title compound was obtained as a light yellow solid (15 mg, 17.2%). LC/MS: [M+1]$^+$, 426.1; $^1$HNMR (300 MHz, DMSO-d6): δ 8.60 (d, J=6.0 Hz, 1H), 8.38 (s, 1H), 8.16 (s, 1H), 8.08-7.98 (m, 2H), 7.54 (s, 1H), 7.45 (dd, J=6.0 and 1.8 Hz, 1H), 2.87 (t, J=8.0 Hz, 2H), 2.51 (s, 3H), 1.88-1.80 (m, 2H), 1.02 (t, J=7.7 Hz, 3H).

Example 59: N-(3-chloro-4-(1-(6-oxo-1-propyl-1,6-dihydropyridin-3-yl)-1H-pyrazol-4-yl)phenyl)cyclopropanesulfonamide

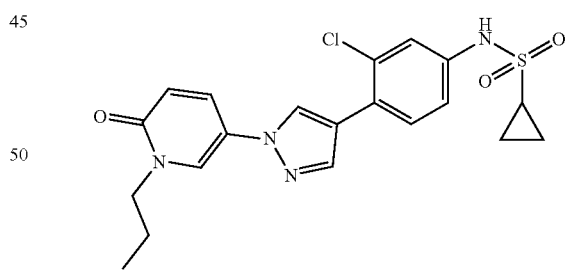

Step 1: 5-(4-(2-chloro-4-nitrophenyl)-1H-pyrazol-1-yl)-1-propylpyridin-2(1H)-one A microwave vial was charged with 5-(4-bromo-1H-pyrazol-1-yl)-1-propylpyridin-2(1H)-one (0.250 g, 0.9 mmol), (2-chloro-4-nitrophenyl)boronic acid (0.196 g, 1.0 mmol), and dioxan (8 mL) and water (2 mL) and the flask was degassed and flushed with argon. PdCl$_2$(dppf) (0.073 g, 0.1 mmol), was added and the reaction flask was again degassed and flushed with argon. The reaction mixture was then heated to 100° C. in a microwave for 45 minutes. The reaction was cooled to room temperature and quenched with sat. NaHCO₃ and extracted with ethyl acetate (3×50 mL). The combined organics were washed with water, brine and dried over MgSO₄. The solvents were evaporated to dryness and the residue purified by flash chromatography (silica gel, 0-60% ethyl acetates in hexanes) to afford the product as yellow solid (170 mg, 54%). LC/MS: [M+1]+, 359.1; ¹H NMR (300 MHz, CDCl₃): δ 8.37 (d, J=3.0 Hz, 1H), 8.24 (s, 1H), 8.18-8.14 (m, 1H), 8.05 (s, 1H), 7.82 (d, J=3.0 Hz, 1H), 7.69-7.65 (m, 2H), 6.70 (d, J=9.3 Hz, 11H), 3.98 (t, J=7.5 Hz, 2H), 1.89-1.82 (m, 2H), 1.01 (t, J=7.5 Hz, 3H).

Step 2: 5-(4-(4-amino-2-chlorophenyl)-1H-pyrazol-1-yl)-1-propylpyridin-2(1H)-one A round bottom flask was charged with 5-(4-(2-chloro-4-nitrophenyl)-1H-pyrazol-1-yl)-1-propylpyridin-2(1H)-one (0.170 g, 0.5 mmol), ethanol (20 mL) and Tin(II) chloride (0.328 g, 1.7 mmol), was added and the reaction mixture heated to 85° C. for 45 min. The reaction mixture was cooled and poured into 50 mL of 2M KOH. This was extracted with IPA/CHCl3 (1:3, 3×50 mL). The combined organics were washed with brine and dried over MgSO4. The solvents were evaporated to give the product as pale yellow solid which was used in the next reaction without further purification (110 mg, 70%). LC/MS: [M+1]⁺, 329.2; ¹H NMR (300 MHz, DMSO-d6): δ 8.42 (s, 1H), 8.26 (d, J=3.0 Hz, 1H), 7.94 (dd, J=7.2 and 3.0 Hz, 1H), 7.90 (s, 1H), 7.25 (d, J=8.7 Hz, 1H), 6.68 (d, J=2.4 Hz, 1H), 6.55 (dd, J=8.1 and 2.4 Hz, 1H), 6.51 (d, J=9.9 Hz, 1H), 5.44 (s, 2H), 3.8 (t, J=7.8 Hz, 2H), 1.73-1.63 (m, 2H), 0.87 (t, J=6.9 Hz, 3H).

Step 3: N-(3-chloro-4-(1-(6-oxo-1-propyl-1,6-dihydropyridin-3-yl)-1H-pyrazol-4-yl)phenyl)cyclopropanesulfonamide A round bottom flask was charged with 5-(4-(4-amino-2-chlorophenyl)-1H-pyrazol-1-yl)-1-propylpyridin-2(1H)-one (0.110 g, 0.3 mmol), dichloromethane (20 mL) and flask was cooled to 0° C. and pyridine (81 µL, 1.0 mmol) followed by cyclopropanesulfonyl chloride (102 µL, 1.0 mmol) were added under argon. The reaction was stirred over night at room temperature. Another portion of Cyclopropanesulfonyl chloride (102 µL, 1.0 mmol) was added followed by addition of DMAP (20 mg). The reaction mixture was stirred for another 24 hours. The reaction mixture was quenched with water and extracted with dichloromethane (3×25 mL). The combined organics were washed with brine and dried over MgSO₄. The solvents were concentrated to dryness and purified by reverse phase HPLC to give the product as white solid (35 mg, 24%). LC/MS: [M+1]+: 433.1; ¹H NMR (300 MHz, CDCl₃): δ 8.07 (s, 1H), 7.93 (s, 1H), 7.79 (d, J=3.0 Hz, 1H), 7.67 (dd, J=9.9 and 3.0 Hz, 1H), 7.46 (d, J=8.1 Hz, 1H), 7.40 (d, J=2.4 Hz, 1H), 7.22 (dd, J=8.4 and 2.4 Hz, 1H), 6.70 (d, J=9.9 Hz, 1H), 6.47 (bs, 1H), 3.98 (t, J=7.5 Hz, 2H), 2.57-2.49 (m, 1H), 1.89-1.81 (m, 2H), 1.27-1.21 (m, 2H), 1.06-0.98 (m, 5H).

Example 60: N-(3-fluoro-4-(1-(6-oxo-1-propyl-1,6-dihydropyridin-3-yl)-1H-pyrazol-4-yl)phenyl)cyclopropanesulfonamide

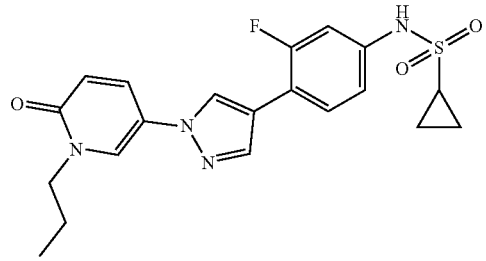 [SMILES: CCCn1cc(-n2cc(-c3ccc(NS(=O)(=O)C4CC4)cc3F)cn2)ccc1=O]

Step 1: 5-(4-(4-amino-2-fluorophenyl)-1H-pyrazol-1-yl)-1-propylpyridin-2(1H)-one A microwave vial was charged with 5-(4-bromo-1H-pyrazol-1-yl)-1-propylpyridin-2(1H)-one (0.200 g, 0.7 mmol), 3-fluoro-4-(4,4,5,5-tetramethyl-1,3,2-dioxaborolan-2-yl)aniline (0.168 g, 0.7 mmol), and dioxan (8 mL) and water (2 mL) and the flask was degassed and flushed with argon. PdCl₂(dppf) (0.058 g, 0.1 mmol) was added and the reaction flask was again degassed and flushed with argon. The reaction mixture was then heated to 100° C. in a microwave for 2 hours. The reaction was cooled to room temperature and quenched with sat. NaHCO₃ and extracted with ethyl acetate (3×50 mL). The combined organics were washed with water, brine and dried over MgSO₄. The solvents were evaporated to dryness and the residue purified by flash chromatography (silica gel, 0-100% ethyl acetates in hexanes) to afford the product as pale yellow oil (100 mg, 45%). LC/MS: [M+1]⁺: 313.1; ¹HNMR (300 MHz, CDCl₃): δ 7.92-7.90 (m, 2H), 7.75 (d, J=3.0 Hz, 1H), 7.66 (dd, J=9.9 and 3.0 Hz, 1H), 7.32 (t, J=8.7 Hz, 1H), 6.66 (d, J+9.9 Hz, 1H), 6.50-6.43 (m, 2H), 3.94 (t, J=6.9 Hz, 2H), 3.87 (bs, 2H), 1.86-1.78 (m, 2H), 0.98 (t, J=7.5 Hz, 3H).

Step 2: N-(3-fluoro-4-(1-(6-oxo-1-propyl-1,6-dihydropyridin-3-yl)-1H-pyrazol-4-yl)phenyl)cyclopropanesulfonamide A round bottom flask was charged with 5-(4-(4-amino-2-fluorophenyl)-1H-pyrazol-1-yl)-1-propylpyridin-2(1H)-one (0.100 g, 0.3 mmol), dichloromethane (20 mL) and flask was cooled to 0° C. and pyridine (74 µL, 0.9 mmol) followed by cyclopropanesulfonyl chloride (93 µL, 0.9 mmol) were added under argon. The reaction was stirred over night at room temperature. Another portion of cyclopropanesulfonyl chloride (93 µL, 0.9 mmol) was added followed by addition of DMAP (20 mg). The reaction mixture was stirred for another 24 hours. The reaction mixture was quenched with water and extracted with DCM (3×25 mL). The combined organics were washed with brine and dried over MgSO₄. The solvents were concentrated to dryness and the residue purified by reverse phase HPLC to give the product as pale yellow solid (35 mg, 23%). LC/MS: [M+1]+: 417.1; ¹H NMR (300 MHz, CD₃OD): δ 8.43 (s, 1H), 8.21 (d, J=2.7 Hz, 1H), 8.08 (s, 1H), 8.01 (dd, J=9.3 and 3.0 Hz, 1H), 7.67 (t, J=8.4 Hz, 1H), 7.18-7.10 (m, 2H), 6.68 (d, J=9.9 Hz, 1H), 4.04 (t, J=6.9 Hz, 2H), 2.64-2.56 (m, 1H), 1.87-1.77 (m, 2H), 1.11-0.94 (m, 7H).

Example 61: N-(3-cyano-4-(1-(6-oxo-1-propyl-1,6-dihydropyridin-3-yl)-1H-pyrazol-4-yl)phenyl)methanesulfonamide

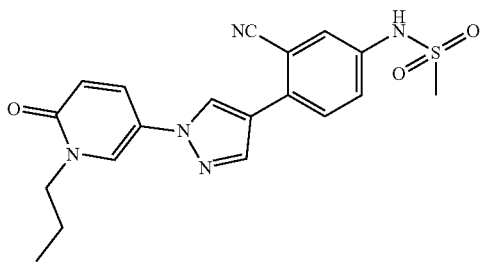 [SMILES: CCCn1cc(-n2cc(-c3ccc(NS(C)(=O)=O)cc3C#N)cn2)ccc1=O]

Step 1: 1-propyl-5-(4-(4,4,5,5-tetramethyl-1,3,2-dioxaborolan-2-yl)-1H-pyrazol-1-yl)pyridin-2(1H)-one A round bottom flask was charged with 5-(4-bromo-1H-pyrazol-1-yl)-1-propylpyridin-2(1H)-one (0.800 g, 2.8 mmol), 4,4,4',4',5,5,5',5'-octamethyl-2,2'-bi(1,3,2-dioxaborolane) (1.440 g, 5.7 mmol), Potassium Acetate (0.835 g, 8.5 mmol) and DMSO (5 mL) and the flask was degassed and flushed with argon. PdCl$_2$(dppf) (0.116 g, 0.1 mmol) was added and the reaction flask was again degassed and flushed with argon. The reaction mixture was then heated to 70° C. overnight under argon. The reaction mixture was cooled to room temperature and quenched with saturated NaHCO3 solution and extracted with ethyl acetate (3×50 mL). The combined organics were washed with water, brine and dried over MgSO4. The solvents were concentrated to dryness and the residue purified by flash chromatography (silica, 0-100% ethyl acetate in hexanes) to get the product as pale brown oil (600 mg, 64.3%). LC/MS: [M+1]:330.3; 1H NMR (300 MHz, CDCl3): δ 7.97 (s, 1H), 7.90 (s, 1H), 7.76 (d, J=3.0 Hz, 1H), 7.61 (dd, J=9.9 and 3.0 Hz, 1H), 6.64 (d, J=9.9 Hz, 1H), 3.93 (t, J=7.8 Hz, 2H), 1.87-1.76 (m, 2H), 1.32 (s, 12H), 0.96 (t, J=7.8 Hz, 3H).

Step 2: 5-nitro-2-(1-(6-oxo-1-propyl-1,6-dihydropyridin-3-yl)-1H-pyrazol-4-yl)benzonitrile A microwave vial was charged with 1-propyl-5-(4-(4,4,5,5-tetramethyl-1,3,2-dioxaborolan-2-yl)-1H-pyrazol-1-yl)pyridin-2(1H)-one (0.200 g, 0.6 mmol), 2-bromo-5-nitrobenzonitrile (0.180 g, 0.8 mmol), and dioxan (8 mL) and water (2 mL) and the flask was degassed and flushed with argon. PdCl$_2$(dppf) (0.058 g, 0.1 mmol) was added and the reaction flask was again degassed and flushed with argon. The reaction mixture was then heated to 100° C. in a microwave for 45 minutes. The reaction was cooled to room temperature and quenched with sat. NaHCO$_3$ and extracted with ethyl acetate (3×50 mL). The combined organics were washed with water, brine and dried over MgSO$_4$. The solvents were evaporated to dryness and the residue purified by flash chromatography (silica gel, 0-60% ethyl acetates in hexanes) to afford the product as yellow solid (170 mg, 80%). LC/MS: [M+1]$^+$, 350.2; $^1$H NMR (300 MHz, CDCl$_3$): δ 8.60 (d, J=2.4 Hz, 1H), 8.47 (t, J=2.4 Hz, 1H), 8.44 (d, J=2.4 Hz, 1H), 8.15 (s, 1H), 7.84-7.82 (m, 2H), 7.70-7.65 (m, 1H), 6.71 (d, J=9.9 Hz, 1H), 3.98 (t, J=7.5 Hz, 2H), 1.89-1.81 (m, 2H), 1.02 (t, J=6.9 Hz, 3H).

Step 3: 5-amino-2-(1-(6-oxo-1-propyl-1,6-dihydropyridin-3-yl)-1H-pyrazol-4-yl)benzonitrile A round bottom flask was charged with 5-nitro-2-(1-(6-oxo-1-propyl-1,6-dihydropyridin-3-yl)-1H-pyrazol-4-yl)benzonitrile (0.170 g, 0.5 mmol), ethanol (20 mL) and Tin(II) chloride (0.328 g, 1.7 mmol) was added and the reaction mixture heated to 85° C. for 45 min. The reaction mixture was cooled and poured into 50 mL of 2M KOH. This was extracted with IPA/CHCl$_3$ (1:3, 3×50 mL). The combined organics were washed with brine and dried over MgSO4. The solvents were evaporated to give the product as pale yellow solid which was used in the next reaction without further purification (120 mg, 77%). LC/MS: [M+1]$^+$, 320.2; $^1$H NMR (300 MHz, CDCl$_3$): δ 8.19 (s, 1H), 8.12 (s, 1H), 7.76 (d, J=3.0 Hz, 1H), 7.69-7.65 (m, 1H), 7.38 (d, J=8.1 Hz, 1H), 6.98 (d, J=2.4 Hz, 1H), 6.91 (dd, J=8.7 and 3.0 Hz, 1H), 6.68 (d, J=9.6 Hz, 1H), 3.99-3.91 (m, 4H), 1.89-1.80 (m, 2H), 1.00 (t, J=7.5 Hz, 3H).

Step 4: N-(3-cyano-4-(1-(6-oxo-1-propyl-1,6-dihydropyridin-3-yl)-1H-pyrazol-4-yl)phenyl)methanesulfonamide A round bottom flask was charged with 5-amino-2-(1-(6-oxo-1-propyl-1,6-dihydropyridin-3-yl)-1H-pyrazol-4-yl)benzonitrile (0.120 g, 0.4 mmol), dichloromethane (20 mL) and flask was cooled to 0° C. and pyridine (89 μL, 1.1 mmol) followed by Methanesulfonyl chloride (112 μL, 1.3 mmol) were added under argon. The reaction was stirred for 2 hours at room temperature. The reaction mixture was quenched with water and extracted with dichloromethane (3×25 mL). Product precipitated out from the organic extract which was collected by filtration and dried under vacuum over night to give the product as tan colored solid (53 mg, 35%). LC/MS: [M+1]+: 398.2; $^1$H NMR (300 MHz, DMSO-d6): δ 10.21 (s, 1H), 8.69 (s, 1H), 8.30 (d, J=2.4 Hz, 1H), 8.15 (s, 1H), 7.93 (dd, J=9.6 and 3.0 Hz, 1H, 7.73 (d, J=8.7 HZ, 1H), 7.58 (d, J=1.8 Hz, 1H), 7.51 (dd, J=8.7 and 2.4 Hz, 1H), 6.55 (d, J=9.6 Hz, 1H), 3.90 (t, J=6.9 Hz, 2H), 3.11 (s, 3H), 1.73-1.65 (m, 2H), 0.88 (t, J=7.5 Hz, 3H).

Example 62: N-(4-(1-(6-oxo-1-propyl-1,6-dihydropyridin-3-yl)-1H-pyrazol-4-yl)-3-(trifluoromethyl)phenyl)methanesulfonamide

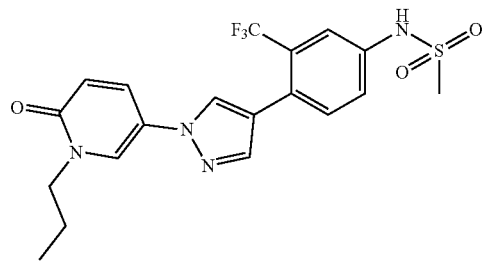 [SMILES: CCCn1cc(-n2cc(-c3ccc(NS(C)(=O)=O)cc3C(F)(F)F)cn2)ccc1=O]

Step 1: 5-(4-(4-nitro-2-(trifluoromethyl)phenyl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl)

pyridin-2(1H)-one (0.200 g, 0.6 mmol), 2-bromo-5-nitrobenzotrifluoride (0.180 g, 0.8 mmol), and dioxan (8 mL) and water (2 mL) and the flask was degassed and flushed with argon. PdCl$_2$(dppf) (0.050 g, 0.1 mmol) was added and the reaction flask was again degassed and flushed with argon. The reaction mixture was then heated to 100° C. in a microwave for 45 minutes. The reaction was cooled to room temperature and quenched with sat. NaHCO3 and extracted with ethyl acetate (3×50 mL). The combined organics were washed with water, brine and dried over MgSO4. The solvents were evaporated to dryness and the residue purified by flash chromatography (silica gel, 0-60% ethyl acetates in hexanes) to afford the product as yellow solid (170 mg, 71%). LC/MS: [M+1]$^+$, 393.3; $^1$H NMR (300 MHz, CDCl$_3$): δ 8.66 (d, J=2.4 Hz, 1H), 8.43 (dd, J=9.0 and 2.4 Hz, 1H), 7.91 (s, 1H), 7.85 (s, 1H), 7.81 (d, J=3.0 Hz, 1H), 7.70-7.62 (m, 2H), 6.70 (d, J=9.3 Hz, 1H), 3.98 (t, J=7.5 Hz, 2H), 1.90-1.81 (m, 2H), 1.02 (t, J=6.9 Hz, 3H).

Step 2: 5-(4-(4-amino-2-(trifluoromethyl)phenyl)-1H-pyrazol-1-yl)-1-propylpyridin-2(1H)-one A round bottom flask was charged with 5-(4-(4-nitro-2-(trifluoromethyl)phenyl)-1H-pyrazol-1-yl)-1-propylpyridin-2(1H)-one (0.170 g, 0.4 mmol), ethanol (20 mL) and Tin(II) chloride (0.328 g, 1.7 mmol) was added and the reaction mixture heated to 85° C. for 45 min. The reaction mixture was cooled and poured into 50 mL of 2M KOH. This was extracted with IPA/CHCl3 (1:3, 3×50 mL). The combined organics were washed with brine and dried over MgSO4. The solvents were evaporated to give the product as pale yellow solid which was used in the next reaction without further purification (120 mg, 76%). LC/MS: [M+1]$^+$, 363.3; $^1$H NMR (300 MHz, CDCl$_3$): δ 7.77 (d, J=3.0 Hz, 1H), 7.70 (d, J=4.5 Hz, 2H), 7.64 (dd, J=9.3 and 3.0 Hz, 1H), 7.20 (d, J=8.1 Hz, 1H), 7.04 (d, J=2.4 Hz, 1H), 6.83 (dd, J=8.4 and 2.4 Hz, 1H), 6.67 (d, J=10.2 Hz, 1H), 3.96 (t, J=7.8 Hz, 2H), 3.92 (bs, 2H), 1.88-1.80 (m, 2H), 1.0 (t, J=7.5 Hz, 3H).

Step 3: N-(4-(1-(6-oxo-1-propyl-1,6-dihydropyridin-3-yl)-1H-pyrazol-4-yl)-3-(trifluoromethyl)phenyl)methanesulfonamide A round bottom flask was charged with 5-(4-(4-amino-2-(trifluoromethyl)phenyl)-1H-pyrazol-1-yl)-1-propylpyridin-2(1H)-one (0.120 g, 0.3 mmol), DCM (20 mL) and flask was cooled to 0° C. and pyridine (89 μL, 1.1 mmol), followed by Methanesulfonyl chloride (112 μL, 1.3 mmol) were added under argon. The reaction was stirred for 2 hours at room temperature. The reaction mixture was quenched with water and extracted with dichloromethane (3×25 mL). Precipitate from the organic extract was collected by filtration and dried to give the product as a yellow solid (43 mg, 29%). LC/MS: [M+1]+: 441.2; $^1$H NMR (300 MHz, DMSO-d6): δ 10.21 (s, 1H), 8.39 (s, 1H), 8.29 (d, J=2.7 Hz, 1H), 7.94 (dd, J=9.9 and 3.0 Hz, 1H), 7.77 (s, 1H), 7.61 (d, J=1.8 Hz, 1H), 7.57-7.49 (m, 2H), 6.53 (d, J=9.9 Hz, 1H), 3.89 (t, J=7.2 Hz, 2H), 3.08 (s, 3H), 1.72-1.64 (m, 2H), 0.872 (t, J=6.9 Hz, 3H).

Example 63: N-(3-chloro-4-(1-(6-oxo-1-propyl-1,6-dihydropyridin-3-yl)-1H-pyrazol-4-yl)phenyl)ethanesulfonamide

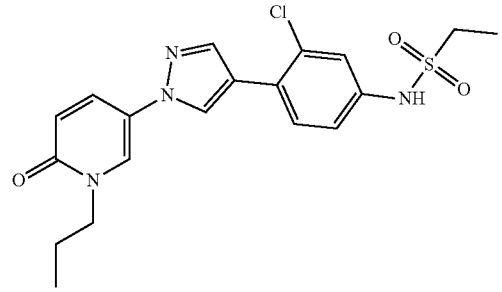 [SMILES: CCCn1cc(-n2cc(-c3ccc(NS(=O)(=O)CC)cc3Cl)cn2)ccc1=O]

Step 1: 5-(4-(2-chloro-4-nitrophenyl)-1H-pyrazol-1-yl)-1-propylpyridin-2(1H)-one A micro wave vial was charged with 5-(4-bromo-1H-pyrazol-1-yl)-1-propylpyridin-2(1H)-one (0.400 g, 1.4 mmol), (2-chloro-4-nitrophenyl)boronic acid (0.29 g, 1.4 mmol), potassium carbonate (0.59 g, 4.3 mmol) and dioxan (12 mL) and water (3 mL) and the flask was degassed and flushed with argon. PdCl$_2$(dppf) (0.116 g, 0.1 mmol) was added and the reaction flask was again degassed and flushed with argon. The reaction mixture was then heated to 100° C. in a microwave for 45 minutes. The reaction was cooled to room temperature and quenched with sat. NaHCO$_3$ and extracted with ethyl acetate (3×50 mL). The combined organics were washed with water, brine and dried over MgSO$_4$. The solvents were evaporated to dryness and the residue purified by flash chromatography (12 g silica gel, 0-60% ethyl acetates in hexanes) to afford the product as yellow solid (160 mg, 32%). $^1$H NMR (300 MHz, CDCl$_3$): δ 8.39 (d, J=2.7 Hz, 1H), 8.25 (s, 1H), 8.17 (dd, J=9.9 and 3.0 Hz, 1H), 8.07 (s, 1H), 7.83 (d, J=3.6 Hz, 1H), 7.72-7.66 (m, 2H), 6.72 (d, J=9.6 Hz, 1H), 3.99 (t, J=7.8 Hz, 2H), 1.91-1.83 (m, 2H), 1.03 (t, J=7.5 Hz, 3H).

Step 2: 5-(4-(4-amino-2-chlorophenyl)-1H-pyrazol-1-yl)-1-propylpyridin-2(1H)-one A round bottom flask was charged with 5-(4-(2-chloro-4-nitrophenyl)-1H-pyrazol-1-yl)-1-propylpyridin-2(1H)-one (0.160 g, 0.4 mmol), ethanol (20 mL) and tin(II) chloride (0.423 g, 2.2 mmol) was added and the reaction mixture heated to 85° C. for 45 min. The reaction mixture was cooled and poured into 20 mL of 2 M KOH. This was extracted with isopropanol/chloroform (1:3, 3×50 mL). The combined organics were washed with brine and dried over MgSO$_4$. The solvents were evaporated to give the product as pale yellow solid which was used in the next reaction without further purification. LC/MS: [M+1]+329.2; $^1$HNMR (300 MHz, CDCl$_3$): δ 7.98 (s, 1H), 7.87 (s, 1H), 7.78 (d, J=3.0 Hz, 1H), 7.67 (dd, J=7.2 and 3.0 Hz, 1H), 7.25 (s, 1H), 6.80 (d, J=2.4 Hz, 1H), 6.69-6.61 (m, 2H), 3.97 (t, J=7.8 Hz, 2H), 3.80 (bs, 2H), 1.87-1.81 (m, 2H), 1.00 (t, J=6.9 Hz, 3H).

Step 3: N-(3-chloro-4-(1-(6-oxo-1-propyl-1,6-dihydropyridin-3-yl)-1H-pyrazol-4-yl)phenyl)ethanesulfonamide A round bottom flask was charged with 5-(4-(4-amino-2-chlorophenyl)-1H-pyrazol-1-yl)-1-propylpyridin-2(1H)-one (0.09 g, 0.2 mmol), dichloromethane (15 mL) and flask was cooled to 0° C. and pyridine (60 μL, 0.7 mmol), followed by ethanesulfonyl chloride (125 μL, 1.2 mmol), were added under argon. The reaction was stirred at room temperature overnight. The reaction mixture was quenched with water and extracted with dichloromethane (3×25 mL). The solvents were removed under reduced pressure. The solid precipitated was collected by filtration and dried in a vacuum oven over night to give the product as tan colored solid (67 mg, 65%). LC/MS: [M+1]+: 421.3; $^1$H NMR (300 MHz, DMSO-$d_6$): δ 10.09 (s, 1H), 8.61 (s, 1H), 8.31 (d, J=3.0 Hz, 1H), 8.06 (s, 1H), 7.97 (dd, J=9.9 and 2.7 Hz, 1H), 7.62 (d, J=8.7 Hz, 1H), 7.36 (s, 1H), 7.23 (d, J=8.7 Hz, 1H), 6.54 (d, J=9.9 Hz, 1H), 3.91 (t, J=6.9 Hz, 2H), 3.17 (q, J=7.4 Hz, 2H), 1.72-1.69 (m, 2H), 1.20 (t, J=6.9 Hz, 3H), 0.90 (t, J=7.5 Hz, 3H).

Using the general procedure of Example 63 the following examples were prepared.

| Example No. | Structure | $^1$H NMR (DMSO-$d_6$, 300 MHz) | LC/MS [M + 1] |
|---|---|---|---|
| 64 | 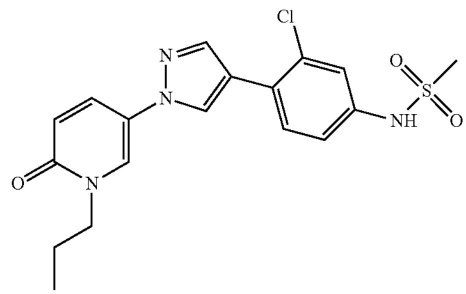 [SMILES: CCCn1cc(-n2cc(-c3ccc(NS(C)(=O)=O)cc3Cl)cn2)ccc1=O] | δ 10.04 (s, 1H), 8.62 (s, 1H), 8.31 (d, J = 2.4 Hz, 1H), 8.07 (s, 1H), 7.97 (dd, J = 9.3 and 2.7 Hz, 1H), 7.63 (d, J = 9.0 Hz, 1H), 7.35 (s, 1H), 7.23 (dd, J = 8.1 and 2.1 Hz, 1H), 6.54 (d, J = 9.3 Hz, 1H), 3.92 (t, J = 6.9 Hz, 2H), 3.07 (s, 3H), 1.74-1.67 (m, 2H), 0.90 (t, J = 7.5 Hz, 3H). | 407.2 |
| 65 | 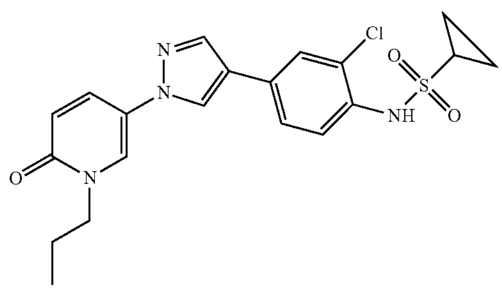 [SMILES: CCCn1cc(-n2cc(-c3ccc(NS(=O)(=O)C4CC4)c(Cl)c3)cn2)ccc1=O] | δ 8.50 (s, 1H), 8.18 (d, J = 2.4 Hz, 1H), 8.08 (s, 1H), 8.00 (dd, J = 9.3 and 2.4 Hz, 1H), 7.77 (s, 1H), 7.58 (s, 2H), 6.68 (d, J = 9.9 Hz, 1H), 4.04 (t, J = 6.9 Hz, 2H), 2.69-2.60 (m, 1H), 1.87-1.80 (m, 2H), 1.29 (t, J = 6.9 Hz, 2H), 1.02-0.96 (m, 5H). (CD$_3$OD) | 433.3 |
| 66 | 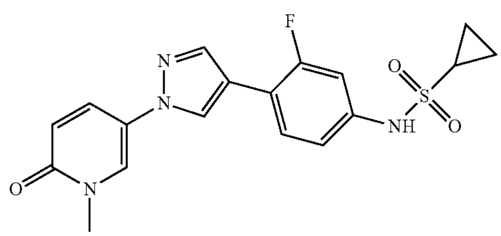 [SMILES: Cn1cc(-n2cc(-c3ccc(NS(=O)(=O)C4CC4)cc3F)cn2)ccc1=O] | δ 10.02 (s, 1H), 8.57 (s, 1H), 8.34 (d, J = 2.7 Hz, 1H), 8.10 (s, 1H), 7.96 (dd, J = 9.9 and 3.0 Hz, 1H), 7.72 (t, J = 8.7 Hz, 1H), 7.14-7.07 (m, 2H), 6.53 (d, J = 9.3 Hz, 1H), 3.49 (s, 3H), 2.73-2.69 (m, 1H), 0.96-0.94 (m, 4H). | 389.1 |
| 67 | 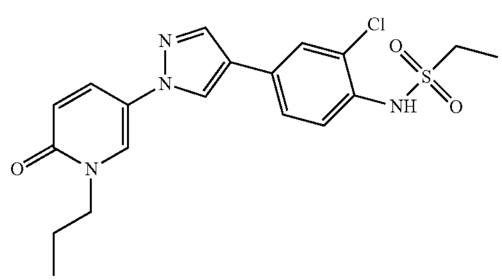 [SMILES: CCCn1cc(-n2cc(-c3ccc(NS(=O)(=O)CC)c(Cl)c3)cn2)ccc1=O] | δ 8.50 (s, 1H), 8.19 (s, 1H), 8.08 (s, 1H), 8.00 (dd, J = 9.9 and 3.0 Hz, 1H), 7.77 (s, 1H), 7.59 (s, 2H), 6.68 (d, J = 9.9 Hz, 1H), 4.04 (t, J = 6.9 Hz, 2H), 3.11 (q, J = 7.8 Hz, 2H), 1.86-1.81 (m, 2H), 1.37 (t, J = 7.4 Hz, 3H), 1.00 (t, J = 7.2 Hz, 3H). (CD$_3$OD) | 421.3 |

-continued

| Example No. | Structure | ¹H NMR (DMSO-d₆, 300 MHz) | LC/MS [M + 1] |
|---|---|---|---|
| 68 | 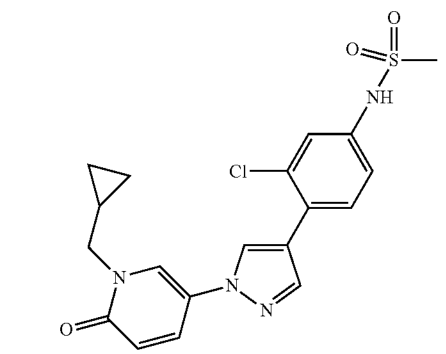 [SMILES: CS(=O)(=O)Nc1ccc(-c2cnn(-c3ccc(=O)n(CC4CC4)c3)c2)c(Cl)c1] | δ 10.08 (s, 1H), 8.65 (s, 1H), 8.38 (d, J = 3.0 Hz, 1H), 8.11 (s, 1H), 8.04-8.00 (m, 1H), 7.67 (d, J = 3.0 Hz, 1H), 7.39 (d, J = 1.5 Hz, 1H), 7.29-7.25 (m, 1H), 6.60 (d, J = 9.0 Hz, 1H), 3.86 (d, J = 6.9 Hz, 2H), 3.11 (s, 3H), 1.34 (s, 1H), 0.55-0.47 (m, 4H). | 419.3 |
| 69 | 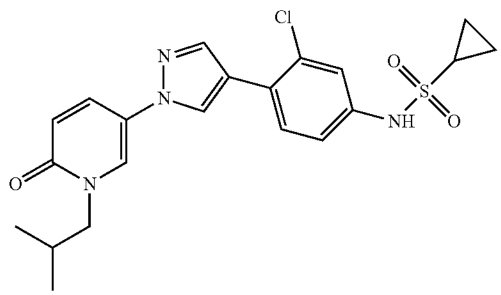 [SMILES: CC(C)Cn1cc(-n2cc(-c3ccc(NS(=O)(=O)C4CC4)cc3Cl)cn2)ccc1=O] | δ 8.42 (s, 1H), 8.16 (d, J = 2.7 Hz, 1H), 8.03-7.99 (m, 2H), 7.56 (d, J = 8.4 Hz, 1H), 7.42 (d, J = 1.8 Hz, 1H), 7.27 (dd, J = 8.7 and 1.8 Hz, 1H), 6.69 (d, J = 9.3 Hz, 1H), 3.90 (d, J = 7.2 Hz, 2H), 2.63-2.58 (m, 1H), 2.25-2.20 (m, 1H), 1.08-.97 (m, 10 H). (CD₃OD) | 447.1 |
| 70 | 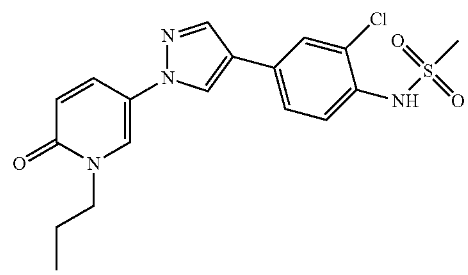 | δ 8.51 (s, 1H), 8.20 (d, J = 3.0 Hz, 1H), 8.08 (s, 1H), 8.00 (dd, J = 9.9 and 3.0 Hz, 1H), 7.79 (d, J = 1.5 Hz, 1H), 7.62-7.55 (m, 2H), 6.68 (d, J = 9.3 Hz, 1H), 4.04 (t, J = 6.9 Hz, 2H), 3.01 (s, 3H), 1.88-1.80 (m, 2H), 1.00 (t, J = 7.5 Hz, 3H). (CD₃OD). | 407.1 |
| 71 | 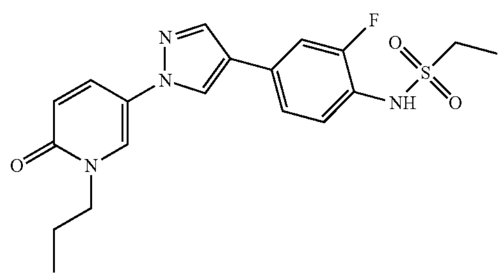 [SMILES: CCCn1cc(-n2cc(-c3ccc(NS(=O)(=O)CC)c(F)c3)cn2)ccc1=O] | δ 8.48 (s, 1H), 8.19 (d, J = 3.0, 1H), 8.07 (s, 1H), 8.00 (dd, J = 9.9 and 3.0 Hz, 1H), 7.55-7.43 (m, 3H), 6.68 (d, J = 9.3 Hz, 1H), 4.04 (t, J = 6.9 Hz, 2H), 3.12 (q, J = 7.8 Hz, 2H), 1.87-1.80 (m, 2H), 1.36 (t, J = 7.2 Hz, 3H), 1.0 (t, J = 7.5 Hz, 3H). (CD₃OD) | 405.2 |
| 72 | 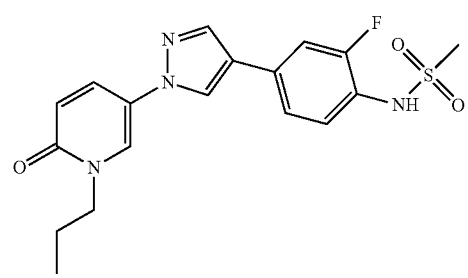 [SMILES: CCCn1cc(-n2cc(-c3ccc(NS(C)(=O)=O)c(F)c3)cn2)ccc1=O] | δ 8.48 (s, 1H), 8.19 (d, J = 3.0, 1H), 8.07 (s, 1H), 8.00 (dd, J = 9.9 and 3.0 Hz, 1H), 7.55-7.43 (m, 3H), 6.68 (d, J = 9.3 Hz, 1H), 4.04 (t, J = 6.9 Hz, 2H), 3.00 (s, 3H), 1.87-1.80 (m, 2H), 1.0 (t, J = 7.5 Hz, 3H). (CD₃OD) | 391.2 |

| Example No. | Structure | $^1$H NMR (DMSO-$d_6$, 300 MHz) | LC/MS [M + 1] |
|---|---|---|---|
| 73 | 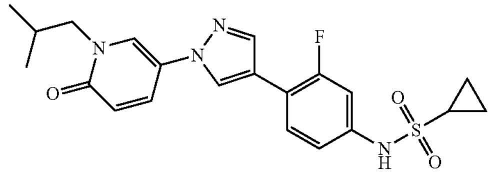 [SMILES: CC(C)Cn1cc(-n2cc(-c3ccc(NS(=O)(=O)C4CC4)cc3F)cn2)ccc1=O] | δ 8.42 (s, 1H), 8.16 (d, J = 2.7 Hz, 1H), 8.08 (s, 1H), 8.02 (dd, J = 10.2 and 3.0 Hz, 1H), 7.68 (t, J = 8.1 Hz, 1H), 7.13 (dt, J = 12.9 and 1.8 Hz, 2H), 6.68 (d, J = 9.9 Hz, 1H), 3.90 (d, J = 7.8 Hz, 2H), 2.65-2.57 (m, 1H), 2.27-2.16 (m, 1H), 1.08-1.05 (m, 2H), 1.02-0.97 (m, 8H). (CD$_3$OD). | 431.1 |
| 74 | 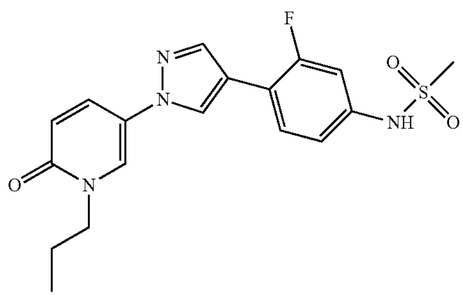 [SMILES: CCCn1cc(-n2cc(-c3ccc(NS(C)(=O)=O)cc3F)cn2)ccc1=O] | δ 8.55 (s, 1H), 8.30 (d, J = 3.0 Hz, 1H), 8.06 (s, 1H), 7.97 (dd, J = 9.9 and 2.7 Hz, 1H), 7.64-7.59 (m, 1H), 7.00-6.91 (m, 2H), 6.54 (d, J = 10.2 Hz, 1H), 3.91 (t, J = 6.9 Hz, 2H), 2.92 (s, 3H), 1.75-1.67 (m, 2H), 0.89 (t, J = 7.5 Hz, 3H). | 391.2 |
| 75 | 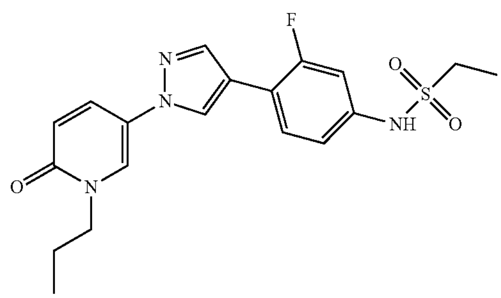 [SMILES: CCCn1cc(-n2cc(-c3ccc(NS(=O)(=O)CC)cc3F)cn2)ccc1=O] | δ 8.59 (s, 1H), 8.31 (d, J = 2.4 Hz, 1H), 8.10 (s, 1H), 7.97 (dd, J = 9.3 and 2.1 Hz, 1H), 7.74-7.68 (m, 1H), 7.11-7.04 (m, 2H), 6.54 (d, J = 9.9 Hz, 1H), 3.91 (t, J = 6.9 Hz, 2H), 3.16-3.11 (m, 2H), 1.74-1.67 (m, 2H), 1.20 (t, J = 6.9 Hz, 3H), 0.89 (t, J = 7.5 Hz, 3H). | 405.2 |

Example 76: N-(3-chloro-4-(1-(1-ethyl-6-oxo-1,6-dihydropyridin-3-yl)-1H-pyrazol-4-yl)phenyl)cyclopropanesulfonamide

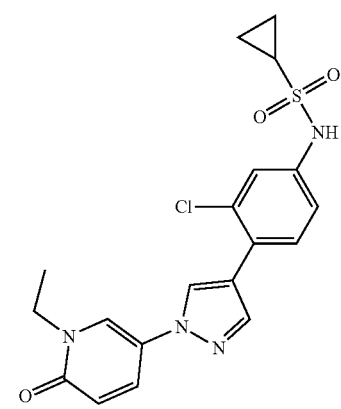 [SMILES: CCn1cc(-n2cc(-c3ccc(NS(=O)(=O)C4CC4)cc3Cl)cn2)ccc1=O]

Step 1: 5-bromo-1-ethylpyridin-2(1H)-one

A round bottom flask was charged with 2-Hydroxy-5-bromopyridine (3.00 g, 17.2 mmol), iodoethane (6.93 mL, 86.2 mmol), potassium carbonate (11.92 g, 86.2 mmol) in acetonitrile (30 mL) under argon. The reaction mixture was stirred at room temperature overnight. The solvents were removed under vacuum and the residue was taken in water and extracted with ethyl acetate. The combined organics were washed with brine and dried over sodium sulfate. The solvents were removed and the residue was purified by flash chromatography (40 g silica, 0-100% ethyl acetate in hexanes) to give a beige solid (1.8 g). LC/MS: [M+] and [M+2] 202.2, 204.1; $^1$H NMR (300 MHz, CDCl$_3$): δ 7.40 (d, J=2.4 Hz, 1H), 7.35-7.31 (m, 1H), 6.48 (d, J=9.9 Hz, 1H), 3.99-3.91 (m, 2H), 1.35 (t, J=7.4 Hz, 3H).

Step 2: 5-(4-bromo-1H-pyrazol-1-yl)-1-ethylpyridin-2(1H)-one

To a stirred solution of 5-bromo-1-ethylpyridin-2(1H)-one (1.08 g, 5.3 mmol.), 4-Bromopyrazole (0.78 g, 5.3 mmol) and cesium carbonate (5.22 g, 16.0 mmol.) in anhydrous dimethyl acetamide (16 mL) under argon was added copper(I) iodide (0.10 g, 0.5 mmol). The mixture was stirred at 135° C. for 2 hours. After cooling the mixture was partitioned between ethyl acetate and water. The organic layer was washed with brine and dried over sodium sulfate. The solvents were removed. The residue was purified by flash chromatography (40 g silica, 0-80% ethyl acetate in hexanes) to give a light yellow solid (340 mg, 24%). LC/MS: [M+], [M+2] 268.3, 270.0; $^1$H NMR (300 MHz, CDCl$_3$): δ 7.71 (d, J=4.2 Hz, 2H), 7.54-7.48 (m, 2H), 6.50 (d, J=9.3 Hz, 1H), 3.95-3.88 (m, 2H), 1.27 (t, J=7.4, 3H).

Step 3: 1-ethyl-5-(4-(4,4,5,5-tetramethyl-1,3,2-dioxaborolan-2-yl)-1H-pyrazol-1-yl)pyridin-2(1H)-one A round bottom flask was charged with 5-(4-bromo-1H-pyrazol-1-yl)-1-ethylpyridin-2(1H)-one (0.34 g, 1.3 mmol), bis(pinacolato)diboron (0.64 g, 2.5 mmol), potassium acetate (0.37 g, 3.8 mmol) in DMSO (4.5 mL) and the flask was degassed and flushed with argon. [1,1'-Bis(diphenylphosphino)ferrocene]dichloropalladium(II) complex with dichloromethane (0.05 g, 0.1 mmol.) was added and the reaction flask was again degassed and flushed with argon. The reaction mixture was then heated to 70° C. over night under argon. The reaction mixture was cooled to room temperature and quenched with saturated NaHCO$_3$ solution and extracted with ethyl acetate. The combined organics were washed with water, brine and dried over sodium sulfate. The solvents were concentrated and the residue purified by flash chromatography (24 g, 0-100% ethyl acetates in hexanes) to give the product as a light yellow solid (130 mg, 32.5%). LC/MS: [M+], [M+2] 316.1, 318.2; $^1$H NMR (300 MHz, CDCl$_3$): δ 7.92 (s, 1H), 7.80 (s, 1H), 7.74 (s, 1H), 7.56 (d, J=9.6 Hz, 1H), 6.54 (d, J=9.3 Hz, 1H), 3.98-3.90 (m, 2H), 1.31-1.14 (m, 15H).

Step 4: N-(3-chloro-4-(1-(1-ethyl-6-oxo-1,6-dihydropyridin-3-yl)-1H-pyrazol-4-yl)phenyl)cyclopropanesulfonamide A micro wave vial was charged with 1-ethyl-5-(4-(4,4,5,5-tetramethyl-1,3,2-dioxaborolan-2-yl)-1H-pyrazol-1-yl)pyridin-2(1H)-one (0.12 g, 0.4 mmol), N-(4-bromo-3-chlorophenyl)cyclopropanesulfonamide (0.12 g, 0.4 mmol.), potassium carbonate (0.16 g, 1.2 mmol) in dioxane (4 mL) and water (0.5 mL) and the flask was degassed and flushed with argon. [1,1'-Bis(diphenylphosphino)ferrocene]dichloropalladium(II) complex with dichloromethane (0.03 g, 0.01 mmol) was added and the reaction flask was degassed and flushed with argon again. The reaction mixture was heated to 100° C. in the microwave for 45 minutes. The reaction was cooled to room temperature and quenched with water and extracted with ethyl acetate. The organics were washed with water, brine and dried over sodium sulfate. The solvents were evaporated and the residue was purified by flash chromatography (24 g silica, 0-10% methanol in dichloromethane) to afford the product as a light brown solid (42.5 mg, 26%). LC/MS: [M+1] 419.4; $^1$H NMR (300 MHz, CD$_3$OD): δ 8.42 (s, 1H), 8.21 (d, J=3.0 Hz, 1H), 8.02 (d, J=4.2 Hz, 1H), 7.98 (d, J=3.0 Hz, 1H), 7.56 (d, J=8.7 Hz, 1H), 7.42 (d, J=1.8 Hz, 1H), 7.29-7.25 (m, 1H), 6.68 (d, J=10.2 Hz, 1H), 4.15-4.08 (m, 2H), 2.63-2.58 (m, 1H), 1.40 (t, J=7.4 Hz, 3H), 1.07 (d, J=4.8 Hz, 2H), 1.00 (d, J=8.1 Hz, 2H).

Using the general procedure of Example 76 the following examples were prepared.

| Example No. | Structure | $^1$H NMR (DMSO-d$_6$, 300 MHz) | LC/MS [M + 1] |
|---|---|---|---|
| 77 | 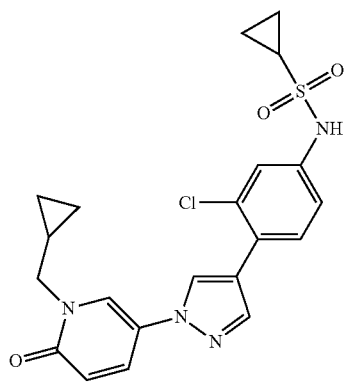 [SMILES: O=c1ccc(-n2cc(-c3ccc(NS(=O)(=O)C4CC4)cc3Cl)cn2)cn1CC1CC1] | δ 10.07 (s, 1H), 8.65 (s, 1H), 8.38 (s, 1H), 8.11 (s, 1H), 8.02 (d, J = 9.3 Hz, 1H), 7.67 (d, J = 8.4 Hz, 1H), 7.42 (s, 1H), 7.30 (d, J = 8.1 Hz, 1H), 6.60 (d, J = 9.9 Hz, 1H), 3.86 (d, J = 6.9 Hz, 2H), 2.76 (s, 1H), 1.34 (s, 1H), 1.01 (d, J = 5.1 Hz, 4H), 0.55-0.48 (m, 4H). | 447.2 [M + 2] |
| 78 | 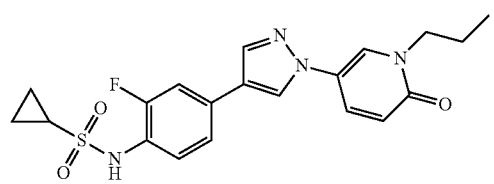 [SMILES: CCCn1cc(-n2cc(-c3ccc(NS(=O)(=O)C4CC4)c(F)c3)cn2)ccc1=O] | δ 7.91 (s, 1H), 7.79 (d, J = 2.7 Hz, 1H), 7.69-7.60 (m, 2H), 7.30 (d, J = 7.2 Hz, 1H), 6.70 (d, J = 9.3 Hz, 1H), 6.47 (s, 1H), 3.98 (t, J = 6.8 Hz, 2H), 2.55-2.50 (m, 1H), 1.90-182 (m, 2H), 1.23-1.17 (m, 2H), 1.04-0.97 (m, 5H). (CDCl$_3$) | 417.4 |

| Example No. | Structure | $^1$H NMR (DMSO-$d_6$, 300 MHz) | LC/MS [M + 1] |
|---|---|---|---|
| 79 | 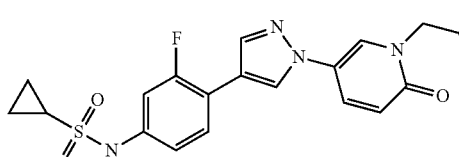 | δ 8.05 (d, J = 1.5 Hz, 1H), 8.00 (s, 1H), 7.75 (d, J = 2.7 Hz, 1H), 7.69 (dd, J = 9.9 and 3.0 Hz, 1H), 7.55 (t, J = 8.3 Hz, 1H), 7.17 (dd, J = 12.0 and 2.1 Hz, 1H), 7.05 (dd, J = 8.7 and 1.8 Hz, 1H), 6.71 (d, J = 8.7 Hz, 1H), 6.49 (s, 1H), 3.84 (d, J = 7.5 Hz, 2H), 2.57-2.52 (m, 1H), 2.28-2.21 (m, 1H), 1.24-1.23 (m, 2H), 1.06-0.99 (m, 8H). | 431.5 |
| 80 | 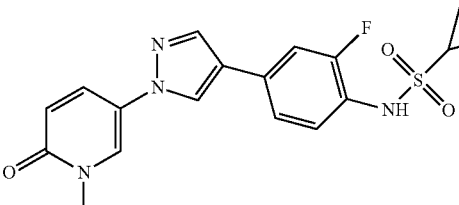 | δ 9.56 (s, 1H), 8.77 (s, 1H), 8.02 (s, 2H), 7.96-7.91 (m, 1H), 7.60 (d, J = 6.9 Hz, 1H), 7.48 (d, J = 8.1 Hz, 1H), 7.43 (t J = 10.2 Hz, 1H), 6.56 (d, J = 9.9 Hz, 1H), 3.78 (d, J = 6.9 Hz, 2H), 2.66-2.61 (m, 1H), 2.15-2.09 (m, 1H), 0.96-0.87 (m, 10H). | 431.4 |
Example 81: N-(3-chloro-4-(1-(1-((1-methylazetidin-3-yl)methyl)-6-oxo-1,6-dihydropyridin-3-yl)-1H-pyrazol-4-yl)phenyl)cyclopropanesulfonamide
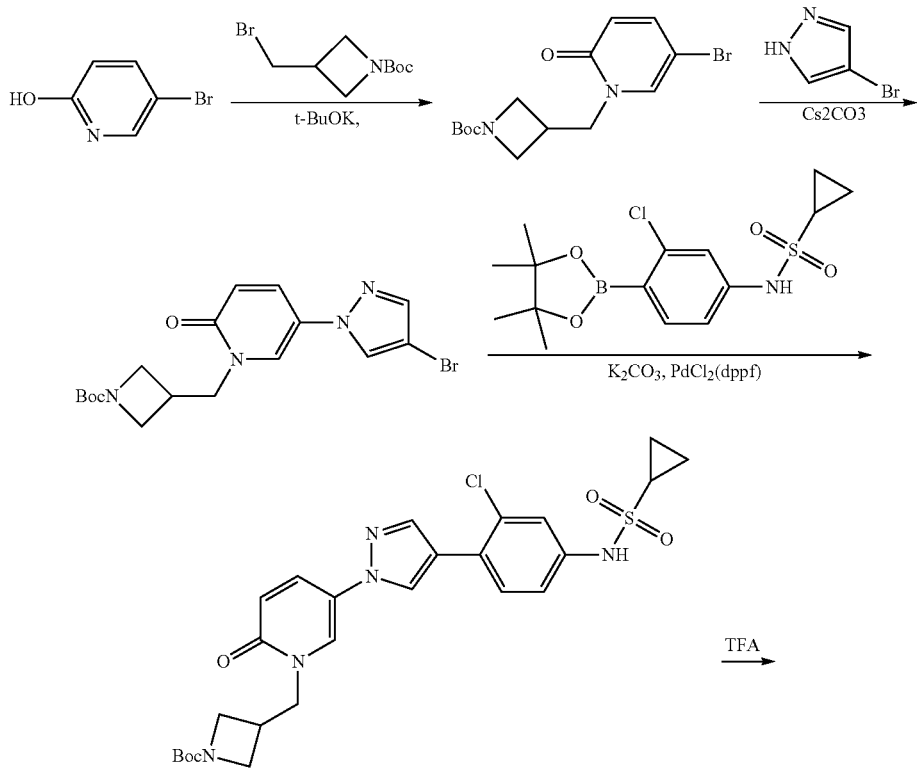

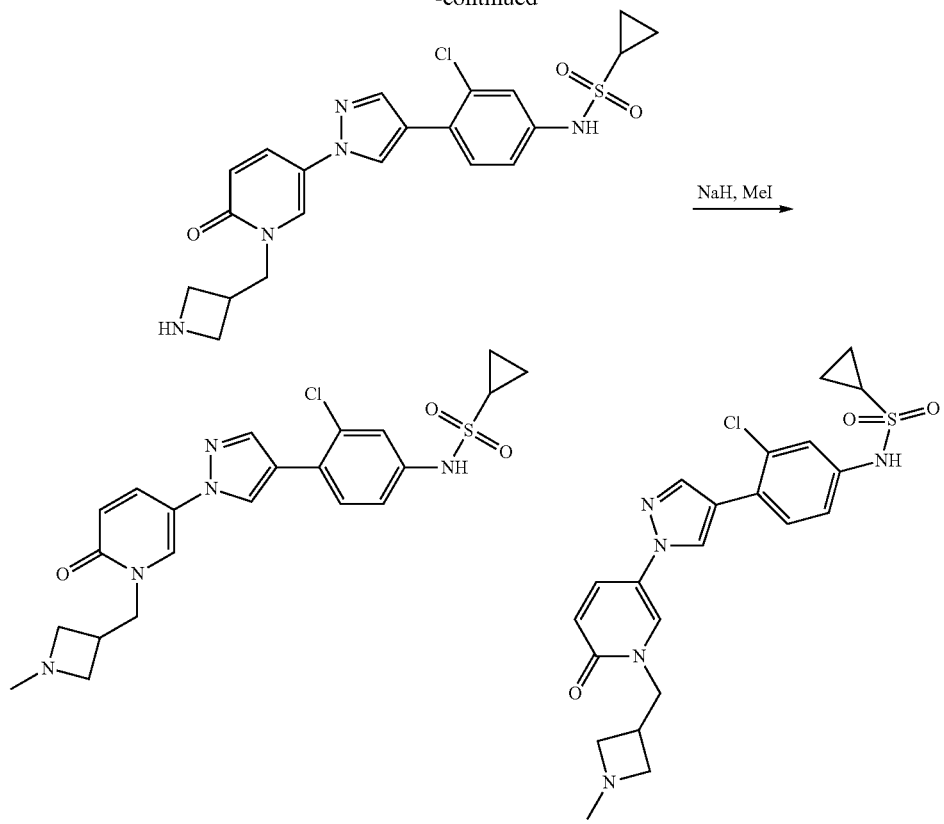

Step 1: tert-butyl 3-((5-bromo-2-oxopyridin-1(2H)-yl)methyl)azetidine-1-carboxylate A round bottom flask was charged with 2-hydroxy-5-bromopyridine (1.0 g, 5.7 mmol) and 1,2-dimethoxyethane (30 mL) and potassium tert-butoxide (0.65 g, 5.7 mmol) was added and the reaction mixture stirred at room temperature for 30 minutes, potassium carbonate (0.56 g, 4.0 mmol) and 1-Boc-3-bromomethylazetidine (2.88 g, 11.5 mmol) were added and the reaction mixture heated to reflux overnight. The reaction mixture was cooled to room temperature and quenched with water and extracted with ethyl acetate (3×100 mL). The combined organics were washed with brine and dried over MgSO$_4$. The solvents were evaporated to dryness and the residue purified by flash chromatography (40 g silica, 0-100% ethyl acetate in hexanes) to give the product as white solid (1.65 g, 84%). LC/MS: [M+]343.2; $^1$H NMR (300 MHz, CDCl$_3$): δ 7.39-7.34 (m, 2H), 6.49 (d, J=9.3 Hz, 1H), 4.08-3.97 (m, 4H), 3.72-3.67 (m, 2H), 3.07-3.05 (m, 1H), 1.44 (s, 9H),

Step 2: tert-butyl 3-((5-(4-bromo-1H-pyrazol-1-yl)-2-oxopyridin-1(2H)-yl)methyl)azetidine-1-carboxylate To a stirred solution of tert-butyl 3-((5-bromo-2-oxopyridin-1(2H)-yl)methyl)azetidine-1-carboxylate (1.65 g, 4.8 mmol), 4-bromopyrazole (1.1 g, 7.6 mmol) and cesium carbonate (7.47 g, 22.9 mmol) in anhydrous dimethyl acetamide (10 mL) under argon was added copper(I) iodide (0.07 g, 0.4 mmol). The mixture was stirred at 130° C. for 2 hours. After cooling, the mixture was partitioned between ethyl acetate and water. The layers were separated and the aqueous layer was extracted twice with ethyl acetate. The combined organics were washed with brine and dried over MgSO$_4$. The solvents were removed and resulting residue was purified by flash chromatography (0-100% ethyl acetate in hexanes) to give the product as oil. LC/MS: [M+], [M+2]$^+$409 and 411; $^1$H NMR (300 MHz, CDCl$_3$): δ 7.71-7.69 (m, 2H), 7.62-7.56 (m, 2H), 6.67 (d, J=9.9 Hz, 1H), 4.18 (m, 2H), 4.03 (t, J=8.7 Hz, 2H), 3.74 (dt, J=6.0 and 3.6 Hz, 2H), 3.11-3.09 (m, 1H), 1.43 (s, 9H).

Step 3: tert-butyl 3-((5-(4-(2-chloro-4-(cyclopropanesulfonamido)phenyl)-1H-pyrazol-1-yl)-2-oxopyridin-1 (2H)-yl)methyl)azetidine-1-carboxylate A round bottom flask was charged with tert-butyl 3-((5-(4-bromo-1H-pyrazol-1-yl)-2-oxopyridin-1(2H)-yl)methyl)azetidine-1-carboxylate (0.20 g, 0.5 mmol), N-(3-chloro-4-(4,4,5,5-tetramethyl-1,3,2-dioxaborolan-2-yl)phenyl)cyclopropanesulfonamide (0.18 g, 0.5 mmol), and dioxan (4 mL) and water (1 mL) and the flask was degassed and flushed with argon. PdCl$_2$(dppf) (0.04 g, 0.05 mmol) was added and the reaction flask was again degassed and flushed with argon. The reaction mixture was then heated to 100° C. for 1 hour in a microwave. The reaction mixture was cooled to room temperature and quenched with water and extracted with isopropanol/dichloromethane (1:3, 3×30 mL). The combined organics were washed with brine and dried over MgSO$_4$. The solvents were evaporated to dryness and the residue was purified by flash chromatography (12 g silica, 0-10% methanol in dichloromethane). The fractions were evaporated to give the product as pale brown oil (150 mg, 55%). LC/MS: [M+1]+ 560.1; ¹HNMR (300 MHz, CDCl₃): δ 8.07 (s, 1H), 7.94 (s, 1H), 7.83 (d, J=2.7 Hz, 1H), 7.72 (dd, J=10.2 and 3.0 Hz, 1H), 7.56-7.41 (m, 2H), 7.25-7.23 (m, 1H), 7.03 (bs, 1H), 6.71 (d, J=9.3 Hz, 1H), 4.21 (bs, 2H), 4.05 (t, J=8.1 Hz, 2H), 3.8-3.75 (m, 2H), 3.18-3.09 (m, 1H), 2.59-2.50 (m, 11H), 1.41 (s, 9H), 1.26-1.20 (m, 2H), 1.05-0.99 (m, 2H).

Step 4: N-(4-(1-(1-(azetidin-3-ylmethyl)-6-oxo-1,6-dihydropyridin-3-yl)-1H-pyrazol-4-yl)-3-chlorophenyl)cyclopropanesulfonamide A round bottom flask was charged with tert-butyl 3-((5-(4-(2-chloro-4-(cyclopropanesulfonamido)phenyl)-1H-pyrazol-1-yl)-2-oxopyridin-1(2H)-yl)methyl)azetidine-1-carboxylate (0.15 g, 0.3 mmol), dichloromethane (15 mL) and trifluoro acetic acid (0.06 mL, 0.8 mmol), was added and the reaction stirred for at room temperature for 3 hours. The solvents were removed and the compound used in the next step without further purification. LC/MS: [M+1]+ 460.7

Step 5: N-(3-chloro-4-(1-(1-((1-methylazetidin-3-yl)methyl)-6-oxo-1,6-dihydropyridin-3-yl)-1H-pyrazol-4-yl)phenyl)cyclopropanesulfonamide A microwave vial was charged with N-(4-(1-(1-(azetidin-3-ylmethyl)-6-oxo-1,6-dihydropyridin-3-yl)-1H-pyrazol-4-yl)-3-chlorophenyl)cyclopropanesulfonamide (0.10 g, 0.2 mmol), iodomethane (0.06 mL, 0.9 mmol), N,N-diisopropylethylamine (0.05 mL, 0.2 mmol), DMSO (2 mL) and heated to 90° C. for 3 hours. The reaction mixture was cooled to room temperature and quenched with water and extracted with isopropanol:chloroform (1:3, 3×50 mL). The combined solvents were washed water, brine and dried over MgSO₄. The solvents were evaporated to dryness and the residue purified by flash chromatography (4 g, 0-20% methanol in dichloromethane) to give the product as an oil. LC/MS: [M+1]+ 474.5; ¹H NMR (300 MHz, CD₃OD): δ 8.62 (s, 1H), 8.45 (d, J=2.4 Hz, 1H), 8.34 (dd, J=9.3 and 2.4 Hz, 1H), 8.14 (s, 1H), 7.66-7.63 (m, 2H), 7.48 (dd, J=8.4 and 2.4 Hz, 1H), 7.11 (d, J=9.9 Hz, 1H), 4.53-4.48 (m, 1H), 4.30-4.23 (m, 1H), 3.76-3.64 (m, 3H), 3.47-3.37 (m, 4H), 2.66-2.47 (m, 2H), 1.01-0.96 (m, 4H).

Example 82: 5-(4-(2-(cyclopentylamino)pyrimidin-5-yl)-1H-pyrazol-1-yl)-1-propylpyridin-2(1H)-one

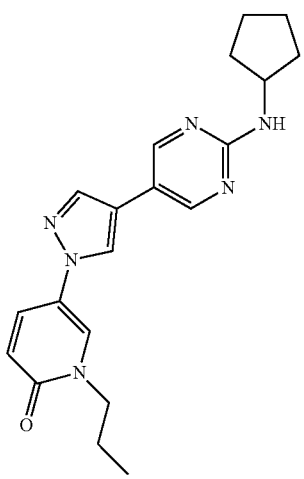 [SMILES: CCCn1cc(-n2cc(-c3cnc(NC4CCCC4)nc3)cn2)ccc1=O]

Step 1: 5-(4-(2-(cyclopentylamino)pyrimidin-5-yl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl)pyridin-2(1H)-one (0.15 g, 0.5 mmol), 5-bromo-N-cyclopentylpyrimidin-2-amine (0.12 g, 0.5 mmol), potassium carbonate (0.19 g, 1.4 mmol) and dioxan (8 mL) and water (2 mL) and the flask was degassed and flushed with argon. PdCl₂(dppf) (0.04 g, 0.05 mmol) was added and the reaction flask was again degassed and flushed with argon. The reaction mixture was then heated to 100° C. in a microwave for 1 hour. The reaction was cooled to room temperature and quenched with sat. NaHCO₃ and extracted with ethyl acetate (3×50 mL). The combined organics were washed with water, brine and dried over MgSO₄. The solvents were evaporated to dryness and the residue purified by flash chromatography (12 g silica gel, 0-100% ethyl acetate in hexanes) to afford the product as yellow solid (52 mg, 27%). LC/MS: [M+1]+ 365.3; ¹HNMR (300 MHz, CDCl₃): δ 8.44 (s, 2H), 7.82 (d, J=4.8 Hz, 2H), 7.77 (d, J=3.0 Hz, 1H), 7.66 (dd, J=9.6 and 2.7 Hz, 1H), 6.69 (d, J=9.9 Hz, 1H), 5.15 (d, J=7.5 Hz, 1H), 4.30-4.28 (m 1H), 3.98 (t, J=7.2 Hz, 2H), 2.10-2.06 (m, 2H), 1.89-1.82 (m, 2H), 1.79-1.67 (m, 4H), 1.54-1.48 (m, 2H), 1.02 (t, J=7.4 Hz, 3H).

Example 83: 5-(4-(2-(tert-butylamino)pyrimidin-5-yl)-1H-pyrazol-1-yl)-1-propylpyridin-2(1H)-one

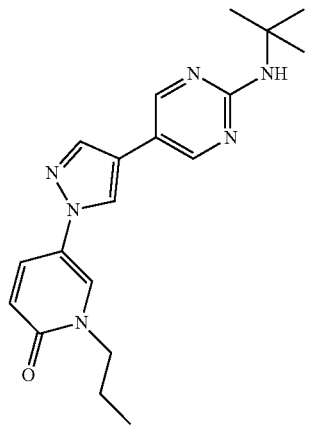 [SMILES: CCCn1cc(-n2cc(-c3cnc(NC(C)(C)C)nc3)cn2)ccc1=O]

The title compound was prepared analogously to Example 82.

LC/MS: [M+1]+353.2; ¹HNMR (300 MHz, CDCl₃): δ 8.42 (s, 2H), 7.82 (d, J=6.0 Hz, 2H), 7.77 (s, 1H), 7.66 (dd, J=9.6 and 2.1 Hz, 1H), 6.69 (d, J=9.9 Hz, 1H), 5.21 (bs, 1H), 3.98 (t, J=7.2 Hz, 2H), 1.89-1.82 (m, 2H), 1.48 (s, 9H), 1.02 (t, J=7.4 Hz, 3H).

Example 84: 5-(4-(6-(tert-butylamino)pyridin-3-yl)-1H-pyrazol-1-yl)-1-propylpyridin-2(1H)-one

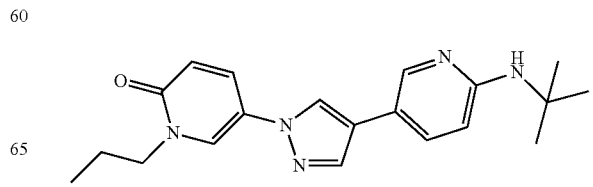

Step 1: 5-bromo-N-(tert-butyl)pyridin-2-amine

A microwave vial was charged with 5-bromo-2-fluoropyridine (1.0 g, 5.7 mmol) and anhydrous dimethyl acetamide (10 mL) and tert-butylamine (3.00 mL, 28.7 mmol.) was added and the reaction mixture heated at 140° C. for 64 h. The reaction mixture was cooled to room temperature and quenched with water (200 mL) and extracted with ethyl acetate (3×100 mL). The combined organics were washed with brine and dried over MgSO$_4$. The solvents were evaporated to dryness and the residue purified by flash chromatography (40 g silica gel, 0-30% ethyl acetate in hexanes) to give the product as colorless liquid (400 mg, 30%). LC/MS: [M+] 229.0; $^1$H NMR (300 MHz, CDCl$_3$): δ 8.08 (d, J=2.1 Hz, 1H), 7.40 (dd, J=8.7 and 3.0 Hz, 1H), 6.32 (d, J=8.1 Hz, 1H), 4.47 (bs, 1H), 1.40 (s, 9H).

Step 2: 5-(4-(6-(tert-butylamino)pyridin-3-yl)-H-pyrazol-1-yl)-1-propylpyridin-2(1H)-one The title compound was prepared in a manner similar to that given for Example 82. LC/MS: [M+1]$^+$ 352.2; $^1$H NMR (300 MHz, CD$_3$OD): δ 8.28 (s, 1H), 8.23 (d, J=1.8 Hz, 1H), 8.13 (d, J=3.0 Hz, 1H), 7.96 (dd, J=9.3 and 3.0 Hz, 1H), 7.92 (s, 1H), 7.59 (dd, J=9.0 and 3.0 Hz, 1H), 6.65 (d, J=9.3 Hz, 1H), 6.57 (d, J=8.7 Hz, 1H), 4.00 (t, J=7.5 Hz, 2H), 1.85-1.77 (m, 2H), 1.43 (s, 9H), 0.98 (t, J=7.5 Hz, 3H).

Example 85: 5-(4-(6-(cyclobutylamino)-4-methylpyridin-3-yl)-1H-pyrazol-1-yl)-1-propylpyridin-2(1H)-one

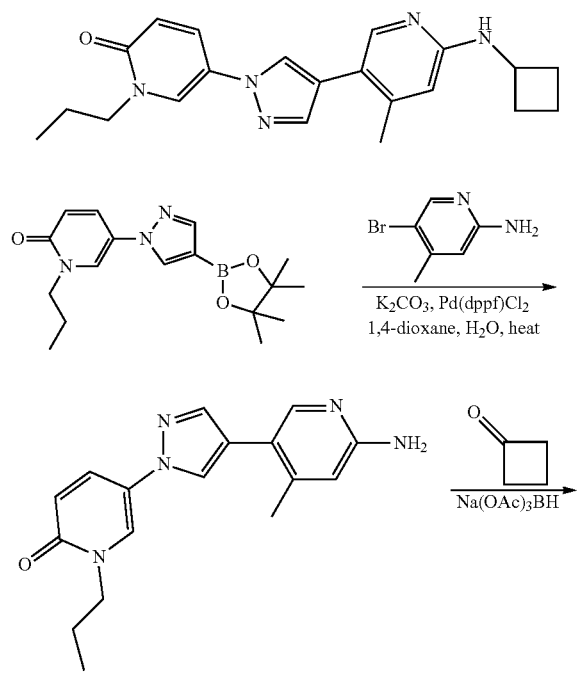

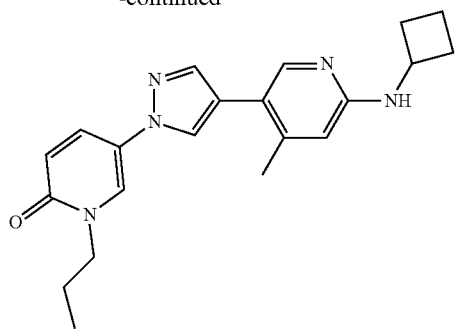

Step 1: 5-(4-(6-amino-4-methylpyridin-3-yl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl)pyridin-2(1H)-one (0.20 g, 0.6 mmol), 2-amino-5-bromo-4-methylpyridine (0.18 g, 0.8 mmol), and dioxan (8 mL) and water (2 mL) and the flask was degassed and flushed with argon. PdCl$_2$(dppf) (0.05 g, 0.05 mmol) was added and the reaction flask was again degassed and flushed with argon. The reaction mixture was then heated to 100° C. in a microwave for 45 minutes. The reaction was cooled to room temperature and quenched with sat. NaHCO$_3$ and extracted with ethyl acetate (3×50 mL). The combined organics were washed with water, brine and dried over MgSO$_4$. The solvents were evaporated to dryness and the residue purified by flash chromatography (12 g silica gel, 0-10% methanol in dichloromethane) to afford the product as yellow solid (160 mg, 80%). LC/MS: [M+1]$^+$310.1; $^1$H NMR (300 MHz, CDCl$_3$): δ 8.00 (s, 1H), 7.78 (d, J=3.0 Hz, 1H), 7.71-7.64 (m, 2H), 6.68 (d, J=9.9 Hz, 1H), 6.43 (s, 1H), 4.42 (bs, 2H), 3.96 (t, J=7.8 Hz, 2H), 2.29 (s, 3H), 1.89-1.78 (m, 2H), 1.0 (t, J=7.5 Hz, 3H).

Step 2: 5-(4-(6-(cyclobutylamino)-4-methylpyridin-3-yl)-1H-pyrazol-1-yl)-1-propylpyridin-2(1H)-one A vial was charged with 5-(4-(6-amino-4-methylpyridin-3-yl)-1H-pyrazol-1-yl)-1-propylpyridin-2(1H)-one (0.07 g, 0.2 mmol), cyclobutanone (0.07 mL, 0.9 mmol) and 1,2-dichloroethane (5 mL) and the reaction mixture was stirred for 15 minutes and sodium triacetoxyborohydride (0.12 g, 0.6 mmol) was added and the reaction mixture stirred at room temperature for 48 hours. The reaction mixture was quenched with water and extracted with dichloromethane (3×25 mL). The combined organics were washed with brine and dried over MgSO$_4$. The solvents were evaporated to dryness and the residue purified by reverse phase HPLC (neutral) to give the product as white solid (10 mg, 12%). LC/MS: [M+1]$^+$364.2; $^1$H NMR (300 MHz, CD$_3$OD): δ 8.17 (d, J=3.0 Hz, 1H), 8.13 (s, 1H), 8.00 (dd, J=9.9 and 3.0 Hz, 1H), 7.89 (s, 1H), 7.78 (s, 1H), 6.67 (d, J=10.2 Hz, 1H), 6.40 (s, 1H), 4.25-4.19 (m, 1H), 4.03 (t, J=7.5 Hz, 2H), 2.42-2.37 (m, 2H), 2.31 (s, 3H), 1.95-1.74 (m, 6H), 1.00 (t, J=7.5 Hz, 3H).

The following compounds are made in a manner similar to that described for Example 85.

| Example No. | Structure | ¹H NMR (CDCl₃, 300 MHz) | LC/MS [M + 1] |
|---|---|---|---|
| 86 | 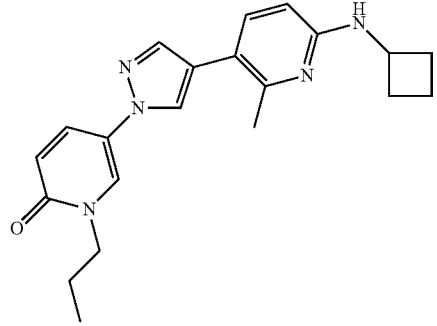 [SMILES: CCCn1cc(-n2cc(-c3ccc(NC4CCC4)nc3C)cn2)ccc1=O] | δ 8.17 (d, J = 3.0 Hz, 1H), 8.13 (s, 1H), 8.00 (dd, J = 9.9 and 3.0 Hz, 1H), 7.89 (s, 1H), 7.78 (s, 1H), 6.67 (d, J = 10.2 Hz, 1H), 6.40 (s, 1H), 4.25-4.19 (m, 1H), 4.03 (t, J = 7.5 Hz, 2H), 2.42-2.337 (m, 2H), 2.31 (s, 3H), 1.95-1.74 (m, 6H), 1.00 (t, J = 7.5 Hz, 3H). (CD₃OD) | 364.2 |
| 87 | 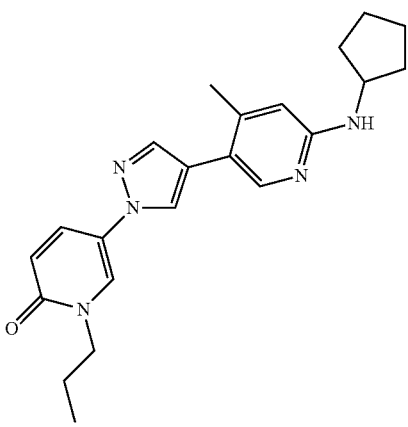 [SMILES: CCCn1cc(-n2cc(-c3cnc(NC4CCCC4)cc3C)cn2)ccc1=O] | δ 8.02 (s, 1H), 7.78 (d, J = 3.0 Hz, 1H), 7.72-7.65 (m, 3H), 6.69 (d, J = 9.3 Hz, 1H), 6.32 (s, 1H), 3.98 9t, J = 7.5 Hz, 2H), 2.32 (s, 3H), 2.1-2.04 (m, 2H), 1.90-1.66 (m, 6H), 1.51 (m, 3H), 1.02 (t, J = 7.5 Hz, 3H). | 378.4 |
| 88 | 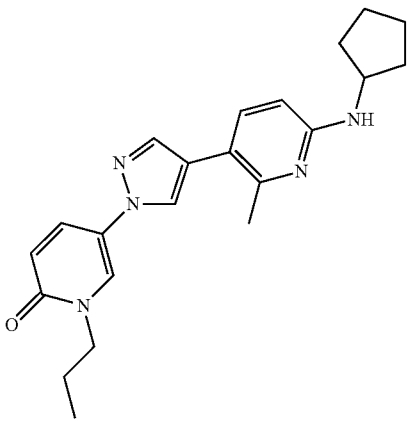 [SMILES: CCCn1cc(-n2cc(-c3ccc(NC4CCCC4)nc3C)cn2)ccc1=O] | δ 7.77 (d, J = 2.4 Hz, 1H), 7.70-7.63 (m, 3H), 7.40 (d, J = 8.1 Hz, 1H), 6.68 (d, J = 10.2 Hz, 1H), 6.31 (d, J = 8.1 Hz, 1H), 4.75 (bs, 1H), 3.99-3.90 (m, 3H), 2.45 (s, 3H), 2.06-1.48 (m, 10H), 1.00 (t, J = 7.5 Hz, 3H). | 378.4 |
| 89 | 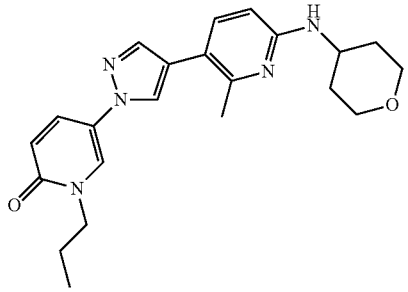 [SMILES: CCCn1cc(-n2cc(-c3ccc(NC4CCOCC4)nc3C)cn2)ccc1=O] | δ 7.76 (d, J = 3.0 Hz, 1H), 7.68-7.62 (m, 3H), 7.39 (d, J = 9.0 Hz, 1H), 6.66 (d, J = 9.3 Hz, 1H), 6.30 (d, J = 8.7 Hz, 1H), 4.01-3.92 (m, 4H), 3.73 (m, 1H), 3.52 (t, J = 9.9 Hz, 2H), 2.45 (s, 3H), 2.04-2.0 (m, 2H), 1.86-1.76 (m, 2H), 1.61-1.48 (m, 2H), 0.98 (t, J = 7.5 Hz, 3H) | 394.1 |

-continued
| Example No. | Structure | ¹H NMR (CDCl₃, 300 MHz) | LC/MS [M + 1] |
|---|---|---|---|
| 90 | 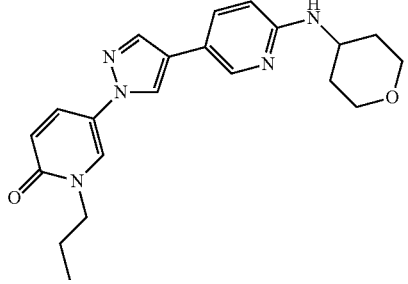 | δ 8.29 (d, J = 2.4 Hz, 1H), 7.84 (s, 1H), 7.80 (s, 1H), 7.77 (d, J = 3.0 Hz, 1H), 7.66 (dd, J = 9.9 and 3.0 Hz, 1H), 7.55 (dd, J = 9.1 and 2.4 Hz, 1H), 6.69 (d, J = 9.9 Hz, 1H), 6.45 (d, J = 8.7 Hz, 1H), 4.43 (brs, 1H), 4.04-3.95 (m, 4H), 3.61-3.53 (m, 2H), 2.09-2.05 (m, 2H), 1.89-1.82 (m, 2H), 1.55-1.50 (m, 3H), 1.01 (t, J = 7.4 Hz, 3H). | 380.4 |
| 91 | 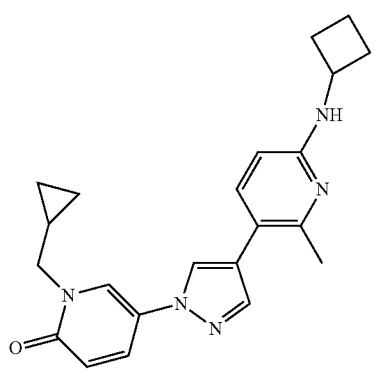 [SMILES: Cc1nc(NC2CCC2)ccc1-c1cnn(-c2ccc(=O)n(CC3CC3)c2)c1] | δ 8.21 (d, J = 2.7 Hz, 1H), 8.12 (s, 1H), 8.01-7.97 (m, 1H), 7.79 (s, 1H), 7.48 (d, J = 8.4 Hz, 1H), 6.68 (d, J = 9.6 Hz, 1H), 6.34 (d, J = 9.0 Hz, 1H), 4.22-4.16 (m, 1H), 3.93 (d, J = 6.9 Hz, 2H), 2.45-2.38 (m, 5H), 1.97-1.87 (m, 2H), 1.83-1.75 (m, 2H), 1.40-1.34 (m, 1H), 0.65-0.58 (m, 2H), 0.52-0.48 (m, 2H). (CD₃OD) | 376.4 |
| 92 | 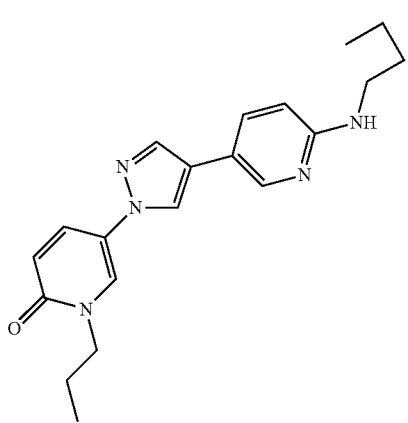 [SMILES: CCCCNc1ccc(-c2cnn(-c3ccc(=O)n(CCC)c3)c2)cn1] | δ 8.35 (d, J = 2.4 Hz, 1H), 7.84 (s, 1H), 7.78-7.76 (m, 2H), 7.67 (dd, J = 9.9, 3.0 Hz, 1H), 7.55 (dd, J = 8.7, 2.4 Hz, 1H), 6.69 (d, J = 9.3 Hz, 1H), 6.52 (d, J = 8.7 Hz, 1H), 3.98 (t, J = 7.4 Hz, 2H), 3.56 (q, J = 7.1 Hz, 4H), 190-1.82 (m, 2H), 1.26-1.20 (m, 6H), 1.02 (t, J = 7.4 Hz, 3H). | 352.4 |

Example 93: 5-(4-(6-(cyclopentylamino)-2-methylpyridin-3-yl)-1H-pyrazol-1-yl)-1-(cyclopropylmethyl)pyridin-2(1H)-one

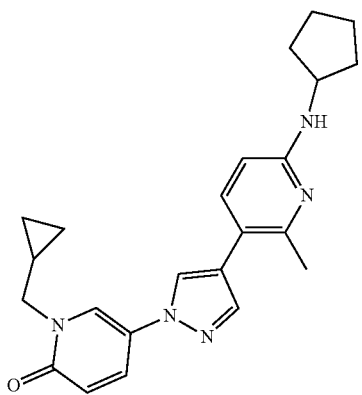 [SMILES: Cc1nc(NC2CCCC2)ccc1-c1cnn(-c2ccc(=O)n(CC3CC3)c2)c1]

Step 1:
5-bromo-N-cyclopentyl-6-methylpyridin-2-amine

A vial was charged with 5-bromo-6-methylpyridin-2-amine (2.00 g, 10.7 mmol), cyclopentanone (4.03 mL, 53.5 mmol) and 1,2-dichloroethane (60 mL) and the reaction mixture was stirred for 15 minutes and sodium triacetoxyborohydride (11.28 g, 53.5 mmol) was added and the reaction mixture stirred at room temperature overnight. The reaction mixture was quenched with water and extracted with dichloromethane (3×25 mL). The combined organics were washed with brine and dried over $MgSO_4$. The solvents were evaporated to dryness and the residue purified by flash chromatography (40 g silica 0-20% ethyl acetate in hexanes) to give the product as light yellow oil. LC/MS: [M+1]$^+$ 257.2; $^1$H NMR (300 MHz, $CDCl_3$): δ 7.49 (d, J=8.7 Hz, 1H), 6.14 (d, J=8.7 Hz, 1H), 3.80-3.76 (m, 1H), 2.43 (s, 3H), 1.99-1.48 (m, 8H).

Step 2: 5-(4-(6-(cyclopentylamino)-2-methylpyridin-3-yl)-1H-pyrazol-1-yl)-1-(cyclopropylmethyl)pyridin-2(1H)-one A micro wave vial was charged with 1-(cyclopropylmethyl)-5-(4-(4,4,5,5-tetramethyl-1,3,2-dioxaborolan-2-yl)-1H-pyrazol-1-yl)pyridin-2(1H)-one (0.13 g, 0.4 mmol.), 5-bromo-N-cyclopentyl-6-methylpyridin-2-amine (0.1 g, 0.4 mmol.) and potassium carbonate (0.16 g, 1.1 mmol.) in dioxane (10 mL) and water (0.5 mL) and the flask was degassed and flushed with argon. [1,1'-Bis(diphenylphosphino)ferrocene]dichloropalladium(II) complex with dichloromethane (0.031 g, 0.01 mmol) was added and the reaction flask was degassed and flushed with argon again. The reaction mixture was heated to 100° C. in the microwave for 90 minutes. The reaction was cooled to room temperature and quenched with water and extracted with ethyl acetate. The organics were washed with water, brine and dried over sodium sulfate. The solvents were evaporated. The residue was purified by flash chromatography (24 g silica, 0-10% methanol in dichloromethane). The product fractions were collected and the solvent was removed by vacuum. The residue was purified again by reverse phase HPLC (neutral, 30-95% Acetonitrile/Water) to give a yellow oil (38.1 mg). LC/MS: [M+1] 390.4; $^1$HNMR (300 MHz, $CD_3OD$): δ 8.20 (d, J=2.4 Hz, 1H), 8.11 (s, 1H), 8.00-7.96 (m, 1H), 7.77 (s, 1H), 7.48 (d, J=8.1 Hz, 1H), 6.67 (d, J=9.3 Hz, 1H), 6.41 (d, J=8.7 Hz, 1H), 4.03-4.01 (m, 1H), 3.91 (d, J=6.9 Hz, 2H), 2.44 (s, 3H), 2.05-1.99 (m, 2H), 1.76-1.66 (m, 4H), 1.64-1.48 (m, 2H), 1.35-1.33 (m, 1H), 0.59 (d, J=6.9 Hz, 2H), 0.47 (d, J=3.9 Hz, 2H).

The following compounds are made in a manner similar to that described for Example 93.

| Example No. | Structure | $^1$H NMR (DMSO-$d_6$, 300 MHz) | LC/MS [M + 1] |
|---|---|---|---|
| 94 | 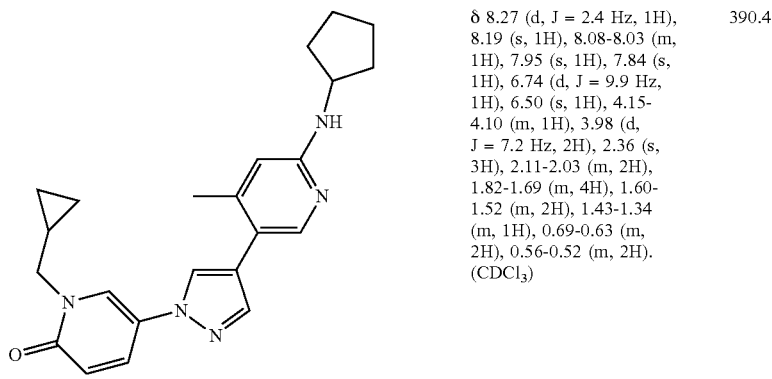 | δ 8.27 (d, J = 2.4 Hz, 1H), 8.19 (s, 1H), 8.08-8.03 (m, 1H), 7.95 (s, 1H), 7.84 (s, 1H), 6.74 (d, J = 9.9 Hz, 1H), 6.50 (s, 1H), 4.15-4.10 (m, 1H), 3.98 (d, J = 7.2 Hz, 2H), 2.36 (s, 3H), 2.11-2.03 (m, 2H), 1.82-1.69 (m, 4H), 1.60-1.52 (m, 2H), 1.43-1.34 (m, 1H), 0.69-0.63 (m, 2H), 0.56-0.52 (m, 2H). ($CDCl_3$) | 390.4 |

-continued

| Example No. | Structure | $^1$H NMR (DMSO-d$_6$, 300 MHz) | LC/MS [M + 1] |
|---|---|---|---|
| 95 | 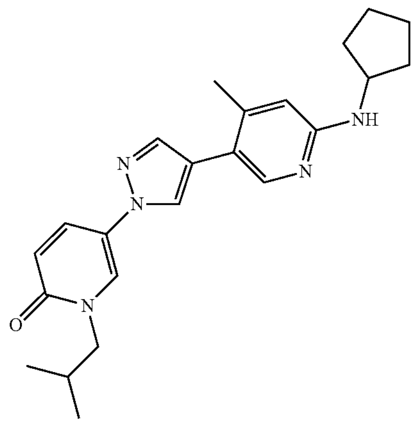 [SMILES: Cc1cc(NC2CCCC2)ncc1-c1cnn(-c2ccc(=O)n(CC(C)C)c2)c1] | δ 8.02 (s, 1H), 7.74-7.65 (m, 4H), 6.69 (d, J = 9.9 Hz, 1H), 6.31 (s, 1H), 4.56 (bs, 1H), 4.04-3.97 (m, 1H), 3.83 (d, J = 7.5 Hz, 2H), 2.32 (s, 3H), 2.28-2.04 (m, 3H), 1.77-1.66 (m, 4H), 1.54-1.48 (m, 2H), 1.00 (d, J = 6.6 Hz, 6H). (CDCl$_3$) | 392.5 |
| 96 | 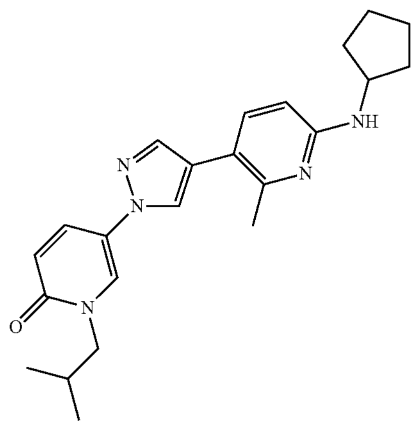 [SMILES: Cc1nc(NC2CCCC2)ccc1-c1cnn(-c2ccc(=O)n(CC(C)C)c2)c1] | δ 7.74-7.65 (m, 4H), 7.41 (d, J = 5.1 Hz, 1H), 6.69 (d, J = 9.3 Hz, 1H), 6.33 (d, J = 8.1 Hz, 1H), 4.68 (bs, 1H), 3.94-3.90 (m, 1H), 3.83 (d, J = 7.5 Hz, 2H), 2.47 (s, 3H), 2.28-2.02 (m, 3H), 1.77-1.48 (m, 6H), 1.00 (d, J = 6.6 Hz, 6H). | 392.5 |
| 97 | 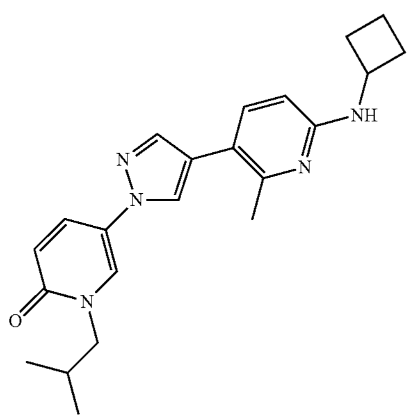 [SMILES: Cc1nc(NC2CCC2)ccc1-c1cnn(-c2ccc(=O)n(CC(C)C)c2)c1] | δ 7.74-7.65 (m, 4H), 7.40 (d, J = 8.4 Hz, 1H), 6.69 (d, J = 9.3 Hz, 1H), 6.22 (d, J = 8.4 Hz, 1H), 4.85 (bs, 1H), 4.12-4.04 (m, 1H), 3.83 (d, J = 7.5 Hz, 2H), 2.47-2.44 (m, 4H), 2.30-1.74 (m, 6H), 1.00 (d, J = 6.6 Hz, 6H). (CD$_3$OD) | 378.5 |
| 98 | 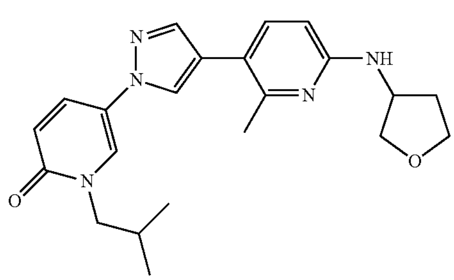 [SMILES: Cc1nc(NC2CCOC2)ccc1-c1cnn(-c2ccc(=O)n(CC(C)C)c2)c1] | δ 8.10 (s, 2H), 8.00-7.95 (m, 1H), 7.77 (s, 1H), 7.45 (d, J = 7.2 Hz, 1H), 6.66 (d, J = 9.9 Hz, 1H), 6.41 (d, J = 8.1 Hz, 1H), 4.43-4.41 (m, 1H), 4.01-3.96 (m, 2H), 3.89-3.82 (m, 3H), 3.82-3.63 (m, 1H), 3.30 (s, 3H), 2.45-2.19 (m, 2H), 1.93-1.83 (m, 1H), 0.97 (d, J = 7.2 Hz, 6H). (CD$_3$OD) | 394.4 |

-continued
| Example No. | Structure | ¹H NMR (DMSO-d₆, 300 MHz) | LC/MS [M + 1] |
|---|---|---|---|
| 99 | 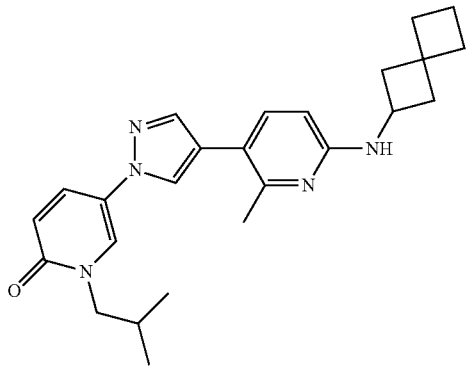 [SMILES: Cc1nc(NC2CC3(CCC3)C2)ccc1-c1cnn(-c2ccc(=O)n(CC(C)C)c2)c1] | δ 8.12 (d, J = 3.3 Hz, 2H), 8.02-7.97 (m, 1H), 7.78 (s, 1H), 7.48 (d, J = 9.0 Hz, 1H), 6.68 (d, J = 9.6 Hz, 1H), 6.32 (d, J = 8.7 Hz, 1H), 4.04-3.99 (m, 1H), 3.90 (d, J = 7.8 Hz, 2H), 2.54-2.47 (m, 2H), 2.44 (s, 3H), 2.25-2.20 (m, 1H), 2.11 (t, J = 7.1 Hz, 2H), 1.98 (t, J = 7.1 Hz, 1H), 1.91-1.82 (m, 5H), 0.97 (d, J = 6.3 Hz, 6H). (CD₃OD) | 418.6 |
| 100 | 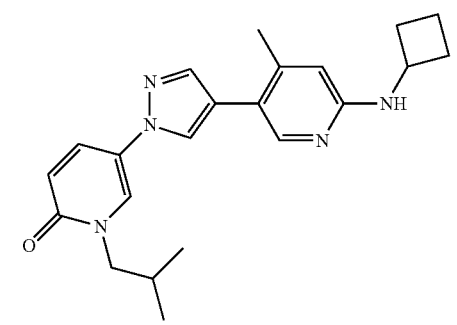 [SMILES: Cc1cc(NC2CCC2)ncc1-c1cnn(-c2ccc(=O)n(CC(C)C)c2)c1] | δ 8.13 (s, 2H), 8.02-7.98 (m, 1H), 7.89 (s, 1H), 7.78 (s, 1H), 6.68 (d, J = 10.2, 1H), 6.40 (s, 1H), 4.24-4.19 (m, 1H), 3.89 (d, J = 7.2 Hz, 2H), 2.43-2.39 (m, 2H), 2.31 (s, 3H), 2.25-2.20 (m, 1H), 1.96-1.89 (m, 2H), 1.82-1.77 (m, 2H), 0.98 (d, J = 6.9 Hz, 6H). (CD₃OD) | 378.5 |
| 101 | 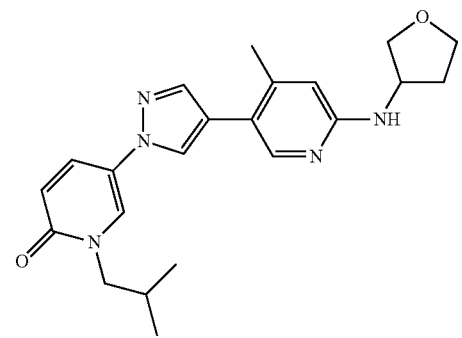 [SMILES: Cc1cc(NC2CCOC2)ncc1-c1cnn(-c2ccc(=O)n(CC(C)C)c2)c1] | δ 8.16 (d, J = 2.1 Hz, 1H), 8.12 (s, 1H), 8.02-7.98 (m, 1H), 7.79 (s, 1H), 7.46 (d, J = 8.7 Hz, 1H), 6.67 (d, J = 9.6 Hz, 1H), 6.43 (d, J = 8.7 Hz, 1H), 4.44-4.42 (m, 1H), 4.06-3.92 (m, 4H), 3.88-3.83 (m, 1H), 3.68-3.65 (m, 1H), 2.46 (s, 3H), 2.33-2.26 (m, 1H), 1.90-1.80 (m, 3H), 0.99 (t, d = 7.5 Hz, 3H). (CD₃OD) | 379.4 |
| 102 | 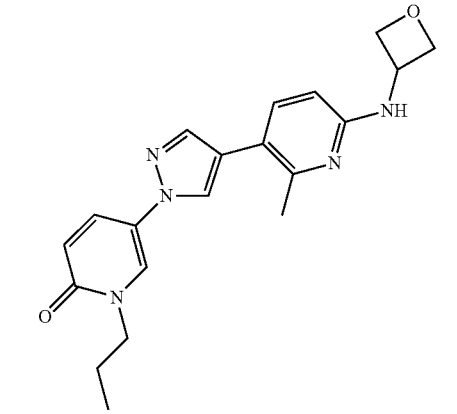 [SMILES: CCCn1cc(-n2cc(-c3ccc(NC4COC4)nc3C)cn2)ccc1=O] | δ 7.82-7.77 (m, 2H), 7.69 (d, J = 10.2 Hz, 1H), 7.57-7.51 (m, 2H), 7.22 (d, J = 6.0 Hz, 1H), 6.71 (d, J = 9.9 Hz, 1H), 4.92 (bs, 2H), 4.00 (t, J = 6.9 Hz, 2H), 2.67 (s, 3H), 1.88-1.83 (m, 4H), 1.27 (bs, 2H), 1.03 (t, J = 7.5 Hz, 3H). (CDCl₃) | 364.4 |

| Example No. | Structure | ¹H NMR (DMSO-d₆, 300 MHz) | LC/MS [M + 1] |
|---|---|---|---|
| 103 | 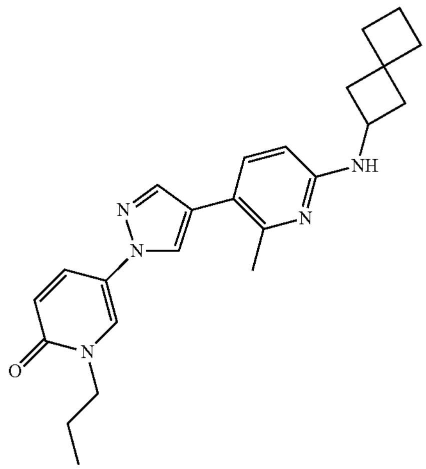 [SMILES: CCCn1cc(-n2cc(-c3ccc(NC4CC5(CCC5)C4)nc3C)cn2)ccc1=O] | δ 7.78 (s, 1H), 7.71-7.67 (m, 3H), 7.39 (d, J = 9.0 Hz, 1H), 6.69 (d, J = 9.9 Hz, 1H), 6.19 (d, J = 8.7 Hz, 1H), 4.73 (bs, 1H), 4.00-3.96 (m, 3H), 2.57-2.50 (m, 2H), 2.46 (s, 3H), 2.09-1.85 (m, 10H), 1.02 (t, J = 7.5 Hz, 3H). (CDCl₃) | 404.6 |
| 104 | 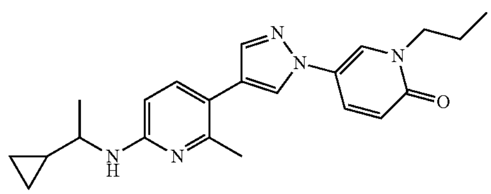 [SMILES: CCCn1cc(-n2cc(-c3ccc(NC(C)C4CC4)nc3C)cn2)ccc1=O] | δ 7.78 (s, 1H), 7.71-7.67 (m, 3H), 7.38 (d, J = 9.7 Hz, 1H), 6.69 (d, J = 9.9 Hz, 1H), 6.27 (d, J = 9.1 Hz, 1H), 4.62 (bs, 1H), 3.98 (t, J = 6.8 Hz, 2H), 3.28-3.26 (m, 1H), 2.47 (s, 3H), 1.90-183 (m, 2H), 1.28 (d, J = 6.3 Hz, 3H), 1.02 (t, J = 7.4 Hz, 3H), 0.52-0.29 (m, 4H). (CDCl₃) | 378.5 |
| 105 | 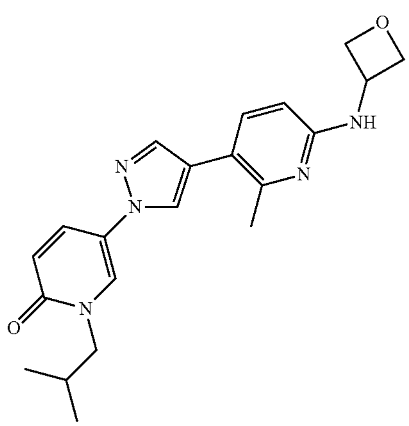 [SMILES: Cc1nc(NC2COC2)ccc1-c1cnn(-c2ccc(=O)n(CC(C)C)c2)c1] | δ 7.77 (bs, 2H), 7.69 (d, J = 9.6 Hz, 1H), 7.57-7.51 (m, 2H), 7.22 (m, 1H), 6.71 (d, J = 9.3 Hz, 1H), 4.92 (bs, 2H), 3.85 (d, J = 6.9 Hz, 2H), 3.65 (bs, 3H), 2.67 (s, 3H), 2.29-2.23 (m, 2H), 1.01 (d, J = 6.6 Hz, 6H). (CDCl₃) | 378.5 |

Example 106: N-(cyclopropylmethyl)-2-methyl-6-(1-(2-propylpyridin-4-yl)-1H-pyrazol-4-yl)pyridin-3-amine

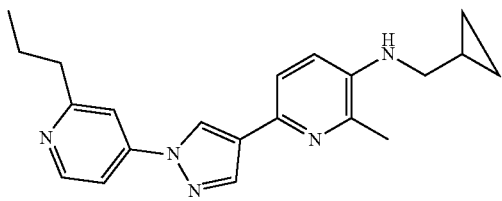 [SMILES: CCCc1cc(-n2cc(-c3ccc(NCC4CC4)c(C)n3)cn2)ccn1]

Step 1:
4-(4-bromo-1H-pyrazol-1-yl)-2-propylpyridine

To a stirred solution of 4-bromo-2-(n-propyl)pyridine (4.0 g, 20.0 mmol), 3-bromopyrazole (3.5 g, 24.0 mmol), potassium carbonate (5.526 g, 40.0 mmol, 2.0 equiv.) in anhydrous toluene (40 mL) under argon were added trans-N,N'-dimethyl-1,2-cyclohexanediamine (0.6 mL, 4.0 mmol) and copper(I) iodide (0.19 g, 1.0 mmol). The mixture was stirred at 100° C. overnight. After cooling, the mixture was partitioned between ethyl acetate and water. The layers were separated and the aqueous layer was extracted twice with ethyl acetate. The combined organics were washed with brine and dried over MgSO₄. The solvents were removed and resulting residue purified by flash chromatography (80 g, 0-40% ethyl acetate in hexanes). The title compound was obtained as a thick oil (2.89 g, 54.3%). LC/MS: [M+1]⁺ 268.1; ¹H NMR (300 MHz, CDCl₃): δ 8.59 (d, J=5.1 Hz, 1H), 8.06 (s, 1H), 7.73 (s, 1H), 7.49 (d, J=1.8 Hz, 1H), 7.38 (dd, J=5.7 and 2.4 Hz, 1H), 2.84 (t, J=7.5 Hz, 2H), 1.85-1.78 (m, 2H), 1.00 (t, J=7.5 Hz, 3H).

Step 2: 2-propyl-4-(4-(4,4,5,5-tetramethyl-1,3,2-dioxaborolan-2-yl)-1H-pyrazol-1-yl)pyridine To a stirred solution of 4-(4-bromo-1H-pyrazol-1-yl)-2-propylpyridine (2.1 g, 7.9 mmol) in DMSO (35 mL) was added 4,4,4',4',5,5,5',5'-octamethyl-2,2'-bi(1,3,2-dioxaborolane) (3.0 g, 11.8 mmol) and potassium acetate (2.3 g, 23.7 mmol) followed by 1,1'-bis(diphenylphosphino)ferrocenedichloro palladium(II) dichloromethane complex, (190 mg) and the flask was degassed and flushed with argon and stirred at 70° C. overnight. After cooling, the mixture was partitioned between ethyl acetate (100 mL) and sat. NaHCO₃. The organic layer was washed with brine, dried over Na₂SO₄ and concentrated. The product was obtained as a yellow oil (3.0 g). The crude was directly used in subsequent reaction without further purification. LC/MS: [M+1]⁺ 314.2.

Step 3: 2-methyl-3-nitro-6-(1-(2-propylpyridin-4-yl)-1H-pyrazol-4-yl)pyridine

A solution of 2-propyl-4-(4-(4,4,5,5-tetramethyl-1,3,2-dioxaborolan-2-yl)-1H-pyrazol-1-yl)pyridine (2.00 g, 5.1 mmol), 6-bromo-2-methyl-3-nitropyridine (1.70 g, 7.7 mmol) and 2.0 M sodium carbonate (7.6 mL, 15.3 mmol) in dimethyl formamide (14 mL) was stirred at room temperature for 5 minutes, then tetrakis(triphenylphosphine) palladium(0) (120 mg, 0.1 mmol) was then added and the flask was degassed and flushed with argon and stirred at 110° C. overnight. After cooling, the mixture was partitioned between ethyl acetate (200 mL) and water. The organic layer was washed with brine, dried over Na₂SO₄ and concentrated. The residue was purified by flash chromatography (40 g, 0-70% ethyl acetate in hexanes) to afford the desired product as a brown solid. ¹H-NMR (300 MHz, CDCl₃): δ 8.70 (s, 1H), 8.64 (d, J=5.7 Hz, 1H), 8.37 (d, J=8.7 Hz, 1H), 8.28 (s, 1H), 7.62 (s, 1H), 7.56-7.53 (m, 2H), 2.95 (s, 3H), 2.88 (t, J=7.8 Hz, 2H), 1.89-1.81 (m, 2H), 1.03 (t, J=7.8 Hz, 3H).

Step 4: 2-methyl-6-(1-(2-propylpyridin-4-yl)-1H-pyrazol-4-yl)pyridin-3-amine

To a yellow suspension of 2-methyl-3-nitro-6-(1-(2-propylpyridin-4-yl)-1H-pyrazol-4-yl)pyridine (1.25 g, 3.9 mmol) in ethanol (50 mL), was added tin(II) chloride (2.4 g, 12.8 mmol), followed by hydrogen chloride (0.13 mL, 3.9 mmol), and the reaction was heated to 80° C. for 6 hours. After the reaction had cooled to ambient temperature, it was poured into an ice-cold solution of 10.0 g potassium hydroxide in 100 mL of water. The basic mixture was diluted with 75 mL of ethyl acetate, the layers separated, and the aqueous layer was extracted with ethyl acetate (3×30 mL). The combined organics were dried over sodium sulfate and concentrated and purified by flash chromatography to afford the desired product as a yellow solid. ¹H NMR (300 MHz, CDCl₃): δ 8.58 (d, J=5.4 Hz, 1H), 8.48 (s, 1H), 8.12 (s, 1H), 7.59 (d, J=1.8 Hz, 1H), 7.49 (dd, J=5.6 and 2.0 Hz, 1H), 7.29 (s, 1H), 6.98 (d, J=8.1 Hz, 1H), 3.67 (bs, 2H), 2.85 (t, J=7.7 Hz, 2H), 1.87-1.79 (m, 2H), 1.01 (t, J=7.4 Hz, 3H).

Step 5: N-(cyclopropylmethyl)-2-methyl-6-(1-(2-propylpyridin-4-yl)-1H-pyrazol-4-yl)pyridin-3-amine To a solution of 2-methyl-6-(1-(2-propylpyridin-4-yl)-1H-pyrazol-4-yl)pyridin-3-amine (0.07 g, 0.2 mmol) in dichloroethane (5 mL) was added cyclopropanecarbaldehyde (22 μL, 0.3 mmol), acetic acid (20 μL, 0.4 mmol) and sodium triacetoxyborohydride (0.15 g, 0.7 mmol). The reaction was stirred at room temperature for 4 hours. The mixture was diluted with saturated sodium bicarbonate and dichloromethane. The organic layer was washed with brine, dried over anhydrous sodium sulfate, filtered and concentrated. The resulting residue was purified by flash chromatography (4 g, 0-50% ethyl acetates in hexanes) to give title compound as a yellow solid (21 mg, 26%). LC/MS: 348.2 [M+1]⁺; ¹H NMR (300 MHz, CDCl₃): δ 8.57 (d, J=5.4 Hz, 1H), 8.47 (s, 1H), 8.11 (s, 1H), 7.59 (s, 1H), 7.49 (d, J=5.1 Hz, 1H), 7.32 (d, J=5.1 Hz, 1H), 6.86 (d, J=8.1 Hz, 1H), 3.02 (d, J=7.2 Hz, 2H), 2.85 (t, J=7.7 Hz, 2H), 2.49 (s, 3H), 1.87-1.77 (m, 2H), 1.19-1.15 (m, 1H), 1.01 (t, J=7.2 Hz, 3H), 0.66-0.60 (m, 2H), 0.34-0.29 (m, 2H).

The following compounds were made in a manner similar to that described for Example 106.

| Example No. | Structure | ¹H NMR (CDCl₃, 300 MHz) | LC/MS [M + 1] |
|---|---|---|---|
| 107 | 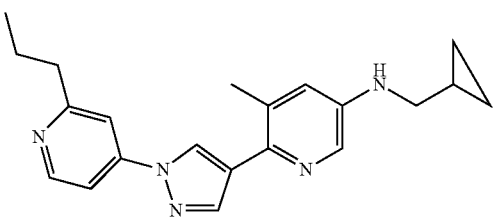 [SMILES: CCCc1cc(-n2cc(-c3ncc(NCC4CC4)cc3C)cn2)ccn1] | δ 8.58 (d, J = 5.4 Hz, 1H), 8.36 (s, 1H), 8.13 (s, 1H), 7.95 (d, J = 2.4 Hz, 1H), 7.59 (d, J = 1.8 Hz, 1H), 7.49 (dd, J = 5.7 and 2.1 Hz, 1H), 6.77 (d, J = 2.4 Hz, 1H), 3.02 (d, J = 7.2 Hz, 2H), 2.85 (t, J = 7.7 Hz, 2H), 2.48 (s, 3H), 1.89-1.77 (m, 2H), 1.16-1.07 (m, 1H), 1.01 (t, J = 7.2 Hz, 3H), 0.64-0.58 (m, 2H), 0.32-0.27 (m, 2H). | 348.2 |

| Example No. | Structure | ¹H NMR (CDCl₃, 300 MHz) | LC/MS [M + 1] |
|---|---|---|---|
| 108 | 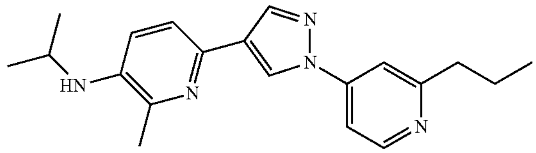 [SMILES: CCCc1cc(-n2cc(-c3ccc(NC(C)C)c(C)n3)cn2)ccn1] | δ 8.57 (d, J = 6.0 Hz, 1H), 8.46 (s, 1H), 8.11 (s, 1H), 7.59 (s, 1H), 7.51-7.49 (m, 1H), 7.32 (d, J = 8.4 Hz, 1H), 6.89 (d, J = 8.4 Hz, 1H), 3.70-3.63 (m, 1H), 2.84 (t, J = 7.7 Hz, 2H), 2.44 (s, 3H), 1.87-1.79 (m, 2H), 1.29 (d, J = 6.3 Hz, 6H), 1.01 (t, J = 7.2 Hz, 3H). | 336.3 |
| 109 | 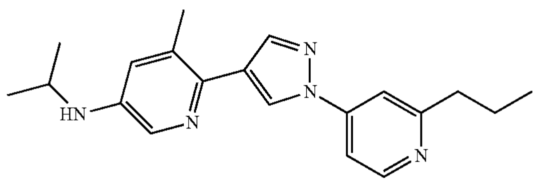 [SMILES: CCCc1cc(-n2cc(-c3ncc(NC(C)C)cc3C)cn2)ccn1] | δ 8.58 (d, J = 5.4 Hz, 1H), 8.35 (s, 1H), 8.13 (s, 1H), 7.92 (d, J = 2.1 Hz, 1H), 7.59 (s, 1H), 7.49 (d, J = 3.6 Hz, 1H), 6.76 (s, 1H), 3.71-3.67 (m, 1H), 2.85 (t, J = 7.7 Hz, 2H), 2.47 (s, 3H), 1.87-1.76 (m, 2H), 1.27 (d, J = 6.6 Hz, 6H), 1.01 (t, J = 7.2 Hz, 3H). | 336.2 |
| 110 | 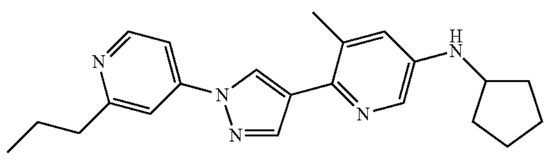 [SMILES: CCCc1cc(-n2cc(-c3ncc(NC4CCCC4)cc3C)cn2)ccn1] | δ 8.57 (d, J = 6.0 Hz, 1H), 8.35 (s, 1H), 8.13 (s, 1H), 7.93 (d, J = 2.4 Hz, 1H), 7.59 (s, 1H), 7.49-7.47 (m, 1H), 6.77 (d, J = 2.4 Hz, 1H), 3.86-3.82 (m, 1H), 2.84 (t, J = 7.7 Hz, 2H), 2.47 (s, 3H), 2.08-2.04 (m, 2H), 1.86-1.67 (m, 8H), 1.01 (t, J = 7.2 Hz, 3H). | 362.3 |
| 111 | 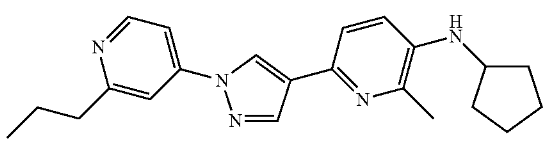 [SMILES: CCCc1cc(-n2cc(-c3ccc(NC4CCCC4)c(C)n3)cn2)ccn1] | δ 8.57 (d, J = 5.4 Hz, 1H), 8.46 (s, 1H), 8.11 (s, 1H), 7.59 (s, 1H), 7.50-7.49 (m, 1H), 7.31 (d, J = 2.4 Hz, 1H), 6.91 (d, J = 8.7 Hz, 1H), 3.85-3.81 (m, 1H), 2.84 (t, J = 7.7 Hz, 2H), 2.43 (s, 3H), 2.12-2.07 (m, 2H), 1.87-1.60 (m, 8H), 1.01 (t, J = 7.2 Hz, 3H). | 362.3 |
| 112 | 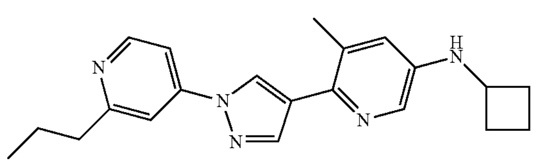 [SMILES: CCCc1cc(-n2cc(-c3ncc(NC4CCC4)cc3C)cn2)ccn1] | δ 8.58 (d, J = 6.0 Hz, 1H), 8.35 (s, 1H), 8.13 (s, 1H), 7.89 (d, J = 2.4 Hz, 1H), 7.59 (s, 1H), 7.49 (d, J = 6.0 Hz, 1H), 6.71 (d, J = 2.4 Hz, 1H), 3.97-3.92 (m, 1H), 2.85 (t, J = 7.7 Hz, 2H), 2.49-2.47 (m, 5H), 1.87-1.77 (m, 6H), 1.01 (t, J = 7.2 Hz, 3H). | 348.2 |
| 113 | 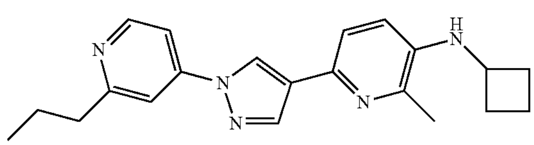 [SMILES: CCCc1cc(-n2cc(-c3ccc(NC4CCC4)c(C)n3)cn2)ccn1] | δ 8.57 (d, J = 5.4 Hz, 1H), 8.46 (s, 1H), 8.10 (s, 1H), 7.59 (s, 1H), 7.49 (d, J = 5.7 Hz, 1H), 7.30 (d, J = 8.1 Hz, 1H), 6.78 (d, J = 8.1 Hz, 1H), 3.97-3.92 (m, 1H), 2.84 (t, J = 7.7 Hz, 2H), 2.49-2.45 (m, 5H), 1.90-1.79 (m, 6H), 1.01 (t, J = 7.2 Hz, 3H). | 348.2 |
| 114 | 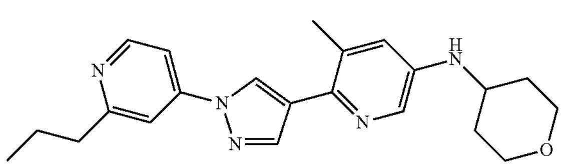 [SMILES: CCCc1cc(-n2cc(-c3ncc(NC4CCOCC4)cc3C)cn2)ccn1] | δ 8.58 (d, J = 5.4 Hz, 1H), 8.35 (s, 1H), 8.13 (s, 1H), 7.95 (d, J = 2.4 Hz, 1H), 7.59 (s, 1H), 7.48 (d, J = 5.2 Hz, 1H), 6.79 (d, J = 2.4 Hz, 1H), 4.06-4.02 (m, 2H), 3.59-3.51 (m, 4H), 2.85 (t, J = 7.7 Hz, 2H), 2.48 (s, 3H), 2.10-2.05 (m, 2H), 1.87-1.79 (m, 2H), 1.52-1.50 (m, 1H), 1.01 (t, J = 7.2 Hz, 3H). (CD₃OD) | 378.2 |

-continued

| Example No. | Structure | $^1$H NMR (CDCl$_3$, 300 MHz) | LC/MS [M + 1] |
|---|---|---|---|
| 115 | 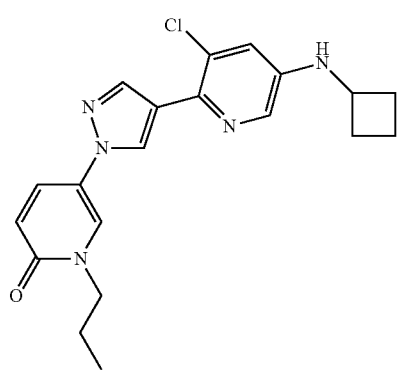 | δ 8.57 (d, J = 6.0 Hz, 1H), 8.47 (s, 1H), 8.11 (s, 1H), 7.59 (s, 1H), 7.49 (d, J = 4.8 Hz, 1H), 7.30 (d, J = 8.4 Hz, 1H), 6.91 (d, J = 9.1 Hz, 1H), 4.07-4.03 (m, 2H), 3.60-3.50 (m, 4H), 2.85 (t, J = 7.7 Hz, 2H), 2.46 (s, 3H), 2.11-2.06 (m, 2H), 1.87-1.79 (m, 2H), 1.52-1.50 (m, 1H), 1.01 (t, J = 7.2 Hz, 3H). | 378.2 |

Example 116: N-(5-methyl-6-(1-(2-propylpyridin-4-yl)-1H-pyrazol-4-yl)pyridin-3-yl)methanesulfonamide

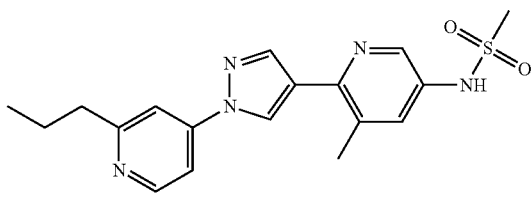 [SMILES: CCCc1cc(-n2cc(-c3ncc(NS(C)(=O)=O)cc3C)cn2)ccn1]

A solution of 5-methyl-6-(1-(2-propylpyridin-4-yl)-1H-pyrazol-4-yl)pyridin-3-amine (0.08 g, 0.3 mmol) and pyridine (62 μL, 0.8 mmol) in dichloromethane (5 mL) was cooled to 0° C. Then, methanesulfonyl chloride (78 μL, 0.9 mmol) was added, and reaction mixture was allowed to warm to room temperature overnight to give a yellow suspension. The reaction mixture was quenched with saturated sodium bicarbonate. The layers were separated, and the aqueous layer was extracted with dichloromethane (2×20 mL). The combined organics were dried over Na$_2$SO$_4$ and concentrated. The resulting residue was purified by flash chromatography (4 g, 0-80% ethyl acetates in hexanes) to give the title compound as a yellow solid (54 mg, 57%). LC/MS: [M+1]$^+$ 372.2; 1HNMR (300 MHz, CDCl$_3$): δ 8.61 (d, J=6.0 Hz, 1H), 8.48 (s, 1H), 8.33 (d, J=2.4 Hz, 1H), 8.22 (s, 1H), 7.60 (s, 2H), 7.51 (d, J=3.6 Hz, 1H), 6.46 (bs, 1H), 3.09 (s, 3H), 2.86 (t, J=7.5 Hz, 2H), 2.59 (s, 3H), 1.87-1.79 (m, 2H), 1.02 (t, J=7.4 Hz, 3H).

Example 117: N-(2-methyl-6-(1-(2-propylpyridin-4-yl)-1H-pyrazol-4-yl)pyridin-3-yl)methanesulfonamide

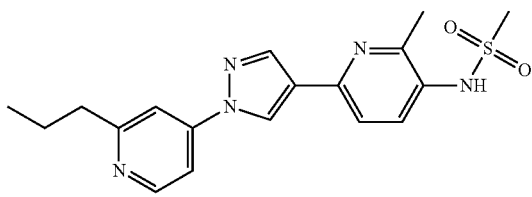 [SMILES: CCCc1cc(-n2cc(-c3ccc(NS(C)(=O)=O)c(C)n3)cn2)ccn1]

The title compound was prepared in a manner analogous to that given for Example 116.
LC/MS: [M+1]$^+$372.2; $^1$HNMR (300 MHz, CDCl$_3$): δ 8.61 (d, J=5.4 Hz, 1H), 8.57 (s, 1H), 8.20 (s, 1H), 7.83 (d, J=5.1 Hz, 1H), 7.60 (s, 1H), 7.53-7.44 (m, 2H), 6.20 (bs, 1H), 3.07 (s, 3H), 2.87 (t, J=7.5 Hz, 2H), 2.62 (s, 3H), 1.88-1.80 (m, 2H), 1.02 (t, J=7.4 Hz, 3H).

Example 118: 5-(4-(3-chloro-5-(cyclobutylamino)pyridin-2-yl)-1H-pyrazol-1-yl)-1-propylpyridin-2(1H)-one Step 1: 5-(4-(3-chloro-5-nitropyridin-2-yl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl)pyridin-2(1H)-one (0.55 g, 1.7 mmol), 2-bromo-3-chloro-5-nitropyridine (0.4 g, 1.7 mmol), potassium carbonate (0.7 g, 5.0 mmol) and dioxan (8 mL) and water (2 mL) and the flask was degassed and flushed with argon. PdCl$_2$(dppf) (0.14 g, 0.2 mmol) and was added and the reaction flask was again degassed and flushed with argon. The reaction mixture was then heated to 100° C. in a microwave for 90 minutes. The reaction was cooled to room temperature and quenched with water and extracted with ethyl acetate (3×50 mL). The combined organics were washed with water, brine and dried over MgSO$_4$. The solvents were evaporated to dryness and the residue purified by flash chromatography (25 g silica gel, 0-70% ethyl acetate in hexanes) to afford the product as yellow solid. LC/MS: [M+1]$^+$, 360.2; $^1$HNMR (300 MHz, CDCl$_3$): δ 9.31 (d, J=2.4 Hz, 1H), 8.63 (s, 1H), 8.56 (s, 2H), 7.88 (d, J=2.4 Hz, 1H), 7.71 (dd, J=9.9 and 3.0 Hz, 1H), 6.72 (d, J=10.2 Hz, 1H), 4.00 (t, J=7.5 Hz, 2H), 1.91-1.83 (m, 2H), 1.03 (t, J=6.9 Hz, 3H).

Step 2: 5-(4-(5-amino-3-chloropyridin-2-yl)-1H-pyrazol-1-yl)-1-propylpyridin-2(1H)-one A round bottom flask was charged with 5-(4-(3-chloro-5-nitropyridin-2-yl)-1H-pyrazol-1-yl)-1-propylpyridin-2

(1H)-one (0.25 g, 0.7 mmol), ethanol (20 mL) and tin(II) chloride (0.65 g, 3.4 mmol) was added and the reaction mixture heated to 85° C. for 45 min. The reaction mixture was cooled and poured into 20 mL of 2M KOH. This was extracted with isopropanol/chloroform (1:3, 3×50 mL). The combined organics were washed with brine and dried over MgSO$_4$. The solvents were evaporated to give the product as pale yellow solid which was used in the next reaction without further purification. LC/MS: [M+1]$^+$ 330.2; $^1$HNMR (300 MHz, CDCl$_3$): 8.29 (s, 1H), 8.02 (d, J=2.4 Hz, 1H), 7.79 (d, J=3.0 Hz, 1H), 7.68 (dd, J=7.2 and 3.0 Hz, 1H), 7.31 (s, 1H), 7.08 (d, J=2.4 Hz, 1H), 6.68 (d, J=9.3 Hz, 1H), 3.96 (t, J=7.8 Hz, 2H), 3.80 (bs, 2H), 1.87-1.81 (m, 2H), 1.00 (t, J=6.9 Hz, 3H).

Step 3: 5-(4-(3-chloro-5-(cyclobutylamino)pyridin-2-yl)-1H-pyrazol-1-yl)-1-propylpyridin-2(1H)-one A vial was charged with 5-(4-(5-amino-3-chloropyridin-2-yl)-1H-pyrazol-1-yl)-1-propylpyridin-2(1H)-one (0.07 g, 0.2 mmol), cyclobutanone (0.08 mL, 1.1 mmol) and 1,2-dichloroethane (5 mL) and the reaction mixture was stirred for 15 min and sodium triacetoxyborohydride (0.14 g, 0.6 mmol) was added and the reaction mixture stirred at room temperature for 48 hours. The reaction mixture was quenched with water and extracted with dichloromethane (3×25 mL). The combined organics were washed with brine and dried over MgSO$_4$. The solvents were evaporated to dryness and the residue purified by reverse phase HPLC to give the product as off-white solid (71 mg, 85%). LC/MS: [M+1]$^+$384.5; $^1$H NMR (300 MHz, CDCl$_3$): δ 8.27 (d, J=3.0 Hz, 2H), 7.91 (d, J=2.4 Hz, 1H), 7.80 (d, J=3.0 Hz, 1H), 7.69 (dd, J=9.9 and 3.0 Hz, 1H), 6.87 (d, J=2.1 Hz, 1H), 6.68 (d, J=9.9 Hz, 1H), 4.05-3.92 (m, 3H), 2.49-2.45 (m, 2H), 1.89-1.82 (m, 6H), 1.01 (t, J=7.4 Hz, 3H).

The following compounds are made in a manner similar to that described for Example 118.

| Example No. | Structure | $^1$H NMR (CDCl$_3$, 300 MHz) | LC/MS [M + 1] |
|---|---|---|---|
| 119 | 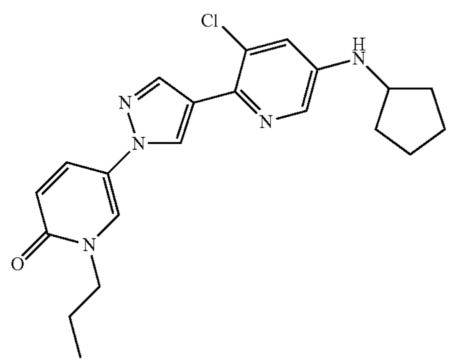 [SMILES: CCCn1cc(-n2cc(-c3ncc(NC4CCCC4)cc3Cl)cn2)ccc1=O] | δ 8.28 (d, J = 3.6 Hz, 2H), 7.94 (d, J = 2.4 Hz, 1H), 7.80 (d, J = 2.4 Hz, 1H), 7.71 (dd, J = 9.3 and 3.0 Hz, 1H), 6.94 (d, J = 2.4 Hz, 1H), 6.68 (d, J = 9.9 Hz, 1H), 3.97 (t, J = 7.4 Hz, 2H), 3.86-3.79 (m, 2H), 2.11-2.05 (m, 2H), 1.89-1.68 (m, 6H), 1.53-1.50 (m, 2H), 1.01 (t, J = 7.4 Hz, 3H). | 398.7 |
| 120 | 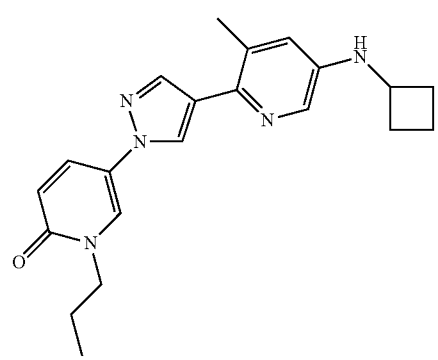 [SMILES: CCCn1cc(-n2cc(-c3ncc(NC4CCC4)cc3C)cn2)ccc1=O] | δ 8.01 (d, J = 10.5 Hz, 2H), 7.87 (d, J = 3.0 Hz, 1H), 7.80 (d, J = 2.7 Hz, 1H), 7.71 (dd, J = 9.9 and 3.0 Hz, 1H), 6.72-6.70 (m, 1H), 6.67 (s, 1H), 3.99-3.95 (m, 3H), 2.49-2.45 (m, 2H), 2.45 (s, 3H), 1.89-1.81 (m, 6H), 1.01 (t, J = 7.4 Hz, 3H). | 364.4 |
| 121 | 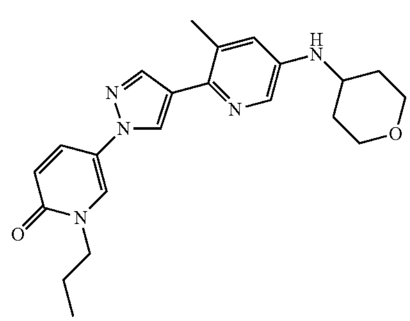 [SMILES: CCCn1cc(-n2cc(-c3ncc(NC4CCOCC4)cc3C)cn2)ccc1=O] | δ 8.02 (d, J = 6.9 Hz, 2H), 7.92 (d, J = 2.4 Hz, 1H), 7.80 (d, J = 2.7 Hz, 1H), 7.71 (dd, J = 9.9 and 3.0 Hz, 1H), 6.78 (d, J = 2.1 Hz, 1H), 6.68 (d, J = 9.6 Hz, 1H), 4.06-3.95 (m, 4H), 3.59-3.50 (m, 4H), 2.46 (s, 3H), 2.09-2.05 (m, 2H), 1.89-1.81 (m, 2H), 1.58-1.50 (m, 2H), 1.01 (t, J = 7.4 Hz, 3H). | 394.1 |

| Example No. | Structure | ¹H NMR (CDCl₃, 300 MHz) | LC/MS [M + 1] |
|---|---|---|---|
| 122 | 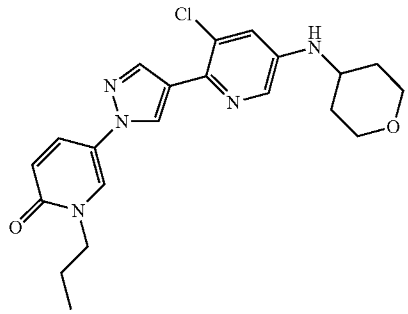 [SMILES: CCCn1cc(-n2cc(-c3ncc(NC4CCOCC4)cc3Cl)cn2)ccc1=O] | δ 8.28 (d, J = 1.8 Hz, 2H), 7.97 (d, J = 2.4 Hz, 1H), 7.80 (d, J = 3.0 Hz, 1H), 7.70 (dd, J = 9.9 and 3.0 Hz, 1H), 6.96 (d, J = 2.4 Hz, 1H), 6.68 (d, J = 9.3 Hz, 1H), 4.07-3.95 (m, 4H), 3.78-3.75 (m, 1H), 3.58-3.51 (m, 3H), 2.09-2.05 (m, 2H), 1.89-1.82 (m, 2H), 1.54-1.49 (m, 2H), 1.01 (t, J = 7.4 Hz, 3H). | 394.5 |
| 123 | 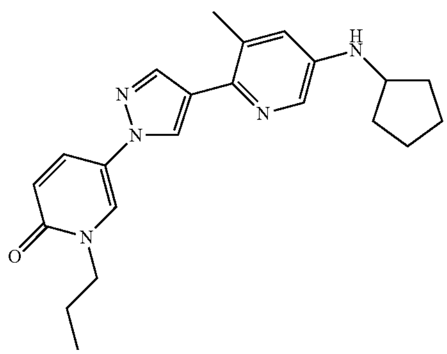 [SMILES: CCCn1cc(-n2cc(-c3ncc(NC4CCCC4)cc3C)cn2)ccc1=O] | δ 8.01 (d, J = 5.7 Hz, 2H), 7.92 (d, J = 2.4 Hz, 1H), 7.80 (d, J = 2.1 Hz, 1H), 7.71 (dd, J = 9.9 and 3.0 Hz, 1H), 6.77 (d, J = 2.1 Hz, 1H), 6.68 (d, J = 9.6 Hz, 1H), 3.97 (t, J = 7.4 Hz, 2H), 3.85-3.81 (m, 1H), 2.45 (s, 3H), 2.08-2.06 (m, 2H), 1.89-1.67 (m, 4H), 1.56-1.40 (m, 4H), 1.01 (t, J = 7.4 Hz, 3H). | 378.3 |
| 124 | 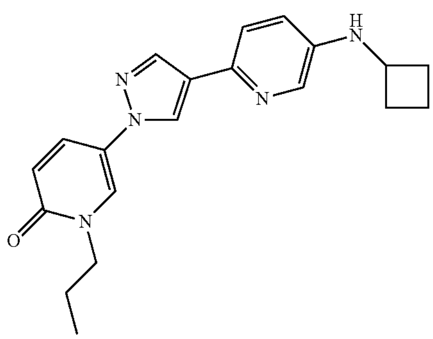 [SMILES: CCCn1cc(-n2cc(-c3ccc(NC4CCC4)cn3)cn2)ccc1=O] | δ 8.12 (s, 1H), 8.01-7.97 (m, 2H), 7.78-7.69 (m, 2H), 7.33 (d, J = 5.7 Hz, 1H), 6.88-6.85 (m, 1H), 6.68 (d, J = 10.2 Hz, 1H), 3.99-3.94 (m, 3H), 1.88-1.81 (m, 6H), 1.63-1.59 (m, 2H), 1.01 (t, J = 7.4 Hz, 3H). | 350.4 |
| 125 | 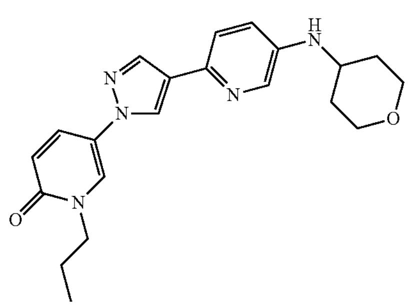 [SMILES: CCCn1cc(-n2cc(-c3ccc(NC4CCOCC4)cn3)cn2)ccc1=O] | δ 8.12 (s, 1H), 8.02 (d, J = 7.2 Hz, 2H), 7.78 (s, 1H), 7.70 (d, J = 9.3 Hz, 1H), 7.35 (d, J = 9.0 Hz, 1H), 6.95 (d, J = 7.5 Hz, 1H), 6.68 (d, J = 9.6 Hz, 1H), 4.06-3.94 (m, 4H), 3.58-3.50 (m, 3H), 2.09-2.05 (m, 2H), 1.89-1.81 (m, 2H), 1.55-1.50 (m, 2H), 1.01 (t, J = 7.4 Hz, 3H). | 380.1 |

| Example No. | Structure | ¹H NMR (CDCl₃, 300 MHz) | LC/MS [M + 1] |
|---|---|---|---|
| 126 | 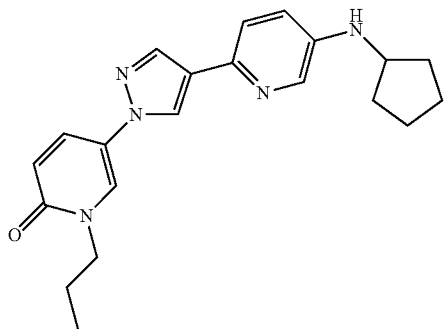 [SMILES: CCCn1cc(-n2cc(-c3ccc(NC4CCCC4)cn3)cn2)ccc1=O] | δ 8.12 (s, 1H), 8.01 (s, 2H), 7.79 (s, 1H), 7.70 (d, J = 9.0 Hz, 1H), 7.34 (d, J = 8.1 Hz, 1H), 6.93 (d, J = 6.0 Hz, 1H), 6.68 (d, J = 9.6 Hz, 1H), 3.97 (t, J = 7.4 Hz, 2H), 3.85-3.81 (m, 1H), 2.08-2.06 (m, 2H), 1.89-1.67 (m, 6H), 1.56-1.40 (m, 2H), 1.01 (t, J = 7.4 Hz, 3H). | 364.4 |
| 127 | 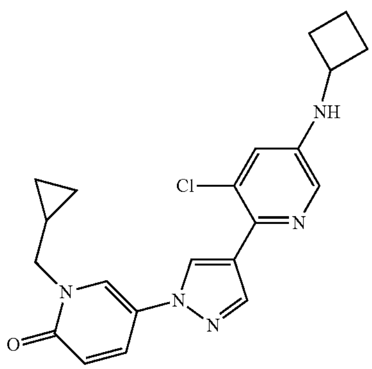 [SMILES: O=c1ccc(-n2cc(-c3ncc(NC4CCC4)cc3Cl)cn2)cn1CC1CC1] | δ 8.48 (s, 1H), 8.24 (s, 1H), 8.18 (s, 1H), 8.01 (d, J = 9.3 Hz, 1H), 7.89 (s, 1H), 6.99 (s, 1H), 6.70 (d, J = 9.9 Hz, 1H), 3.95 (d, J = 7.2 Hz, 3H), 2.45 (s, 1H), 1.98-1.1.86 (m, 4H), 1.39 (s, 1H), 0.64 (d, J = 6.9 Hz, 2H), 0.51 (d, J = 3.6 Hz, 2H). (CD3OD) | 396.6 |
| 128 | 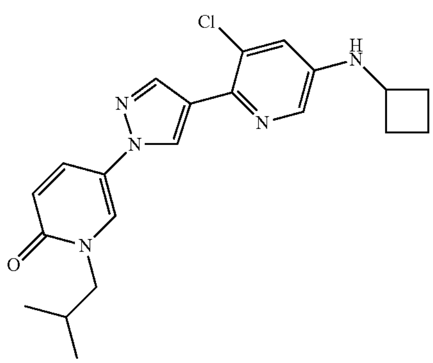 [SMILES: CC(C)Cn1cc(-n2cc(-c3ncc(NC4CCC4)cc3Cl)cn2)ccc1=O] | δ 8.27 (d, J = 4.8 Hz, 2H), 7.91 (d, J = 3.0 Hz, 1H), 7.75-7.69 (m, 2H), 6.87 (d, J = 2.7 Hz, 1H), 6.68 (d, J = 9.9 Hz, 1H), 4.05-3.92 (m, 2H), 3.82 (d, J = 7.8 Hz, 2H), 2.49-2.45 (m, 2H), 2.29-2.20 (m, 1H), 1.90-1.83 (m, 4H), 0.99 (d, J = 6.9 Hz, 6H). | 398.5 |
| 129 | 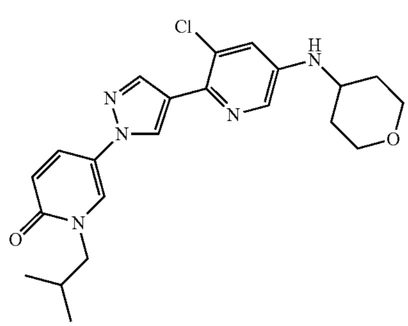 [SMILES: CC(C)Cn1cc(-n2cc(-c3ncc(NC4CCOCC4)cc3Cl)cn2)ccc1=O] | δ 8.28 (d, J = 3.6 Hz, 2H), 7.97 (s, 1H), 7.75-7.69 (m, 2H), 6.96 (s, 1H), 6.68 (d, J = 9.3 Hz, 1H), 4.07-4.03 (m, 2H), 3.82 (d, J = 7.8 Hz, 2H), 3.75-3.67 (m, 1H), 3.59-351 (m, 4H), 2.25-2.04 (m, 4H), 1.00 (d, J = 6.3 Hz, 6H). | 428.6 |

| Example No. | Structure | ¹H NMR (CDCl₃, 300 MHz) | LC/MS [M + 1] |
|---|---|---|---|
| 130 | 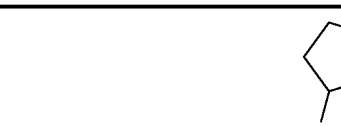 | δ 8.48 (s, 1H), 8.25 (d, J = 2.4 Hz, 1H), 8.17 (s, 1H), 8.03-7.98 (m, 1H), 7.92 (d, J = 2.4 Hz, 1H), 7.06 (d, J = 2.4 Hz, 1H), 6.69 (d, J = 9.3 Hz, 1H), 3.94 (d, J = 7.2 Hz, 2H), 3.82-3.77 (m, 1H), 2.07-2.01 (m, 2H), 1.78-1.67 (m, 4H), 1.57-1.51 (m, 2H), 1.39-1.35 (m, 1H), 0.65-0.59 (m, 2H), 0.52-0.48 (m, 2H). (CD₃OD) | 410.5 |
Additional compounds of the invention (Table A), which can be prepared using methods disclosed herein and known to one of ordinary skill in the art, include
Embodiment A
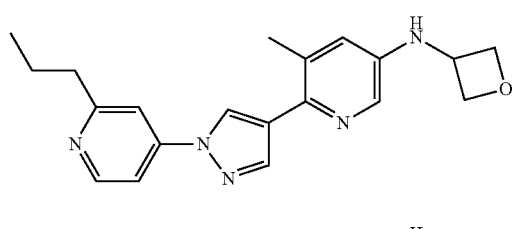
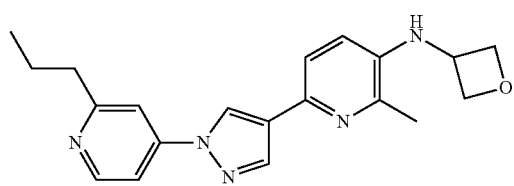
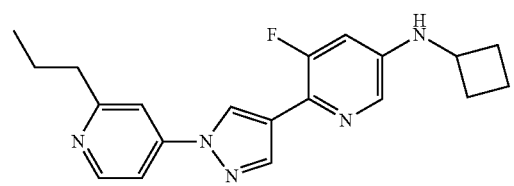
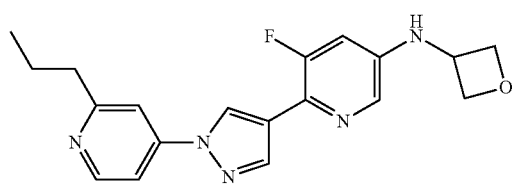
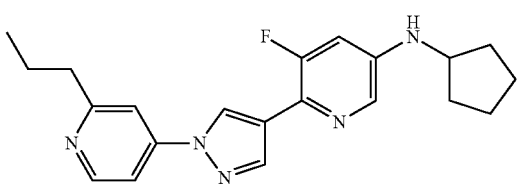
-continued
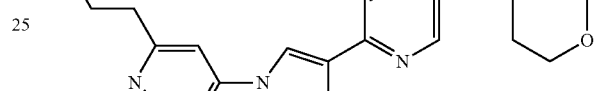
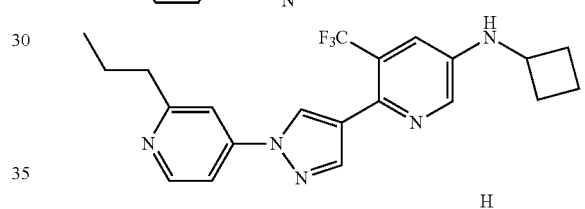
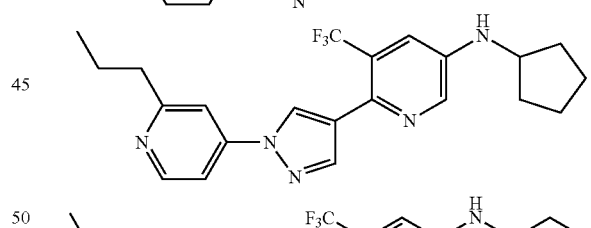
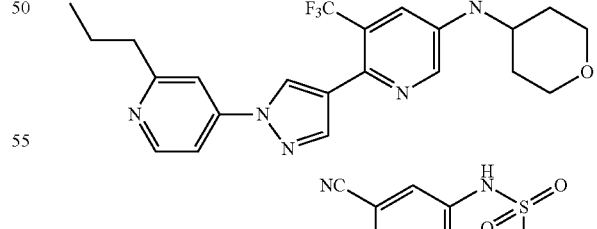
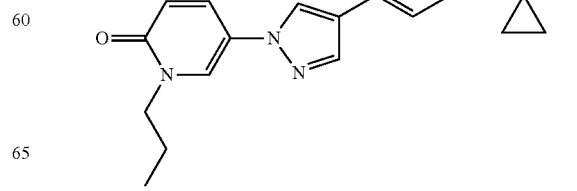

191
-continued
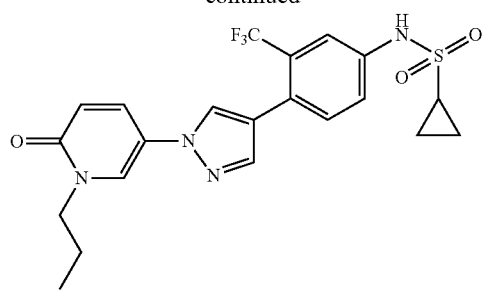
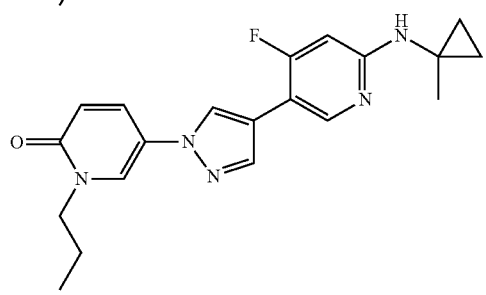
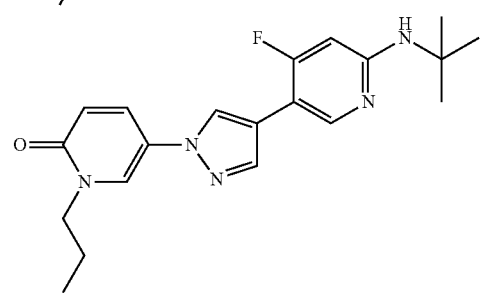
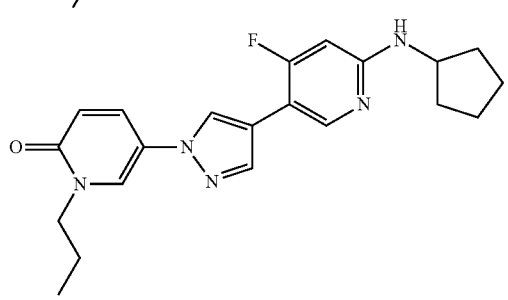
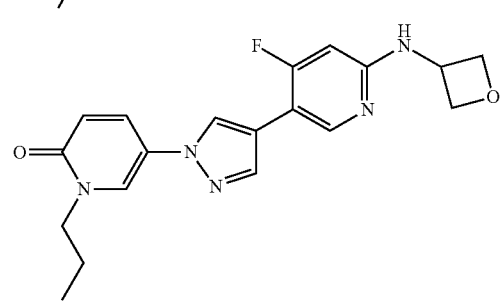
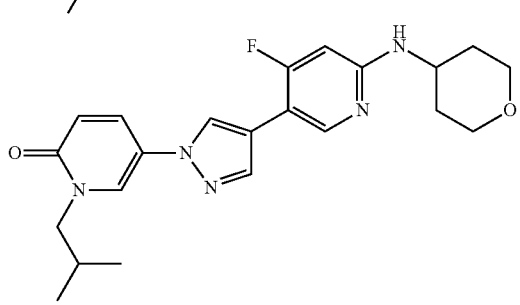
192
-continued
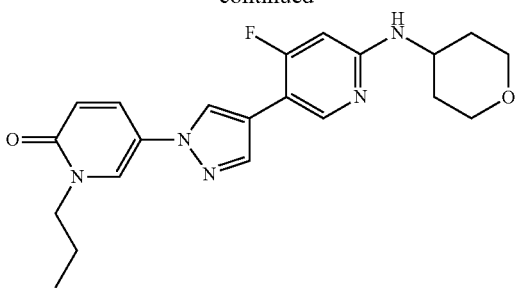
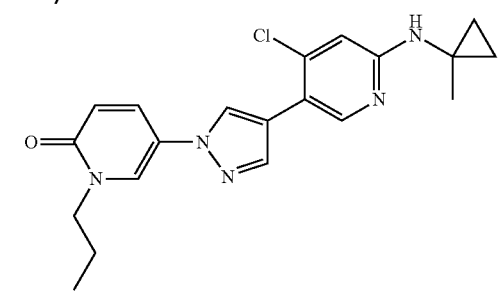
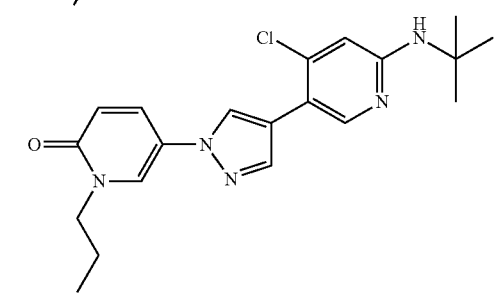
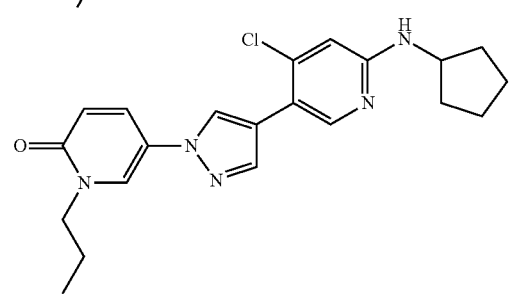
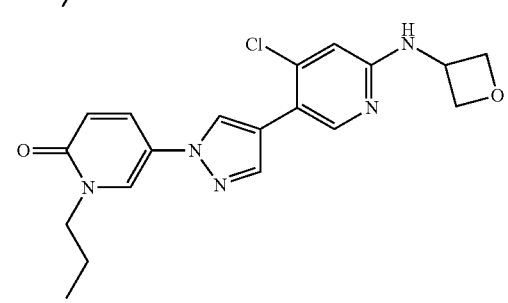
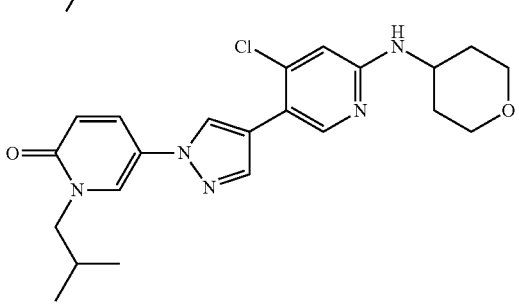

193
-continued
194
-continued
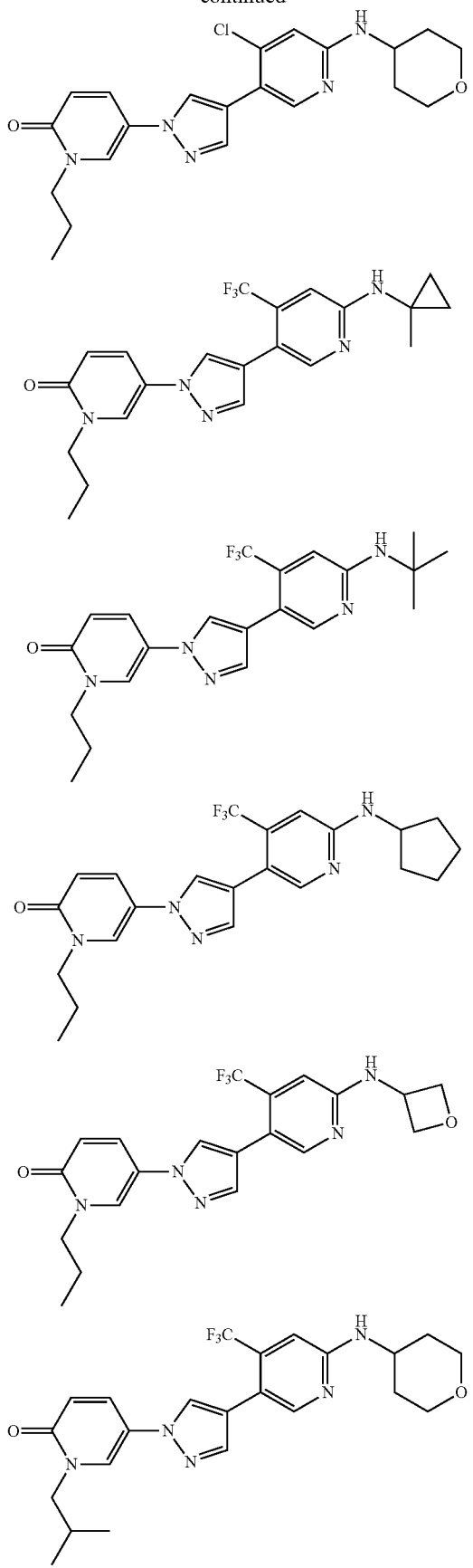
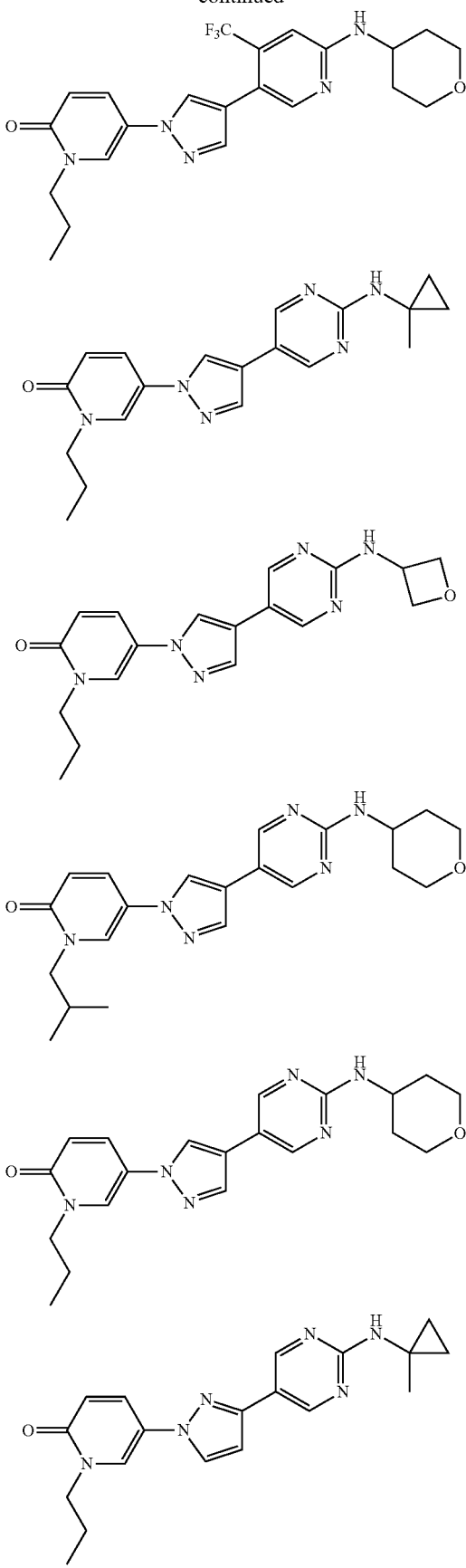

195
-continued
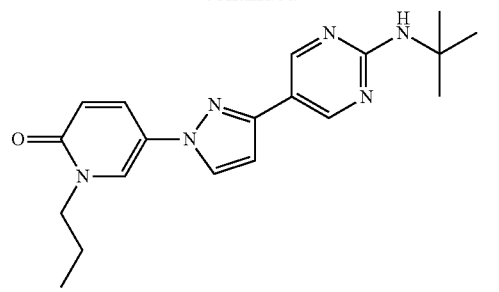
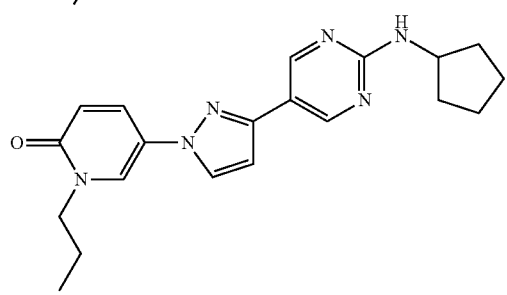
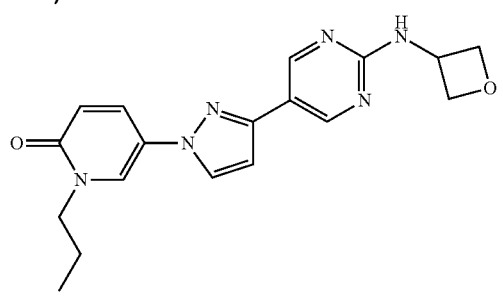
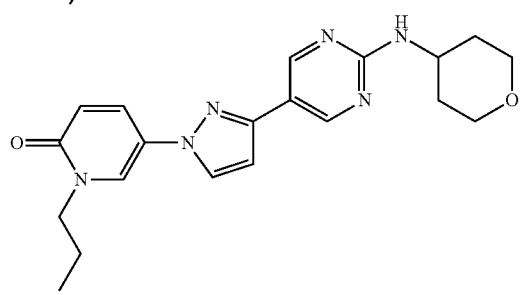
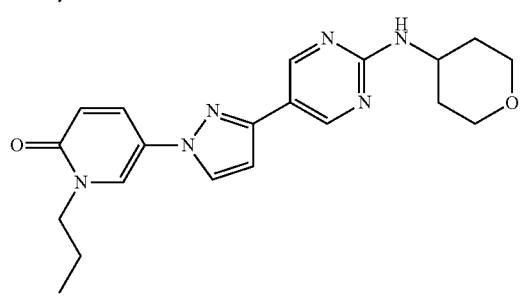
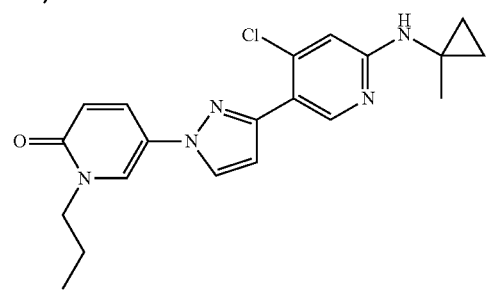
196
-continued
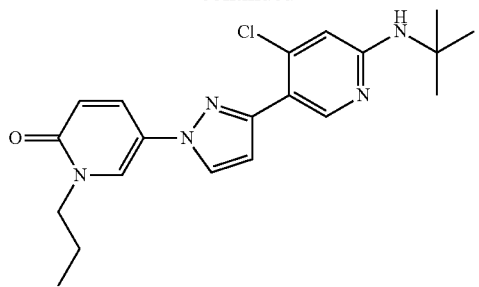
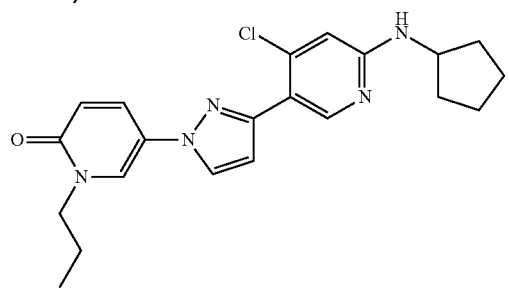
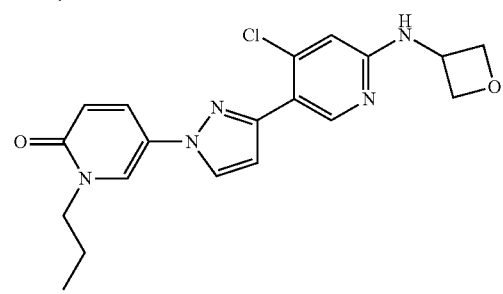
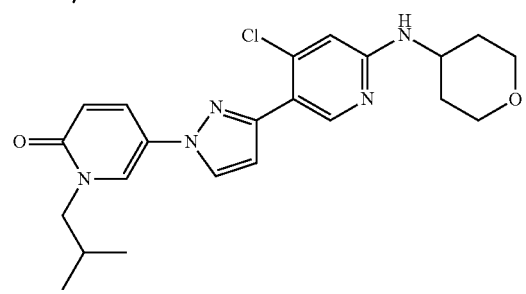
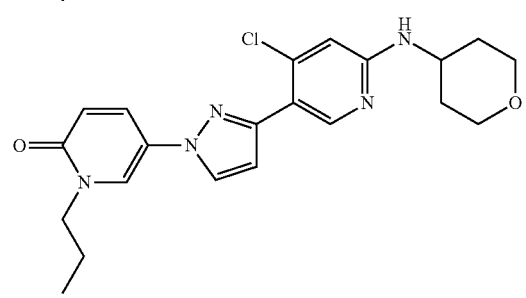
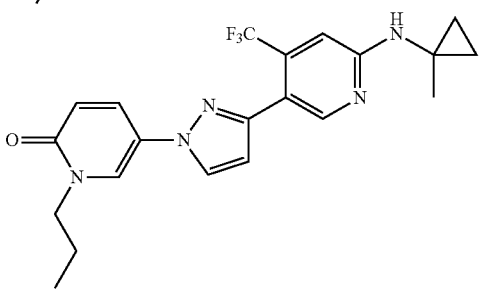

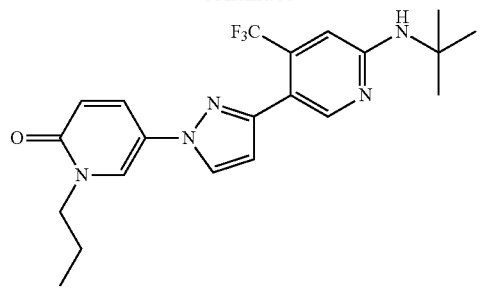
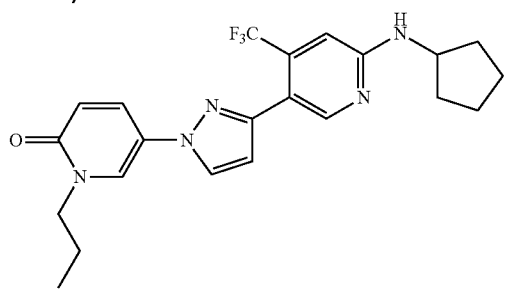
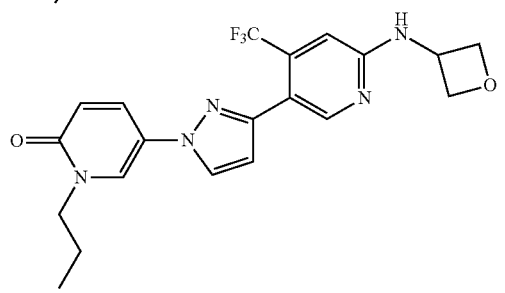
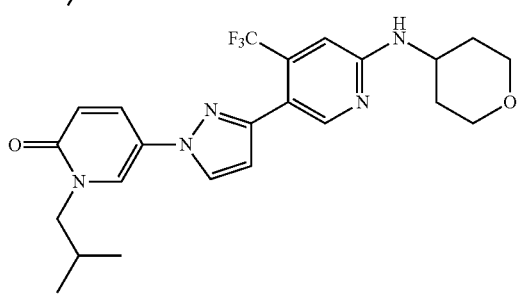
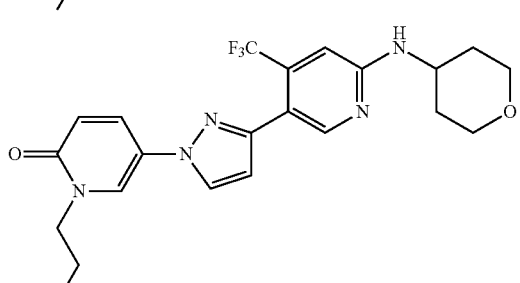
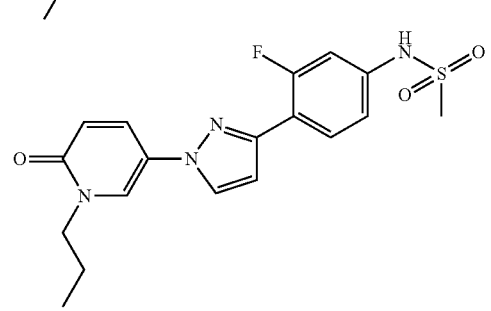
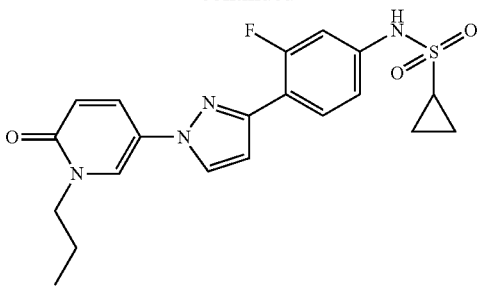
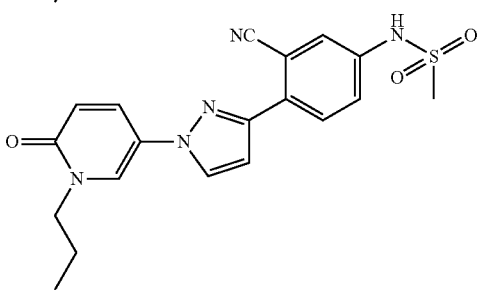
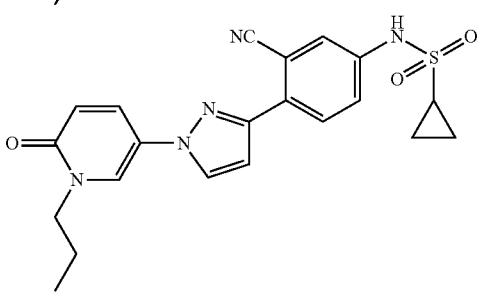
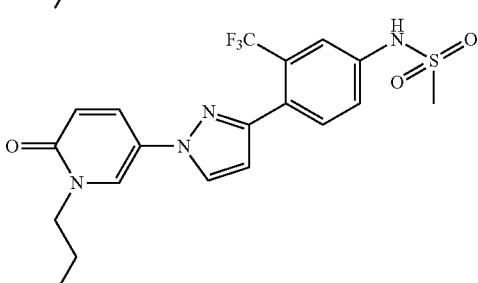
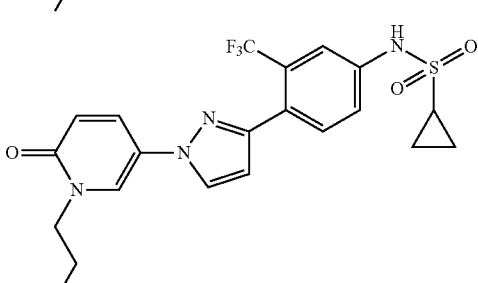
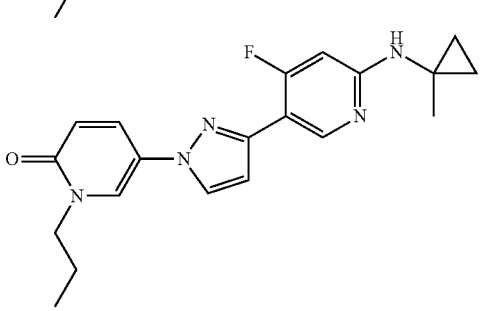

199
-continued
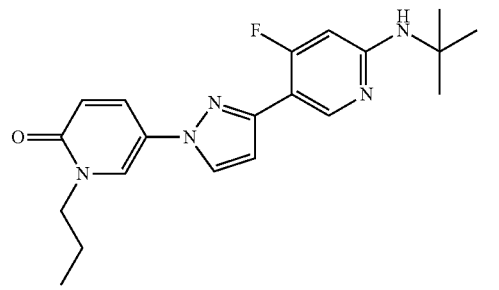
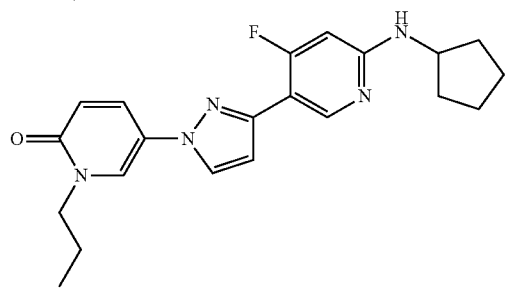
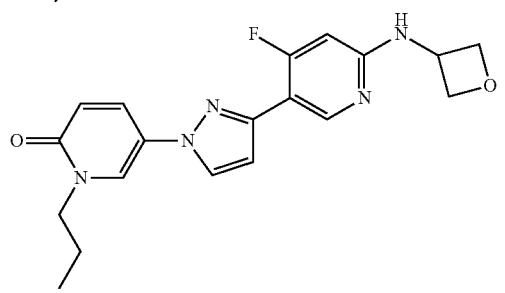
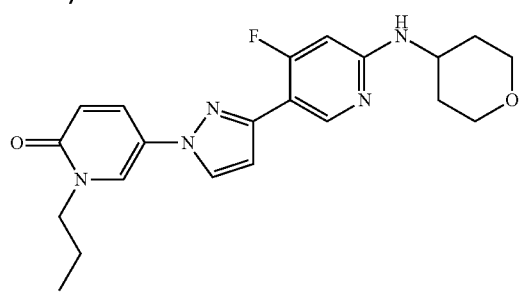
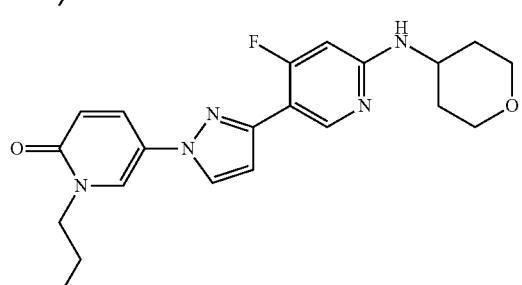
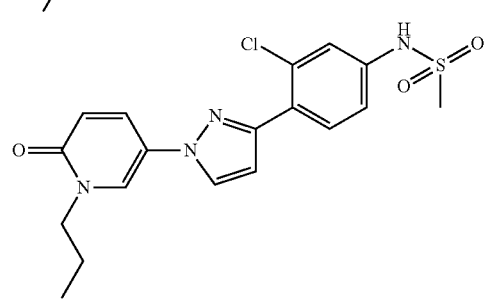
200
-continued
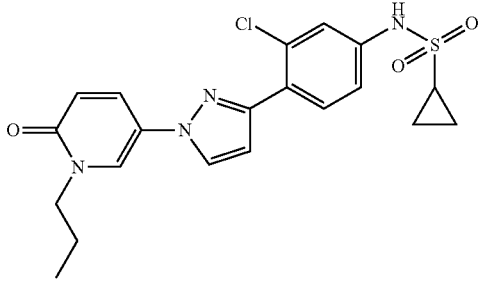
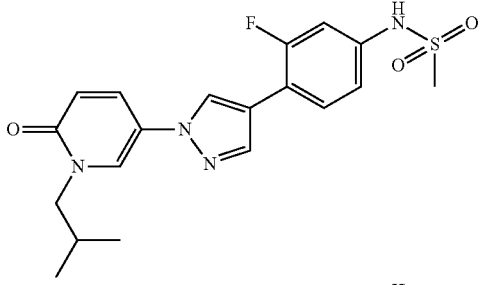
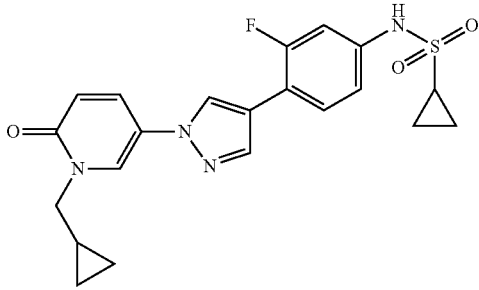
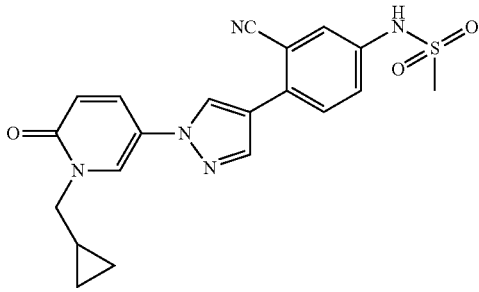
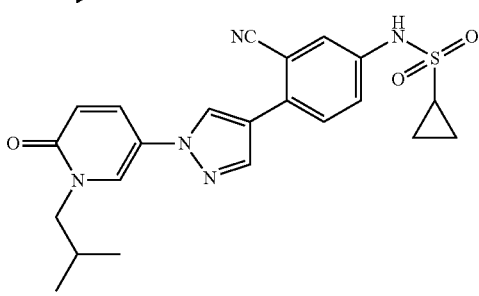
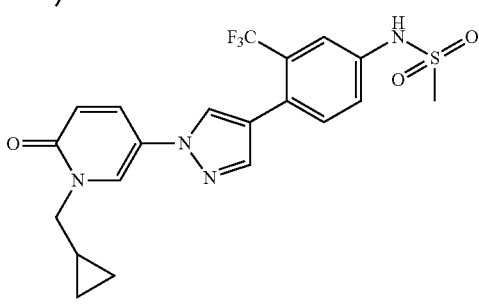

-continued

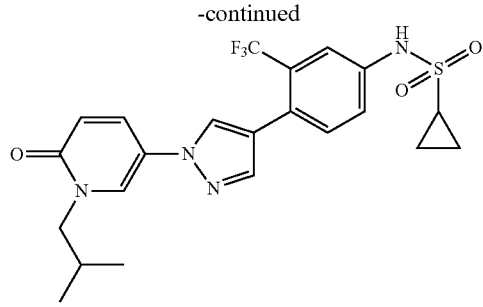

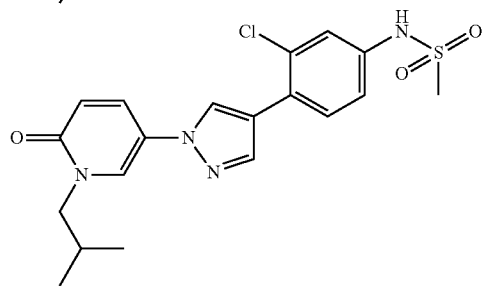

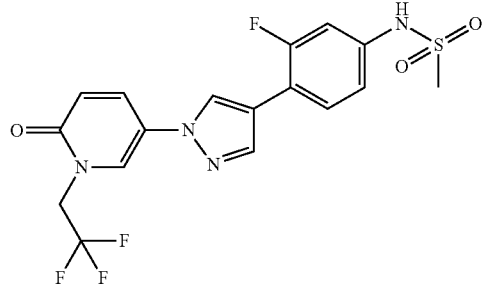

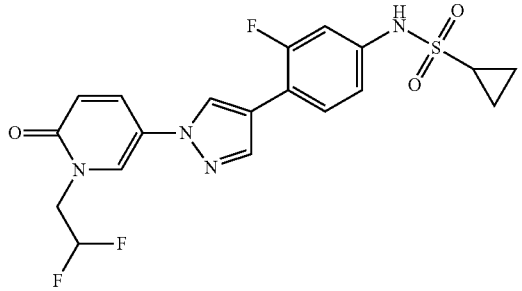

Biological Example 1

Inhibition Assay

Quantitative PCR (qPCR)

HepG2 cells were grown in Dulbecco's Modified Eagle Medium (DMEM) containing 5% FBS and antibiotic-antimycotic in a humidified incubator at 37° C. with 5% $CO_2$. All three components were purchased from ThermoFisher Scientific (Catalog numbers are 11995073, 26140079, and 15240062, respectively). Treatments were done in duplicates for each dose of each compound. For control and treated each treatment, 400,000 HepG2 cells were seeded onto 1 well of 24-well plate. After one day in culture, cells were treated with the test compound (1 μM and/or 10 μM, as indicated below in Table 1) for 24 hours in DMEM with 5% FBS. Compounds were diluted using DMSO from 20 mM stocks. Total RNAs were extracted using RNA extraction kit (Cat #: 45001163, Fisher Scientific) or Trizol. If Trizol was used, RNAs were treated with DNase I (cat #: 18068015, ThermoFisher Scientific) before qPCR. RNA concentrations were measured on a Nanodrop. One-step qPCR were performed using SYBR Green One Step qPCR Kit (Cat #: B25002, Biotool). 10 ng RNA was used in each 10-ul reaction. Triplicate reactions were done for each RNA sample. qPCR was performed on an ABI StepOnePlus using the program: Holding stage step 1, 50° C. 3 min, step 2, 95° C. 5 min; Cycling stage (40 cycles) step 1, 95° C. 10 sec, step 2, 60° C. 30 sec. Primer sequence was as follows: SCD1, 5'-cctggtatttctgggtgaa-3'/5'-gggggctaatgttcttgtca-3'.

All data was measured in HepG2 cells. % inhibition data of SCD1 expression are provided in Table 1. % inhibition at 10 μM is provided as follows: A≥75%; 75%>B≥50%; 50%>C≥10%. % inhibition at 1 μM is provided as follows: A1≥30%; 30%>B1≥2%. NI means no inhibition in the assay at the indicated concentration of compound tested. NT means not tested.

| | Inhibition Percentage (%) | |
|---|---|---|
| Ex. No. | 1 μM | 10 μM |
| 1 | NT | A |
| 2 | NT | A |
| 3 | NT | A |
| 4 | NT | A |
| 5 | NT | C |
| 6 | NT | A |
| 7 | NI | A |
| 8 | NT | A |
| 9 | A1 | A |
| 10 | A1 | A |
| 11 | NT | C |
| 12 | NT | NI |
| 13 | A1 | A |
| 14 | A1 | A |
| 15 | B1 | A |
| 16 | B1 | A |
| 17 | A1 | A |
| 18 | NI | A |
| 19 | B1 | A |
| 20 | NT | C |
| 21 | B1 | A |
| 22 | NT | NI |
| 23 | B1 | A |
| 24 | A1 | A |
| 25 | A1 | A |
| 26 | A1 | A |
| 27 | A1 | A |
| 28 | B1 | A |
| 29 | B1 | A |
| 30 | NT | B |
| 31 | NT | NI |
| 32 | NT | A |
| 33 | A1 | A |
| 52 | A1 | A |
| 34 | B1 | B |
| 35 | B1 | B |
| 36 | NI | B |
| 53 | B1 | A |
| 54 | NI | B |
| 37 | NI | NI |
| 38 | A1 | A |
| 44 | B1 | A |
| 45 | A1 | A |
| 39 | B1 | C |
| 55 | B1 | A |
| 40 | A1 | B |
| 56 | B1 | A |
| 57 | B1 | A |
| 47 | NI | C |

Biological Example 2

Gene Expression Assay

Quantitative PCR (qPCR)

HepG2 cells were obtained from ATCC and grown in Dulbecco's Modified Eagle Medium (DMEM) supplemented with 10% FBS in a 5% $CO_2$ incubator at 37° C. For the assay, the cells were plated in 96-well plates at a concentration of 75,000 cells/well in DMEM with 5% FBS. The compounds were serially diluted in DMSO from 30 to 0.1 mM, and then diluted 1:1000 in growth medium. The medium was added to the cells in duplicate 24 h after plating. After 24 h of incubation, the RNA was isolated from the cells using the RNAqueous®-96 Total RNA Isolation Kit (Ambion). The eluted RNA was reverse transcribed using the Cells-to-Ct kit reverse transcriptase (Ambion). For the quantitative PCR, the cDNA was analysed using the Power SYBR® Green PCR Master Mix (Applied Biosystems) and gene specific primers. The reaction was run on an ABI7300 thermocycler and the instrument software was used to determine Ct values. The fold change of mRNA expression relative to the vehicle control was calculated using the method by Livak. Primer sequence was as follows: SCD1, 5'-cctggtatttctggggtgaa-3'/5'-gggggctaatgttcttgtca-3'. FBS: Hyclone, lot #FRG26939.

All data was measured in HepG2 cells. % inhibition data of SCD1 expression are provided in Table 2. % inhibition at 10 µM is provided as follows: A≥75%; 75%>B≥50%; 50%>C>25%; and 25%>D>1%. NI means no inhibition in the assay at the indicated concentration of compound tested. NT means not tested.

TABLE 2

| Ex. No. | Inhibition Percentage (%) at 1 µM |
|---|---|
| 59 | A |
| 106 | D |
| 107 | C |
| 108 | D |
| 109 | C |
| 110 | B |
| 111 | D |
| 112 | D |
| 113 | D |
| 114 | C |
| 115 | D |
| 60 | B |
| 61 | D |
| 62 | B |
| 70 | D |
| 84 | A |
| 71 | C |
| 72 | C |
| 69 | A |
| 79 | A |
| 116 | C |
| 74 | C |
| 75 | C |
| 117 | A |
| 63 | A |
| 64 | A |
| 65 | A |
| 85 | B |
| 86 | A |
| 66 | D |
| 82 | NI |
| 83 | C |
| 67 | C |
| 87 | A |
| 88 | A |
| 89 | B |

TABLE 2-continued

| Ex. No. | Inhibition Percentage (%) at 1 µM |
|---|---|
| 76 | B |
| 118 | NI |
| 119 | B |
| 120 | C |
| 121 | D |
| 122 | C |
| 123 | B |
| 124 | NI |
| 125 | NI |
| 126 | C |
| 77 | A |
| 68 | B |
| 127 | B |
| 128 | B |
| 129 | B |
| 130 | B |
| 90 | D |
| 91 | A |
| 93 | A |
| 92 | NI |
| 94 | B |
| 95 | A |
| 96 | A |
| 78 | C |
| 97 | A |
| 80 | B |
| 98 | B |
| 81 | C |
| 99 | C |
| 100 | A |
| 101 | B |
| 102 | C |
| 103 | C |
| 104 | A |
| 105 | D |

Biological Example 3

Cell Viability Assay

HepG2, Huh7, Hep3B2.1-7, SK-HEP-1, MDA-MB-231, T47D, MCF7, DU145 cells are cultured in DMEM containing 5% FBS and antibiotic-antimycotic. MOLT4, RPMI8226, and LNCaP cells are cultured in RPMI1640 (Cat #: A1049101, Fisher Scientific) containing 5% FBS and antibiotic-antimycotic. HepaRG cells are cultured in William E medium (Cat #: A1217601, Fisher Scientific) containing 5% FBS, glutaMAX (cat #: 35050061, Fisher Scientific), and antibiotic-antimycotic. All cells are grown in a humidified incubator at 37° C. with 5% CO2. For the assay, 2,000 HepG2, MDA-MB-231, T47D, MCF7, and DU145 cells, 3,000 Huh7, Hep3B2.1-7, and SK-HEP-1 cells and 10,000 cells of MOLT4, RPMI8226, and LNCaP cells are seeded into each well of 96 well plates. After one day in culture, cells are treated with a test compound (0, 1, 10, 32, 100, 320, 1000, 3200, 10000, and 20000 nM) for 48 and 72 hr. The cell viability is assessed using Thiazolyl Blue Tetrazolium Bromide (MTT) assay. 5 mg/mL MTT is added in an amount equal to 10% of the culture medium volume after 48- and 72-hr treatment with the test compound. After the plates are incubated at 37° C. for 3.5 hours for HepG2, Huh7, Hep3B2.1-7, SK-HEP-1, MDA-MB-231, T47D, MCF7, DU145 HepaRG the medium is removed and formazan crystals are dissolved in 100 µL. The absorbance is measured on a Cytation 5 epi-fluorescence microscope in the BCM Integrated Microscopy core at wavelengths of 550 nm, and 690 nm. The absorbance at 550 nm subtracted by the absorbance at 690 nm is used for graphing. Curves are plotted using GraphPad Prism program. For MOLT4, RPMI8226, and LNCaP the medium was not removed and equal volume of 10% SDS with 0.01 HCL was added and incubated at 37 C overnight. The absorbance at 570 nm subtracted by the absorbance at 690 nm is used for graphing. Curves are plotted using GraphPad Prism program.

Results

Figure 1B:
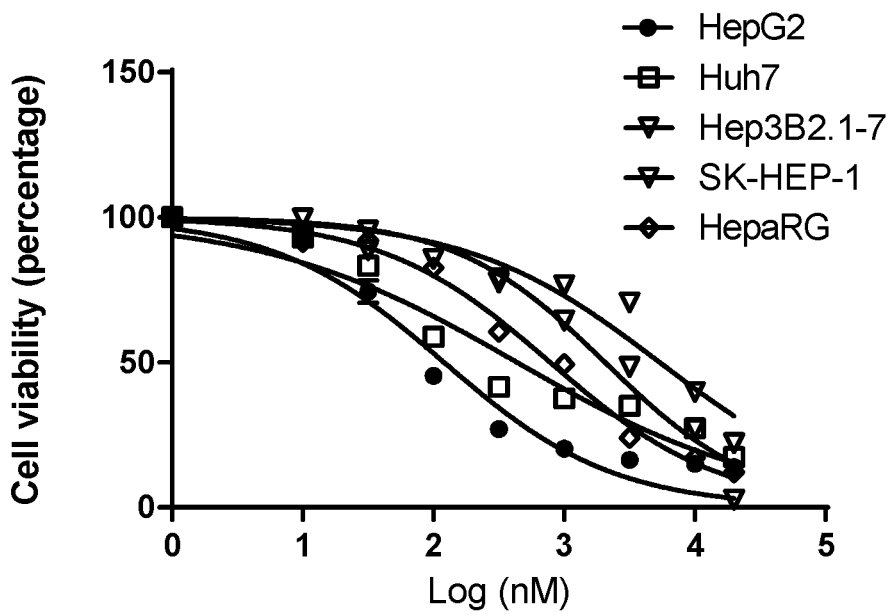

Effect of a test compound on the growth of liver cancer cell lines: Several liver cancer cell lines were tested for growth inhibition by a test compound after 48 and 72 hours treatment. After 48 hours treatment, the test compound inhibited the growth at $IC_{50}$'s of 0.37, 1.2, 4.4, 6.6 and 1.2 µM in liver cell lines HepG2, Huh7, Hep3B2.1-7, SK-HEP-1, and the terminally-differentiated hepatic stem cells HepaRG, respectively (FIG. 1A). When these cells were treated for 72 hours the $IC_{50}$'s were significantly lower at 0.12, 2.1, 5.4, 1.2, and 0.79 µM respectively (FIG. 1B).

Figure 2A:
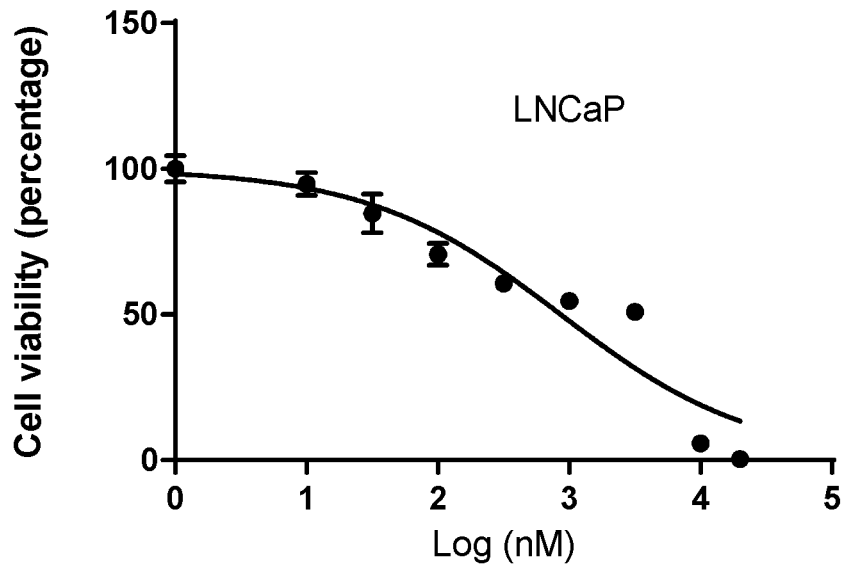
FIG. 2 depicts results for prostate cancer cell lines tested for growth inhibition by a test compound within the scope for Formula I.
Figure 2B:
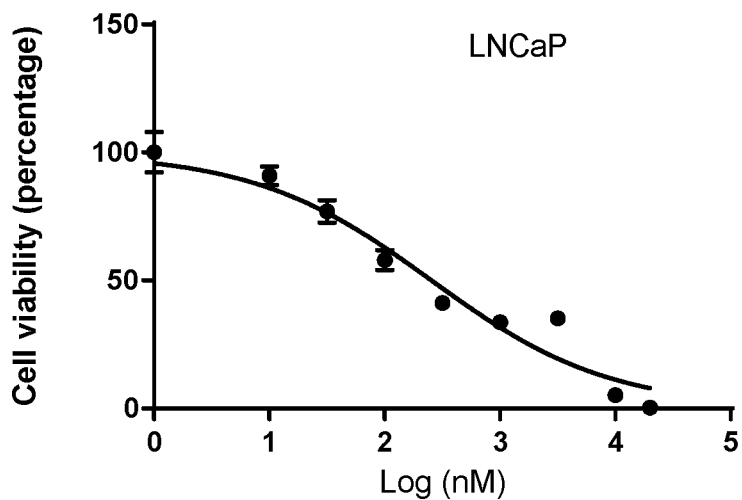

Effect a test compound on the viability of prostate cancer cell lines: Human prostate cancer cells LNCap were cultured in in RPMI1640 with 5% FBS and treated for 48 and 72 hours. The cell viability was determined using MTT assay; N=3). Curves were plotted using GraphPad Prism program. $IC_{50}$'s were determined under conditions described above. The inhibition of this cell line was dose dependent and $IC_{50}$ was 0.86 and 0.25 µM after 48 and 72 hours, respectively. See FIGS. 2A and 2B.

Figure 3A:
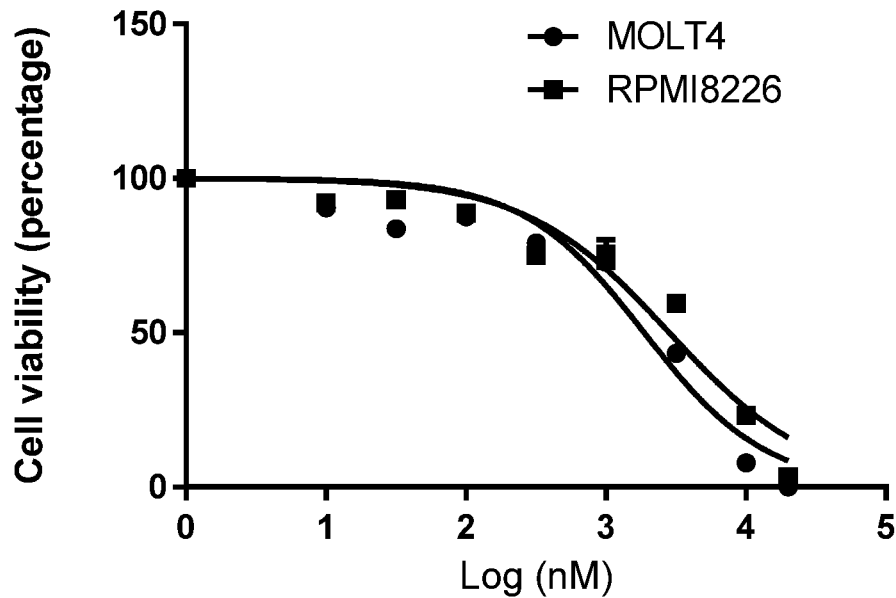
FIG. 3 depicts results for leukemia cell lines tested for growth inhibition by a test compound within the scope for Formula I.
Figure 3B:
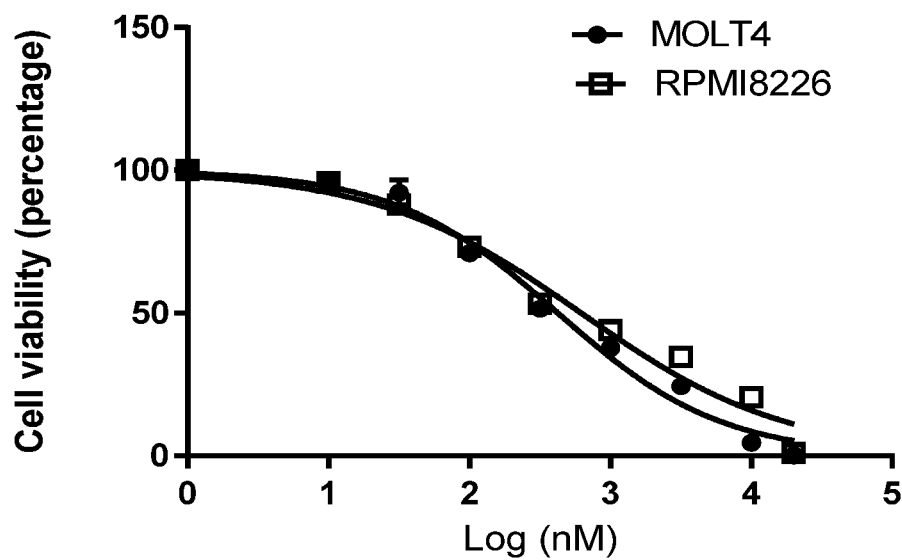

Effect of a test compound on the viability of Leukemia cells: Leukemia cell lines MOLT4 and RPMI8226 were cultured in RPMI1640 with 5% FBS and treated with either 0.1% DMSO (control) and different doses for 48 or 72 hours of the test compound as described above. The cell viability was determined using MTT assay; N=3). Curves were plotted using GraphPad Prism program. As shown in FIG. 3A cell viability of MOLT4 and RPMI8226 Cells was 1.9 and 2.8 µM, respectively after 48 hours treatment. The cell viability was significantly lower after 72 hour treatment and $IC_{50}$ was 0.43 and 0.62 uM respectively (FIG. 3B).

Biological Example 4

Immunoblotting Assay

For the experiment, $3*10^5$ cells are seeded in 6 well plates cultured in complete medium with 5% fetal bovine serum at 37° C., 5% CO2, 95% air and 100% relative humidity for 24 hours, then treated with different dosage of the test compound (0, 5, 10 or 20 µM) for another 6, 24 or 48 h. After treatment, cells are washed once with ice-cold PBS and scraped into radioimmunoprecipitation assay (RIPA) lysis buffer, with addition of protease and phosphatase inhibitor cocktail. The extract is sonicated (3*10 sec) and centrifugation at 12,000 rpm for 10 min. The protein concentration of each total cell extract is measured by BCA kit (Bio-red protein assay). Equal amounts of protein extracts are separated on gradient 4% to 12% Bis-Tris SDS-PAGE gel (Bio-red) and then transferred to a PVDF membrane. After blocking for 1 hour in a PBS containing 0.1% Tween 20 and 5% nonfat milk, the membrane is probed with indicated antibodies, followed by secondary antibodies conjugated to IRDye 800CW and then used ODYSSEY imaging system to detect MVD, SCD1, SREBP1, SREBP2, and/or PCSK9 protein expression.

Biological Example 5

In Vivo Model

Sprague-Dawley rats (100-200 gm) will be obtained from Charles River Breeding Laboratories, Wilmington, Mass. Commercial laboratory chow and water will be provided ad libitum. ob/ob Mice (10 per group) are fed normal chow (control diet) or chow that contains 100 mg/kg, 200 mg/kg, 300 mg/kg or 400 mg/kg of the test compound. The test compound is administered orally to ob/ob mice daily over a period of 8 weeks. Daily food intake and water consumption are carefully monitored. Mice are weighed daily, and fat and lean body content are determined by dual-energy X-ray absorptiometry (DEXA). % fat is calculated as fat weight/fat+lean weight. Blood constituents are determined using standard procedures. Glucose tolerance is measured in order to investigate the ability of treated mice to clear blood glucose compared to control animals. Three groups (10 per group) of mice are fasted overnight and blood glucose levels are measured at 0, 30, 60, and 120 minutes after the injection of glucose (2 g/kg body weight).

Biological Example 6

In Vivo Model

Sprague-Dawley rats have been used to study human obesity induced by a Western diet (WD) (high-fat, high-carbohydrate diet). Twenty 5- to 6-week-old male rats are fed a WD ad libitum for 3 weeks. Food consumption and body weight are measured every 3 days. Obesity and weight gain are first seen after 2 weeks and become most apparent after 4-5 weeks of this diet. This diet brings about insulin resistance in about 2 weeks. After 3 weeks of feeding WD, the test compound is administered daily at 10 mg/kg to the experimental group (20 rats) by oral gavage. The control group (n=20) is given vehicle only at the same time. Animals are treated for 2 months.

Food intake, water consumption, and body weight are determined and recorded every 3 days for the duration of the experiment. Rats are fed the WD diet for a total of 2 months and 3 weeks. The first 3 weeks are WD alone. After the first 3 weeks, the experimental groups receives the test compound daily.

Before the start of dosing with the test compound, baseline blood constituents are determined. The animals are fasted for 8 hours, and TG, HDL, LDL, VLDL, cholesterol, glucose and insulin levels are determined using standard methods. A glucose tolerance test (GTT) is carried out using standard methods. Body composition (lean and body fat) is determined using dual-energy X-ray absorptiometry on live animals, using standard methods. Body weight and food intake are measured every week, and 1 month after the start of the treatment, blood constituents are determined to measure glucose, TG, HDL, LDL and VLDL in addition to the liver enzymes: aspartate aminotransferase (AST) and alanine aminotransferase (ALT). GTT is also performed in order to assess the insulin-resistant state 4 and 8 weeks after the start of the treatment. Fat and lean body mass are assessed by $^1$H magnetic resonance spectroscopy (Bruker BioSpin, Billerica, Mass., USA) before and after 4 weeks of treatment. A comprehensive animal metabolic monitoring system (CLAMS: Columbus Instruments, Columbus, Ohio, USA) is used to evaluate activity, food consumption and energy expenditure before and after 4 weeks of treatment. Energy expenditure and food intake data is normalized with respect to body weight. Energy expenditure and respiratory quotient (RQ) are calculated from the gas exchange data. Energy expenditure=$(3.815+1.232*RQ)*VO_2$. RQ is the ratio of $VCO_2$ to $VO_2$, which changes depending on the energy source the animal is using. When carbohydrates are the only substrate being oxidized, the RQ is 1.0, and it is 0.7 when only fatty acids are oxidized. Activity is measured on an x and z-axis using infrared beams to count the amount of beam breaks during the specified measurement period. Feeding is measured by recording the difference in the scale measurement of the Center-Feeder from one time point to another.

Following the 2 months of treatment, rats are sacrificed to determine the biochemical and histopathological impact of the test compound on liver, muscle, heart and adipose tissues. The tissues are collected, weighed and kept at −80° C. for further analyses, as follows:

Histological staining for lipid, glycogen and general tissue structure.

TG and cholesterol levels using biochemical methods.

Assays for lipogenic enzymes, such as fatty acid synthase (FAS), acetyl-CoA carboxylases (ACC1 and ACC2), stearoyl-CoA desaturase (SCD1), and enzymes of cholesterol synthesis, 3-hydoxy 3-methyl glutaryl-CoA synthase and reductase, among others.

Expression level of genes previously found to be modulated by fatostatin in both cell culture and mouse studies, including SREBP1 and -2, done using real-time PCR for RNA levels and Western blot assays for protein.

Statistical analyses are performed with commercially available software. Data are expressed as mean+SD. Statistical comparison of changes between control and treated animals are analyzed by one-way ANOVA. Unpaired Student t-test is used to compare the treated animals and the controls. Values of $P<0.05$ are considered statistically significant.

Biological Example 7

In Vivo Model

Animals:

The ob/ob mice were purchased from Jackson's Laboratory when they are about 5-6 weeks old males matched and weighed about 28-31 gram. The mice were housed as group of 4-5 mice per cage. After receiving the mice, they were housed at animal facility under controlled conditions of temperature and day and night cycle. After a week period of adapting to the new facility mice weight were recorded before the experiments start and body composition (fat and lean) were determined by Echo MRI (reference: Galgani J E, Smith S R & Ravussin E (2011) Assessment of EchoMRI-AH versus dual-energy X-ray absorptiometry to measure human body composition. Int J Obes 35, 1241-1246.

Test Compound Formulation:

Compounds were weighed and mixed with a solution containing 40% (V/V) PEG400, 18% solutol, and 42% water. The test compound was weighed and freshly prepared prior to each treatment by mixing the vehicle with the compound followed by a brief sonication for 30 seconds and the doses were calculated according to the body weight. Two doses, 0.25 and 2.5 mg/kg, in addition to placebo were used.

Food Intake:

Food consumptions and body weights were determined at about 3 pm daily. Food consumption is measured by weighing the food that is added daily to the cages minus the food that is left in the cages.

Body Weight and Composition:

Mice-weights were determined daily at 3-4 pm and doses delivered and calculated according to the weight. Ob/Ob mice weight increases significantly on a daily bases. The well-being of the mice was closely monitored, including any obvious health issues such as morbidity, movement an extreme reduction in food intake etc In order to determine the effect of the test compound on reducing total body fat body composition was determined using ECHOMRI method every two weeks.

Blood Constituents:

In order to determine blood constituents, mice were fasted for six hours and blood was withdrawn to measure Glucose and other blood constituents such as TG, LDL, HDL, VLDL and Liver enzymes were performed.

In order to determine the effect of the test compound on reducing total body fat body composition was determined using ECHOMRI method every two weeks.

Results

Food Intake:

Food consumptions and body weights were determined at about 10 am daily. Food consumptions were measured by weighing the food that was added daily to the cages minus the food that was left in the cages. No spillages were noticed in the cages. Food consumption was very similar in all groups: 263, 267 and 273 gram/mouse after 11 weeks, suggesting that the test compound at doses of 0 mg/kg, 0.25 mg/kg, and 2.5 mg/kg did not affect food intake (appetite).

Fat, Lean and Body Weight after Ten Weeks of Treatment with the Test Compound.

Figure 4A:
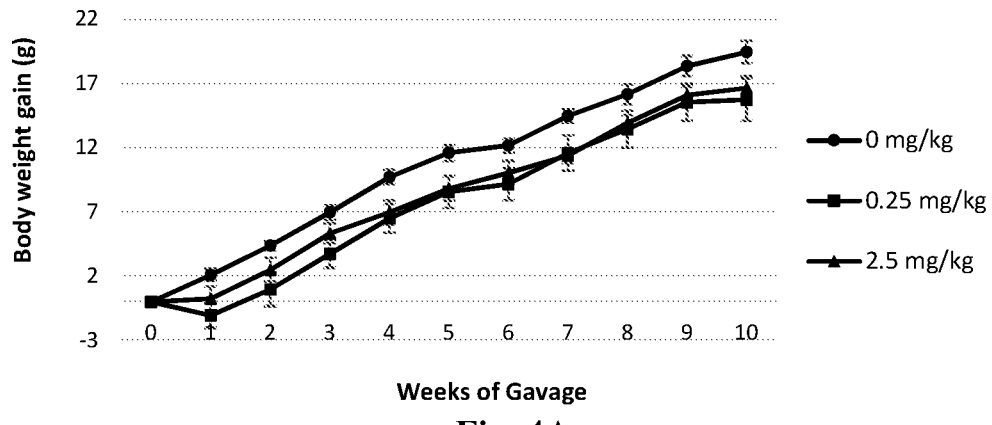
FIG. 4 depicts results for fat content, lean content, and body weight after ten weeks of treatment within a test compound with the scope for Formula I.
Figure 4B:
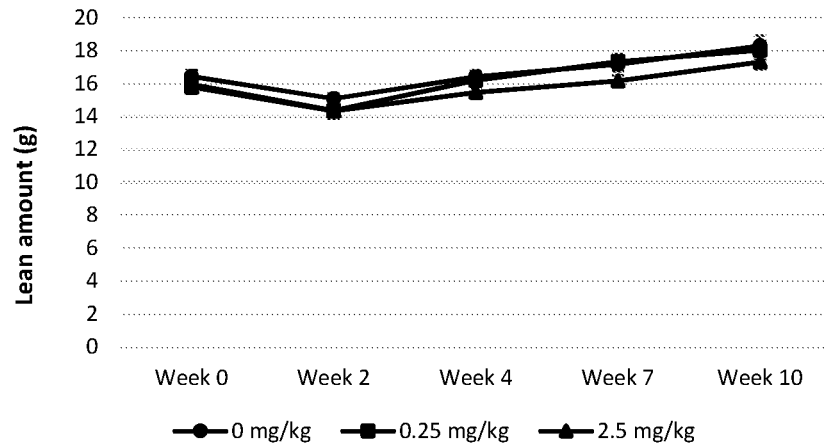
Figure 4C:
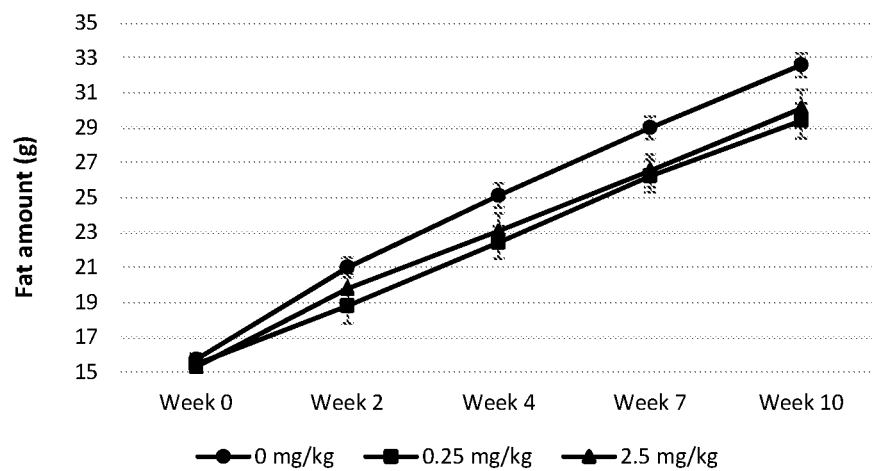

The initial weights of the mice upon arrival were about 28-30 gram, and the mice were divided into 3 groups of five mice in each cage. Mouse weights were determined daily at around 10 am. FIG. 4A shows the increases in body weights of each experimental group (n=7). Interestingly, the treated groups gained similar weights, at about 15-20% less weight than the controls (19.4±0.9, 15.7±1.6 and 16.6±0.9 gram/mouse for control, 0.25 and 2.5 mg/kg groups respectively). There was no significant change in lean content between the three groups (FIG. 4B). When fat content was determined by Echo MRI every 2-3 weeks, the fat amount in both treated groups was similar (FIG. 4C). The fat amount was consistently lower compared to the controls and after 10 weeks the fat weights were 32.6±0.7, 29.4±1.0 and 30.1±1.1-gram fat/mouse of control, 0.25 and 2.5 mg doses respectively. These results suggest that the decreased in weight gained in the treated groups was mainly due to reduced fat accumulation. In the figures, values are mean±SE (n=7).

Blood Analyses after Nine Weeks of Treatment.

Figure 5:
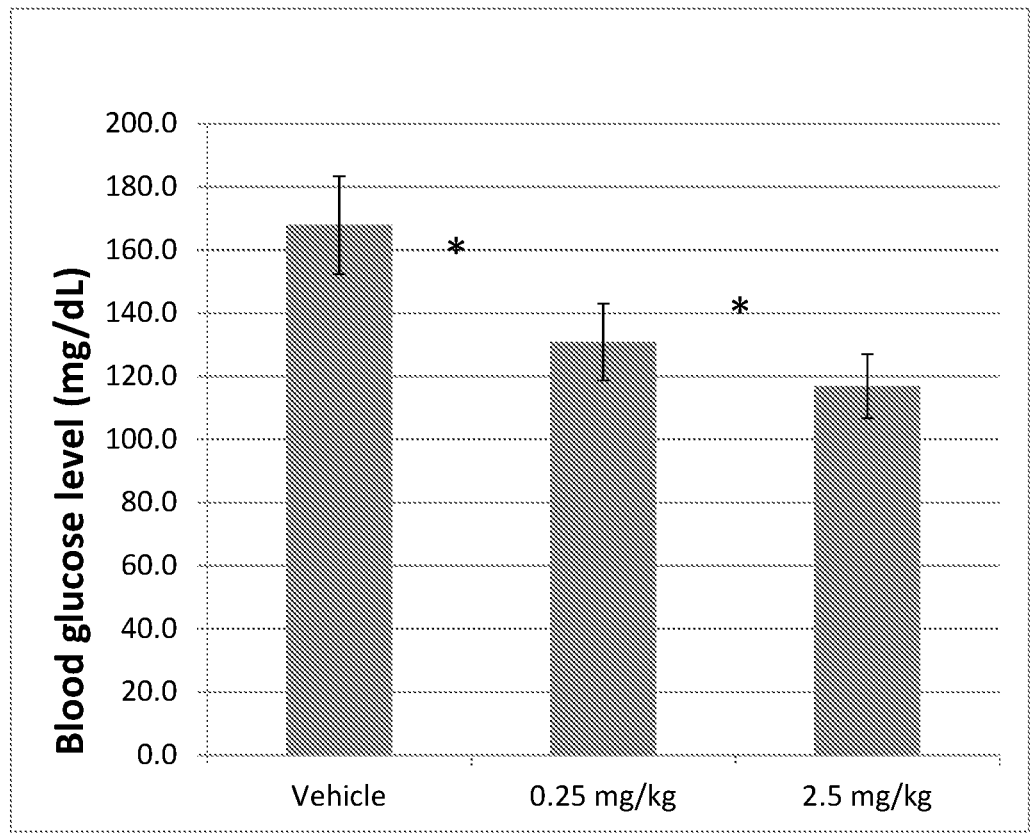
FIG. 5 depicts results for glucose levels in blood of mice treated with 0.25 and 2.5 mg/kg of a test compound within the scope for Formula I.

The effect of the test compound on blood glucose and serum lipid levels were determined after nine weeks of treatment. Blood was withdrawn from the mouse submandibular vein after 6 hours fasting conditions. Glucose levels was determined using McKesson blood glucose meter and serum was separated for determination of lipids, and liver enzymes Lipids and liver enzymes were determined by Mouse Metabolism Core (Baylor College of Medicine). As shown in FIG. 5, the glucose levels in blood of treated 0.25 and 2.5 mg/kg groups were 22% and 30% lower than the controls respectively (0.25 mg/kg: 130.9±12.2; 2.5 mg/kg: 116.9±10.1, controls: 167.9±15.5 mg/dl).

Figure 6A:
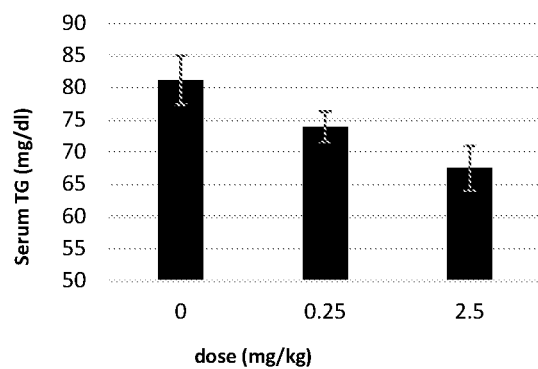
FIG. 6 depicts results for triglyceride levels, total cholesterol levels, HDL levels, and LDL levels in mice treated with a test compound within the scope for Formula I.
Figure 6B:
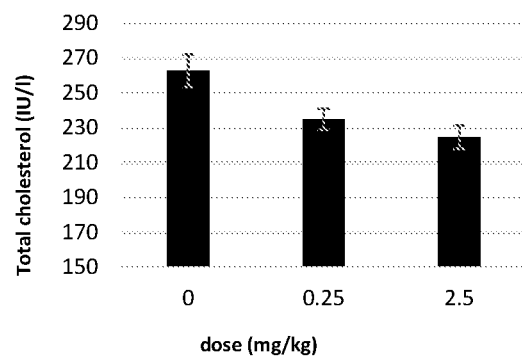
Figure 6C:
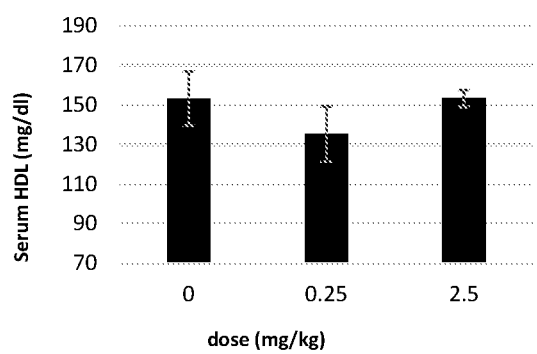
Figure 6D:
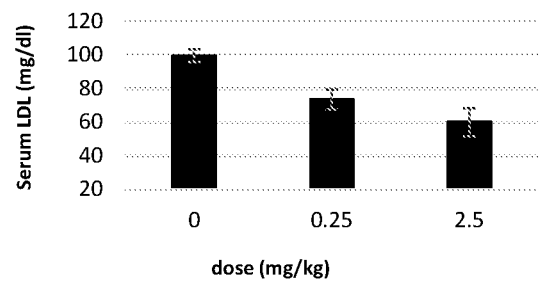

The triglycerides level decreased about 10 and 17% in serum of 0.25 mg/kg and 2.5 mg/kg compared to the controls (73.91±2.37, 67.47±3.50 and 81.17±3.81 mg/dl respectively) (FIG. 6A). Total cholesterol was about 10 and 15% lower in the 0.25 and 2.5 mg/kg compared to controls (235.03±6.02, 224.77±6.68 and 262.86±9.34 mg/dl respectively) (FIG. 6B). There were no significant differences at the level of HDL between the three groups (FIG. 6C). However the level of LDL was lower in the blood of the compound-treated groups which was about 27 and 40% lower for 0.25 and 2.5 mg/kg respectively compared to controls (73.6±5.90, 60.14±8.39, and 99.69±3.75 mg/dl respectively) (FIG. 6D). Values are mean±SE. *P<0.05).

Figure 7A:
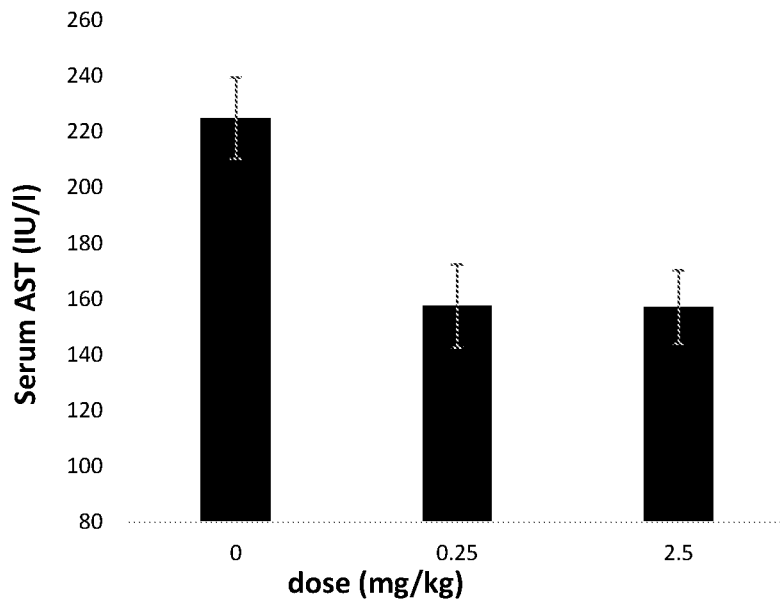
FIG. 7 depicts results for levels of aspartate aminotransferase (AST) and alanine aminotransferase (ALT) in serum of mice after nine weeks of treatment with a test compound within the scope for Formula I.
Figure 7B:
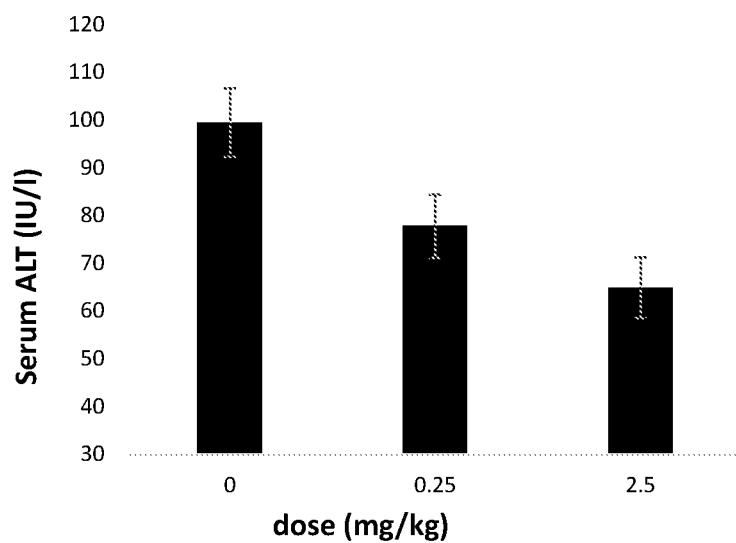

Levels of aspartate aminotransferase (AST) and alanine aminotransferase (ALT) in serum of mice were determined after nine weeks of treatment. As shown in FIGS. 7A and 7B, the level of both enzymes were lower than the control animals, suggesting that the test compound did not cause liver toxicity and may actually improve the liver condition as evident by lower AST and ALT values. AST was about 35% lower in 0.25 and 2.5 mg/kg compared to control (158±14.92, 157±13.18 and 225±14.60 IU/L respectively). ALT was lower by 22% and 35% compared to controls (78±6.63, 65±6.37, and 99±7.15 IU/L respectively). Values are mean±SE. *P<0.05

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A Compound of Formula (I):

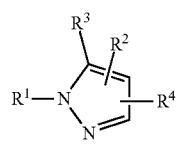

(I)

where
$R^1$ is phenyl, pyridinonyl, pyridinyl, pyrimidinyl, pyridazinyl, or pyrazinyl; where the phenyl, pyridinyl, pyrimidinyl, pyridazinyl, and pyrazinyl rings are optionally substituted with 1, 2, or 3 $R^{1a}$ and where the pyridinonyl is substituted on the nitrogen with $R^{1b}$ and is additionally optionally substituted with 1, 2, or 3 $R^{1a}$;
each $R^{1a}$ is independently halo, alkyl, alkenyl, haloalkyl, cycloalkyl, cycloalkylalkyl, heterocycloalkyl, or heterocycloalkylalkyl;
$R^{1b}$ is hydrogen, alkyl, alkenyl, haloalkyl, cycloalkyl, cycloalkylalkyl, heterocycloalkyl, or heterocycloalkylalkyl;
$R^2$ is

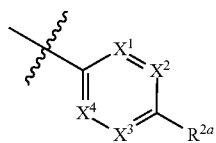

where 0, 1, or 2 of $X^1$-$X^4$ are nitrogen and the remaining are CH or $CR^{2b}$, provided that 0-2 $CR^{2b}$ are present;
$R^{2a}$ is $NR^{5a}S(O)_2R^{5b}$ or $NR^{6a}R^{6b}$;
each $R^{2b}$ is independently halo, alkyl, haloalkyl, —$NO_2$, or cyano;
$R^3$ is hydrogen, halo, alkyl, or haloalkyl;
$R^4$ is hydrogen, halo, alkyl, or haloalkyl;
$R^{5a}$ and $R^{6a}$ are independently hydrogen or alkyl; and $R^{5b}$ and $R^{6b}$ are independently alkyl; haloalkyl; cycloalkyl; cycloalkylalkyl; heterocycloalkyl; or heterocycloalkylalkyl; and
wherein each cycloalkyl, either alone or as part of another group, is independently optionally substituted with one or two groups independently selected from the group consisting of alkyl, halo, and haloalkyl; or
a pharmaceutically acceptable salt thereof;
provided that the compound is not N-methyl-6-(1-phenyl-1H-pyrazol-4-yl)pyridazin-3-amine; N-ethyl-6-(1-phenyl-1H-pyrazol-4-yl)pyridazin-3-amine; N-propyl-6-(1-phenyl-1H-pyrazol-4-yl)pyridazin-3-amine;

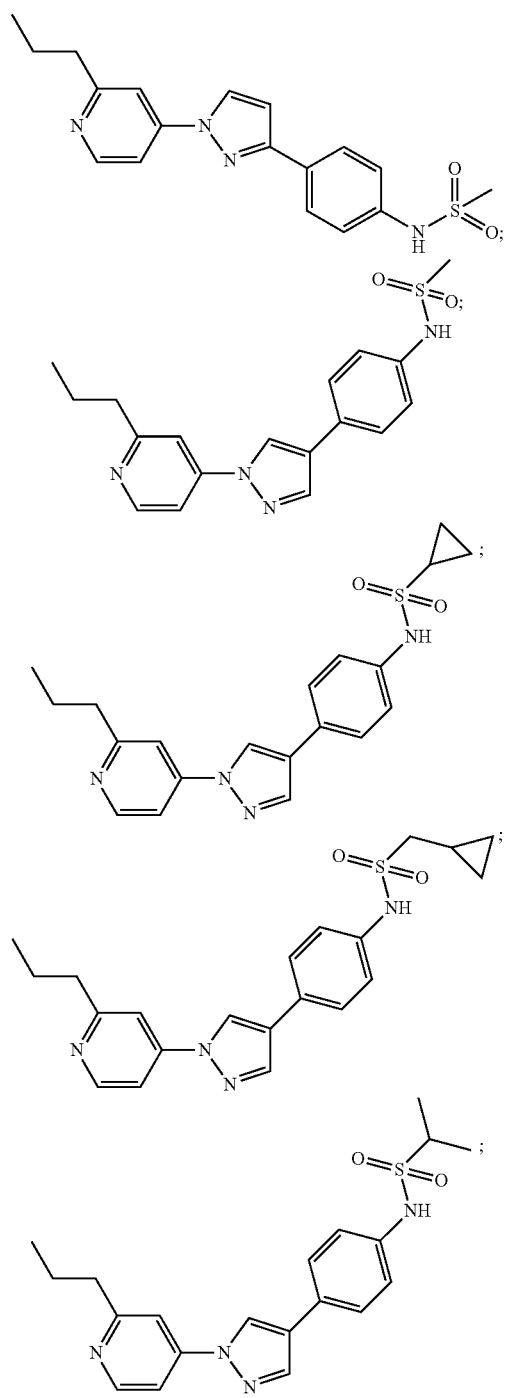

-continued

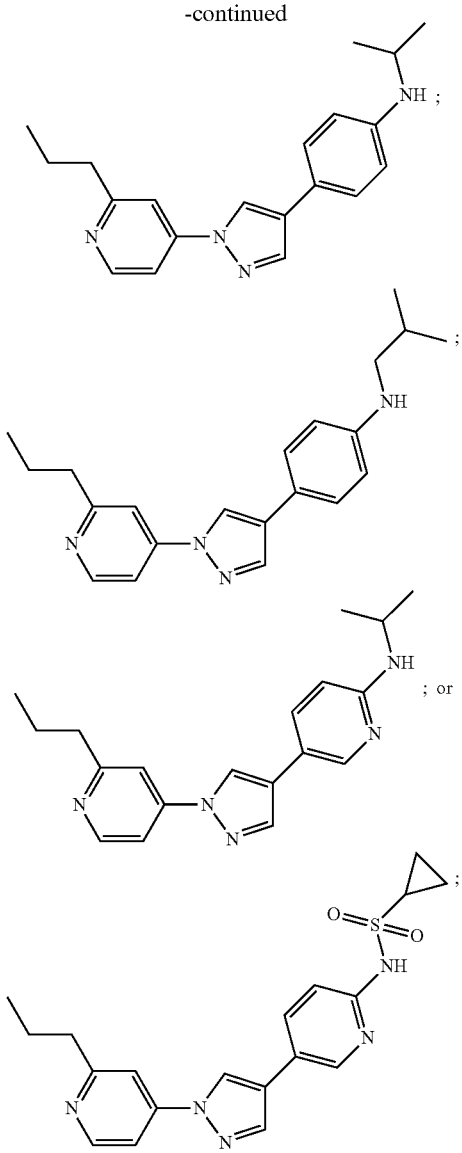

or a pharmaceutically acceptable salt thereof.

2. The Compound of claim 1 according to Formula (Ic):

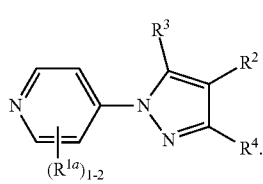

3. The Compound of claim 1 according to Formula (Ib):

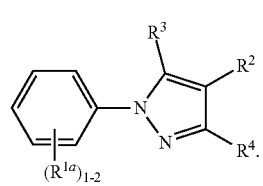

4. The Compound of claim 1 according to Formula (Id):

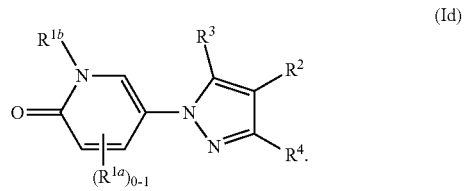

5. The Compound of claim 1, where $R^3$ and $R^4$ are hydrogen.

6. The Compound of claim 1, where $R^2$ is

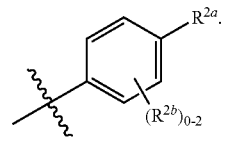

7. The Compound of claim 1, where $R^2$ is

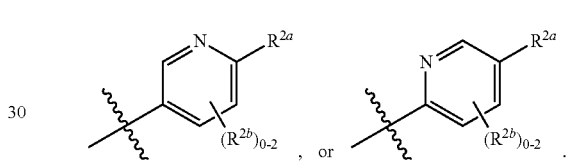

8. The Compound of claim 1, where $R^2$ is substituted with a first $R^{2b}$; and when the $R^2$ ring is phenyl or pyridinyl, $R^2$ is additionally optionally substituted with a second $R^{2b}$.

9. The Compound of claim 8, where the first $R^{2b}$ is halo.

10. The Compound of claim 8, where the first $R^{2b}$ is —CN, —CH$_3$, or —CF$_3$.

11. The Compound of claim 1, where $R^{2a}$ is —NHS(O)$_2$R$^{5b}$.

12. The Compound of claim 1, where $R^{2a}$ is —NHR$^{6b}$.

13. The Compound of claim 1, where $R^{1a}$ is alkyl.

14. The Compound of claim 1, where $R^{1b}$ is alkyl, haloalkyl, cycloalkylalkyl, or heterocycloalkylalkyl where the heterocycloalkylalkyl is optionally substituted with an alkyl group on a ring nitrogen of the heterocycloalkyl ring.

15. The compound of claim 1 selected from the following formula:

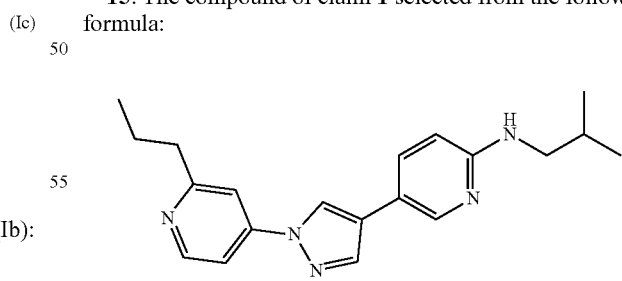

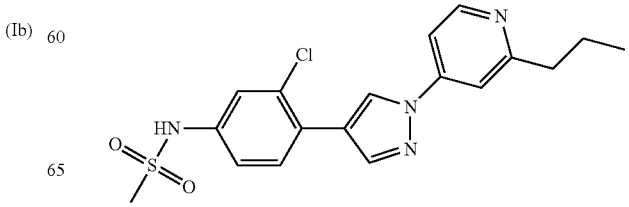

213
-continued
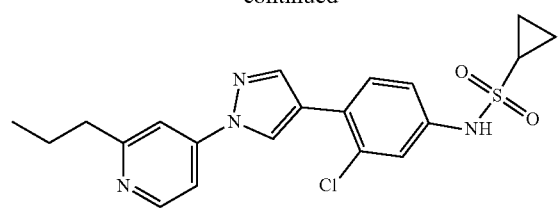
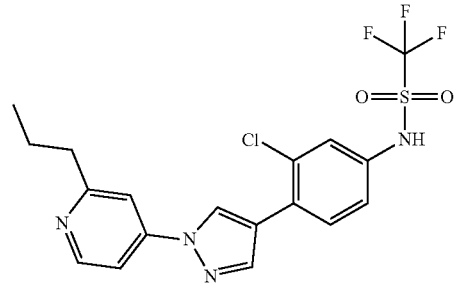
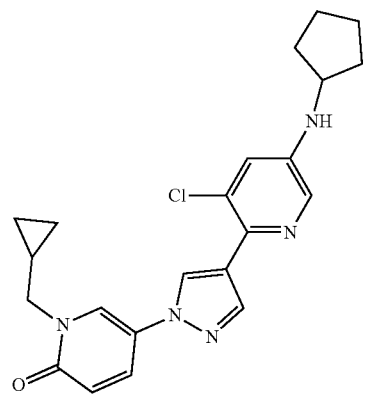
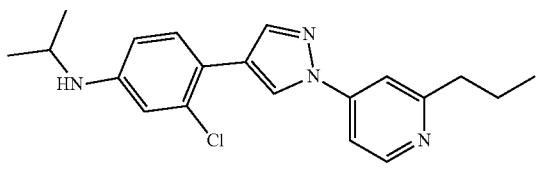
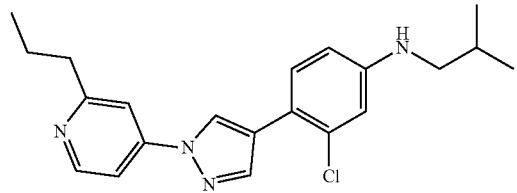
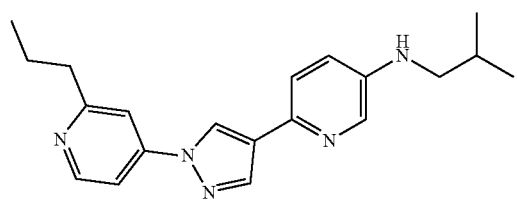
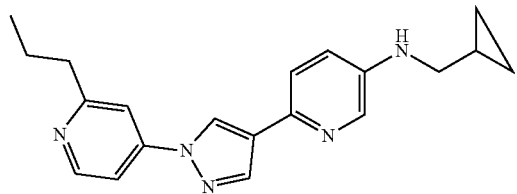
214
-continued
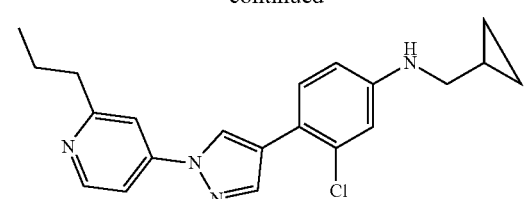
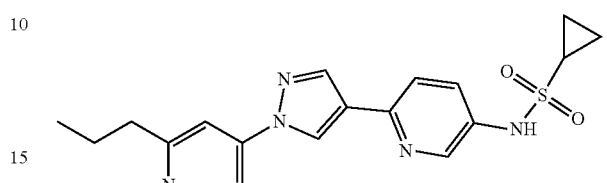
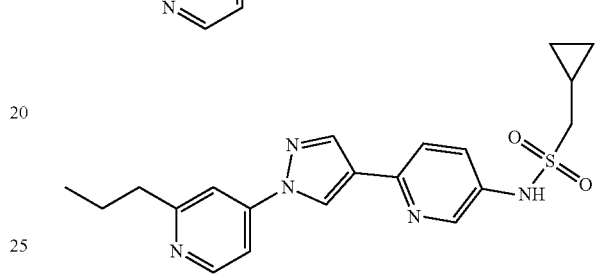
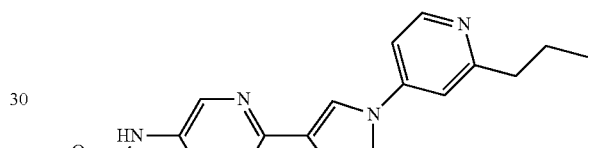
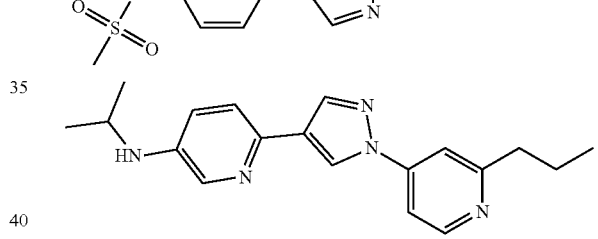
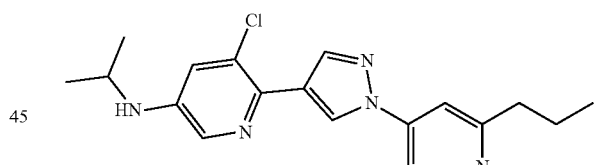
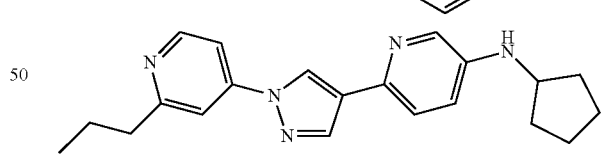
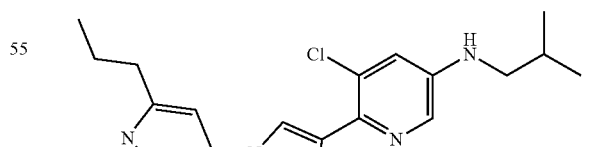
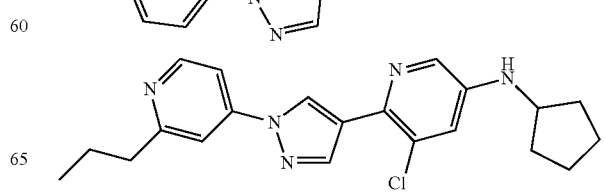

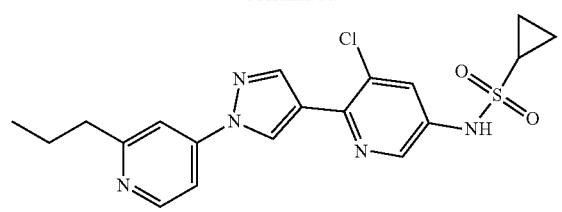
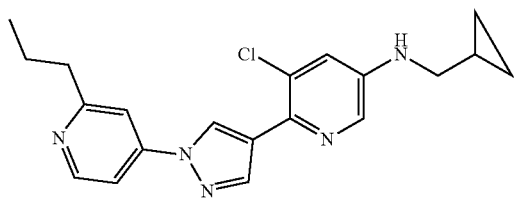
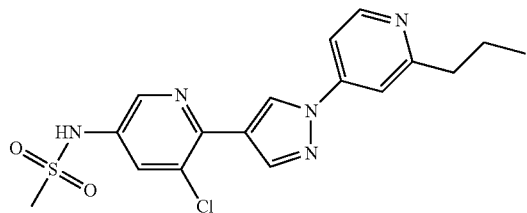
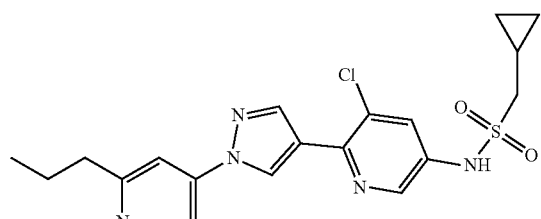
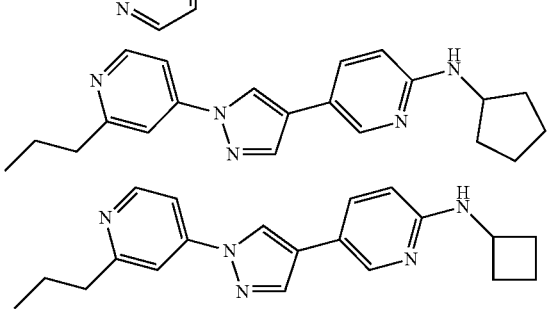
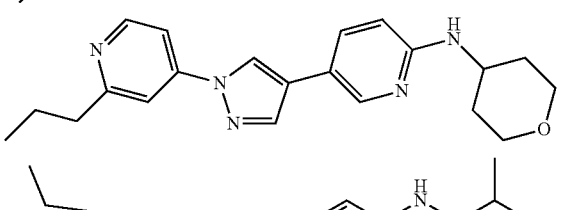
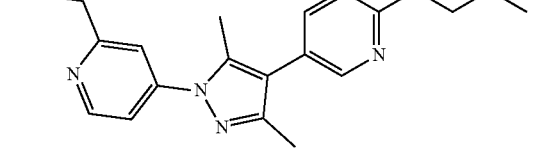
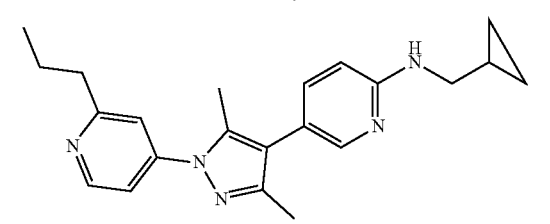
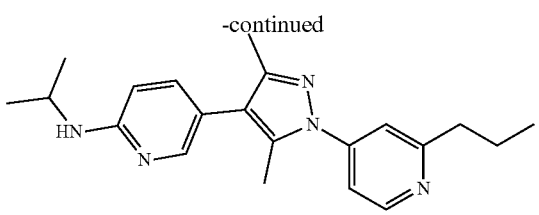
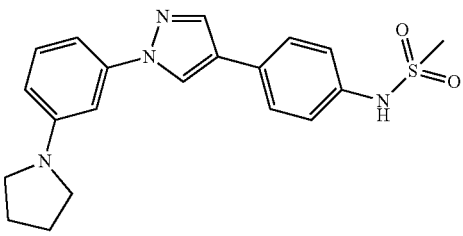
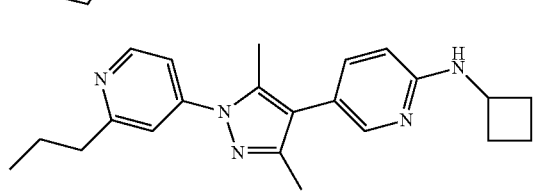
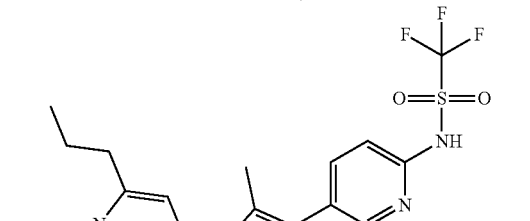
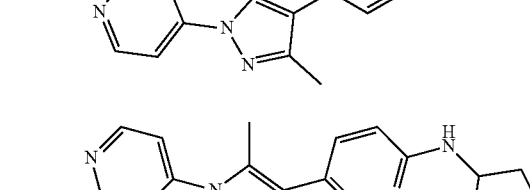
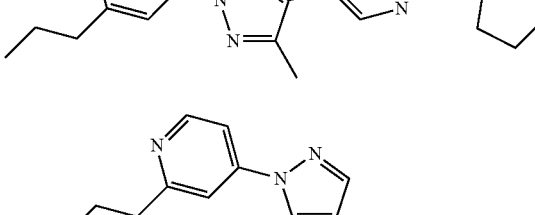
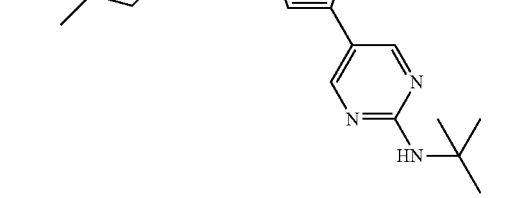
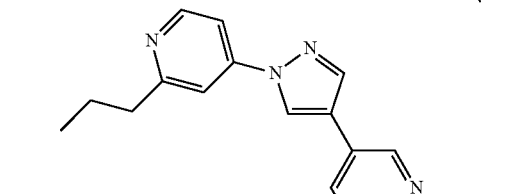

217
-continued
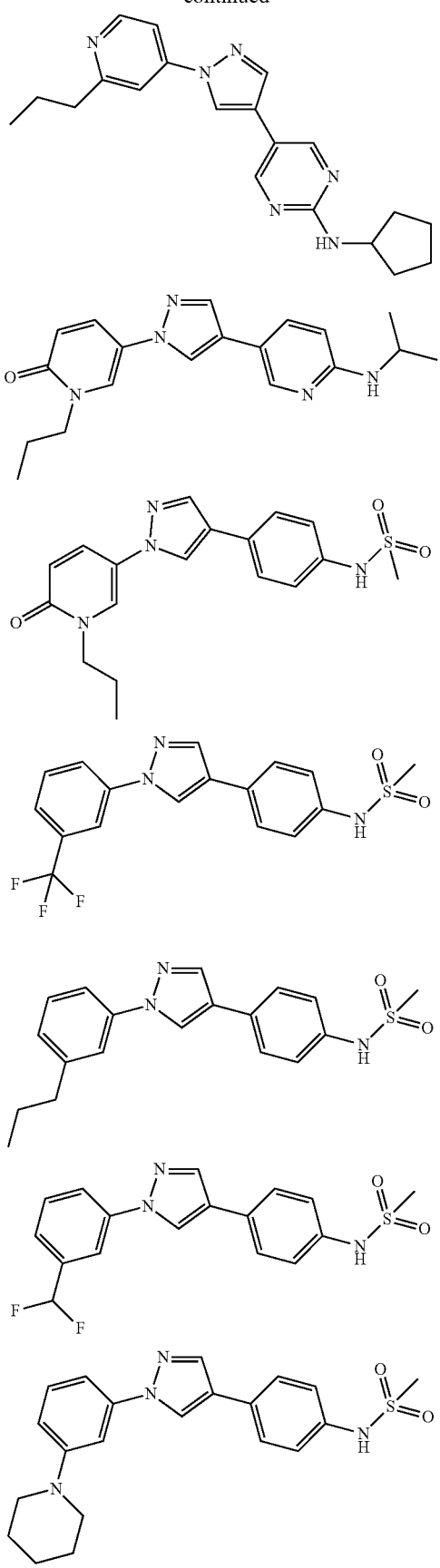
218
-continued
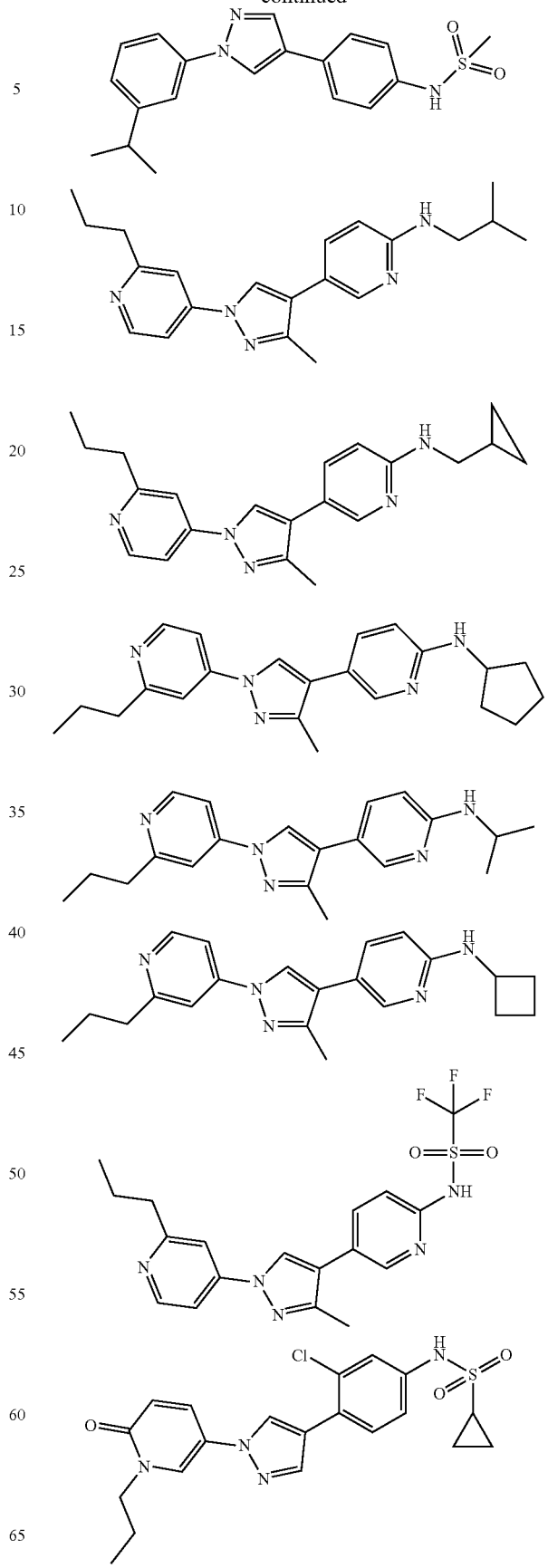

219
-continued
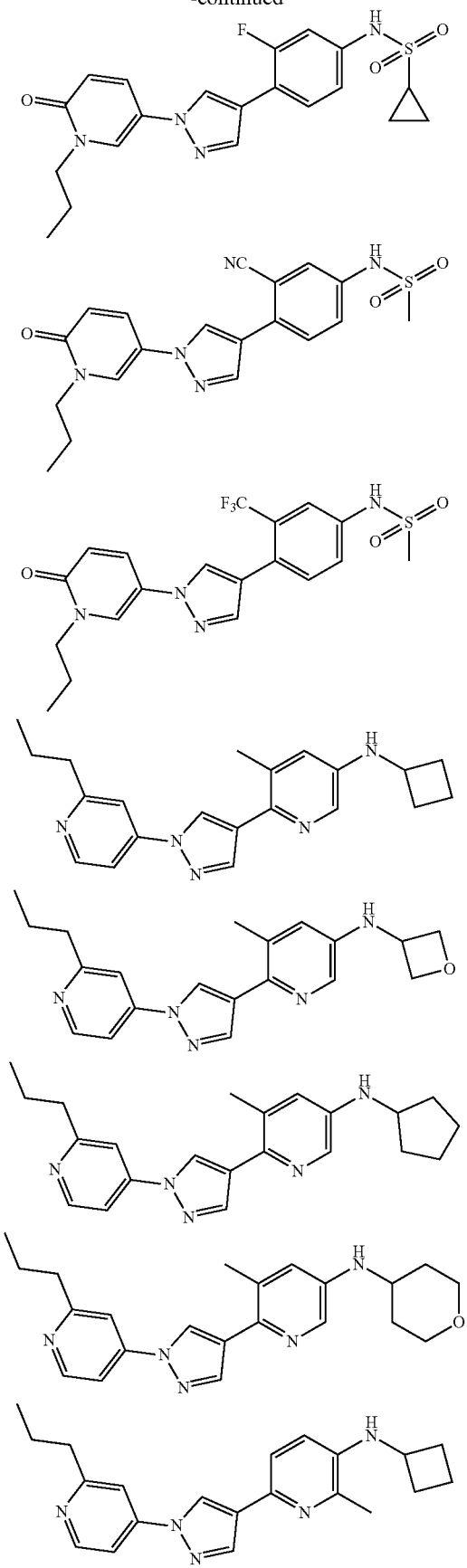
220
-continued
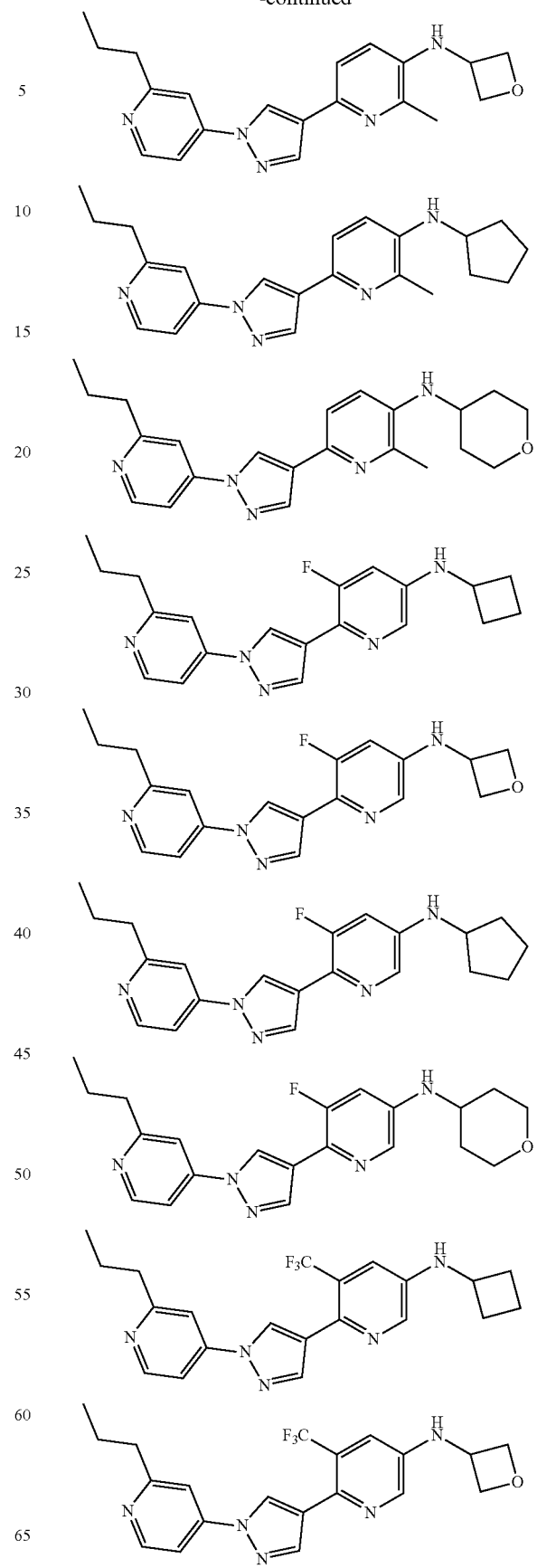

221
-continued
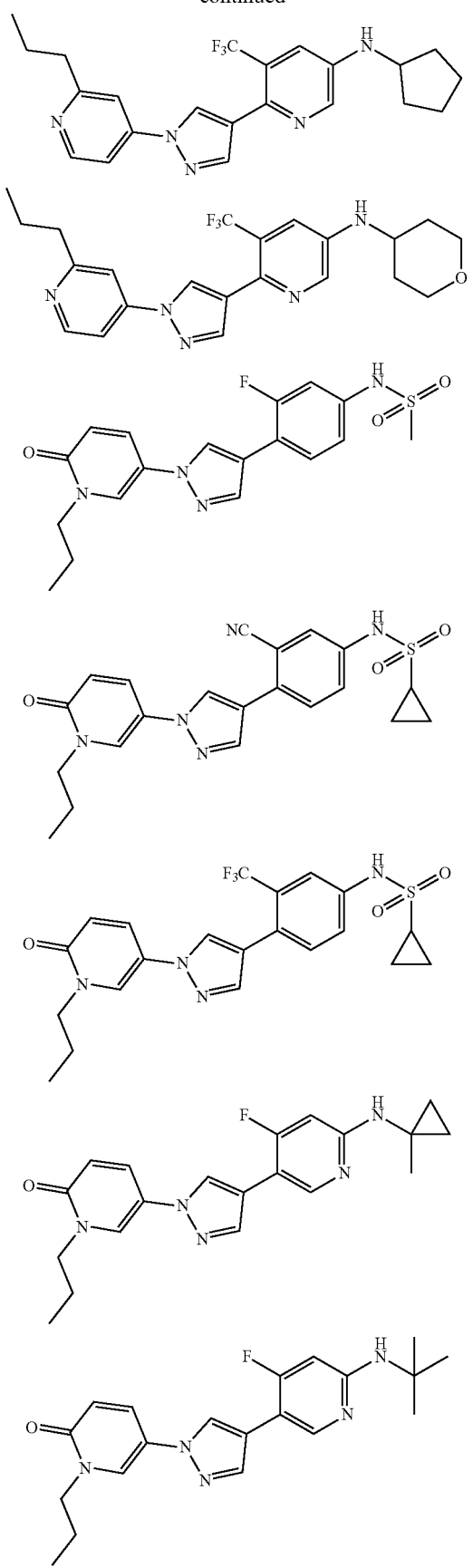
222
-continued
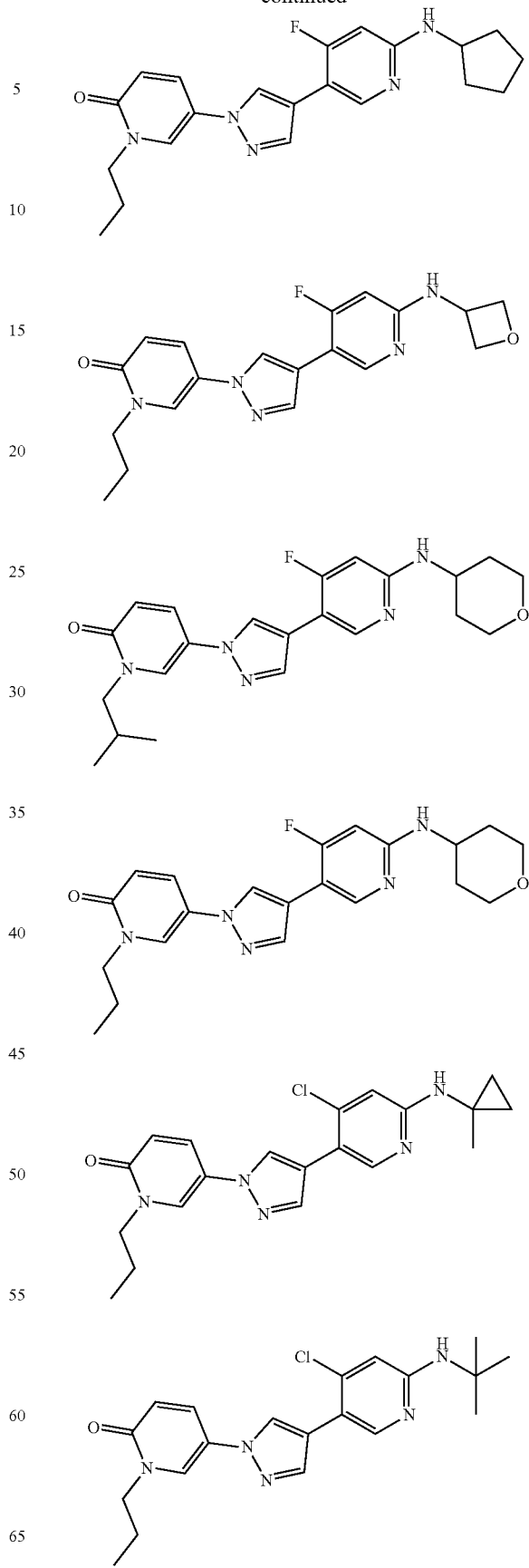

223
-continued
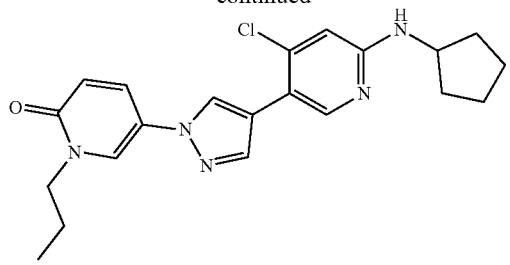
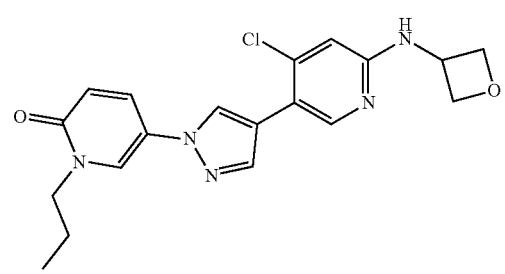
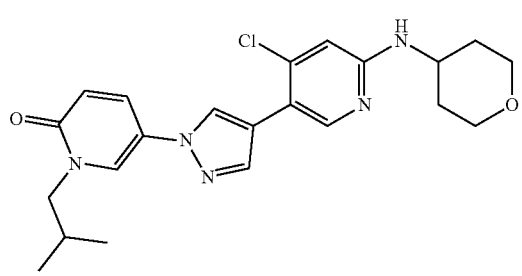
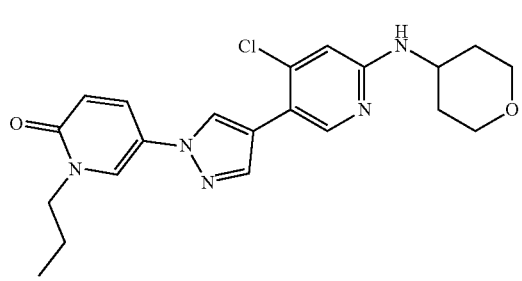
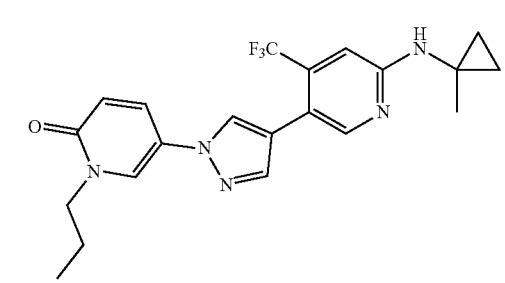
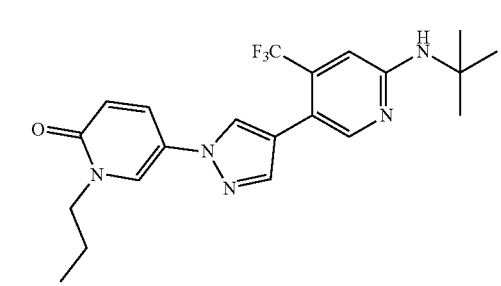
224
-continued
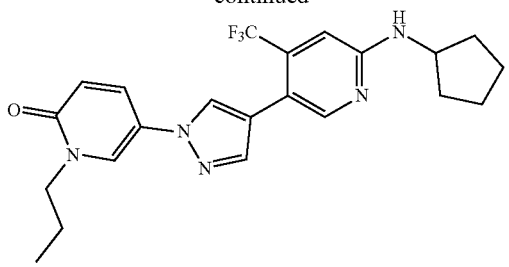
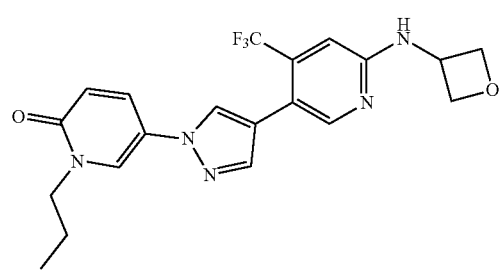
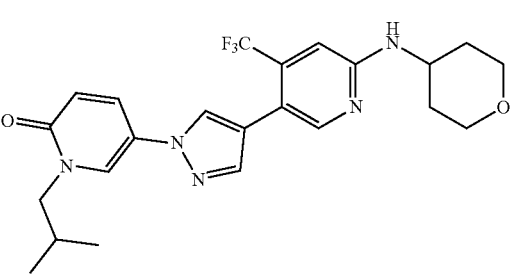
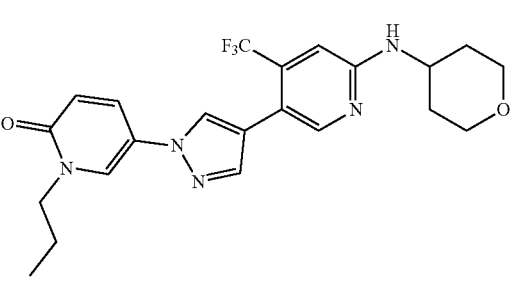
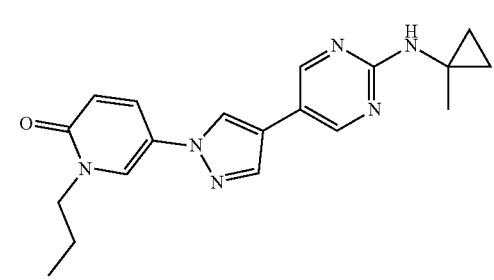
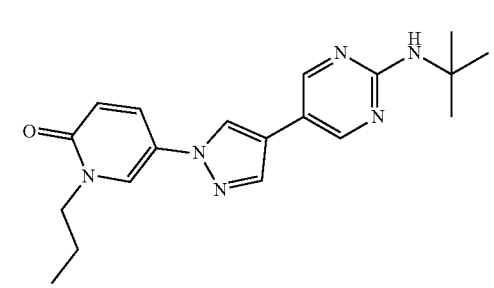

225
-continued
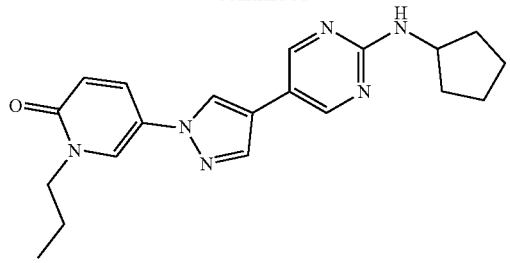
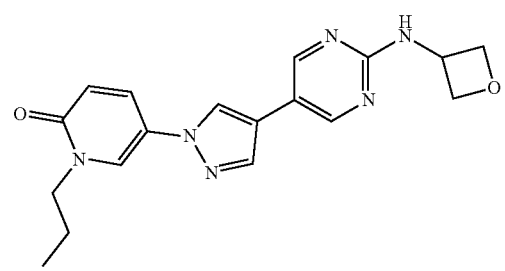
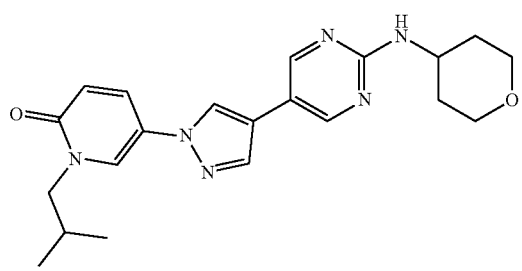
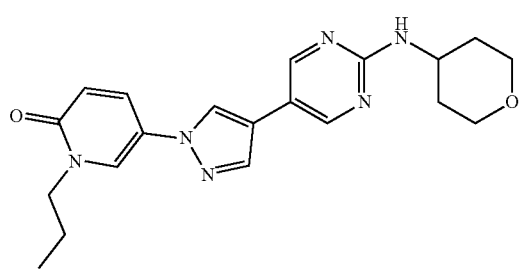
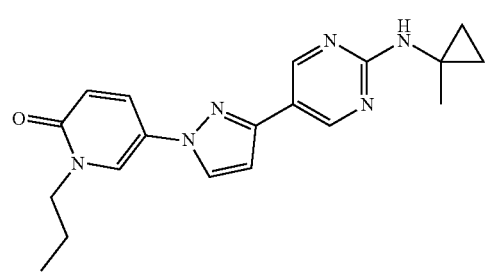
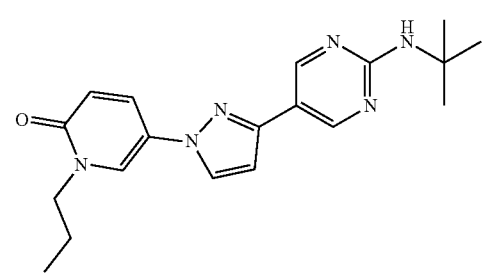
226
-continued
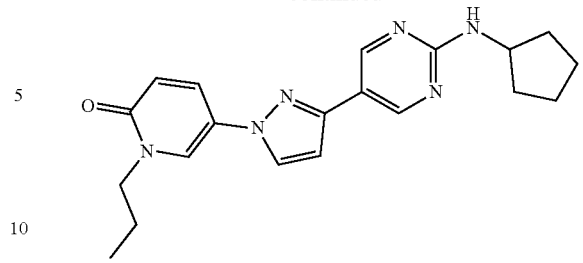
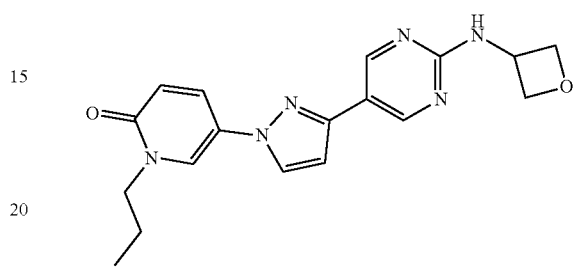
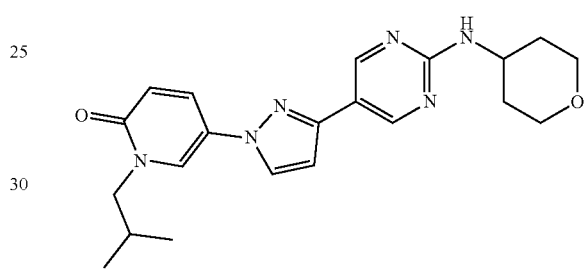
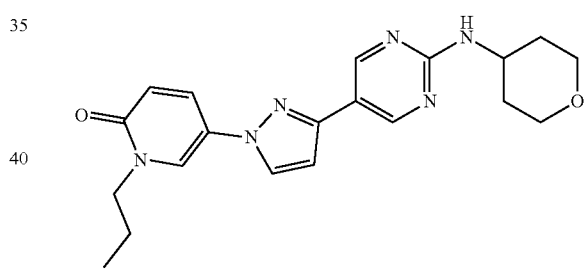
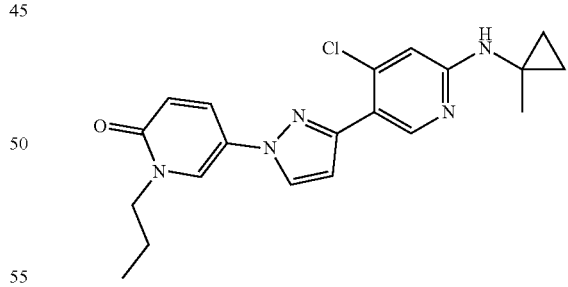
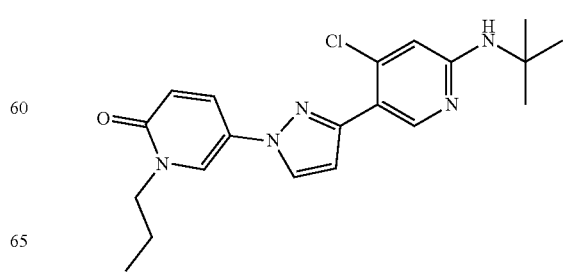

227
-continued
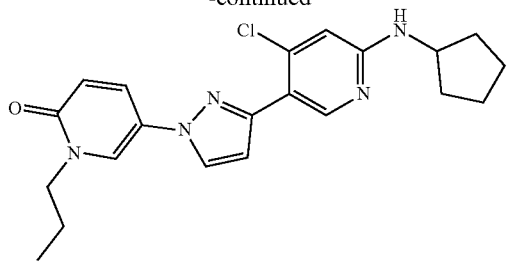
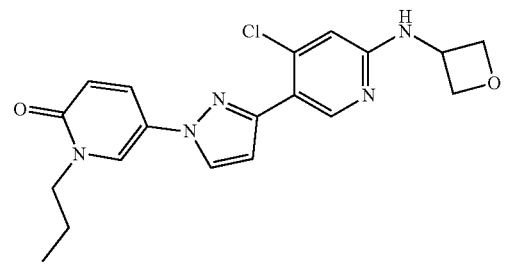
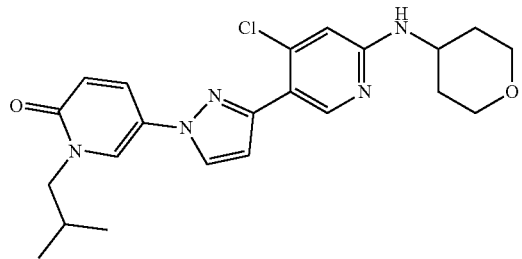
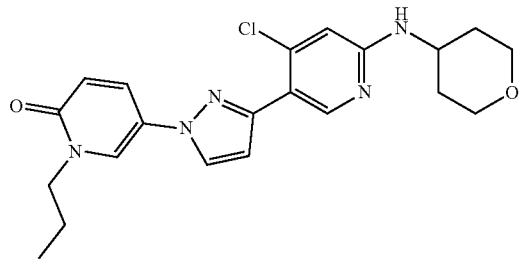
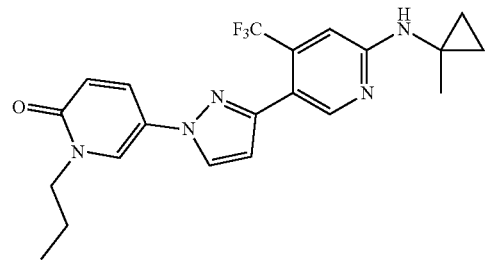
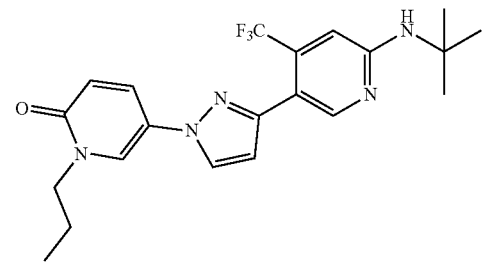
228
-continued
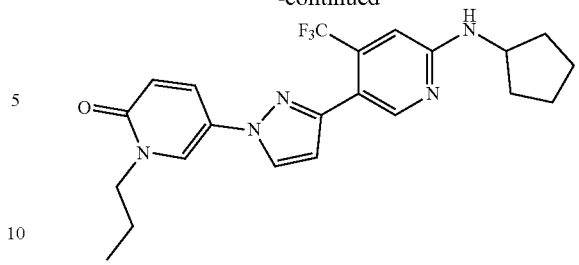
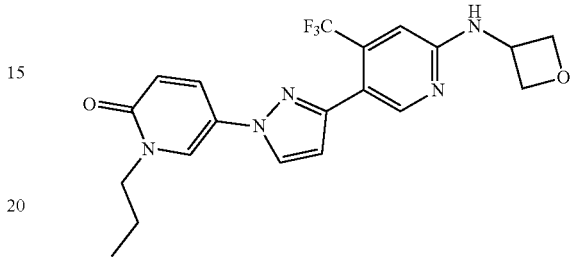
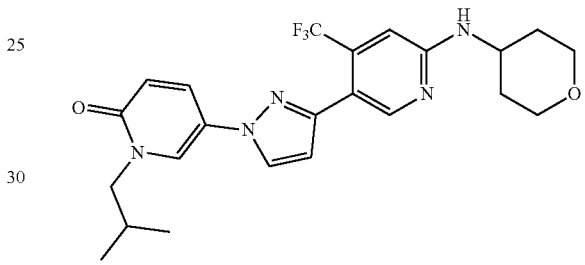
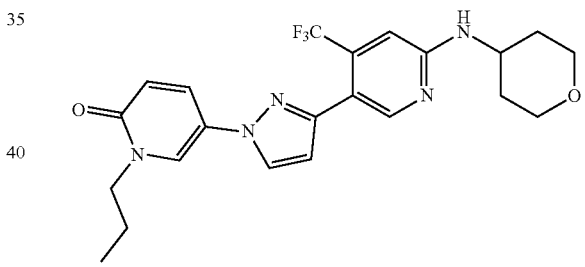
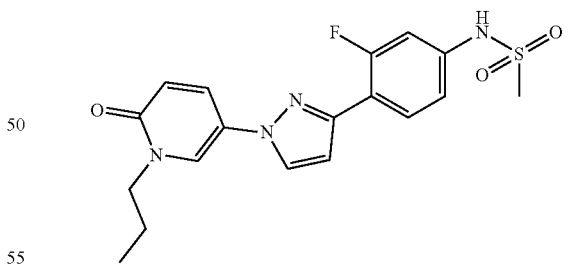
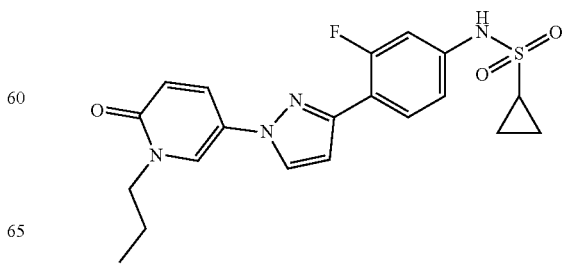

229
-continued
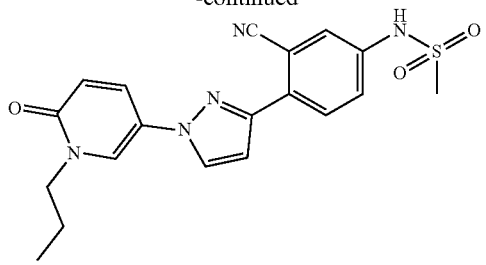
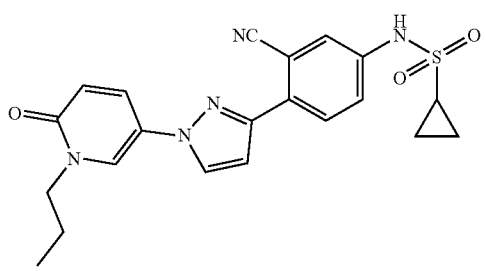
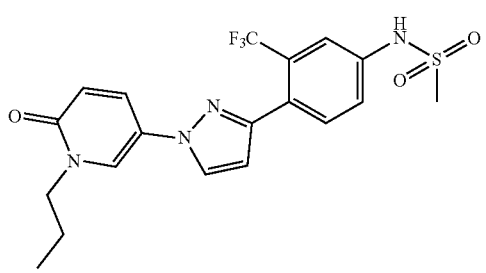
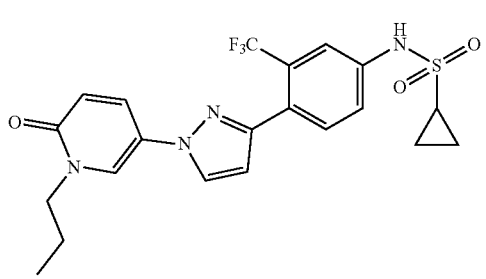
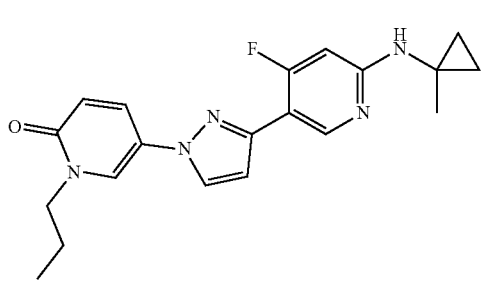
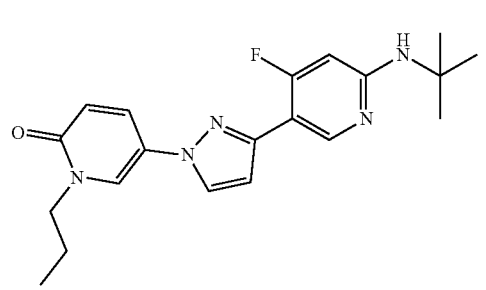
230
-continued
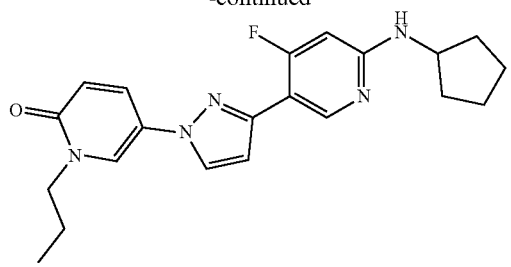
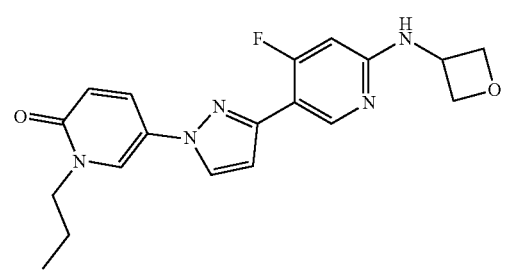
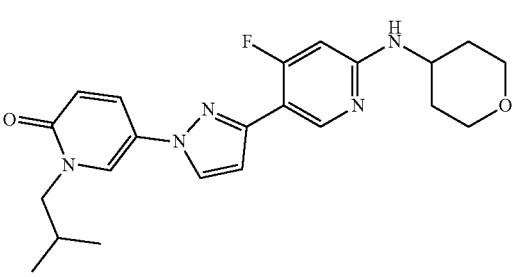
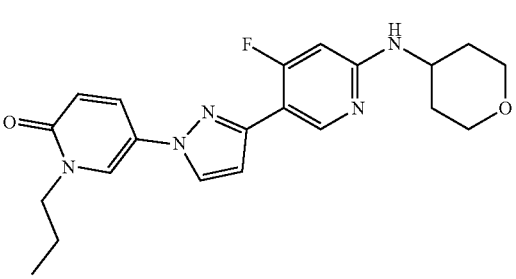
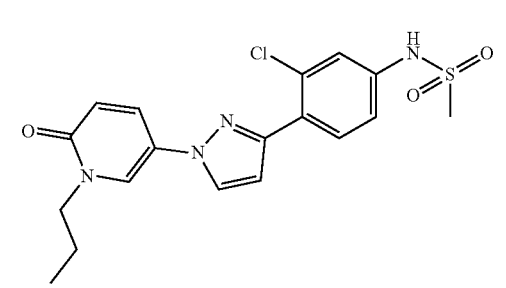
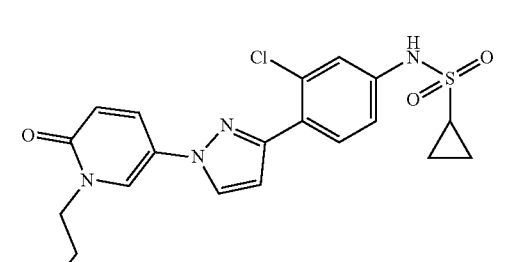

231
-continued
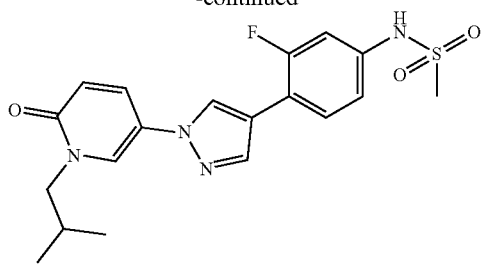
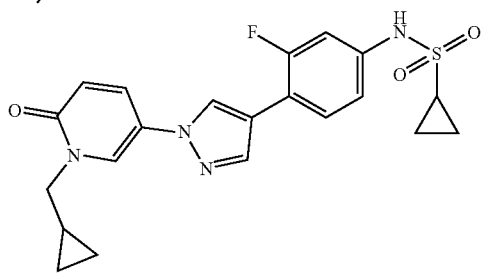
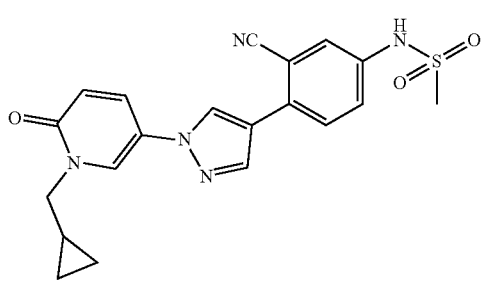
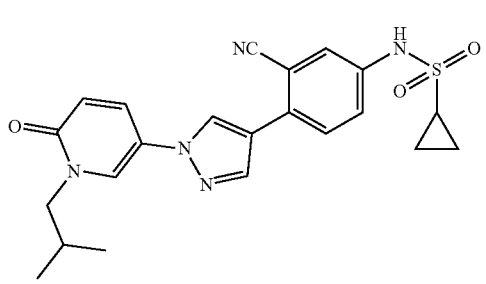
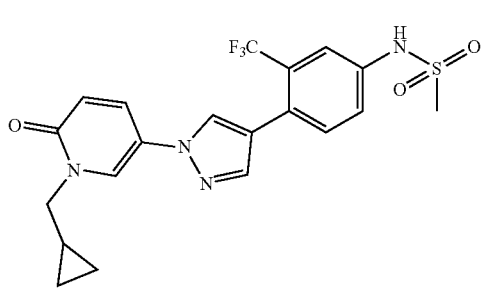
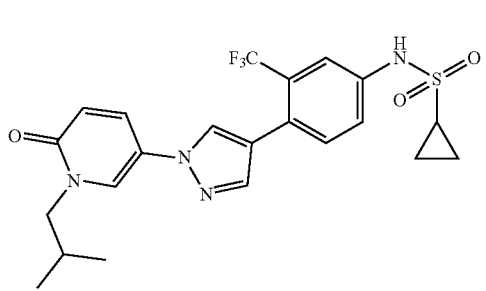
232
-continued
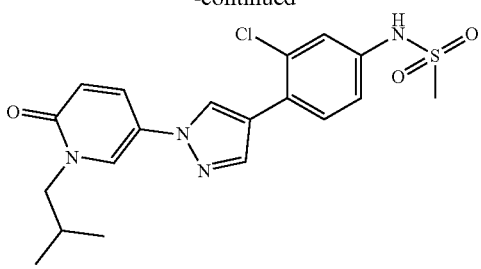
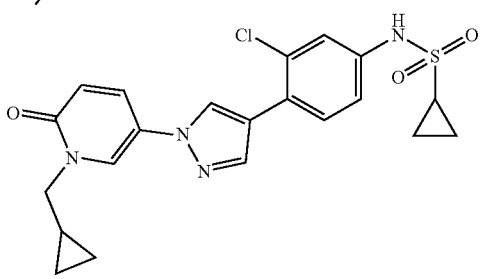
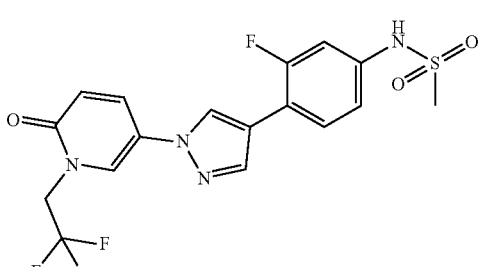
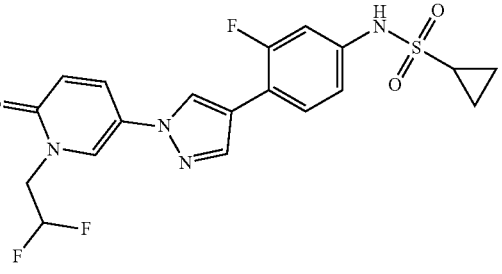
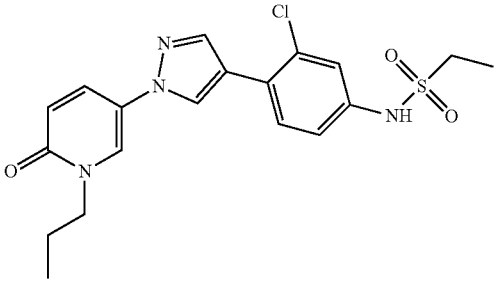
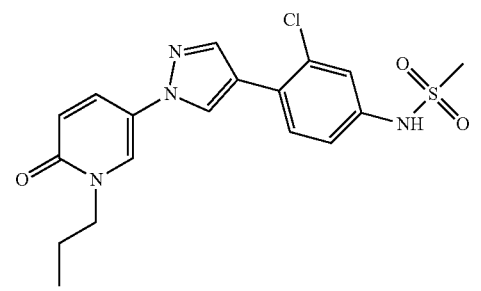

233
-continued
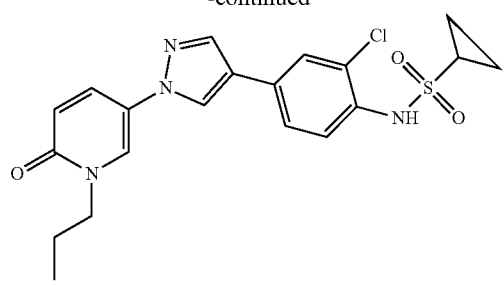
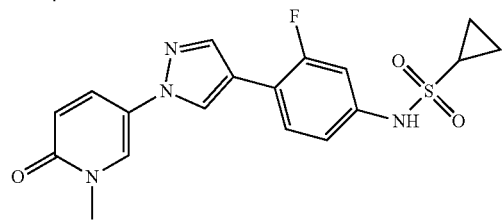
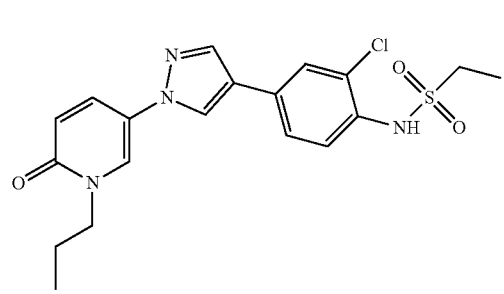
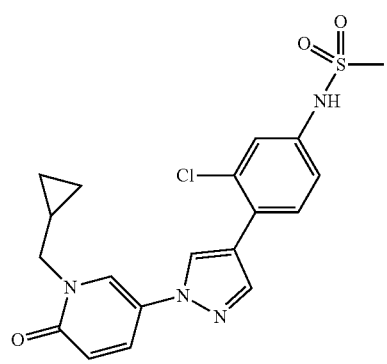
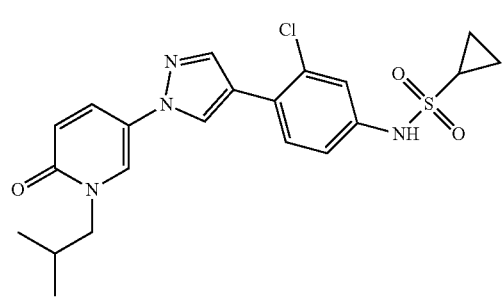
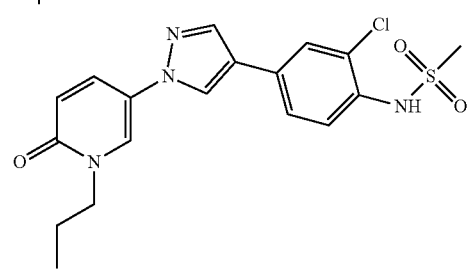
234
-continued
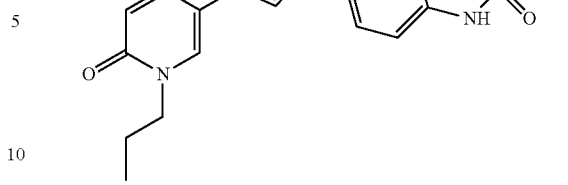
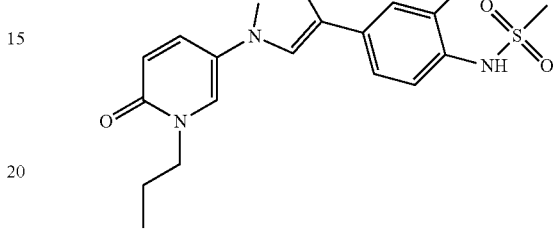
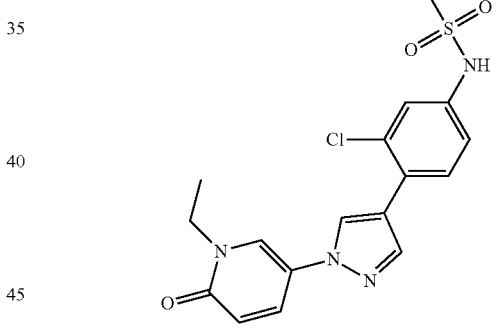
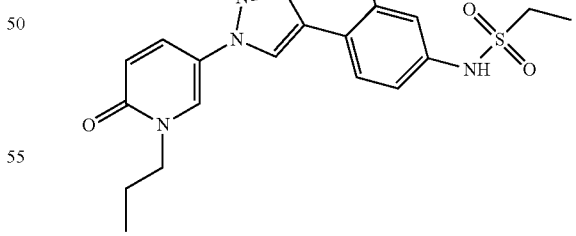
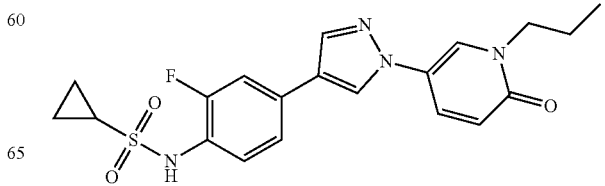

235
-continued
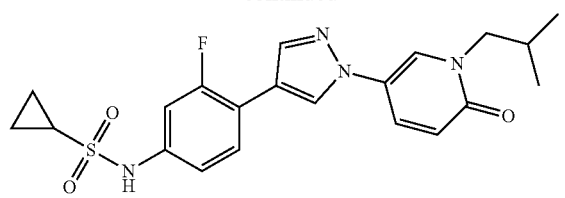
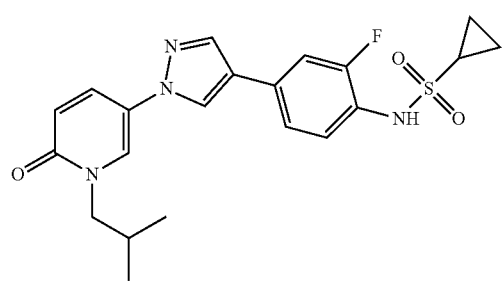
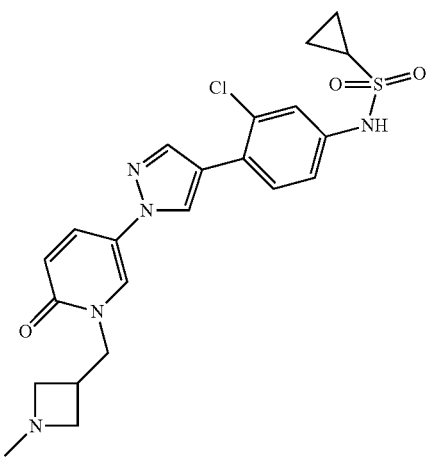
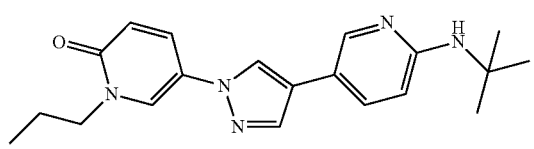
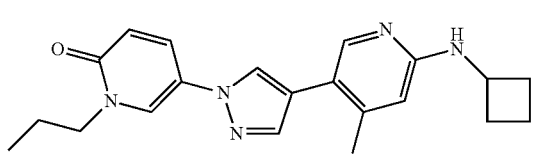
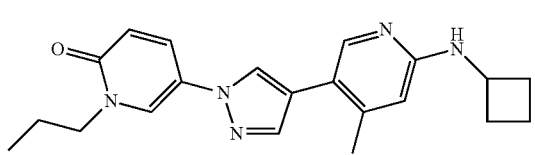
236
-continued
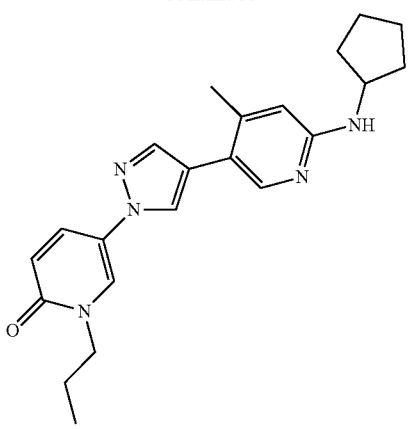
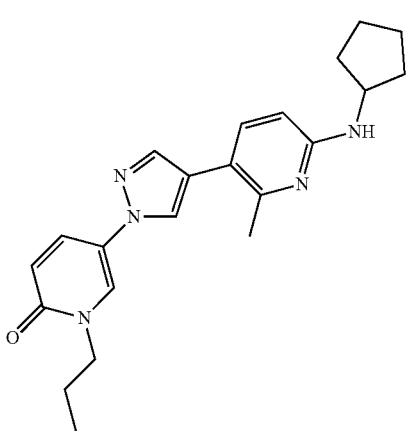
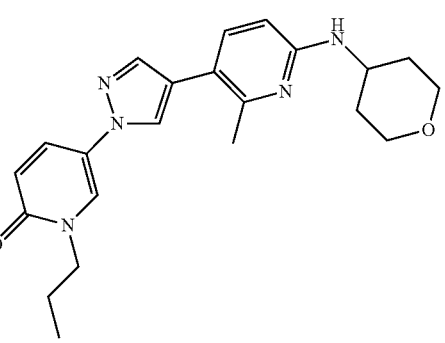
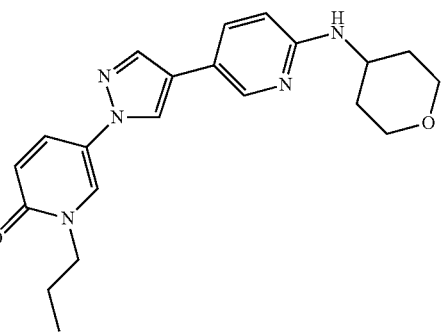

237
-continued
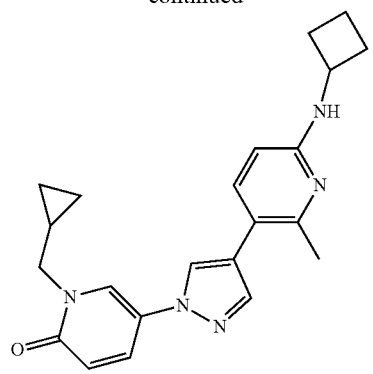
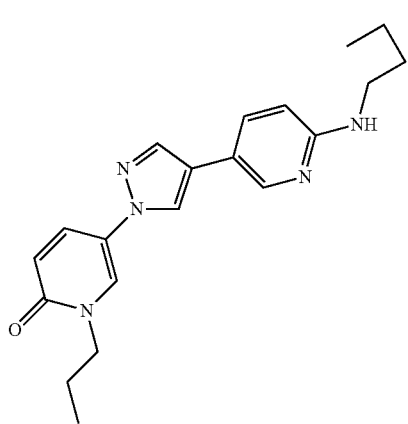
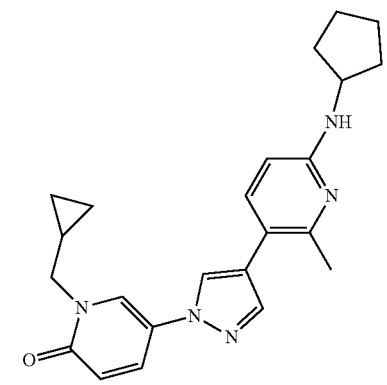
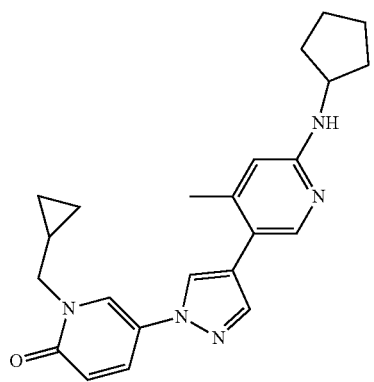
238
-continued
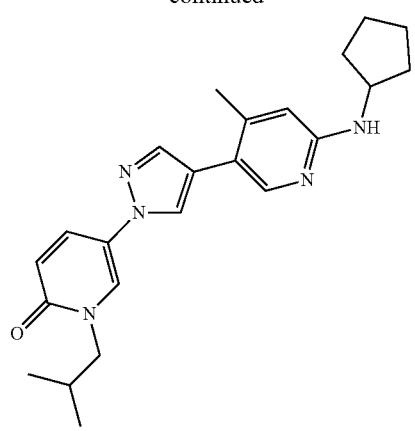
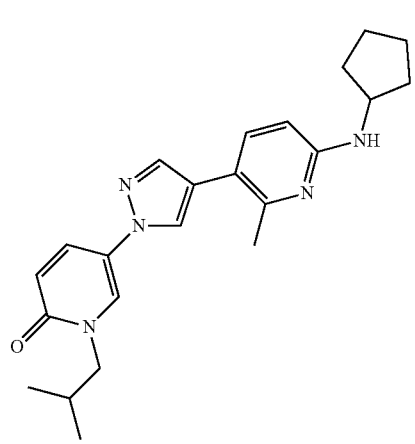
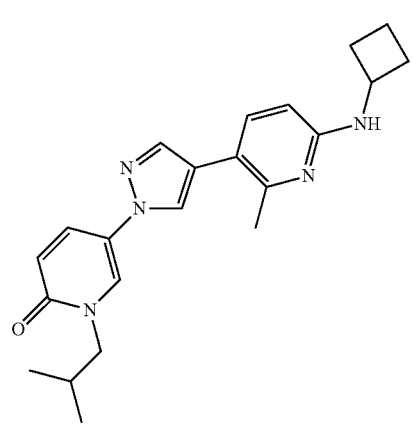
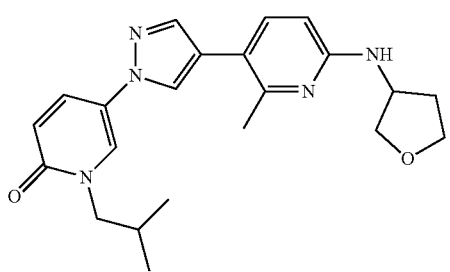

239
-continued
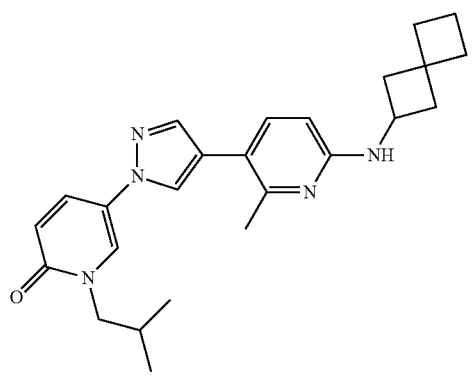
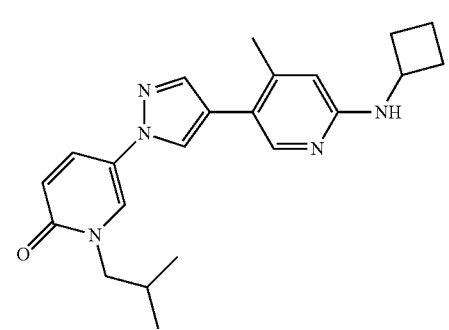
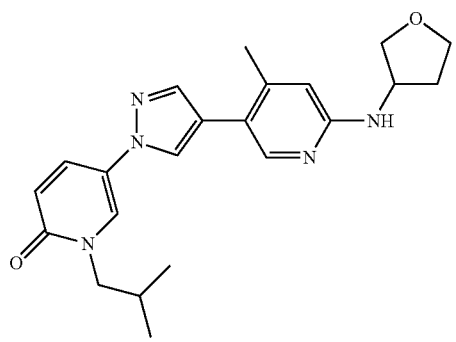
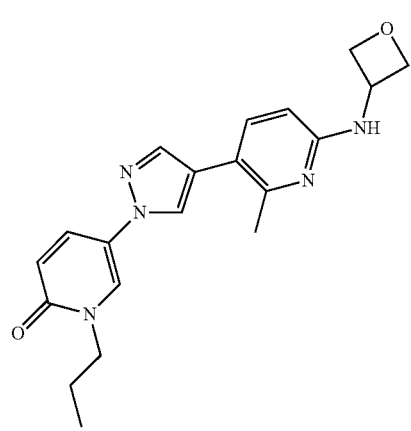
240
-continued
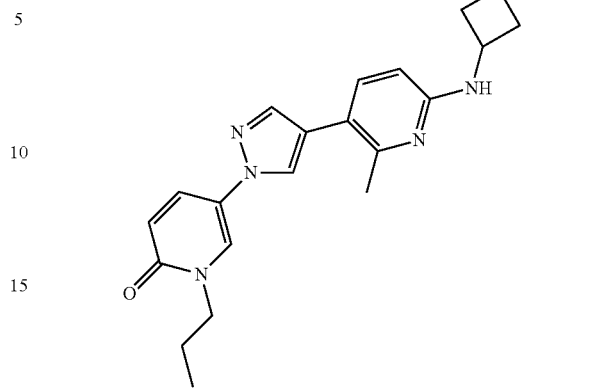
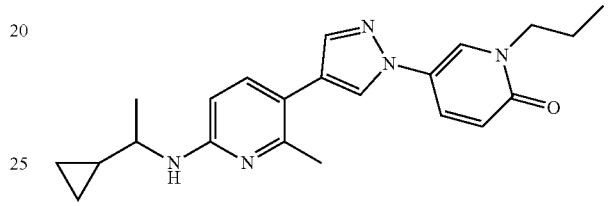
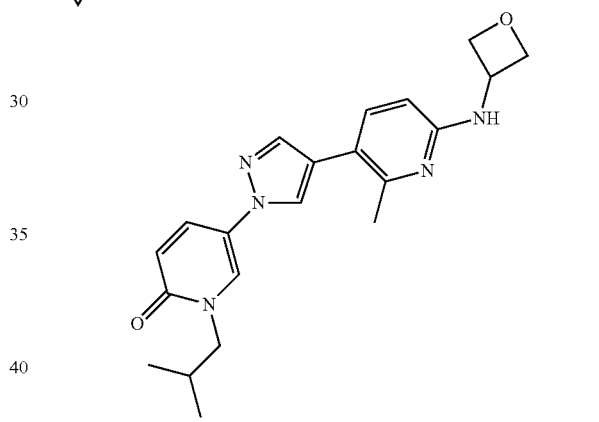
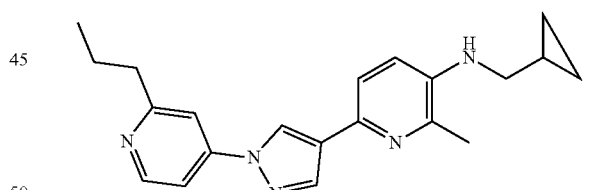
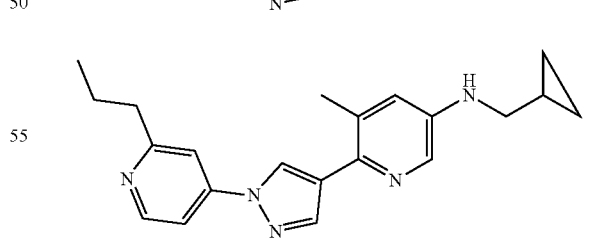
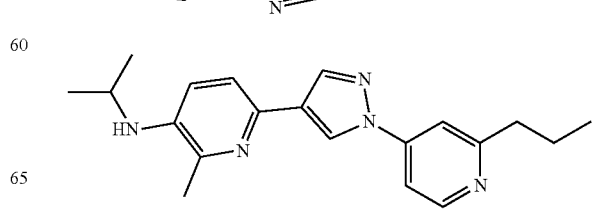

241
-continued
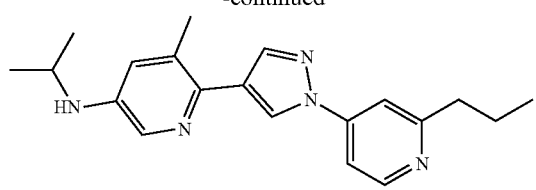
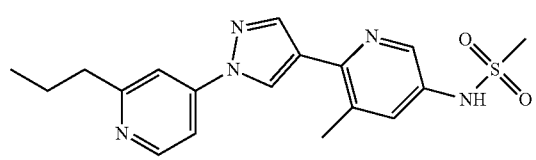
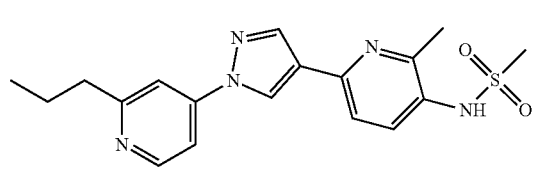
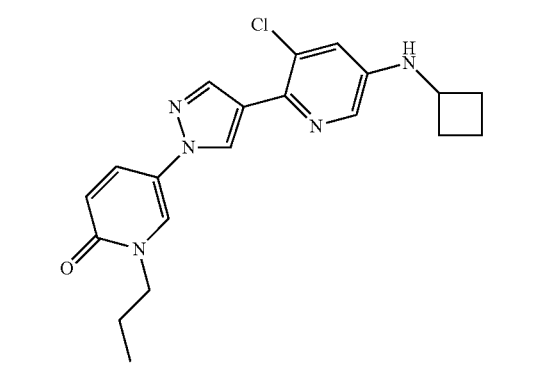
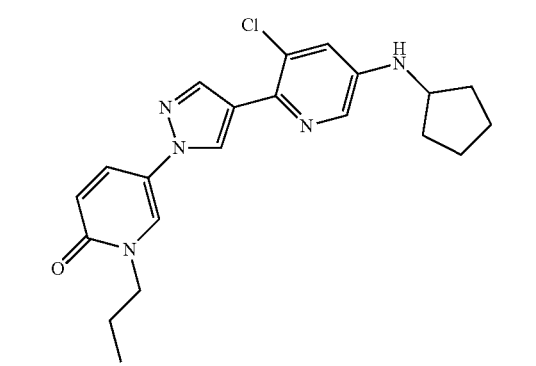
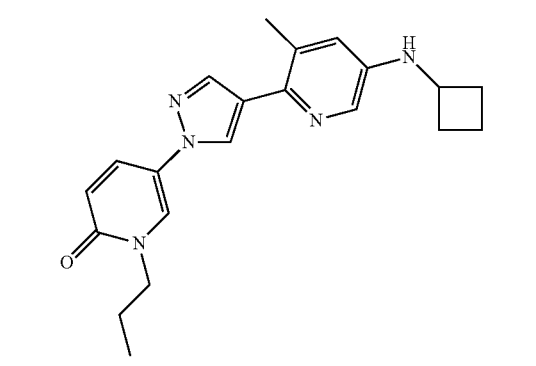
242
-continued
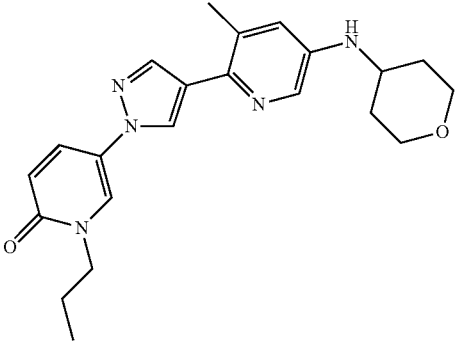
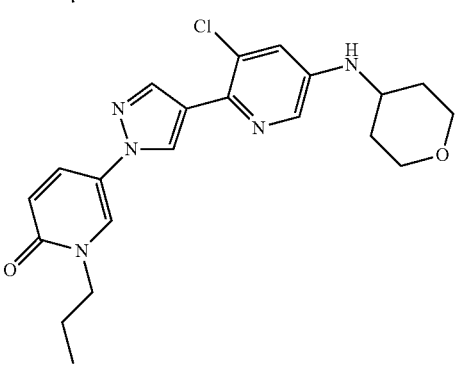
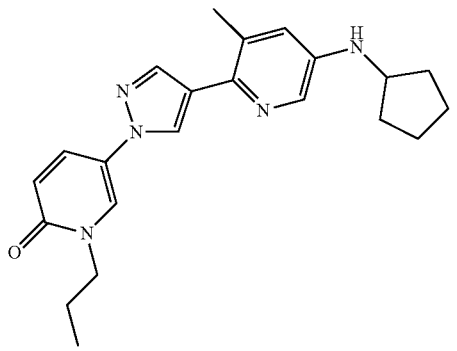
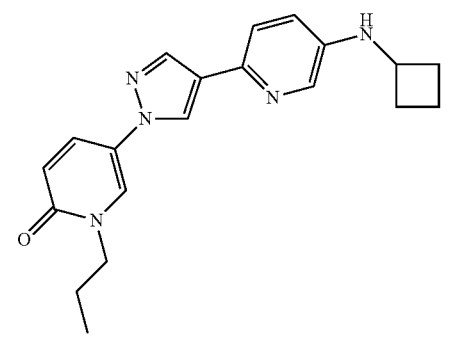
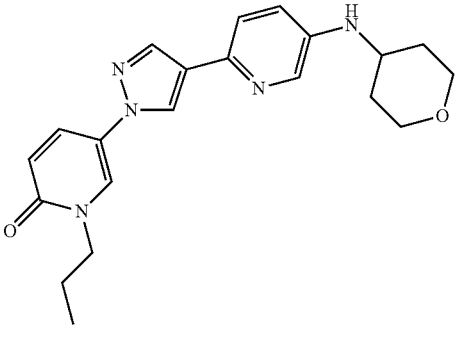

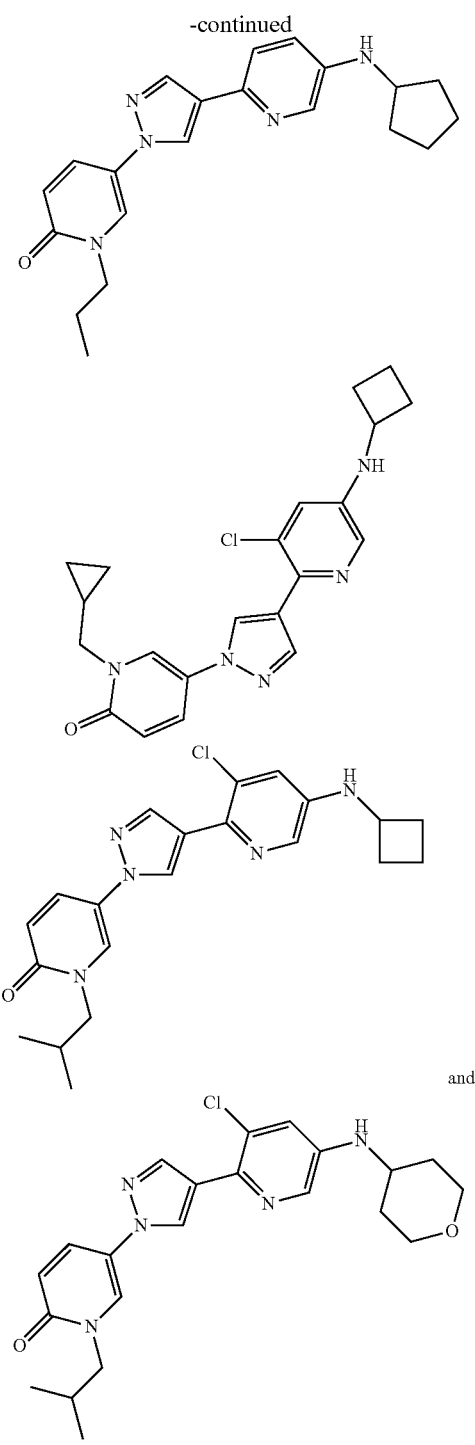

or a pharmaceutically acceptable salt thereof.

16. A pharmaceutical composition comprising a Compound of claim 1 or a pharmaceutically acceptable salt thereof and a pharmaceutically acceptable carrier.

17. A method of inhibiting or relieving a condition, disease, or disorder associated with abnormal activation of the SREBP pathway comprising administering to a patient in need thereof an effective amount of the Compound of claim 1 wherein the condition, disease, or disorder is selected from metabolic syndrome, hypertension, type 2 diabetes, dyslipidemia, obesity, reducing body weight, a metabolic disease, hyperlipidemia, a lipoprotein related disease, combined elevated cholesterol and elevated triglycerides, Frederickson Type IIb, familial combined hyperlipidemia, familial hypertriglyceridemia, Frederickson Type IV, hyperlipoproteinemia Type V, mixed hyperlipidemia, acquired hyperlipidemia, Fatty Liver Disease, Nonalcoholic Steatohepatitis, Neutral Lipid Storage Diseases, Chanarin-Dorfman Syndrome, post myocardial infarction management, peripheral vascular disease, cerebrovascular disease—thrombotic, type II diabetes mellitus, diabetic nephropathy, and cancer; or wherein the patient is in need of increased thermogenesis or in need of reducing body weight.

18. The method of claim 17, wherein the cancer is selected from hepatocellular carcinoma, prostate cancer, post menopausal breast carcinoma, pancreatic adenocarcinoma, ovarian cancer, B cell lymphoma, leukemia, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach cancer, gastric cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer.

19. The method of claim 17, wherein the condition, disease, or disorder is selected from metabolic syndrome, Frederickson Type IIb, familial combined hyperlipidemia, Frederickson Type IV, hyperlipoproteinemia Type V, mixed hyperlipidemia, Aquired hyperlipidemia, Fatty Liver Disease, nonalcoholic steatohepatitis, Neutral Lipid Storage Diseases, Chanarin-Dorfman Syndrome, hypertension, type 2 diabetes, dyslipidemia, obesity, hepatocellular carcinoma, prostate cancer, post-menopausal breast carcinoma, pancreatic adenocarcinoma, ovarian cancer, B cell lymphoma, leukemia, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach cancer, gastric cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer; or wherein the patient is in need of increased thermogenesis or in need of reducing body weight.

20. The method of claim 17, where the compound is selected from the following formula:

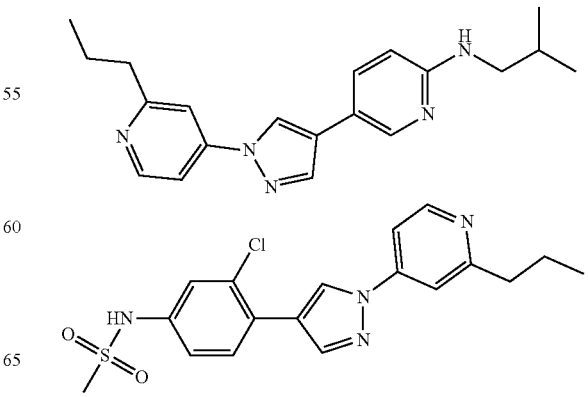

245
-continued
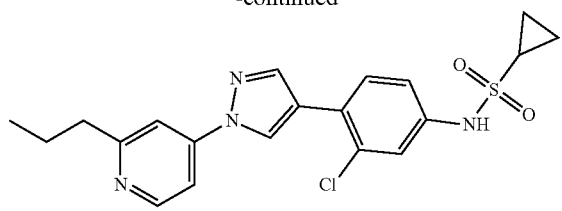
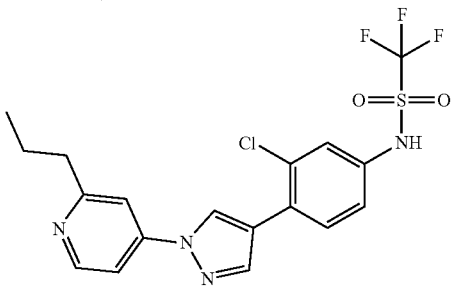
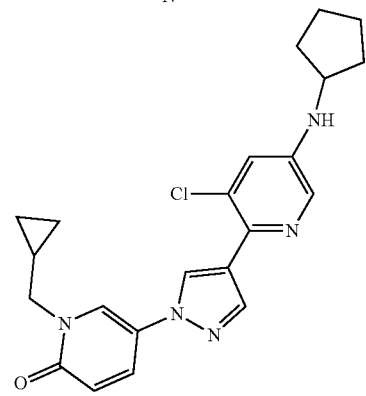
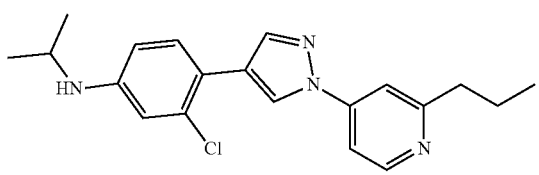
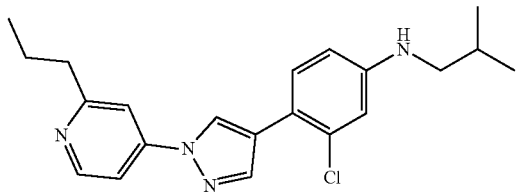
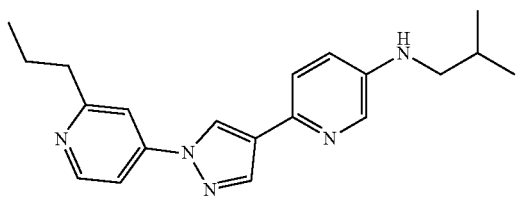
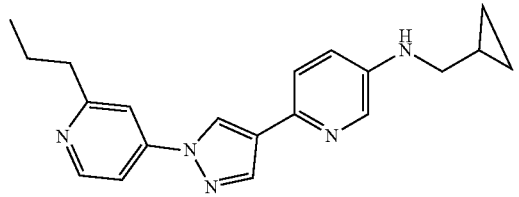
246
-continued
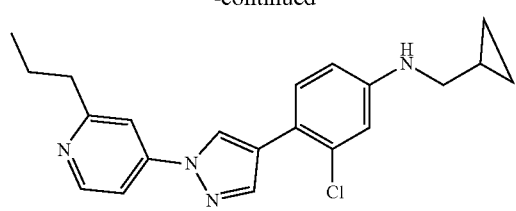
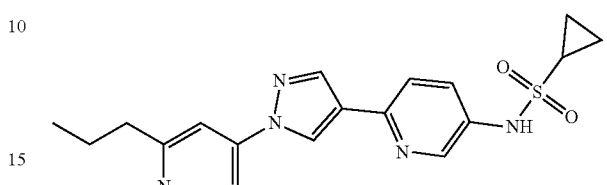
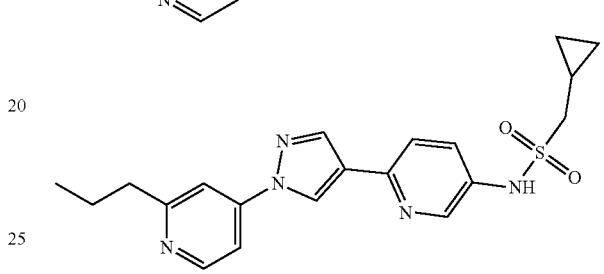
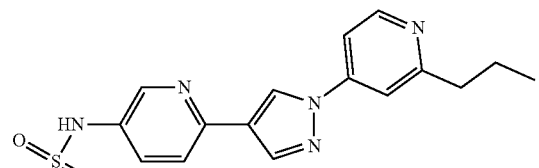
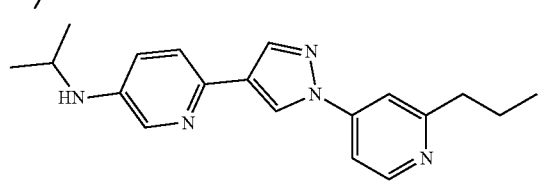
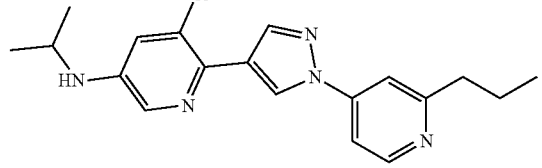
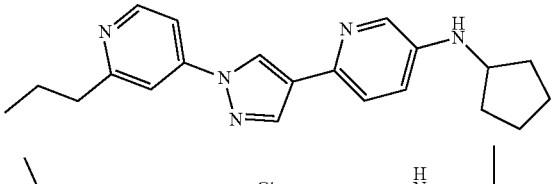
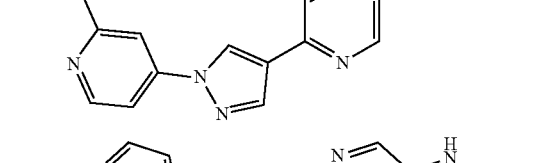
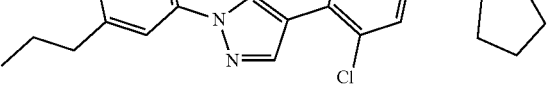

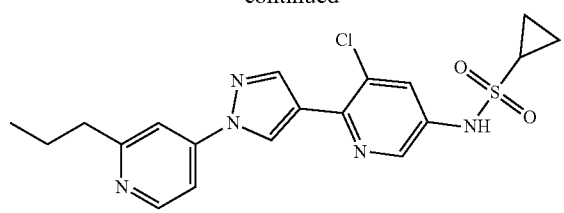
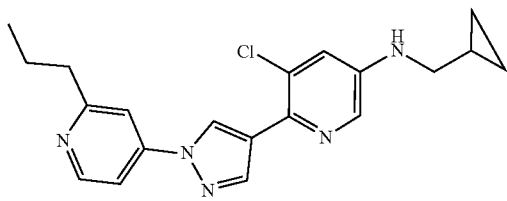
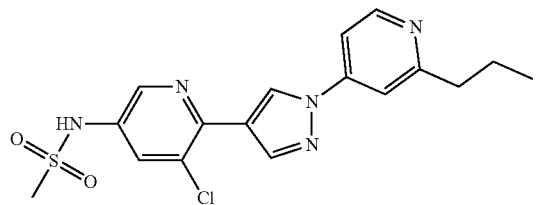
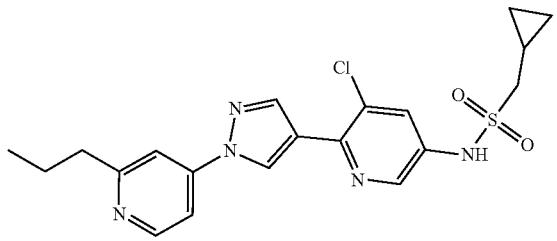
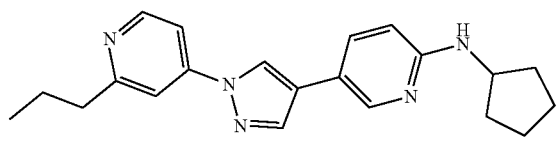
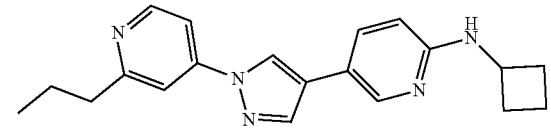
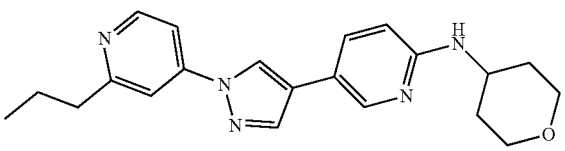
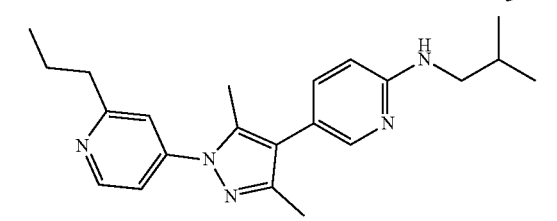
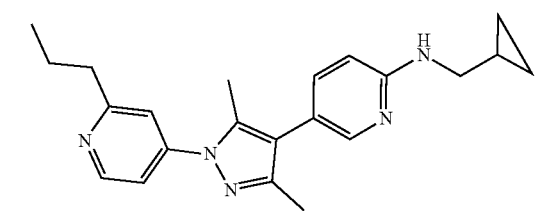
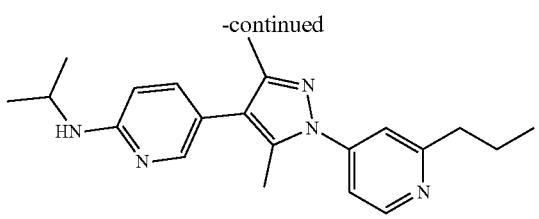
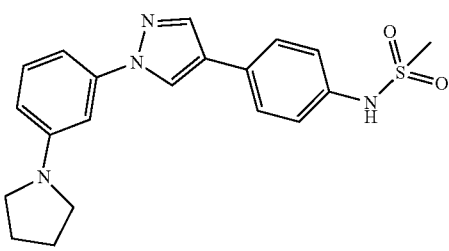
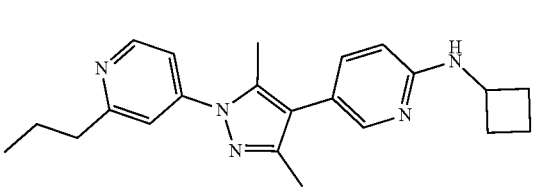
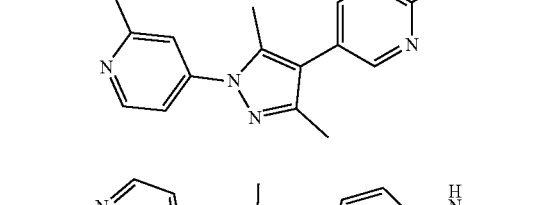
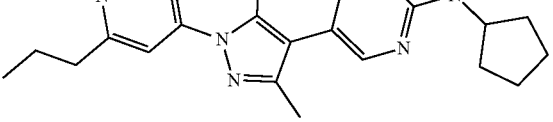
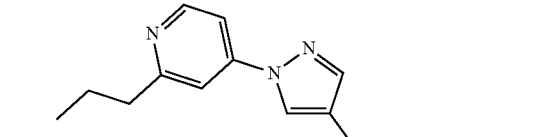
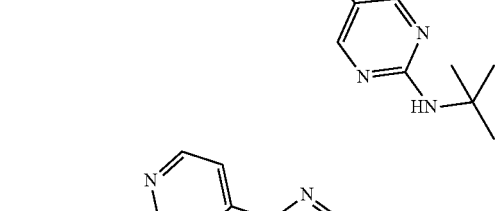
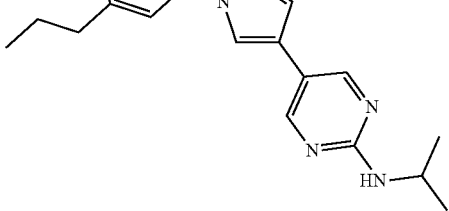

249
-continued
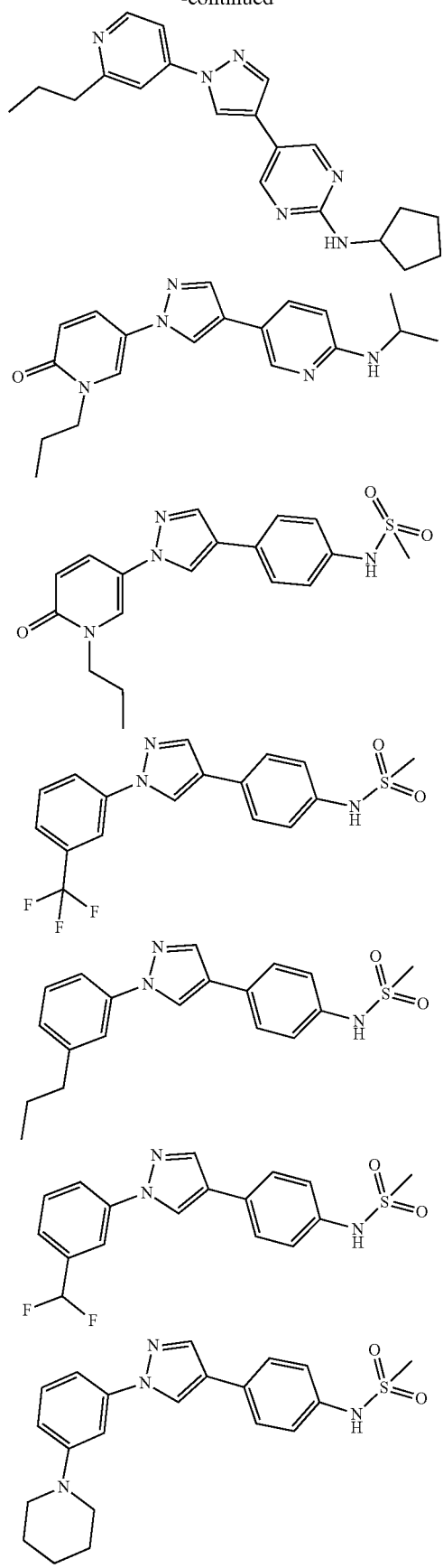
250
-continued
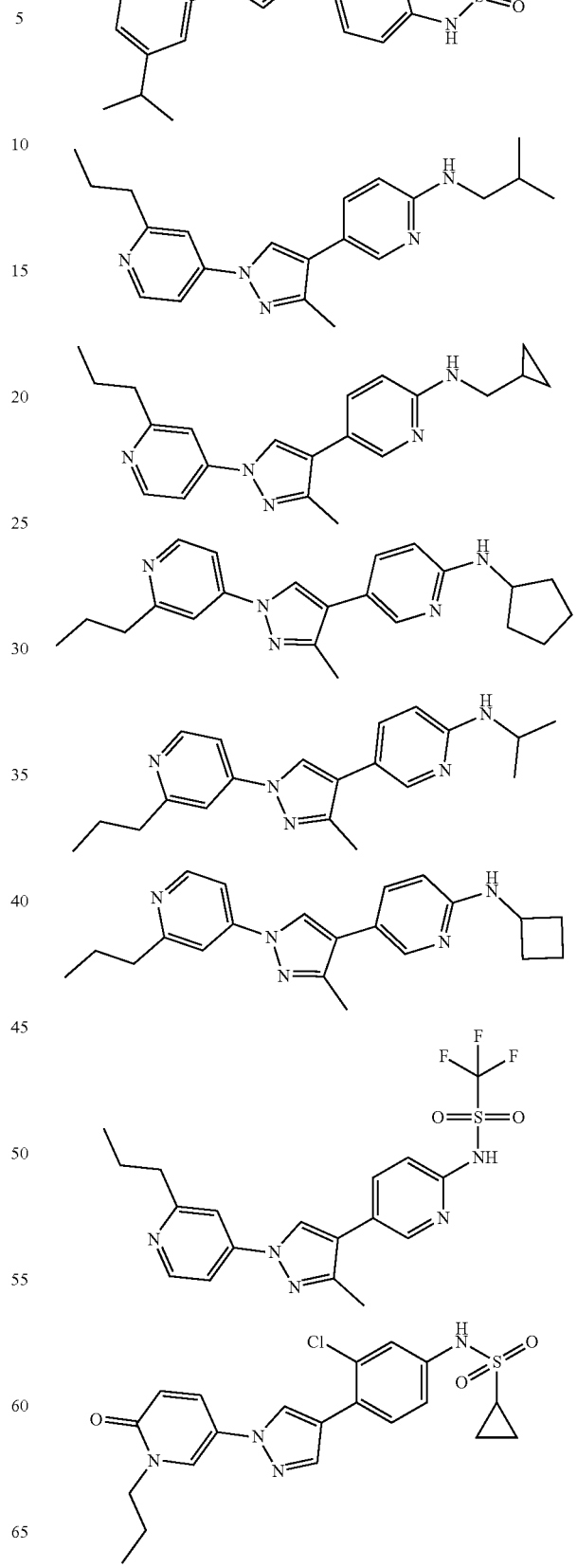

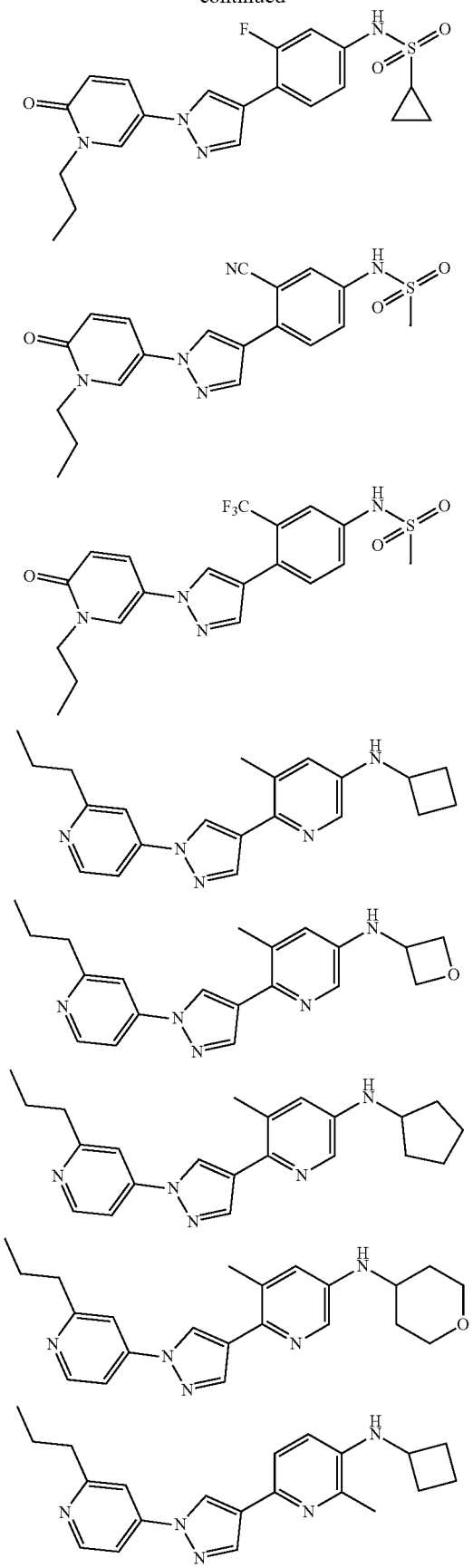
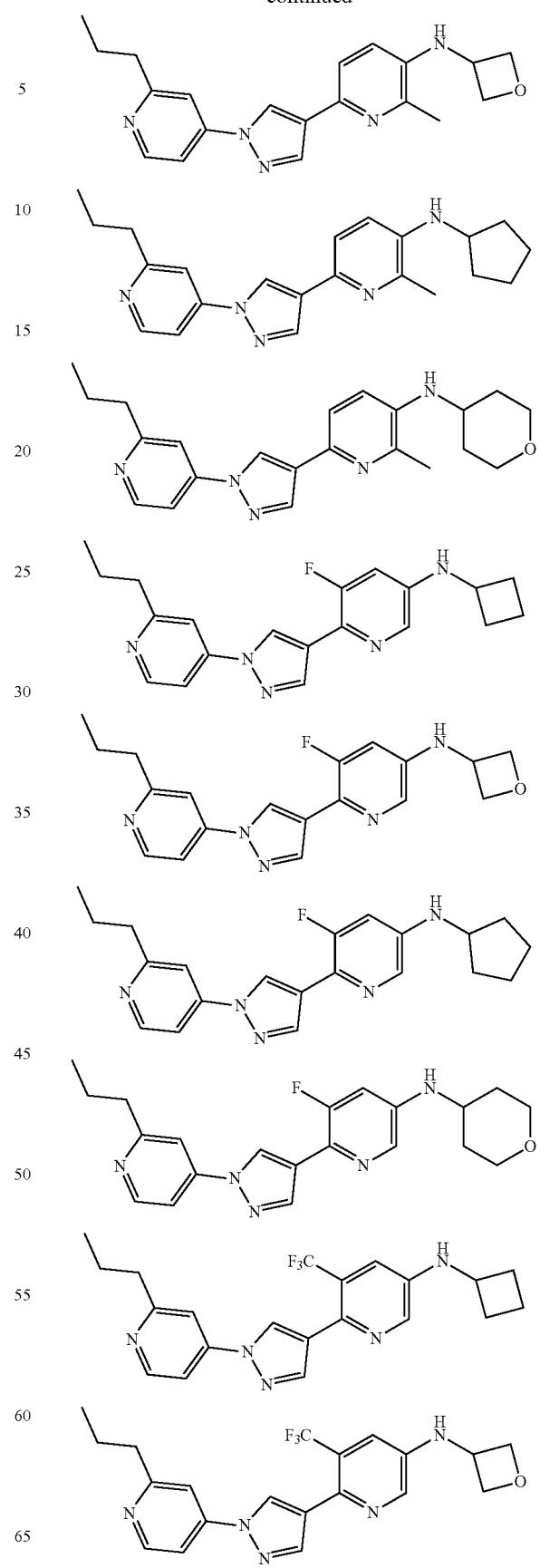

253
-continued
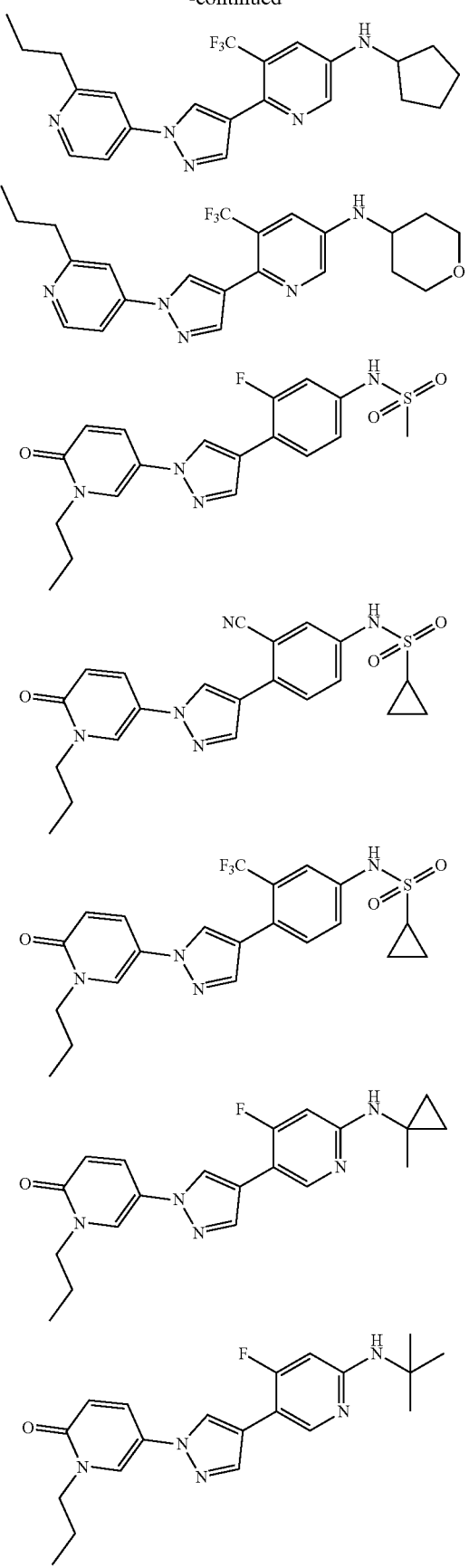
254
-continued
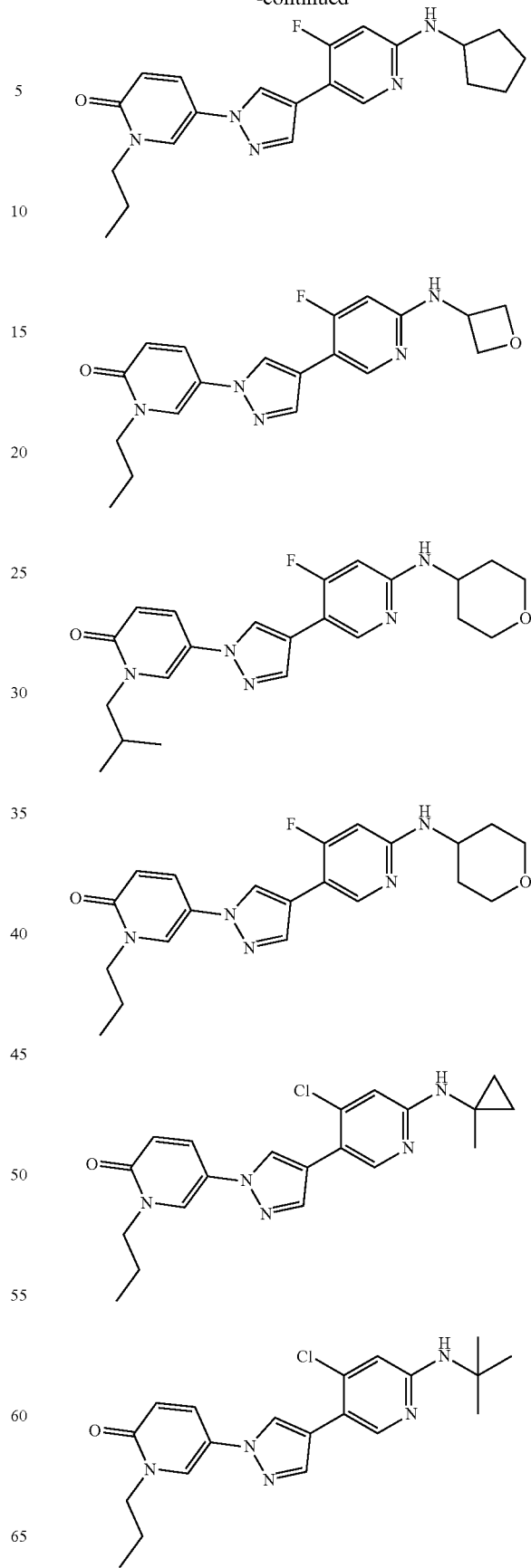

255
-continued
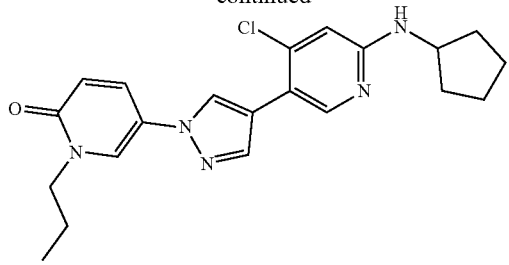
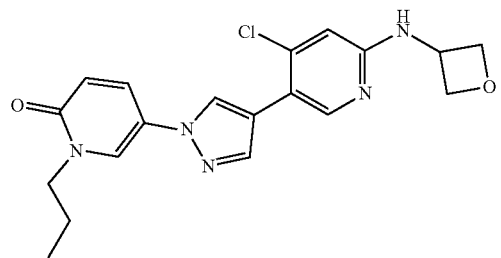
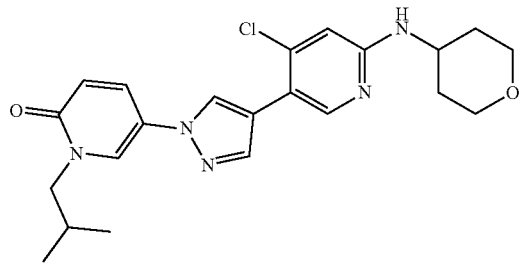
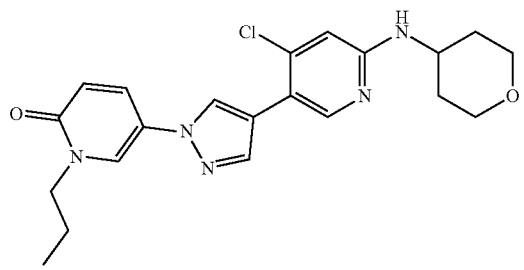
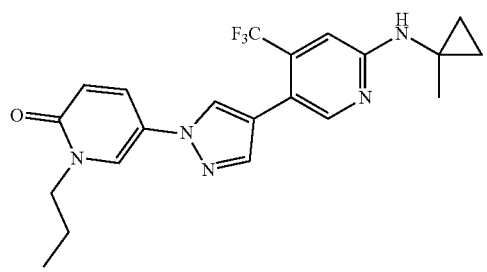
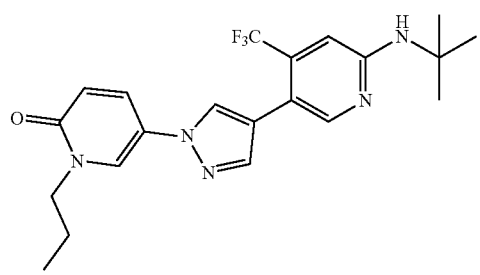
256
-continued
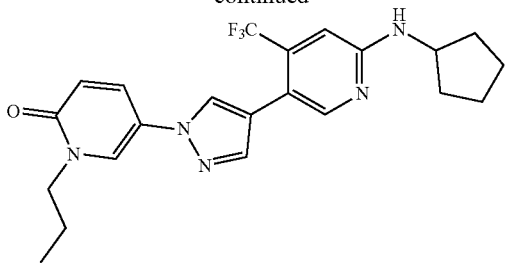
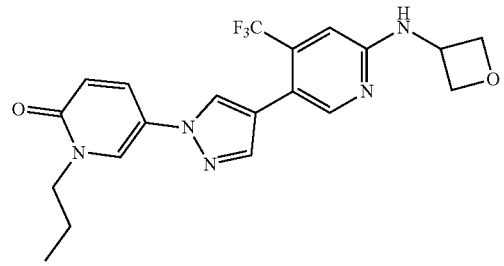
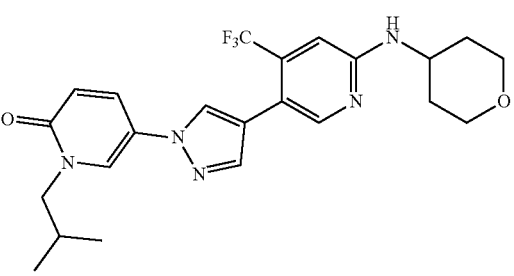
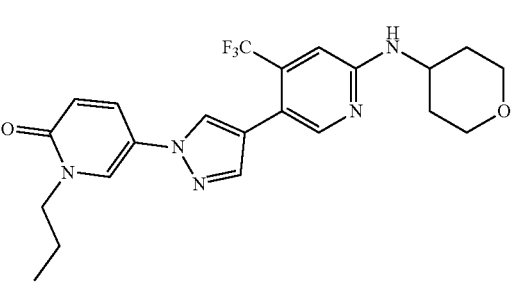
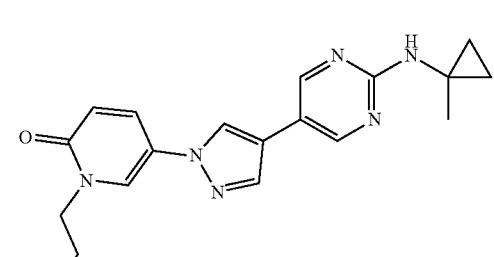
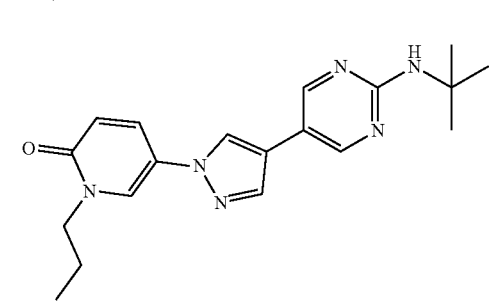

257
-continued
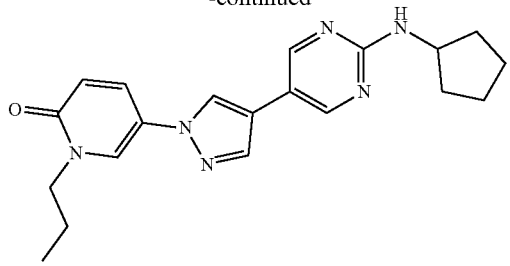
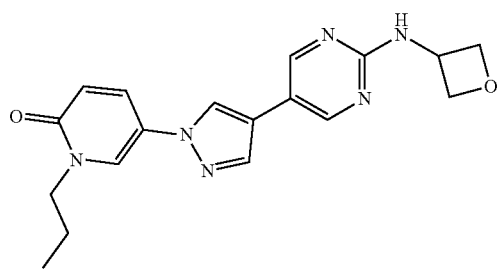
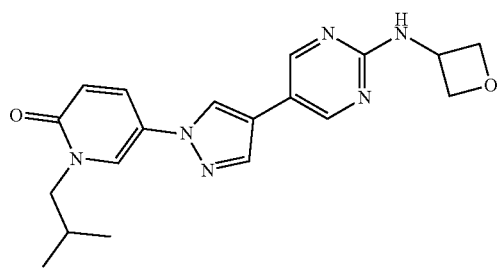
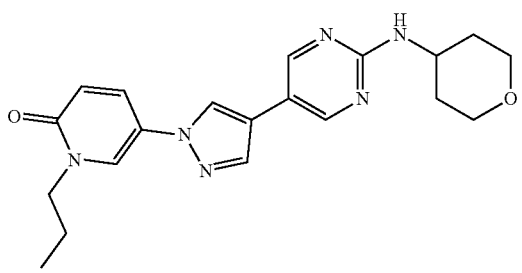
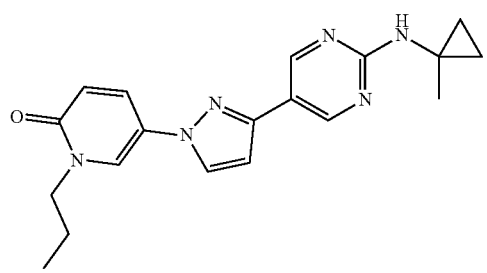
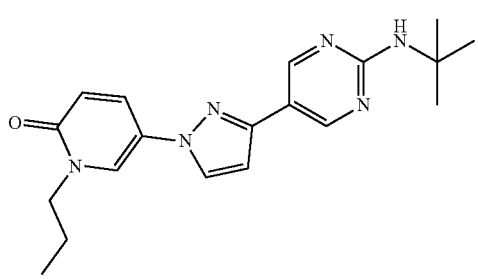
258
-continued
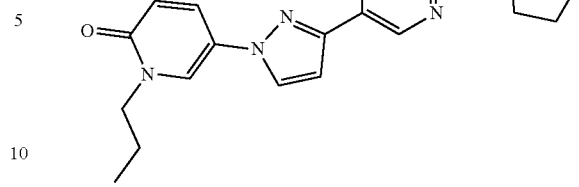
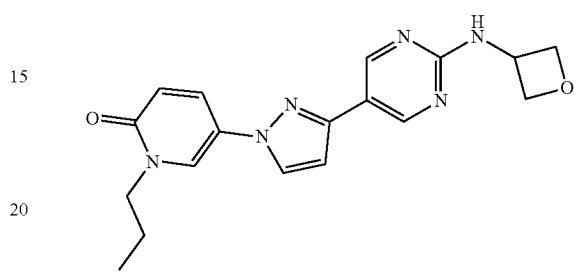
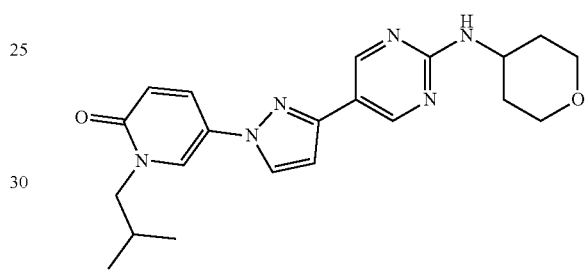
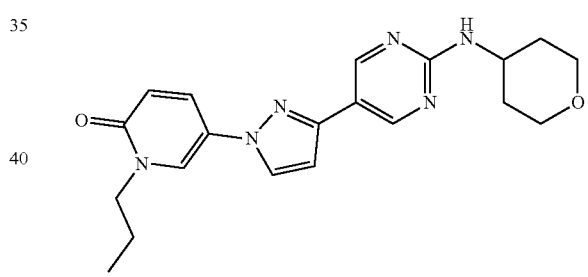
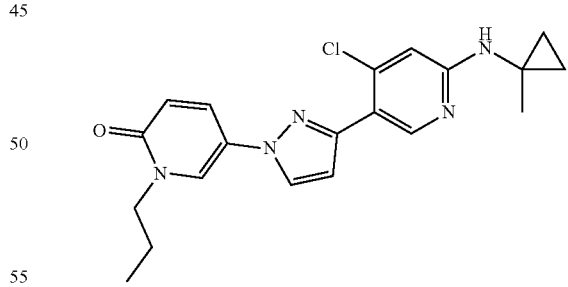
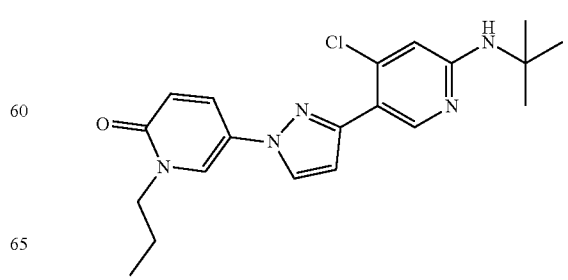

259
-continued
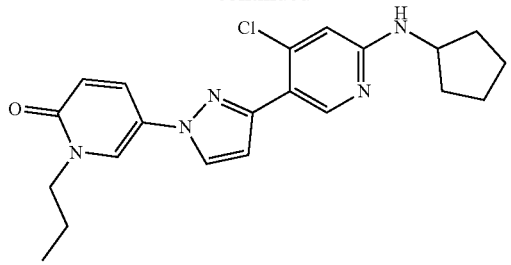
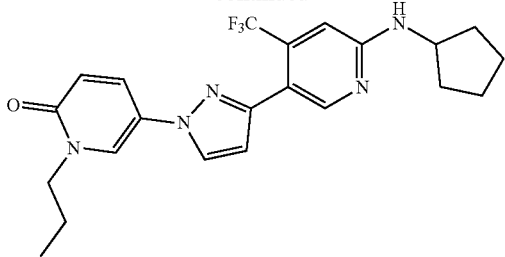
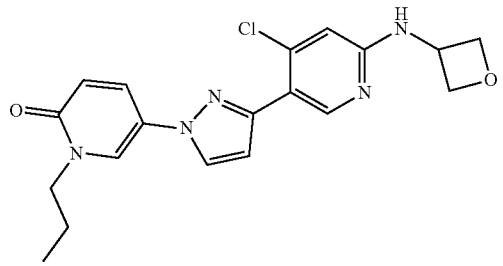
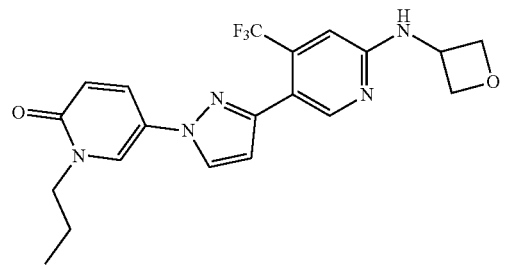
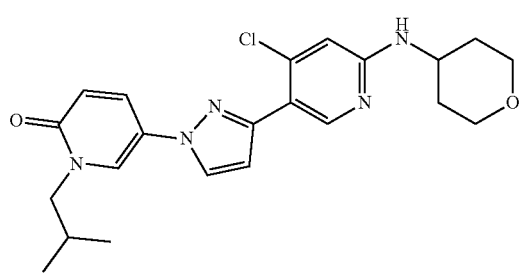
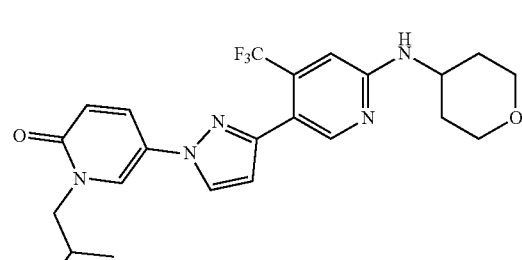
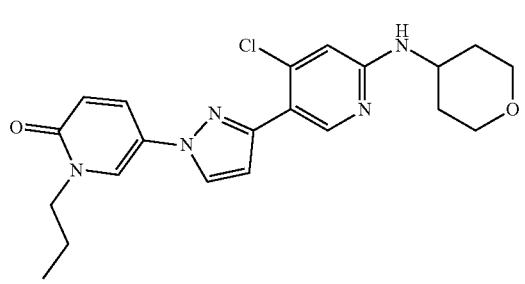
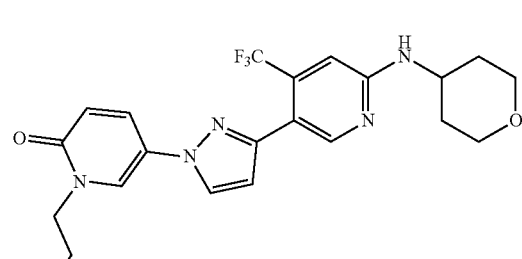
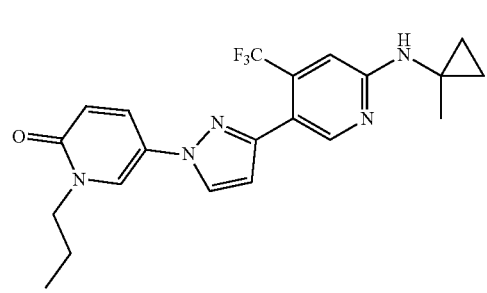
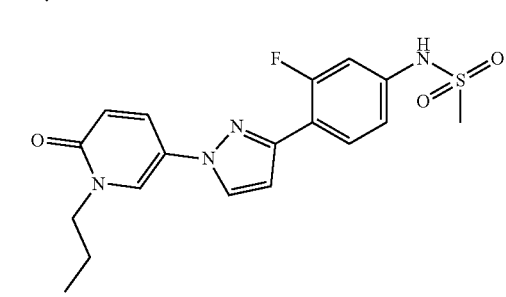
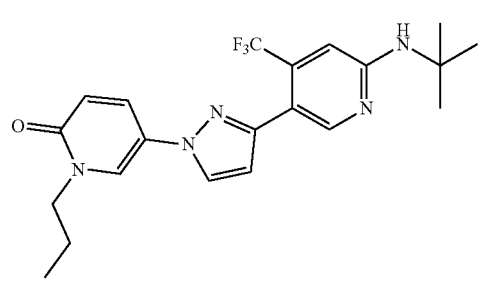
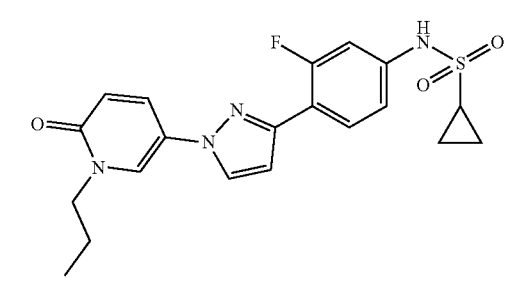
260
-continued 261
-continued
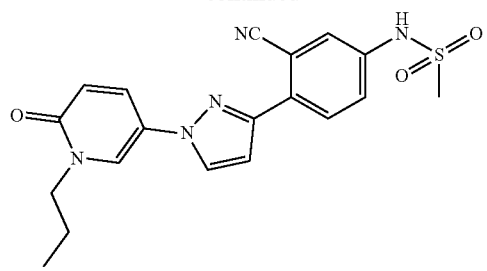
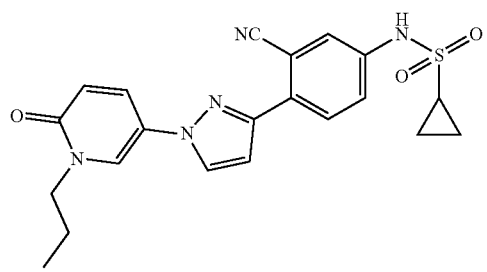
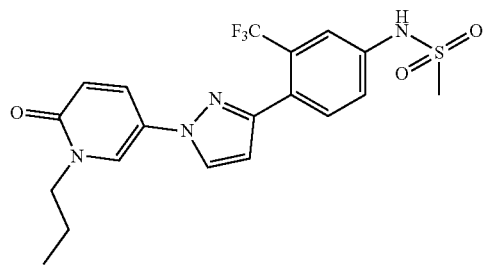
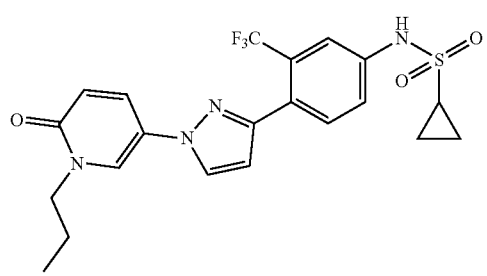
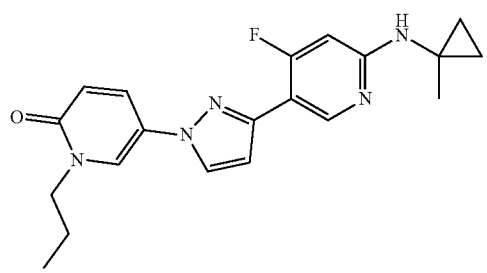
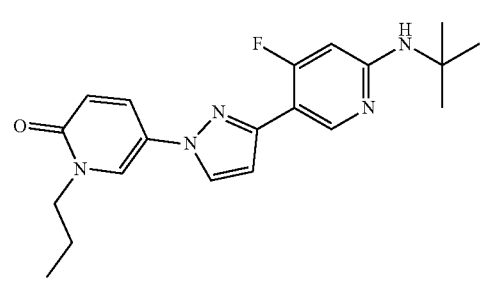
262
-continued
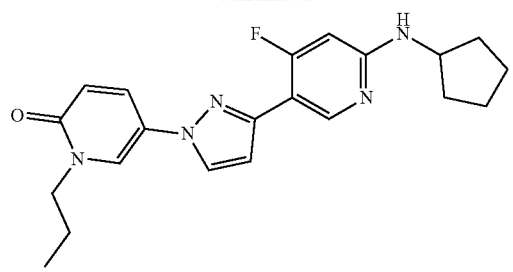
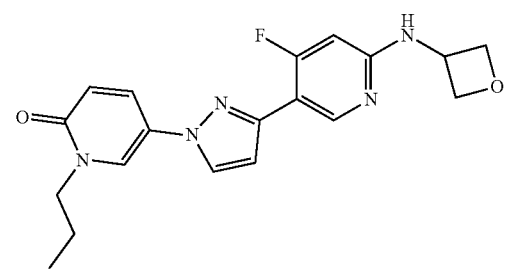
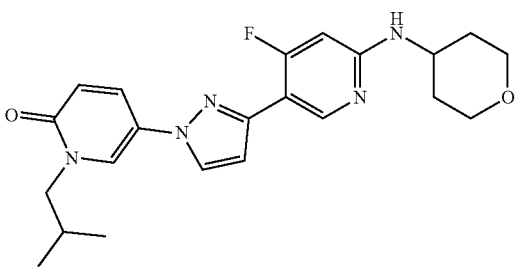
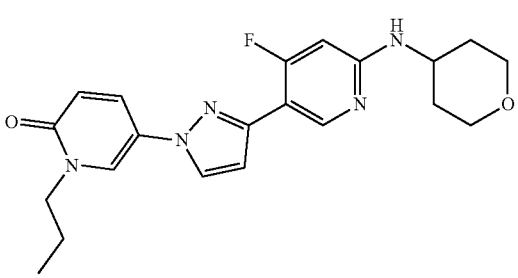
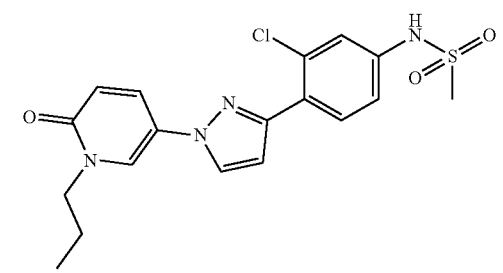
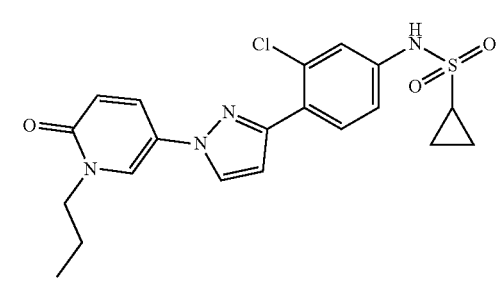

263
-continued
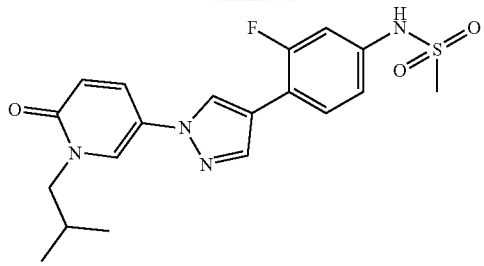
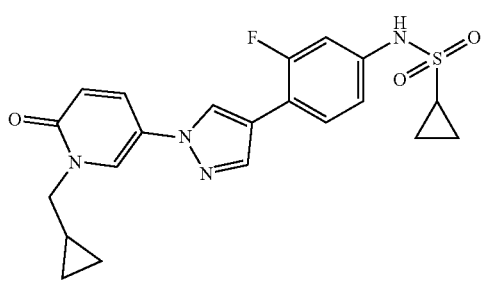
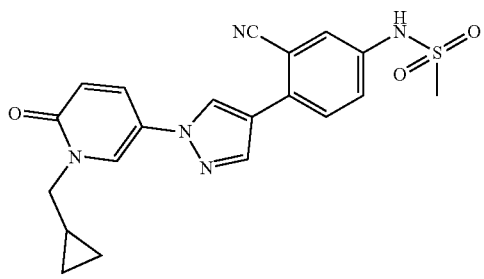
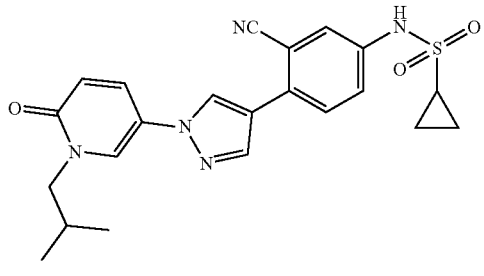
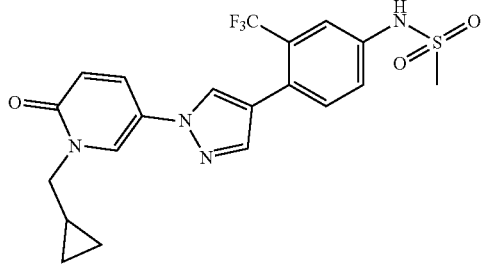
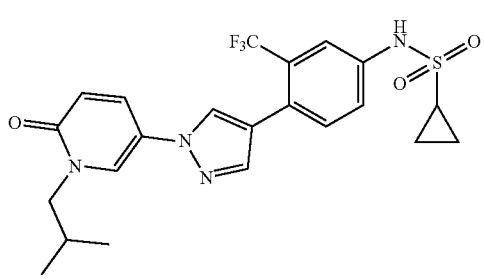
264
-continued
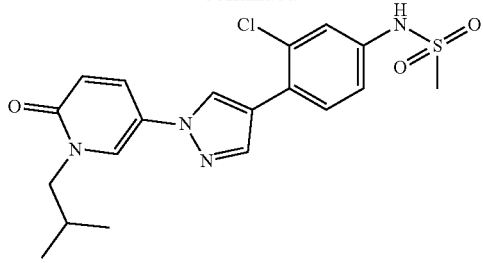
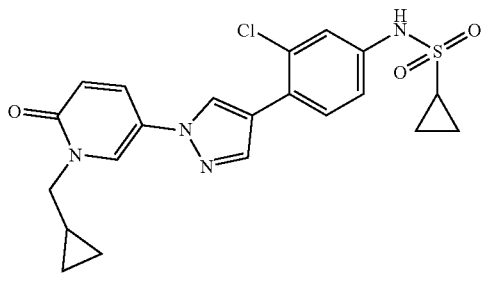
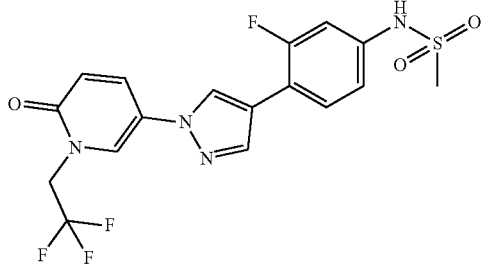
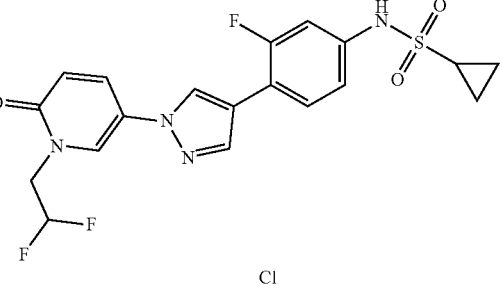
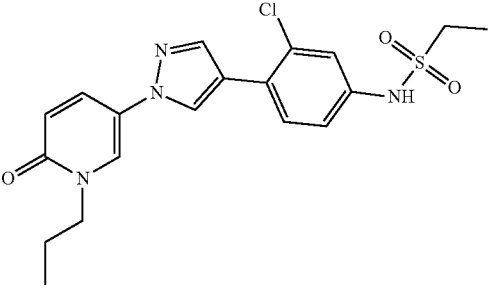
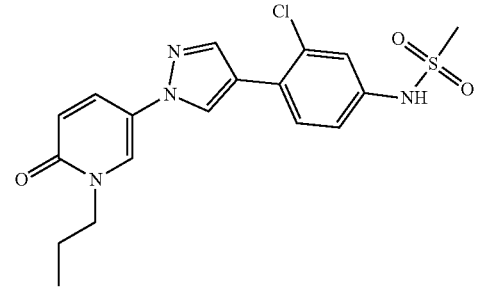

265
-continued
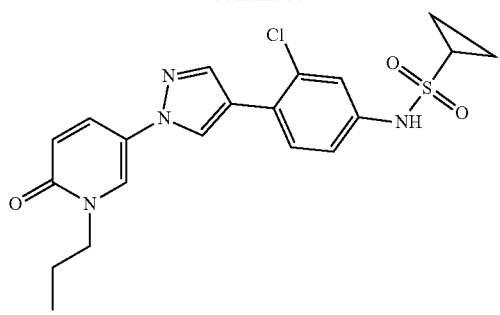
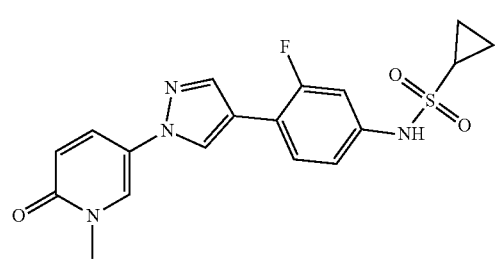
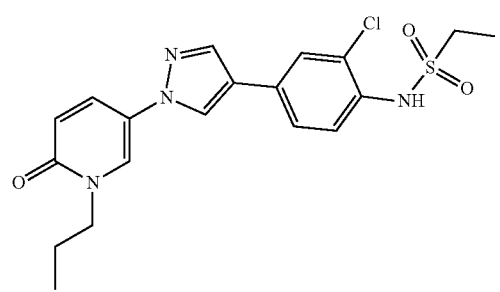
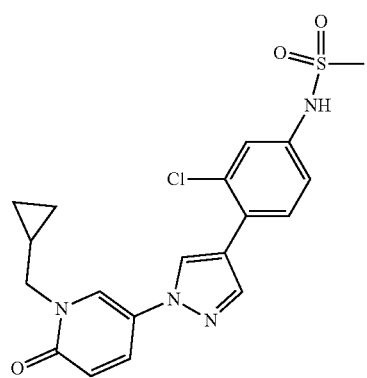
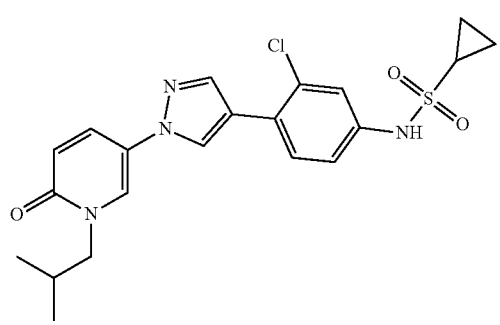
266
-continued
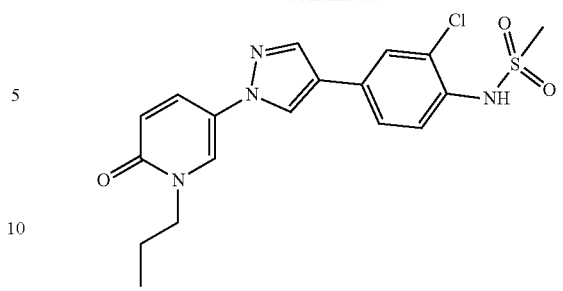
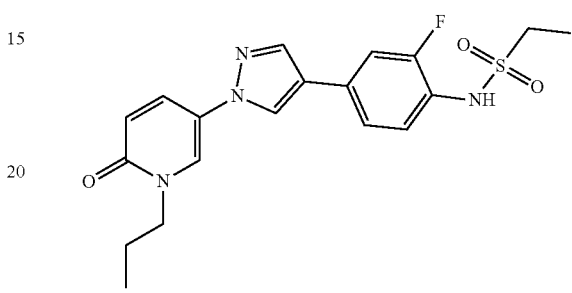
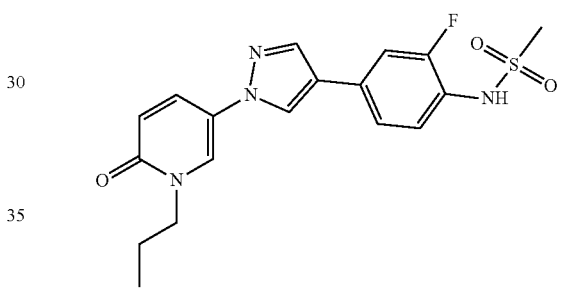
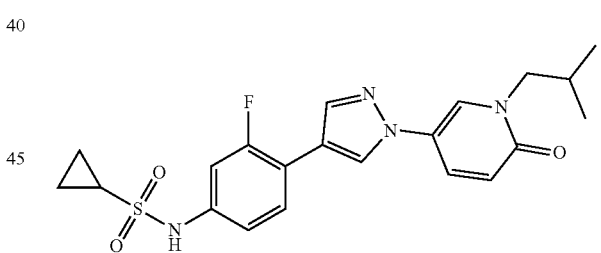
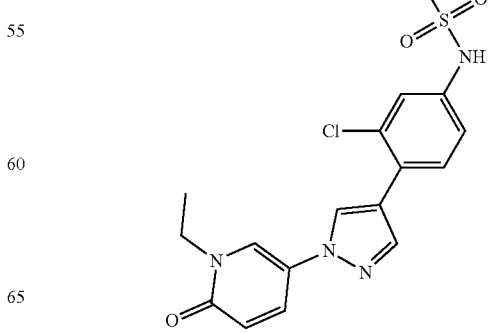

267
-continued
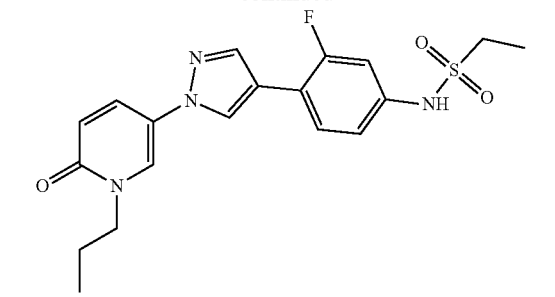
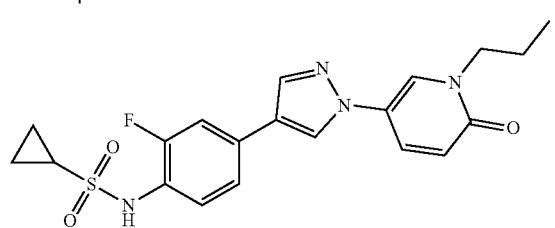
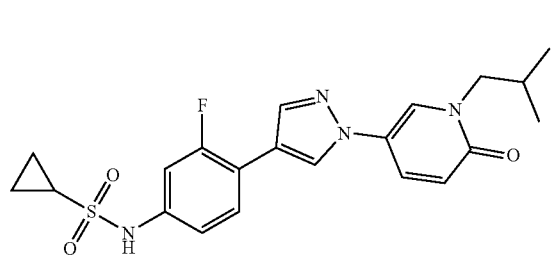
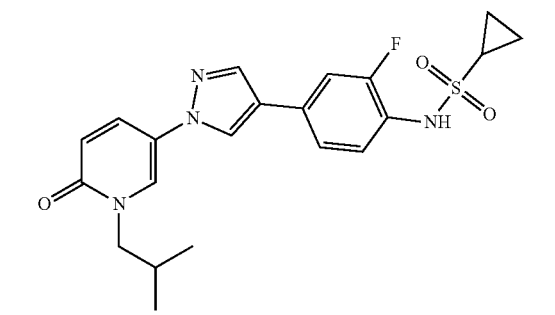
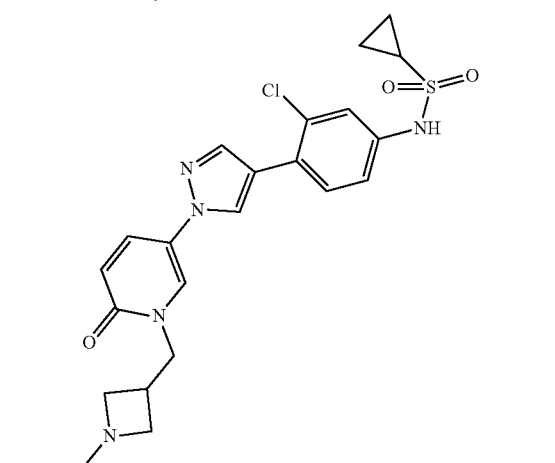
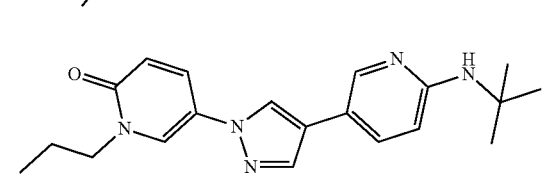
268
-continued
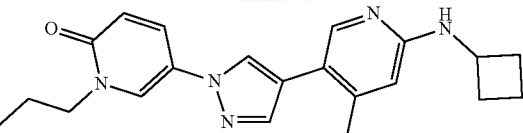
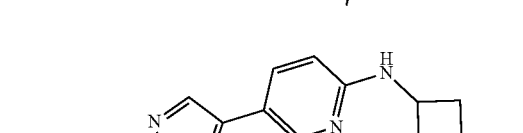
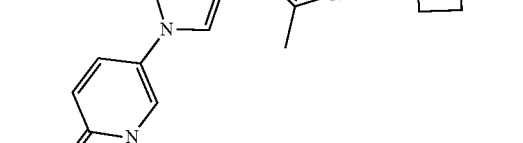
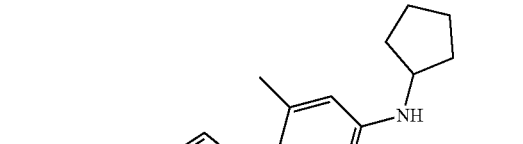
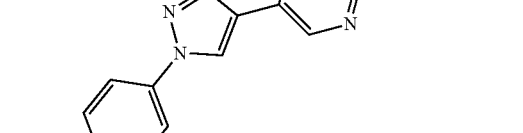
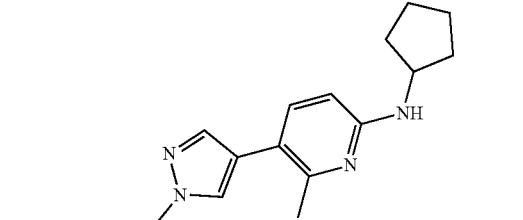
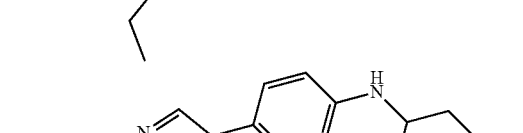
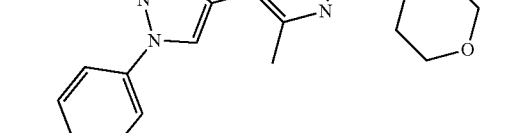

269
-continued
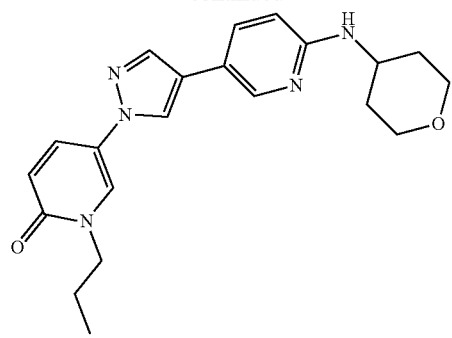
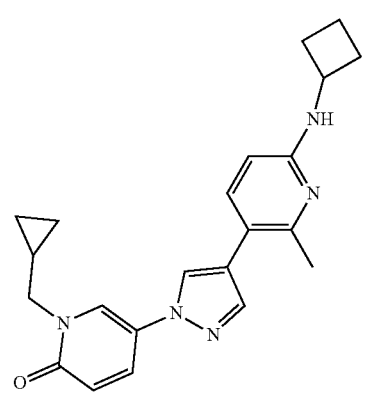
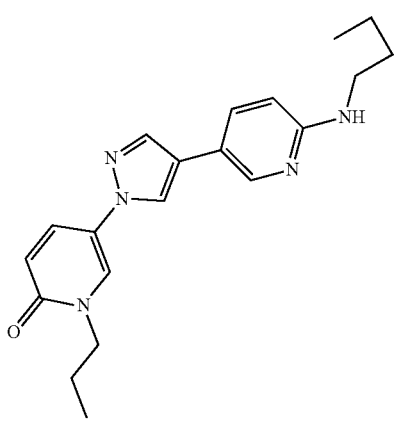
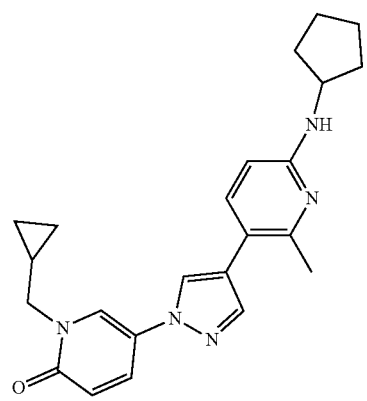
270
-continued
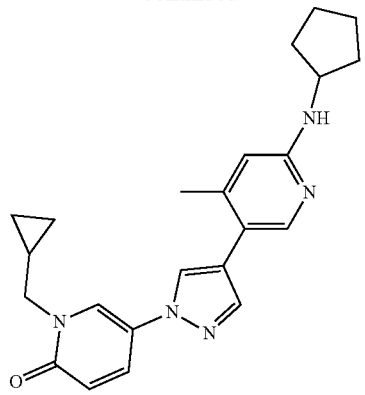
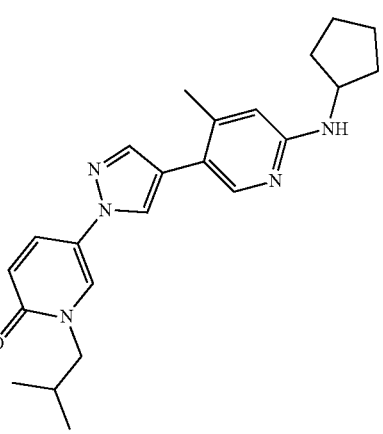
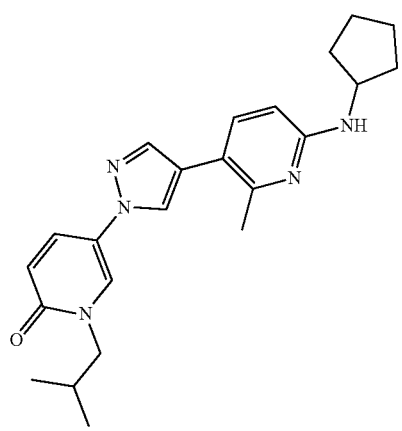
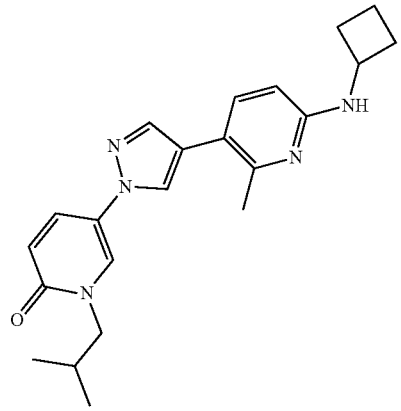

271
-continued
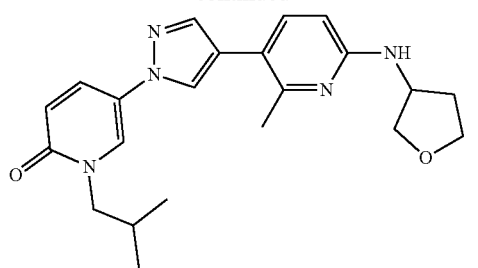
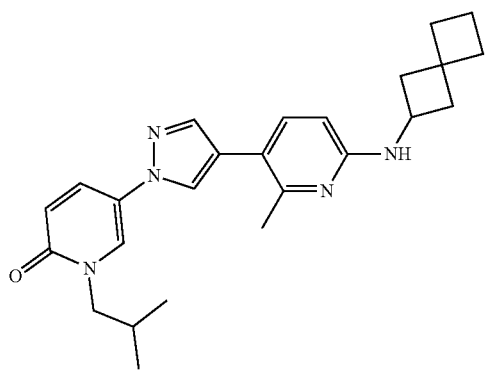
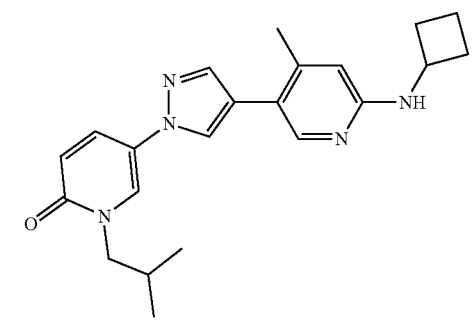
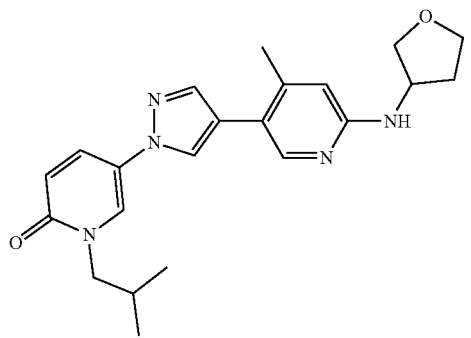
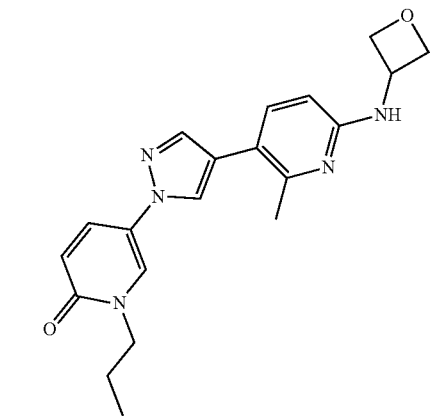
272
-continued
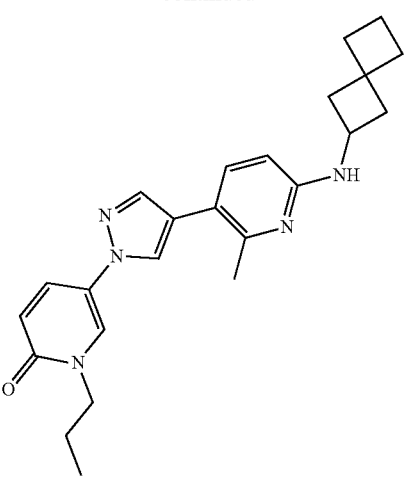
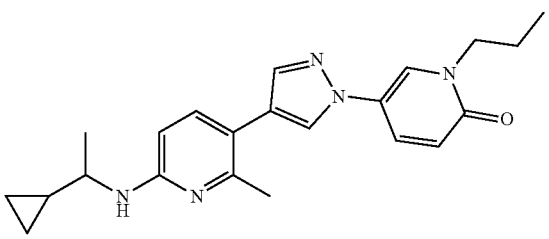
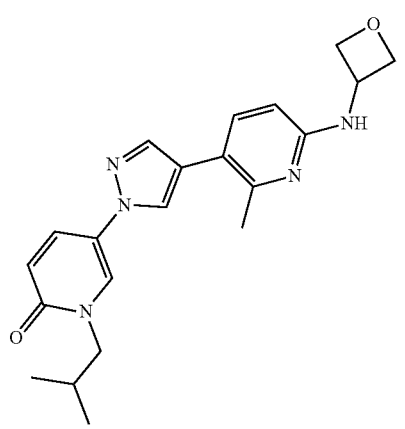
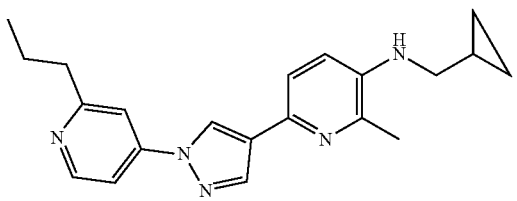
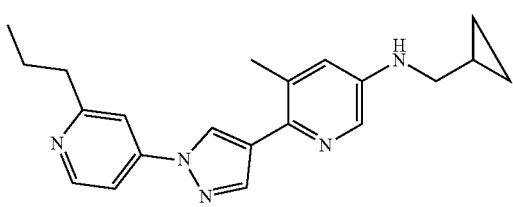
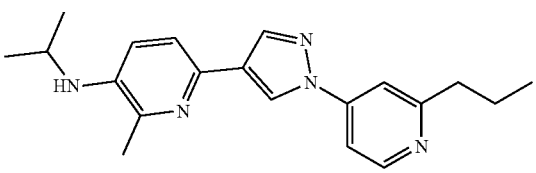

273
-continued
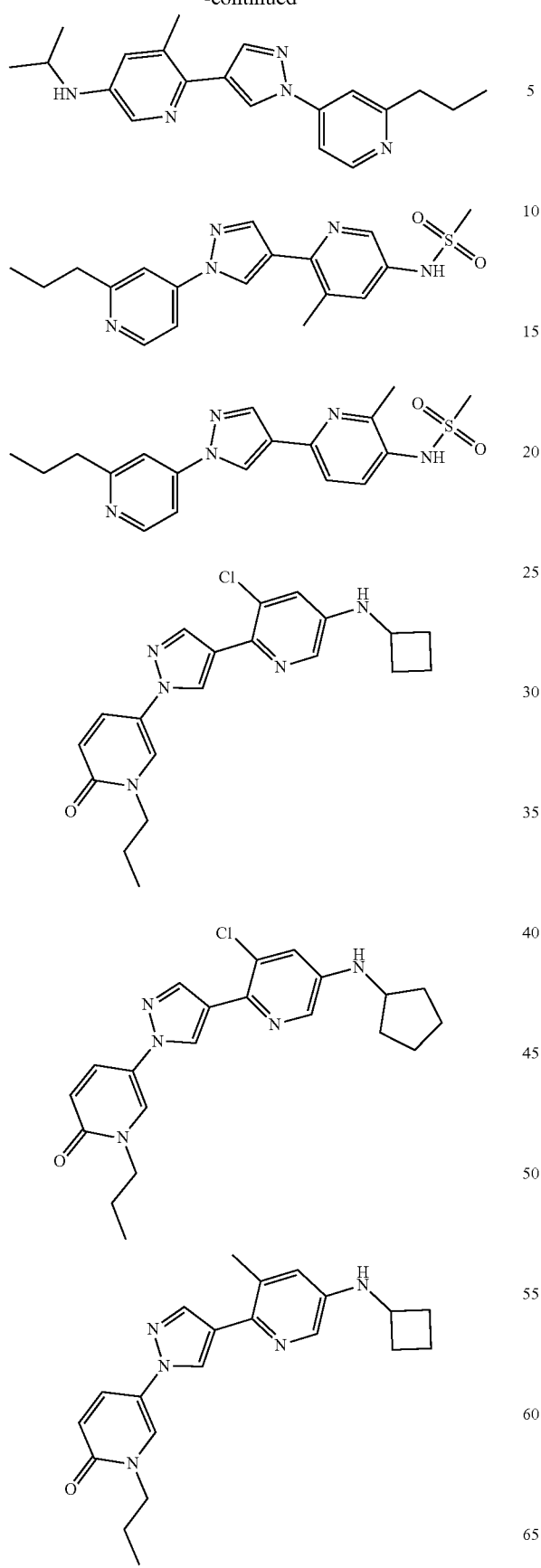
274
-continued
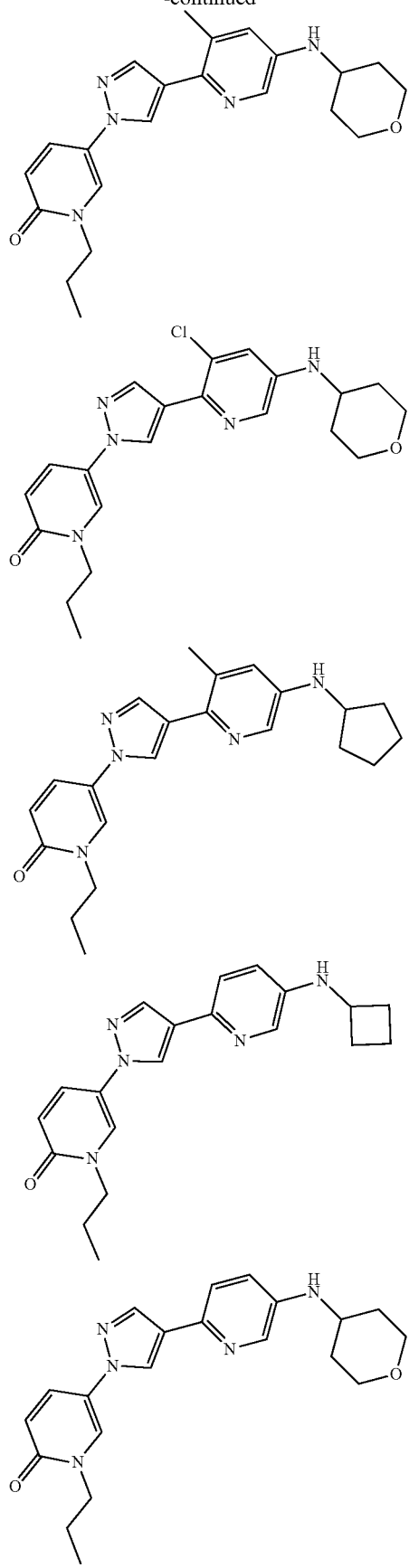

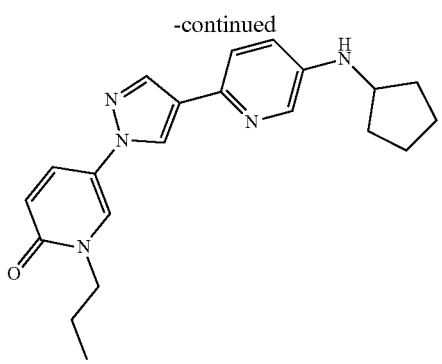

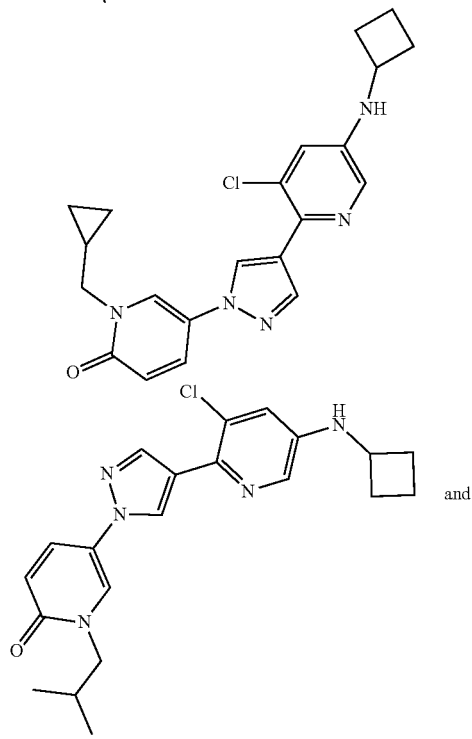

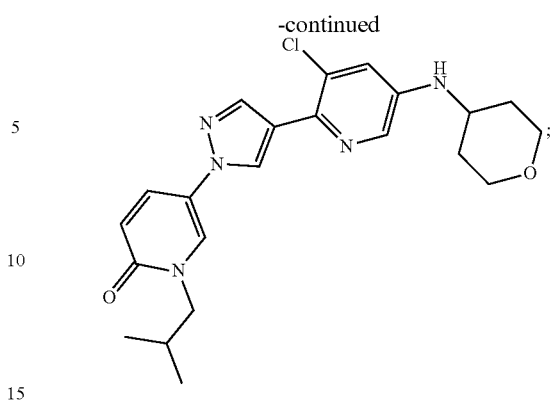

or a pharmaceutically acceptable salt thereof.

21. The method of claim 20, wherein the condition, disease, or disorder is selected from prostate cancer, post-menopausal breast carcinoma, pancreatic adenocarcinoma, leukemia, and liver cancer.

22. A method of reducing glucose, triglyceride, cholesterol, low-density lipoprotein, aspartate aminotransferase, and/or alanine aminotransferase levels, comprising administering to a patient in need thereof an effective amount of the Compound of claim 1.

23. A method of reducing glucose, triglyceride, cholesterol, low-density lipoprotein, aspartate aminotransferase, and/or alanine aminotransferase levels, comprising administering to a patient in need thereof an effective amount of the Compound of claim 15.

\* \* \* \* \*